(12) United States Patent
Vincent et al.

(10) Patent No.: US 9,738,610 B2
(45) Date of Patent: Aug. 22, 2017

(54) INDAZOLE DERIVATIVES AND USES THEREOF

(71) Applicants: Whitehead Institute for Biomedical Research, Cambridge, MA (US); The Broad Institute, Inc., Cambridge, MA (US); Massachusetts Institute of Technology, Cambridge, MA (US)

(72) Inventors: Benjamin Vincent, Cambridge, MA (US); Luke Whitesell, Somerville, MA (US); Susan L. Lindquist, Cambridge, MA (US); Willmen Youngsaye, Cumberland, RI (US); Stephen L. Buchwald, Newton, MA (US); Jean-Baptiste Langlois, Cambridge, MA (US); Partha P. Nag, Somerville, MA (US); Amal Ting, Newton, MA (US); Barbara J. Morgan, Mayfield Heights, OH (US); Benito Munoz, Newtonville, MA (US); Sivaraman Dandapani, Malden, MA (US); Bruce Tidor, Lexington, MA (US); Raja R. Srinivas, Cambridge, MA (US)

(73) Assignees: Whitehead Institute for Biomedical Research, Cambridge, MA (US); The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/430,308

(22) PCT Filed: Sep. 24, 2013

(86) PCT No.: PCT/US2013/061508
§ 371 (c)(1),
(2) Date: Mar. 23, 2015

(87) PCT Pub. No.: WO2014/047662
PCT Pub. Date: Mar. 27, 2014

(65) Prior Publication Data
US 2015/0353503 A1    Dec. 10, 2015

Related U.S. Application Data

(60) Provisional application No. 61/798,321, filed on Mar. 15, 2013, provisional application No. 61/705,099, filed on Sep. 24, 2012.

(51) Int. Cl.
| | |
|---|---|
| C07D 231/56 | (2006.01) |
| C07D 403/06 | (2006.01) |
| C07D 413/06 | (2006.01) |
| A61K 31/416 | (2006.01) |
| A61K 31/422 | (2006.01) |
| A61P 31/10 | (2006.01) |

(Continued)

(52) U.S. Cl.
CPC ......... C07D 231/56 (2013.01); C07D 401/04 (2013.01); C07D 401/06 (2013.01); C07D 403/06 (2013.01); C07D 405/04 (2013.01); C07D 409/04 (2013.01); C07D 413/06 (2013.01); C07D 417/06 (2013.01)

(58) Field of Classification Search
CPC .. C07D 231/56; C07D 403/06; C07D 413/06; A61K 31/416; A61K 31/422
USPC ....................................... 548/361.1; 514/404
See application file for complete search history.

(56) References Cited

U.S. PATENT DOCUMENTS

| | | |
|---|---|---|
| 5,571,902 A | 11/1996 | Ravikumar et al. |
| 6,462,068 B1 | 10/2002 | Straub et al. |

FOREIGN PATENT DOCUMENTS

WO  WO 2012/021982 A1   2/2012

OTHER PUBLICATIONS

Roemer et al. Cold Spring Harb Perspect Med 2014, 4, 1-14.*
(Continued)

*Primary Examiner* — Venkataraman Balasubramanian
(74) *Attorney, Agent, or Firm* — Wolf, Greenfield & Sacks, P.C.

(57) ABSTRACT

The present invention provides novel compounds (e.g., compounds of Formula (I)), and pharmaceutically acceptable salts, solvates, hydrates, polymorphs, co-crystals, tautomers, stereoisomers, isotopically labeled derivatives, prodrugs, and compositions thereof. Also provided are methods and kits comprising the inventive compounds, or compositions thereof, for treating and/or preventing a fungal or protozoan infection, inhibiting the activity of a fungal or protozoan enzyme, killing a fungus or protozoon, or inhibiting the growth of a fungus or protozoon. The fungus may be a *Candida* species, *Aspergillus* species, or other pathogenic fungal species. The compounds of the invention may inhibit the activity of fungal or protozoan cytochrome b and/or fungal or protozoan Hsp90. The present invention also provides synthetic methods of the inventive compounds.

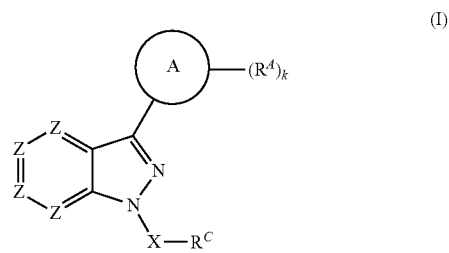

19 Claims, 20 Drawing Sheets

(51) Int. Cl.
 C07D 409/04 (2006.01)
 C07D 401/04 (2006.01)
 C07D 401/06 (2006.01)
 C07D 405/04 (2006.01)
 C07D 417/06 (2006.01)

(56) References Cited

OTHER PUBLICATIONS

Song et al. Crit Rev Microbiol, Early Online 1-34, 2015.*
Hartland et al. http://www.ncbi.nlm.nih.gov/books/NBK98920, Dec. 12, 2011; Full document provided.*
BioAssay: AID50504, <URL: http://pubchem.ncbi.nlm.nih.gov/assay/assay.cgi?aid=504504, deposit date Mar. 21, 2011, modified Date Mar. 13, 2011. BioAssay Test compounds List provided.*
International Search Report and Written Opinion, mailed Apr. 24, 2014, in connection with Application No. PCT/US2013/061508.
International Preliminary Report on Patentability, mailed Apr. 2, 2015, in connection with Application No. PCT/US2013/061508.
[No Author Listed], Antifungal Drug Resistance—Resistant Strain Measured in Microorganism System Using Plate Reader—2037-02_Inhibitor_Dose_DryPowder_Activity_Set10. BioAssay: AID 504504. Mar. 21, 2011. http://pubchem.ncbi.nlm.nih.gov/assay/assay.cgi?aid=504504 [last accessed Jun. 10, 2015]. 4 pages.
[No Author Listed], CID 49835841. Compound Summary. Jul. 11, 2011. http://pubchem.ncbi.nlm.nih.gov/compound/49835841 [last accessed Jun. 10, 2015]. 11 pages.
[No Author Listed], CID 49868638. Compound Summary. Jul. 11, 2011. http://pubchem.ncbi.nlm.nih.gov/compound/49868638 [last accessed Jun. 10, 2015]. 11 pages.
[No Author Listed], CID 53245458. Compound Summary. Jul. 11, 2011. http://pubchem.ncbi.nlm.nih.gov/compound/53245458 [last accessed Jun. 10, 2015]. 10 pages.
[No Author Listed], CID 53245464. Compound Summary. Jul. 11, 2011. http://pubchem.ncbi.nlm.nih.gov/compound/53245464#section=Top [last accessed Jun. 10, 2015]. 10 pages.
[No Author Listed], CID 53245469. Compound Summary. Jul. 11, 2011. http://pubchem.ncbi.nlm.nih.gov/compound/53245469 [last accessed Jun. 10, 2015]. 11 pages.
[No Author Listed], CID 53245471. Compound Summary. Jul. 11, 2011. http://pubchem.ncbi.nlm.nih.gov/compound/53245471 [last accessed Jun. 10, 2015]. 10 pages.
[No Author Listed], CID 53245478. Compound Summary. Jul. 11, 2011. http://pubchem.ncbi.nlm.nih.gov/compound/53245478 [last accessed Jun. 10, 2015]. 10 pages.
[No Author Listed], CID 53245479. Compound Summary. Jul. 11, 2011. http://pubchem.ncbi.nlm.nih.gov/compound/53245479 [last accessed Jun. 10, 2015]. 10 pages.
[No Author Listed], CID 53245485. Compound Summary. Jul. 11, 2011. http://pubchem.ncbi.nlm.nih.gov/compound/53245485 [last accessed Jun. 10, 2015]. 11 pages.
[No Author Listed], CLSI M27-A2: Reference Method for Broth Dilution Antifungal Susceptibility Testing of Yeasts; Approved Standard—Second Edition. Clinical and Laboratory Standards Institute. Aug. 2002;22(15). 51 pages.
[No Author Listed], CLSI M27-A3: Reference Method for Broth Dilution Antifungal Susceptibility Testing of Yeasts; Approved Standard—Third Edition. Clinical and Laboratory Standards Institute. Apr. 28, 2008;28(14). 40 pages.
Berge et al., Pharmaceutical Salts. J Pharm Sci. Jan. 1977;66(1):1-19.
Cernicka et al., Chemosensitisation of drug-resistant and drug-sensitive yeast cells to antifungals. Int J Antimicrob Agents. Feb. 2007;29(2):170-8. Epub Jan. 3, 2007.
Courchesne, Characterization of a novel, broad-based fungicidal activity for the antiarrhythmic drug amiodarone. J Pharmacol Exp Ther. Jan. 2002;300(1):195-9.
DiGirolamo et al., Reversal of fluconazole resistance by sulfated sterols from the marine sponge *Topsentia* sp. J Nat Prod. Aug. 2009;72(8):1524-8. doi: 10.1021/np900177m. Epub Jul. 1, 2013. 12 pages.
Gallo et al., 4-alkoxy and 4-thioalkoxyquinoline derivatives as chemosensitizers for the chloramphenicol-resistant clinical Enterobacter aerogenes 27 strain. Int J Antimicrob Agents. Sep. 2003;22(3):270-3.
Gamarra et al., Mechanism of the synergistic effect of amiodarone and fluconazole in Candida albicans. Antimicrob Agents Chemother. May 2010;54(5):1753-61. doi: 10.1128/AAC.01728-09. Epub Mar. 1, 2010.
Guo et al., Plagiochin E, a botanic-derived phenolic compound, reverses fungal resistance to fluconazole relating to the efflux pump. J Appl Microbiol. Mar. 2008;104(3):831-8. doi: 10.1111/j.1365-2672.2007.03617.x. Epub Jan. 9, 2008.
Hartland et al., Identification of small molecules that selectively inhibit fluconazole-resistant Candida albicans in the presence of fluconazole but not in its absence. Oct. 29, 2010 [updated Nov. 7, 2012]. Probe Reports from the NIH Molecular Libraries Program [Internet]. Bethesda (MD): National Center for Biotechnology Information (US); 2010-. 92 pages.
Hawkey et al., The changing epidemiology of resistance. J Antimicrob Chemother. Sep. 2009;64 Suppl 1:i3-10. doi: 10.1093/jac/dkp256. Review.
Johnson et al., Novel mitochondrial substrates of omi indicate a new regulatory role in neurodegenerative disorders. PLoS One. Sep. 18, 2009;4(9):e7100. doi: 10.1371/journal.pone.0007100. 12 pages.
Kim et al., Chemosensitization prevents tolerance of Aspergillus fumigatus to antimycotic drugs. Biochem Biophys Res Commun. Jul. 18, 2008;372(1):266-71. doi: 10.1016/j.bbrc.2008.05.030. Epub May 16, 2008.
Kinzel et al., A new palladium precatalyst allows for the fast Suzuki-Miyaura coupling reactions of unstable polyfluorophenyl and 2-heteroaryl boronic acids. J Am Chem Soc. Oct. 13, 2010;132(40):14073-5. doi: 10.1021/ja1073799. Epub Oct. 13, 2011. 12 pages.
Lavigne et al., Squalamine, an original chemosensitizer to combat antibiotic-resistant gram-negative bacteria. J Antimicrob Chemother. Apr. 2010;65(4):799-801. doi: 10.1093/jac/dkq031. Epub Feb. 10, 2010.
Mai et al., Discovery of uracil-based histone deacetylase inhibitors able to reduce acquired antifungal resistance and trailing growth in Candida albicans. Bioorg Med Chem Lett. Mar. 1, 2007;17(5):1221-5. Epub Dec. 12, 2006.
Pfaller et al., Epidemiology of invasive candidiasis: a persistent public health problem. Clin Microbiol Rev. Jan. 2007;20(1):133-63. Review.
Redding et al., Resistance of Candida albicans to fluconazole during treatment of oropharyngeal candidiasis in a patient with AIDS: documentation by in vitro susceptibility testing and DNA subtype analysis. Clin Infect Dis. Feb. 1994;18(2):240-2.
Sanglard et al., Resistance of Candida species to antifungal agents: molecular mechanisms and clinical consequences. Lancet Infect Dis. Feb. 2002;2(2):73-85. Review.
Spinks et al., Design, synthesis and biological evaluation of Trypanosoma brucei trypanothione synthetase inhibitors. ChemMedChem. Jan. 2, 2012;7(1):95-106. doi: 10.1002/cmdc.201100420. Epub Dec. 8, 2011.
Wilen et al., Strategies in Optical Resolutions. Tetrahedron. 1977;33:2725-36.
PCT/US2013/061508, Apr. 24, 2014, International Search Report and Written Opinion.
PCT/US2013/061508, Apr. 2, 2015, International Preliminary Report on Patentability.

* cited by examiner

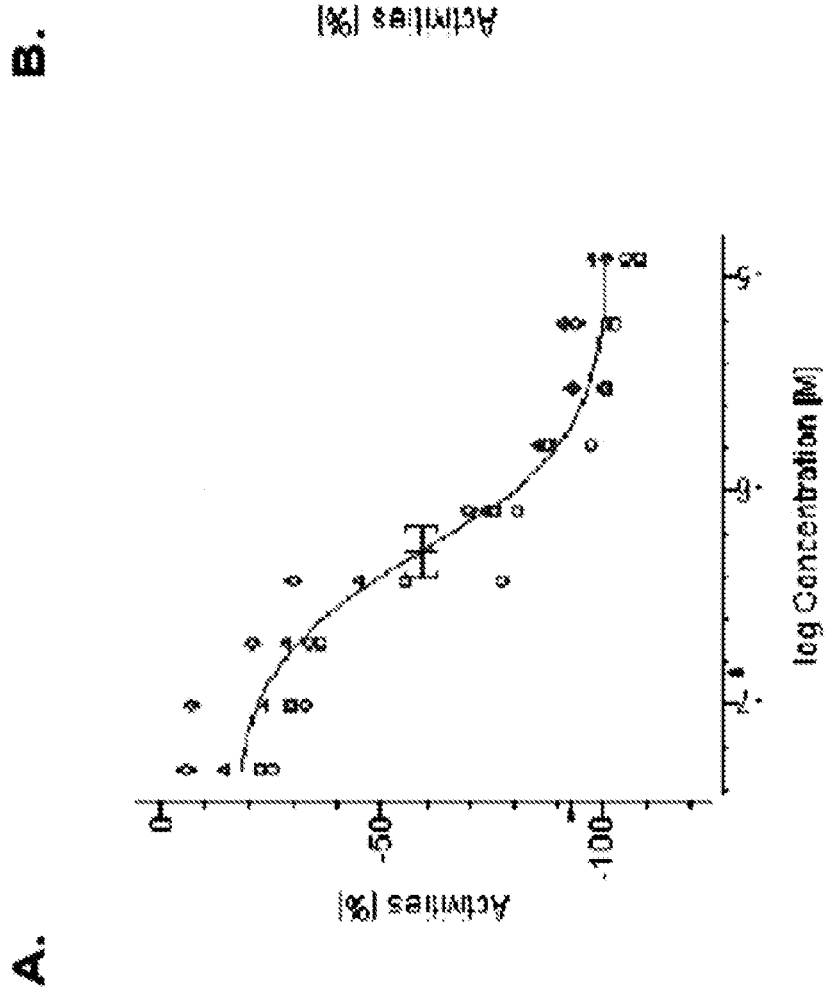
Figure 6A-B

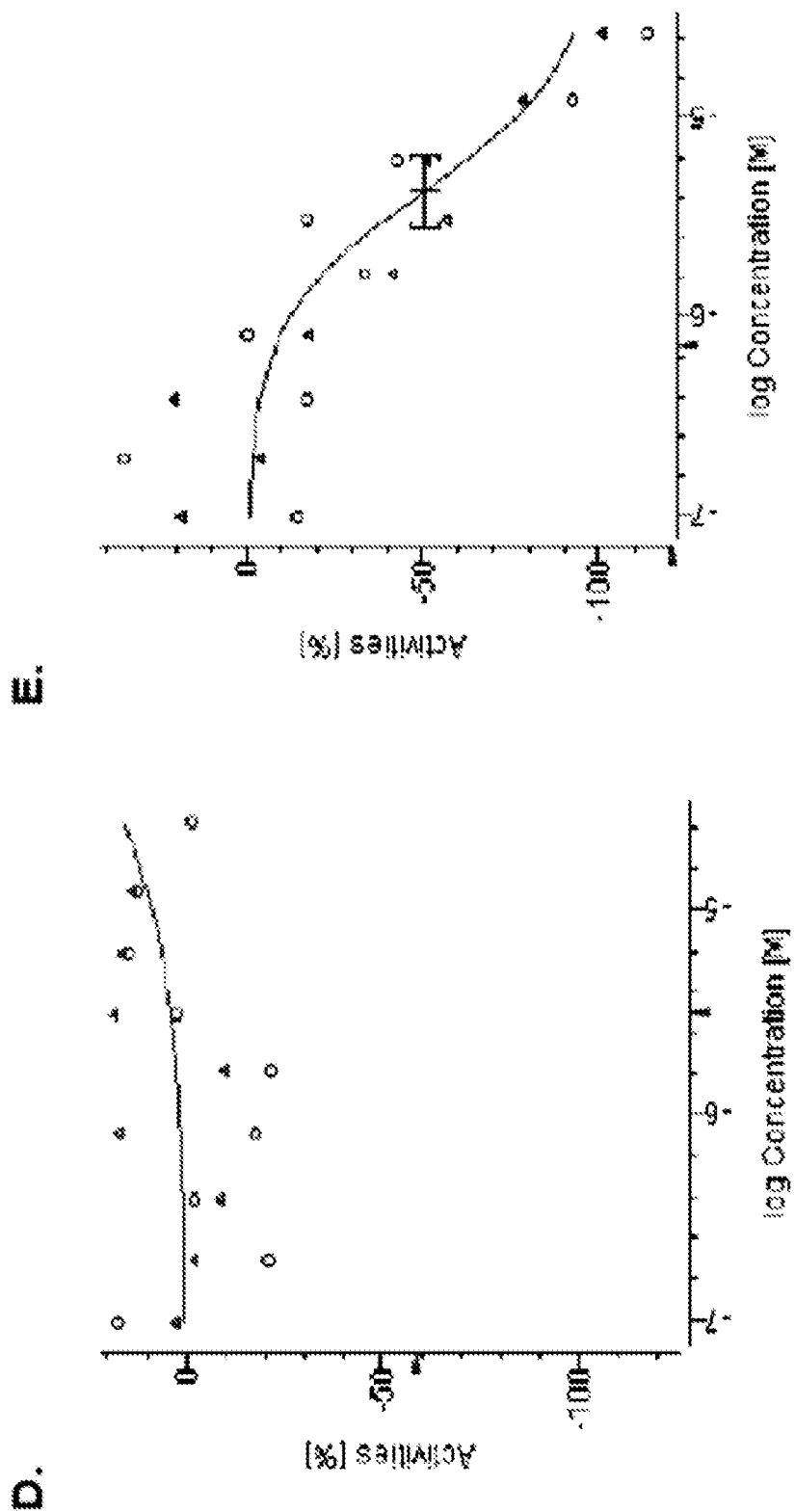
Figure 6D-E

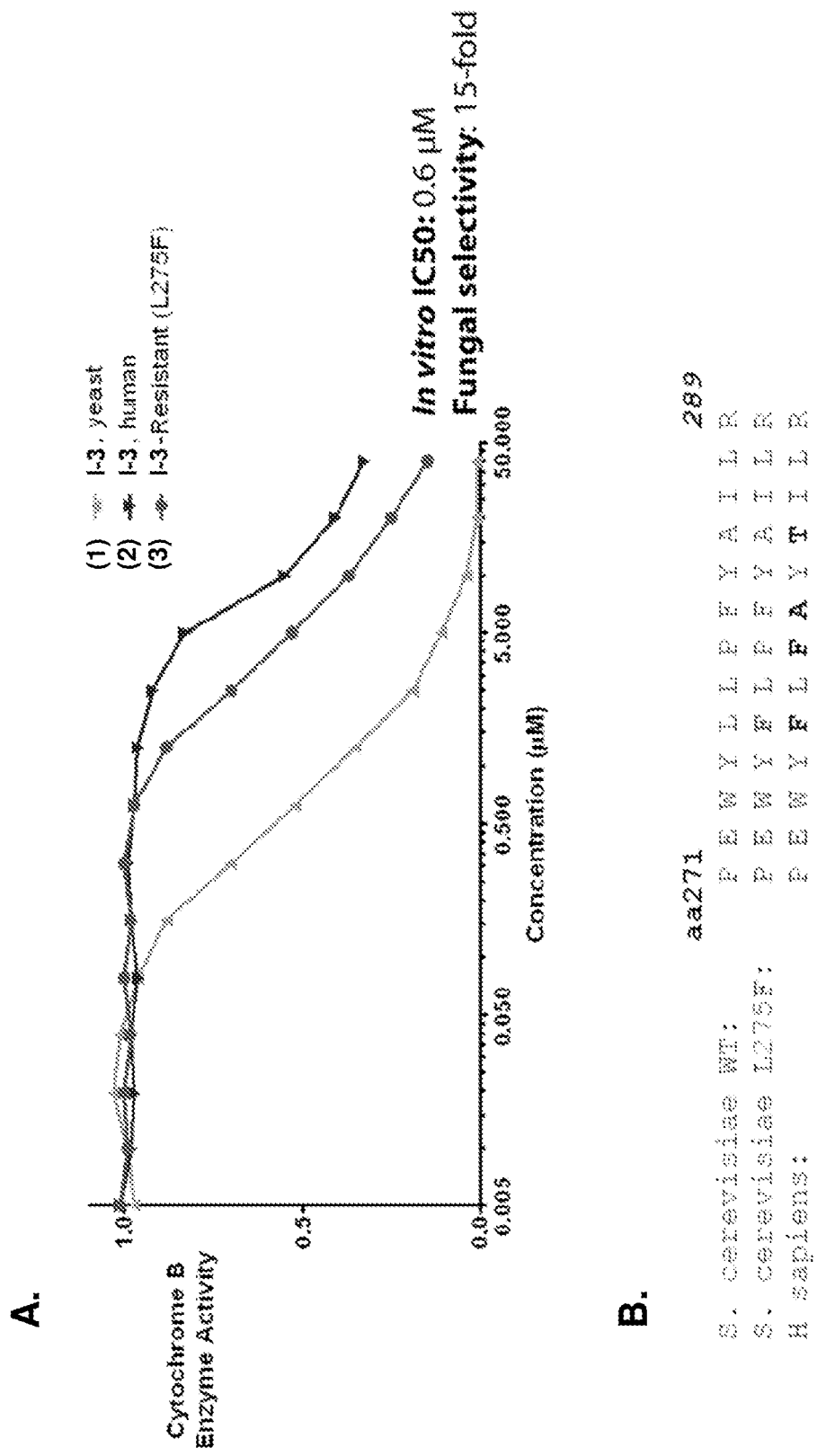
Figure 14A-B

SEQUENCE LISTING

```
<160> NUMBER OF SEQ ID NOS: 3

<210> SEQ ID NO 1
<211> LENGTH: 13
<212> TYPE: PRT
<213> ORGANISM: Saccharomyces cerevisiae

<400> SEQUENCE: 1

Pro Glu Trp Tyr Leu Leu Pro Phe Tyr Ala Ile Leu Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 2

Pro Glu Trp Tyr Phe Leu Pro Phe Tyr Ala Ile Leu Arg
1               5                   10

<210> SEQ ID NO 3
<211> LENGTH: 13
<212> TYPE: PRT
<213> ORGANISM: Homo sapiens

<400> SEQUENCE: 3

Pro Glu Trp Tyr Phe Leu Phe Ala Tyr Thr Ile Leu Arg
1               5                   10
```

INDAZOLE DERIVATIVES AND USES THEREOF

RELATED APPLICATIONS

The present application is a national stage filing under 35 U.S.C. §371 of international PCT application, PCT/US2013/061508, filed Sep. 24, 2013, which claims priority under 35 U.S.C. §119(e) to U.S. provisional patent applications, U.S. Ser. No. 61/798,321, filed Mar. 15, 2013, and U.S. Ser. No. 61/705,099, filed Sep. 24, 2012, each of which is incorporated herein by reference.

GOVERNMENT SUPPORT

This invention was made with government support under Grant Nos. MH086456 and HG005032 awarded by the National Institutes of Health. The government has certain rights in the invention.

BACKGROUND OF THE INVENTION

The discovery of antimicrobial agents possessing unique structural motifs or a novel mechanism of action is critical to counter and control the rising incidence of drug-resistant pathogens (Hawkey et al., *J. Antimicrob. Chemother.* 2009, 64, i3-i10; Gould, *Int. J. Antimicrob. Agents* 2008, 32, S2-S9; Pfaller et al., *Clin. Microbiol. Rev.* 2007, 20, 133-163; Sanglard et al., *Lancet Infect. Dis.* 2002, 2, 73-85). Chemosensitization of resistant organisms is a complementary approach that capitalizes upon the existing arsenal of antimicrobials to combat this medical dilemma (Lavigne et al., *J. Antimicrob. Chemother.* 2010, 65, 799-801; Gallo et al., *Int. J. Antimicrob. Agents* 2003, 22, 270-273; Kim et al., *Biochem. Biophys. Res. Commun.* 2008, 372, 266-271; Cernicka et al., *Int. J. Antimicrob. Agents* 2007, 29, 170-178). By undermining the target pathogen's resistance mechanisms, it is possible to restore efficacy to previously ineffective drugs thereby prolonging their status as frontline treatments. This, in turn, affords critical lead time towards the development of novel antimicrobial drugs.

Fungi are a prominent cause of hospital-acquired infections that are becoming increasingly difficult to control (Pfaller, et al., *Clin. Microbiol. Rev.* 2007, 20, 133-163). Several compounds have been previously identified as chemosensitizers, increasing the susceptibility of various strains of pathogenic fungus *Candida albicans* (*C. albicans*) to fluconazole (FIG. 1) treatment (DiGirolamo et al., "Reversal of fluconazole resistance by sulfated sterols from the marine sponge *Topsentia* sp." *J. Nat. Prod.* 2009, 72(8):1524-28; Cernicka et al., "Chemosensitisation of drug-resistant and drug-sensitive yeast cells to antifungals." *Int. J. Antimicrobial Agents* 2007, 29(2):170-8; Gamarra et al., "Mechanism of the synergistic effect of amiodarone and fluconazole in *C. albicans*. Antimicrob Agents." *Chemother.* 2010, 54(5): 1753-61; Guo et al., "Plagiochin E, a botanic-derived phenolic compound, reverses fungal resistance to fluconazole relating to the efflux pump." *J. Appl. Microbio.* 2008, 104(3):831-38). Cernicka et al. previously reported that the compound 7-chlorotetrazolo[5,1-c]benzo[1,2,4]triazine (CTBT, FIG. 1) was capable of chemosensitizing *C. albicans* strains to fluconazole (Cernicka et al., "Chemosensitisation of drug-resistant and drug-sensitive yeast cells to antifungals." *Int. J. Antimicrobial Agents* 2007, 29(2):170-8). Against fluconazole-susceptible *C. albicans* strain 90028 and fluconazole-resistant *C. albicans* strain Gu5, CTBT was effective with a minimum inhibitory concentration (MIC) value of 2.4 µM when combined with fluconazole. In the absence of fluconazole, CTBT demonstrated no activity against *C. albicans* strain 90028 but did inhibit growth of *C. albicans* strain Gu5 at concentrations greater than 2.4 µM. The anti-arrhythmic drug amiodarone was recently demonstrated to act synergistically with fluconazole in *C. albicans* with MIC values ranging between 1.6 µM to 18.8 µM (Gamarra et al., "Mechanism of the synergistic effect of amiodarone and fluconazole in *C. albicans*. Antimicrob Agents." *Chemother.* 2010, 54(5):1753-61). Plagiochin E, a natural product isolated from liverwort, increased yeast susceptibility to fluconazole at 2.4 µM (Guo et al., "Plagiochin E, a botanic-derived phenolic compound, reverses fungal resistance to fluconazole relating to the efflux pump." *J. Appl. Microbio.* 2008, 104(3):831-38). These agents have been reported to show single-agent antifungal activity. For example, amiodarone shows an $MIC_{50}$ value of 3.1 µM (Courchesne, "Characterization of a novel, broad-based fungicidal activity for the antiarrhythmic drug amiodarone." *J. Pharmacol. Exp. Ther.* 2002, 300:195-99;), and plagiochin E shows an $IC_{50}$ value of 3.8 µM (Guo et al., "Plagiochin E, a botanic-derived phenolic compound, reverses fungal resistance to fluconazole relating to the efflux pump." *J. Appl. Microbio.* 2008, 104(3):831-38).

There remains a need for new classes of antifungal agents or chemosensitizers that increase the effect of existing antifungals agents.

The most potent compounds currently known are several HDAC inhibitors previously reported by Mai et al. ("Discovery of uracil-based histone deacetylase inhibitors able to reduce acquired antifungal resistance and trailing growth in *C. albicans.*" *Bioorg. Med. Chem. Lett.* 2007, 17(5):1221-25). As depicted in FIG. 2, compounds 4 and 5 are uracil-derived hydroxamic acids that exhibited MIC values ranging from 1.2 µM to 1.4 µM when combined with fluconazole. When tested independently, neither compound demonstrated activity against *C. albicans* at concentrations up to 368 µM. When compounds 4 and 5 were evaluated in a biochemical binding assay with murine histone deacetylase 1 (HDAC1), their $IC_{50}$ values were measured at 37 nM and 51 nM, respectively (Mai et al., "Discovery of uracil-based histone deacetylase inhibitors able to reduce acquired antifungal resistance and trailing growth in *C. albicans.*" *Bioorg. Med. Chem. Lett.* 2007, 17(5):1221-25). This finding suggests that these HDAC inhibitors would not be particularly selective for fungal protein targets and diminishes their potential as fungal-selective chemosensitizers. At the present time, neither compound 4 nor 5 has been registered with Molecular Libraries Small Molecule Repository (MLSMR) and was not available for evaluation.

SUMMARY OF THE INVENTION

National Institutes of Health Molecular Libraries and Probe Production Centers Network (NIH-MLPCN) recently performed a high-throughput screening (HTS) campaign to search for potential chemosensitizers of *C. albicans* (pubchem.ncbi.nlm.nih.gov/assay/assay.cgi?aid=1979). The *C. albicans* clinical isolates used in this study demonstrate a range of resistance to the widely prescribed triazole antimycotic fluconazole (Flc) (Redding et al., *Clin. Infect. Dis.* 1994, 18, 240-242), and the objective was to identify novel small molecules capable of surmounting this inherent resistance (DiGirolamo et al., *J. Nat. Prod.* 2009, 72, 1524-1528; Gamarra et al., *Antimicrob. Agents Chemother.* 2010, 54, 1753-1761; Guo et al., *J. Appl. Microbiol.* 2008, 104, 831-838; Mai, et al., *Bioorg. Med. Chem. Lett.* 2007, 17, 1221-1225). The screen was conducted using a phenotypic assay with integrated counter screens to remove compounds acting through previously established methods for overturning drug resistance in *C. albicans*.

A high-throughput screening of 300,000 compounds from the NIH's MLSMR collection identified several substances that potentiate the effect of fluconazole in fluconazole-resistant *Candida albicans* (*C. albicans*) clinical isolates. Among the numerous hits, compound I-16 (see below) was selected for chemical optimization, resulting in the identification of compound I-4 (ML212; see below), which may, among other things, be used as a new small molecule probe to facilitate investigation of the various mechanisms employed by *C. albicans* to withstand fluconazole. Elucidation of compound I-4's mechanism of action may afford new targets to exploit in the continuing efforts to develop novel antimycotics and combat increasingly prevalent drug-resistance.

(I-16)

In one aspect, the present invention provides compounds developed from the identification of compounds I-4 and I-16 for treating fungal injections. In certain embodiments, the present invention provides compounds of Formula (I):

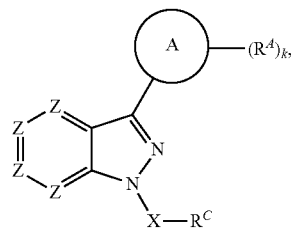

(I)

wherein X, Z, ring A, $R^A$, $R^C$, and k are defined herein, and pharmaceutically acceptable salts, solvates, hydrates, polymorphs, co-crystals, tautomers, stereoisomers, isotopically labeled derivatives, and prodrugs thereof.

Exemplary compounds of Formula (I) include, but are not limited to:

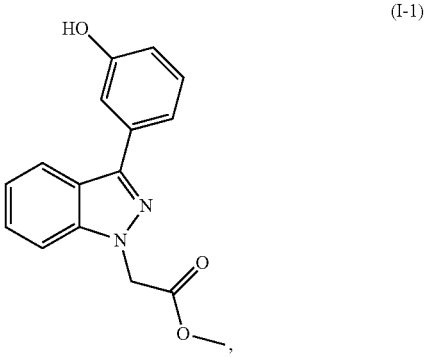

(I-1)

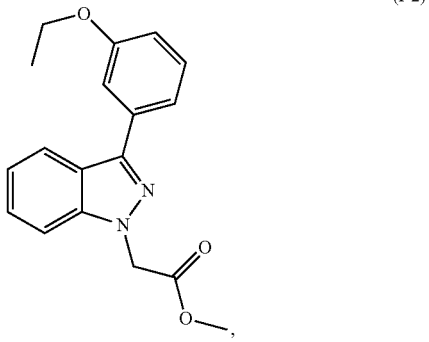

(I-2)

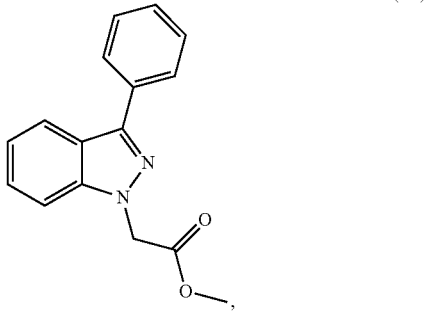

(I-3)

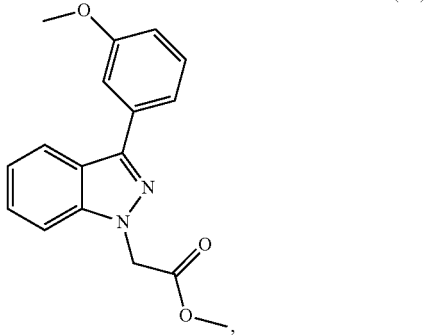

(I-4)

(I-5)
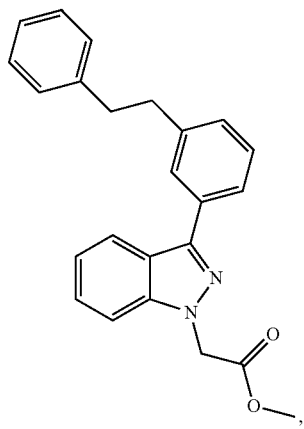
(I-6)
(I-7)
(I-8)
(I-9)
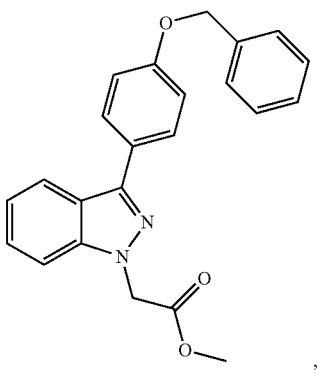
(I-10)
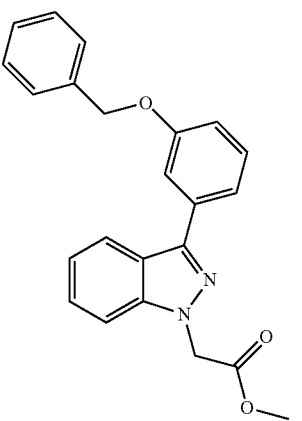
(I-11)
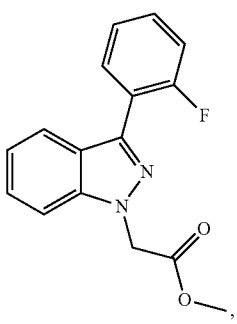
(I-12)
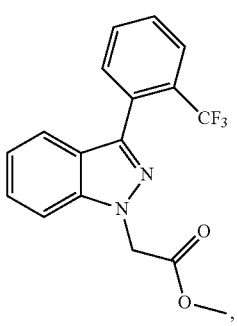

-continued
(I-13)
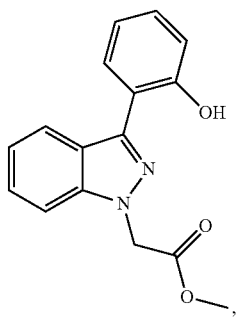
(I-14)
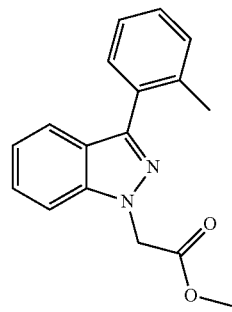
(I-15)
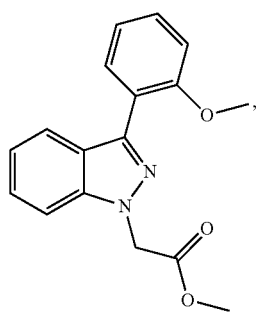
(I-16)
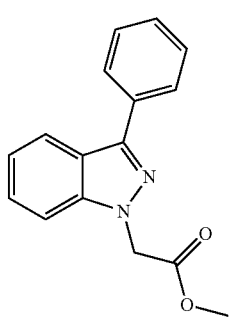
(I-17)
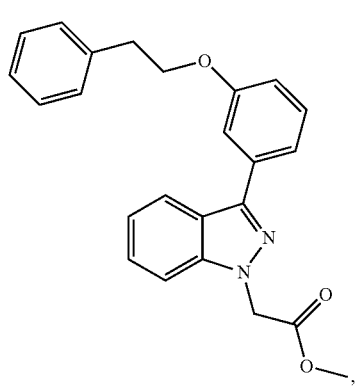
-continued
(I-18)
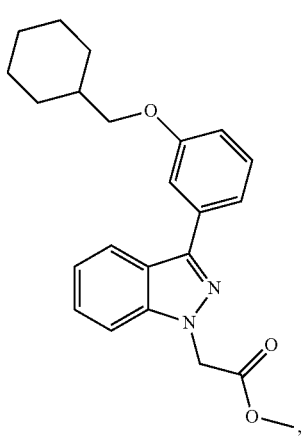
(I-19)
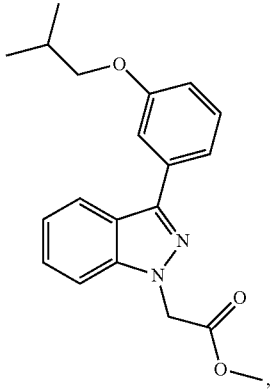
(I-20)
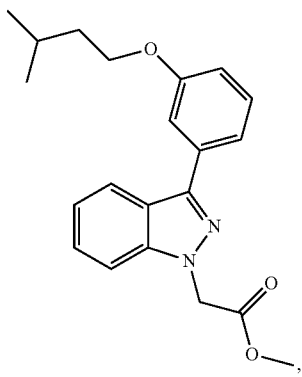
(I-21)
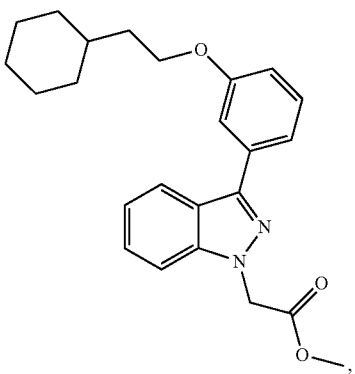

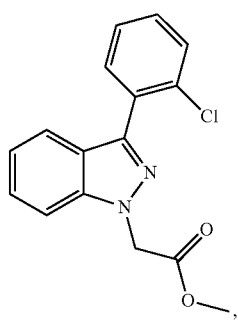
(I-22)
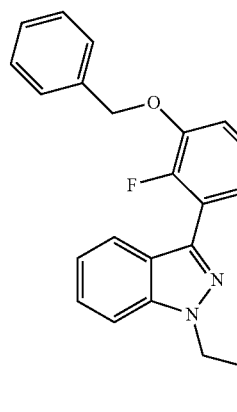
(I-26)
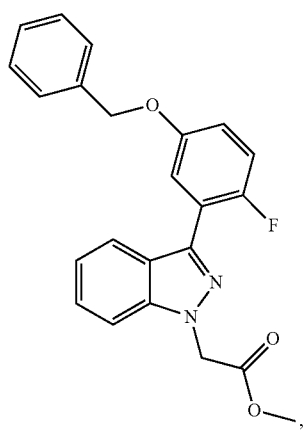
(I-23)
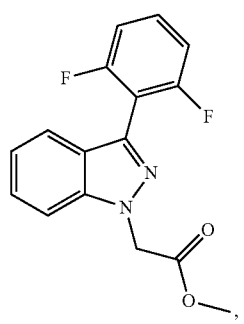
(I-27)
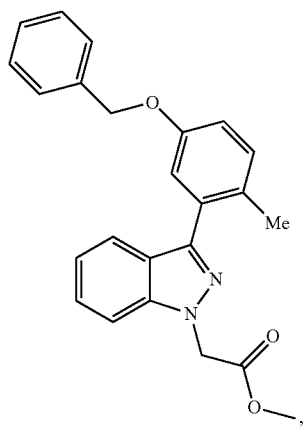
(I-24)
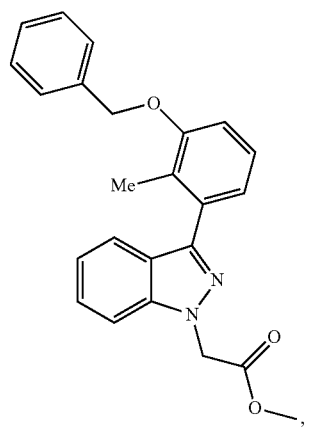
(I-28)
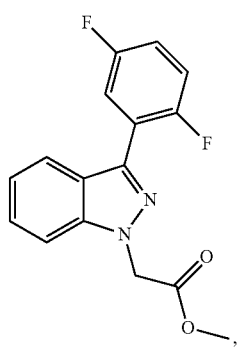
(I-25)
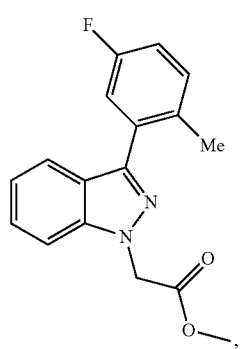
(I-29)

| | |
|---|---|
| (I-30) 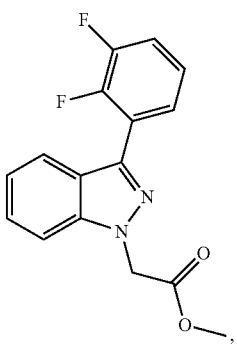 | (I-35) 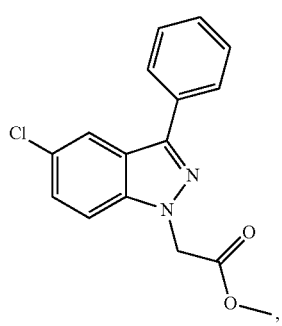 |
| (I-31) 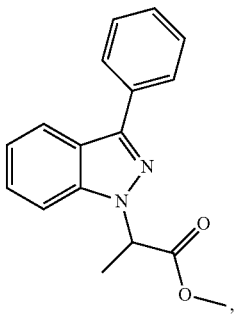 | (I-36) 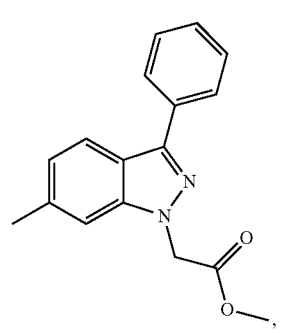 |
| (I-32) 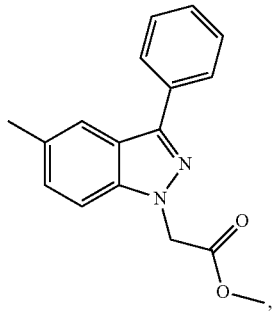 | (I-37) 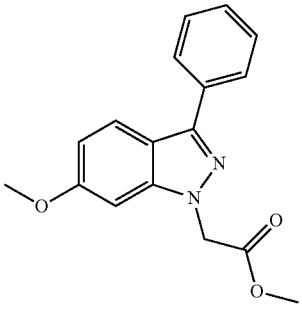 |
| (I-33) 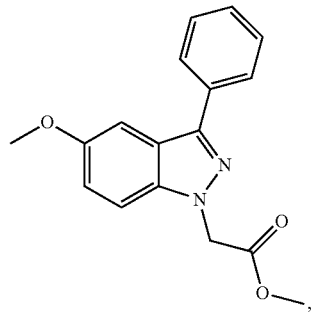 | (I-38) 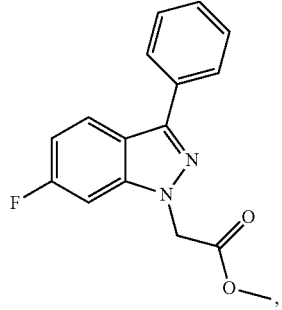 |
| (I-34) 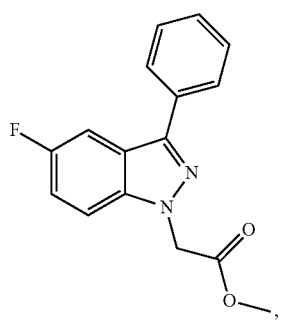 | (I-39) 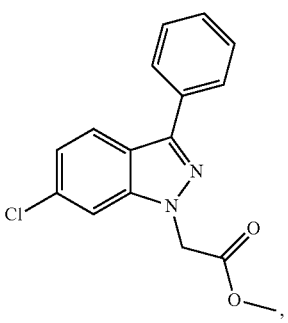 |

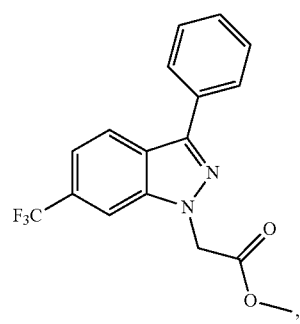
(I-40)
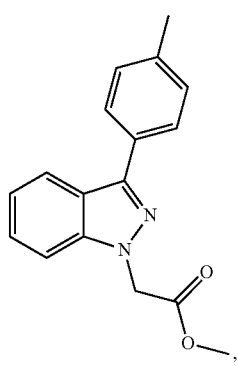
(I-41)
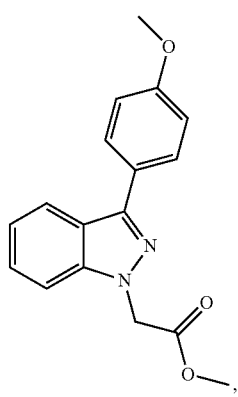
(I-42)
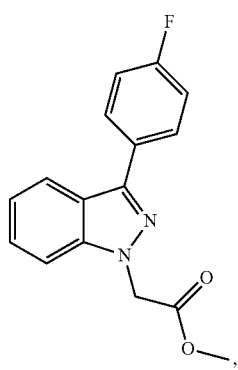
(I-43)
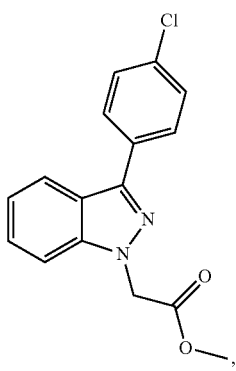
(I-44)
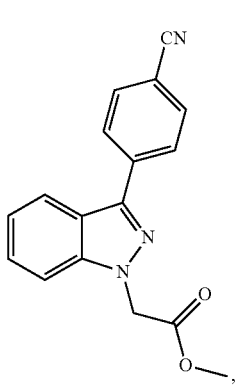
(I-45)
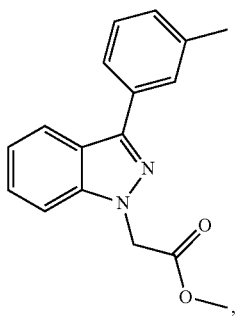
(I-46)
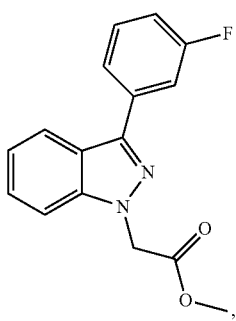
(I-47)

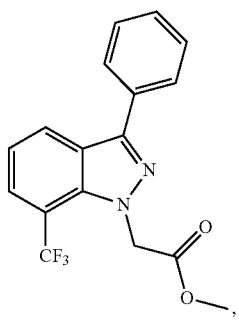 (I-48)
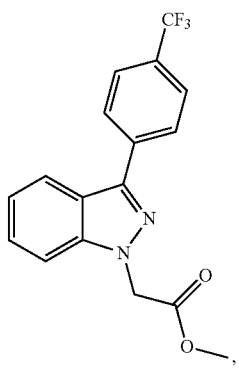 (I-49)
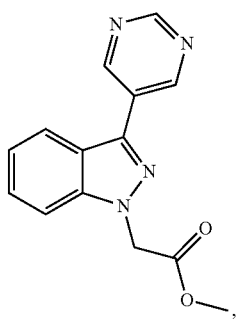 (I-50)
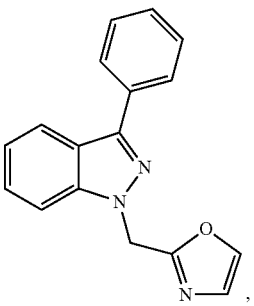 (I-51)
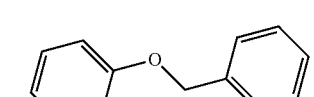
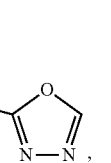 (I-52)
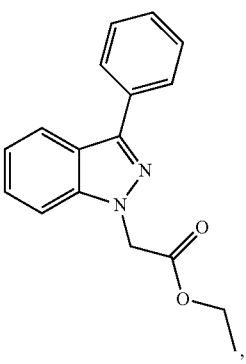 (I-53)
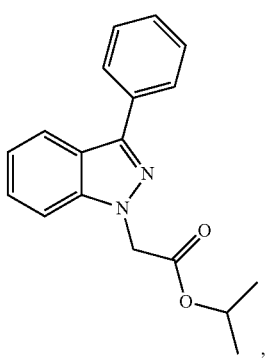 (I-54)
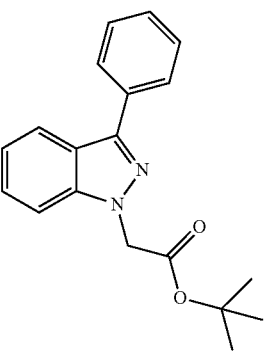 (I-55)
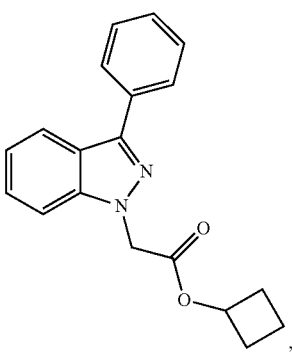 (I-56)

(I-57)
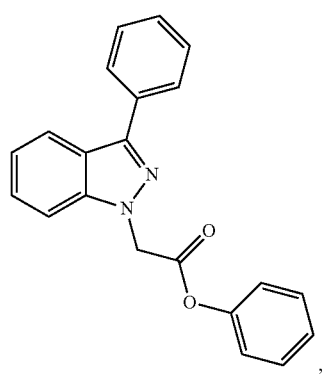
(I-58)
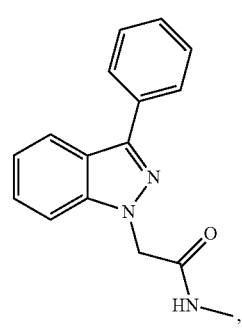
(I-59)
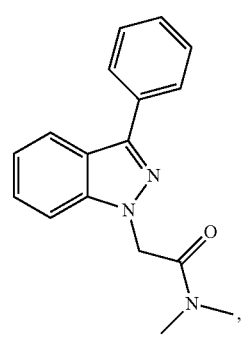
(I-60)
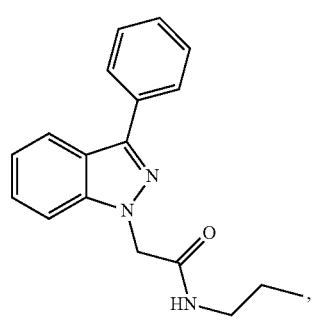
(I-61)
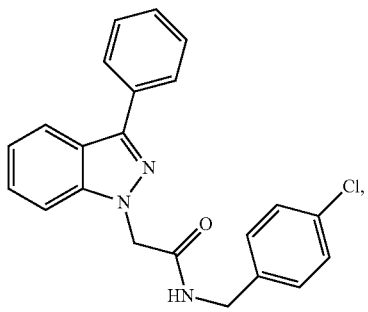
(I-62)
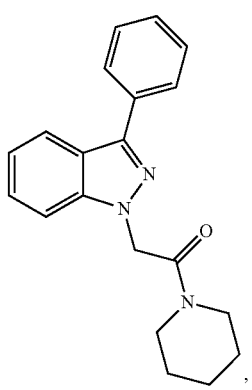
(I-63)
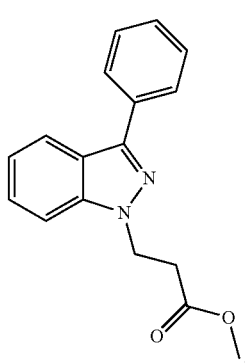
(I-64)
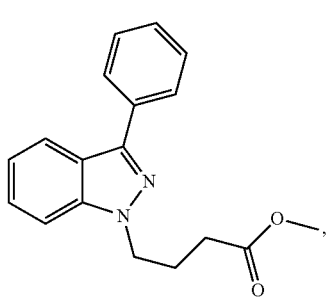

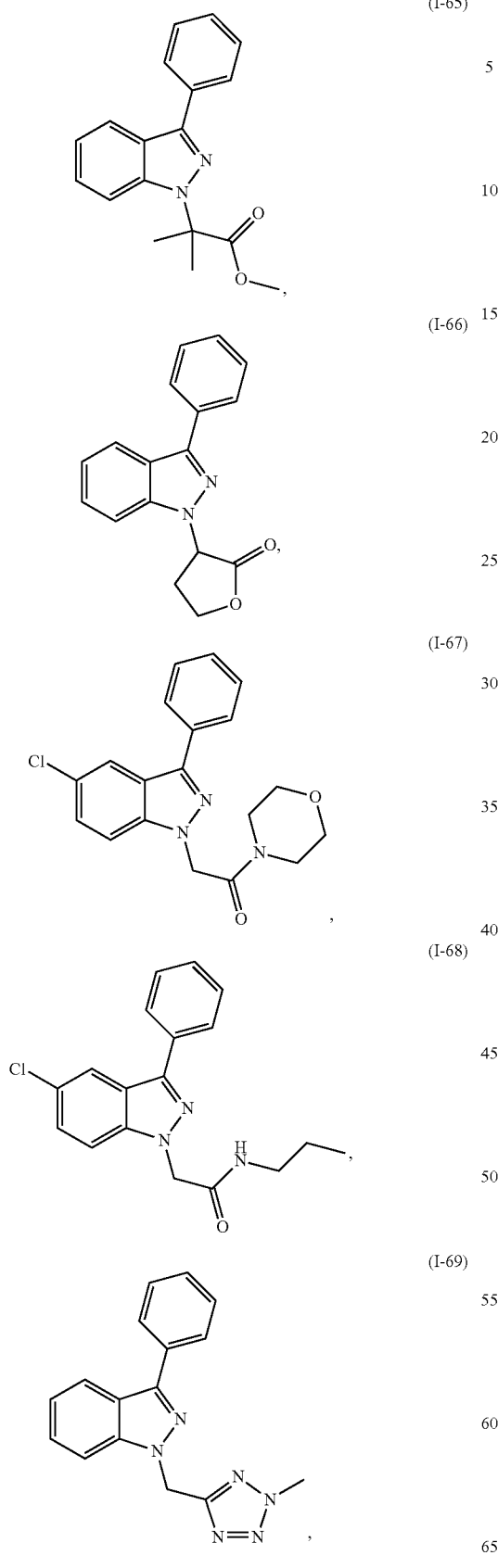
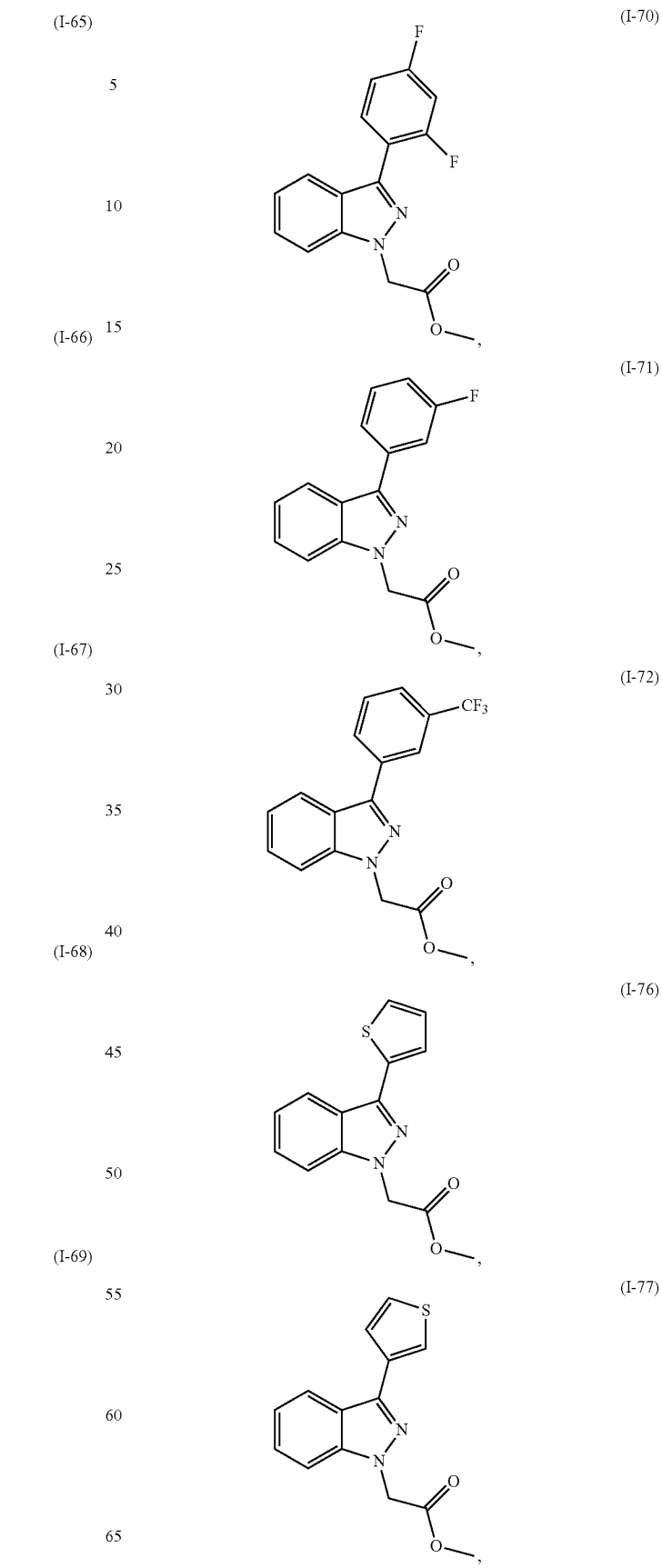

-continued
(I-78)
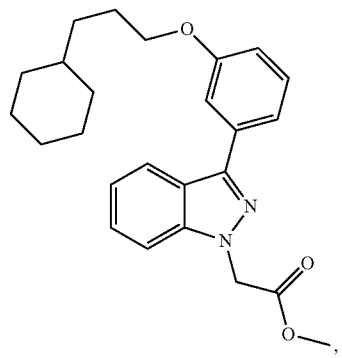
(I-79)
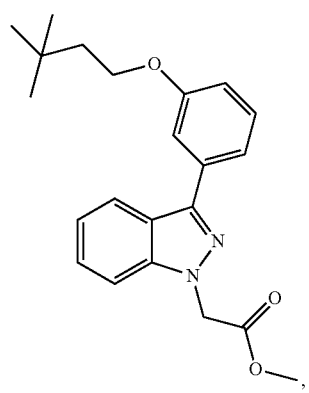
(I-80)
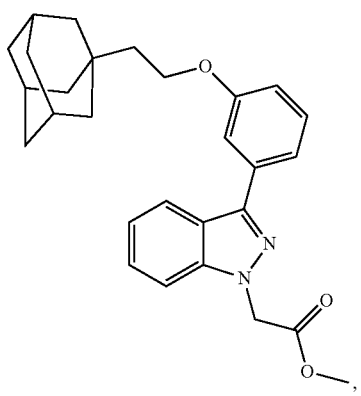
(I-81)
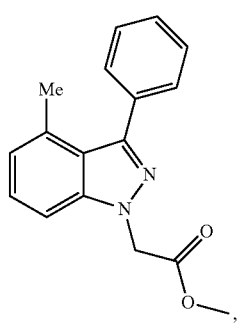
-continued
(I-82)
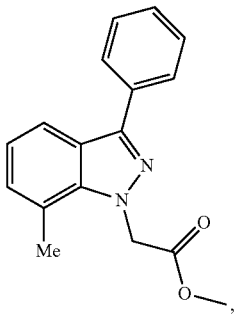
(I-83)
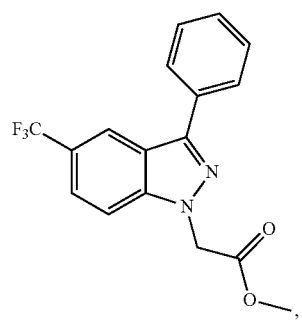
(I-88)
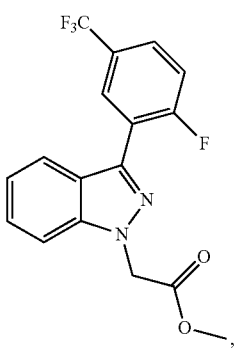
(I-89)
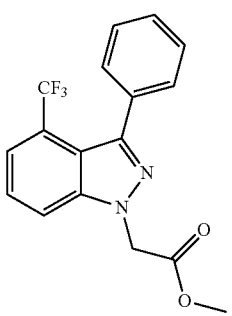
(I-96)
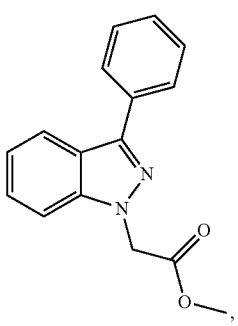

(I-97)
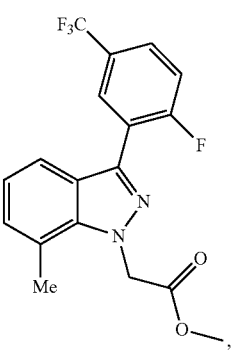
(I-100)
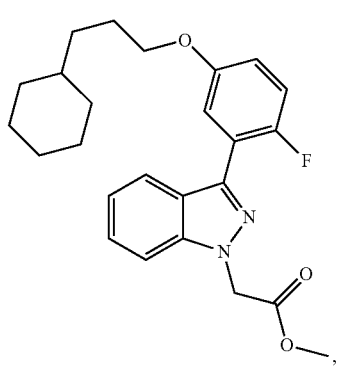
(I-101)
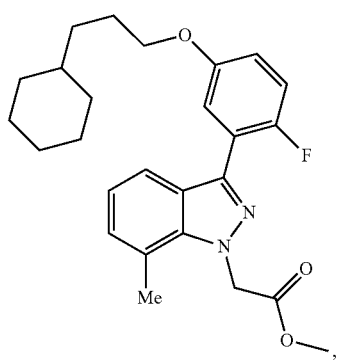
(I-117)
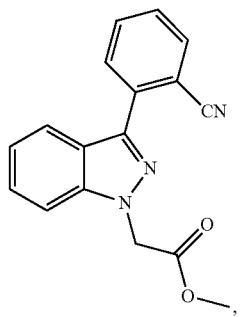
(I-118)
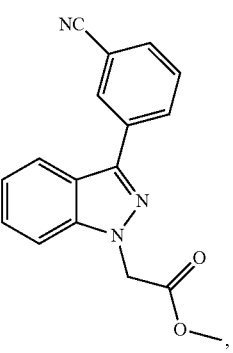
(I-119)
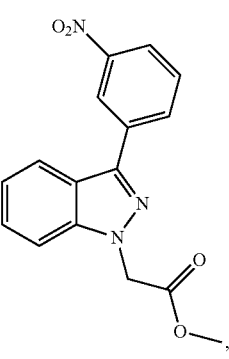
(I-120)
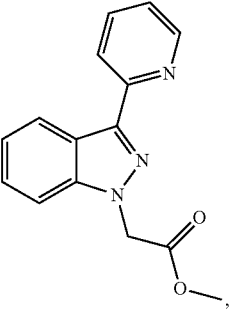
(I-121)
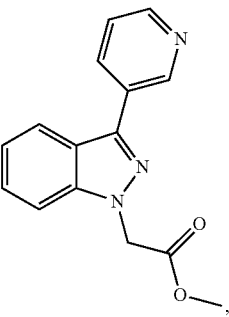

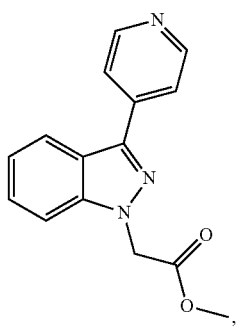
(I-122)
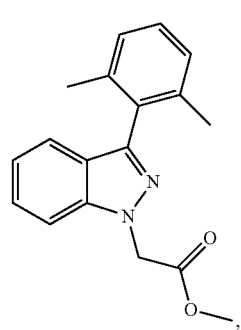
(I-127)
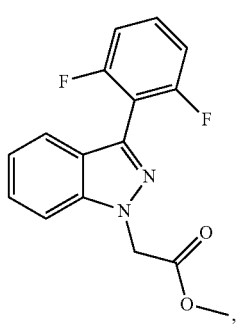
(I-128)
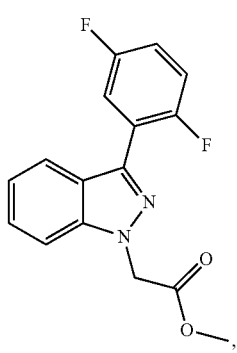
(I-129)
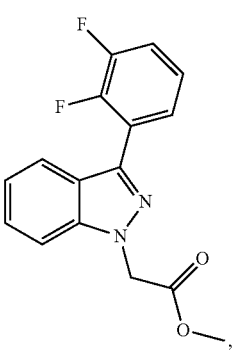
(I-130)
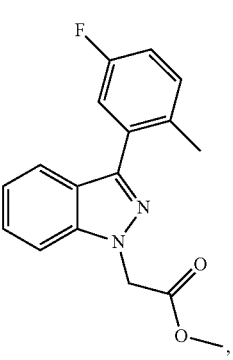
(I-131)
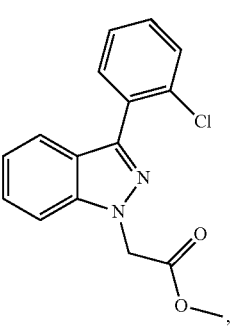
(I-132)
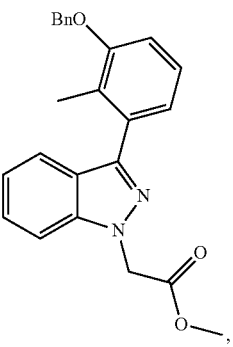
(I-133)

27
-continued
(I-134)
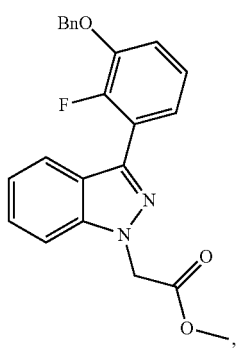
(I-135)
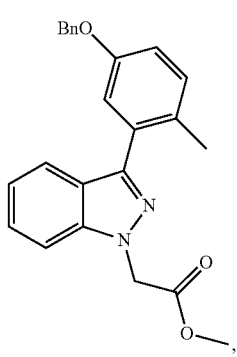
(I-136)
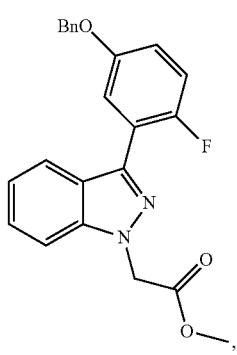
(I-137)
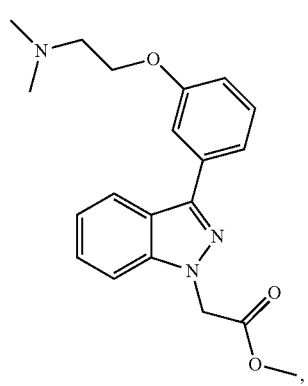
28
-continued
(I-138)
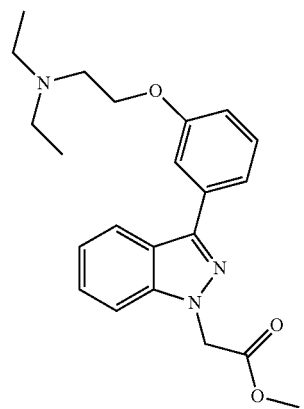
(I-139)
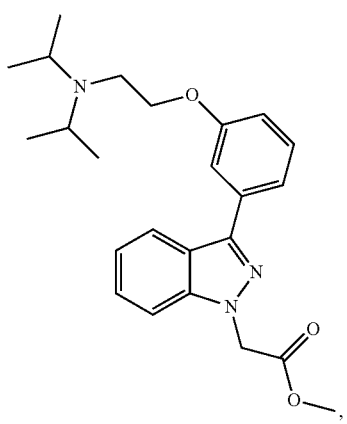
(I-140)
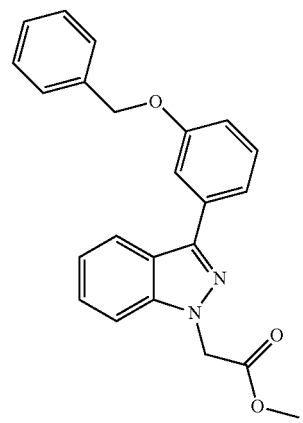
(I-141)
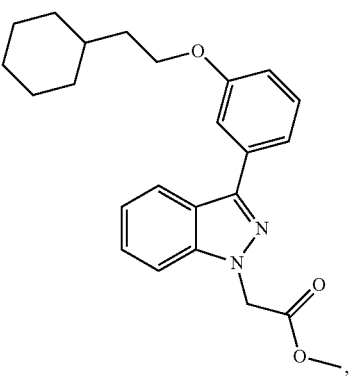

(I-74) 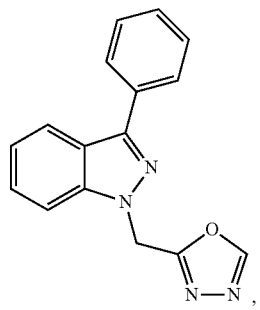
(I-84) 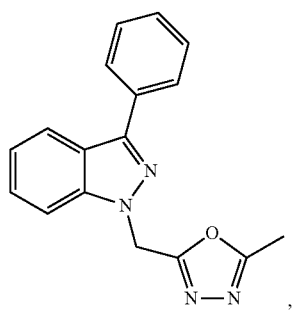
(I-85) 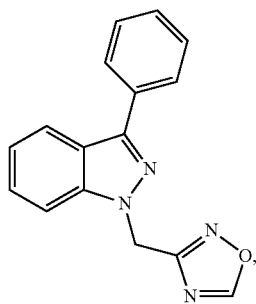
(I-86) 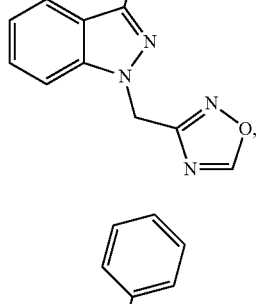
(I-87) 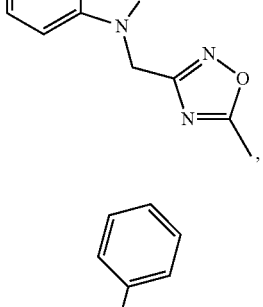
(I-90) 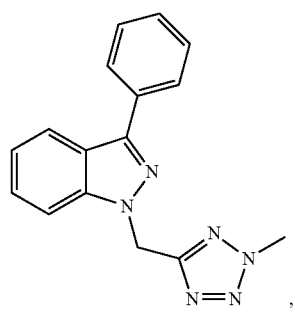
(I-91) 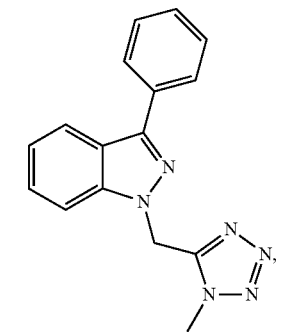
(I-92) 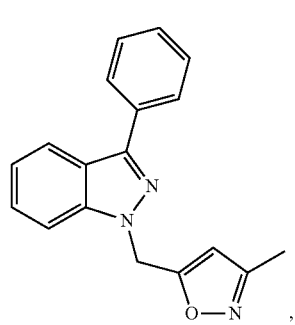
(I-93) 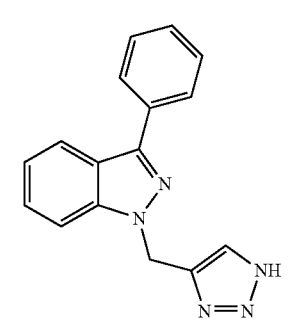
(I-94) 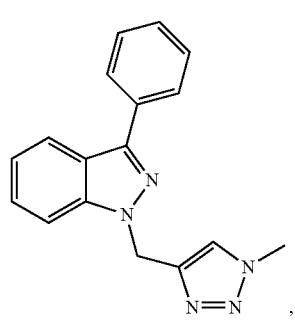

(I-95)
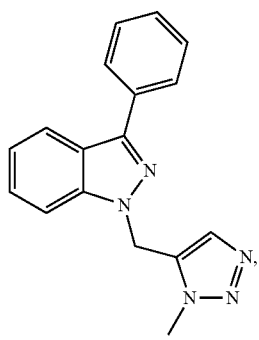
(I-98)
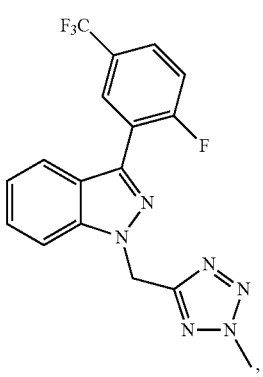
(I-99)
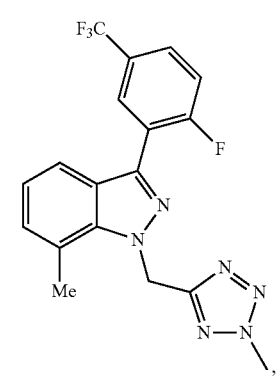
(I-102)
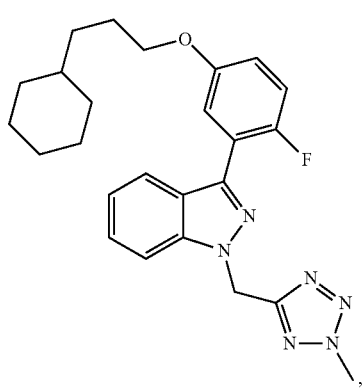
(I-103)
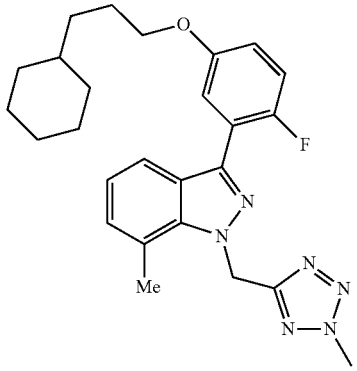
(I-108)
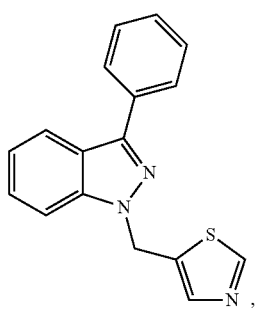
(I-109)
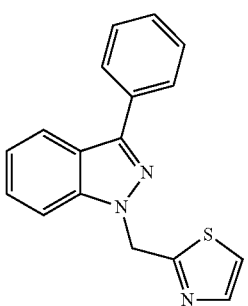
(I-112)
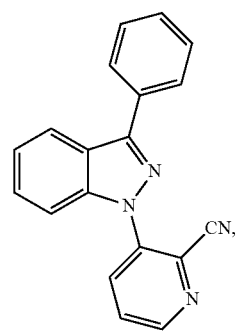

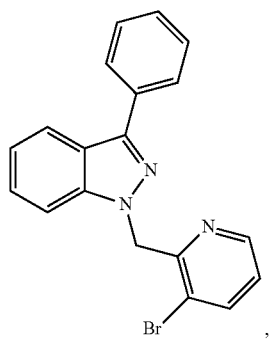
(I-113)
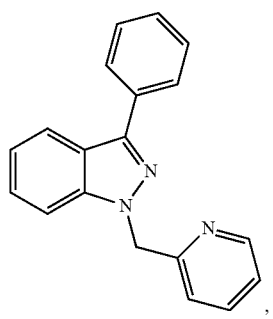
(I-114)
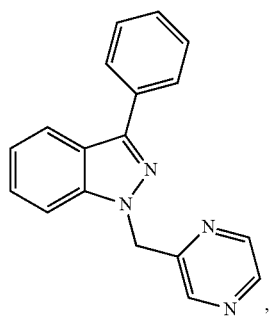
(I-115)
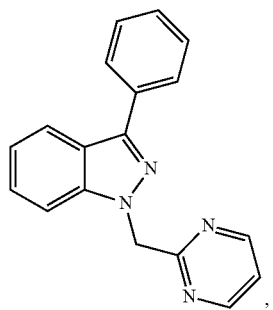
(I-123)
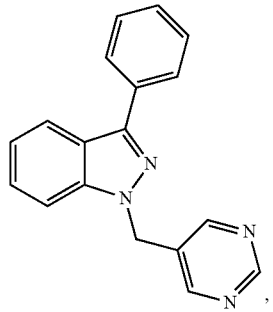
(I-124)
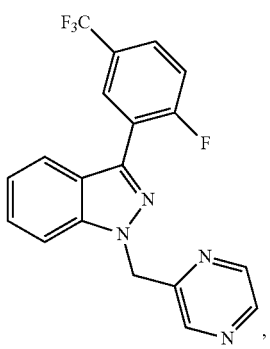
(I-125)
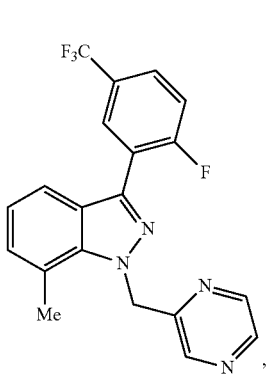
(I-126)
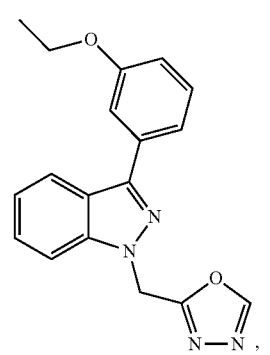
(I-142)
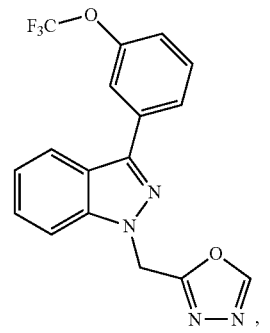
(I-143)

(I-144)
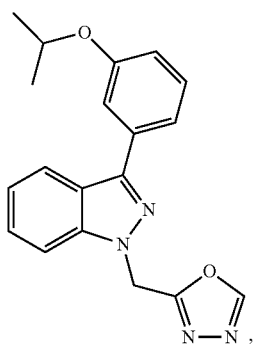
(I-145)
(I-146)
(I-147)
(I-148)
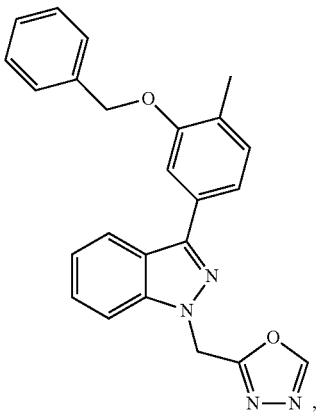
(I-149)
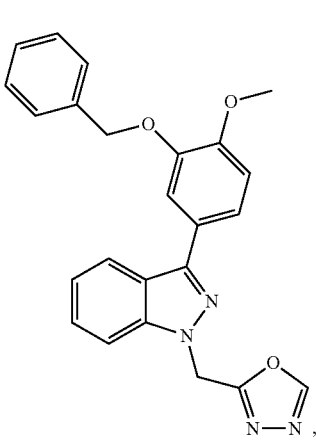
(I-150)
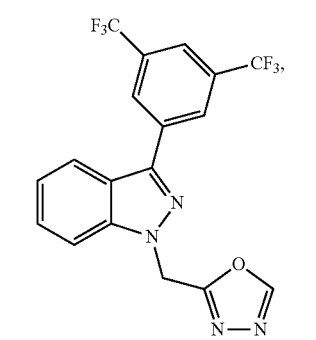
(I-151)
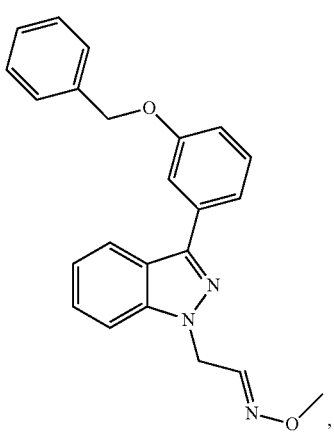

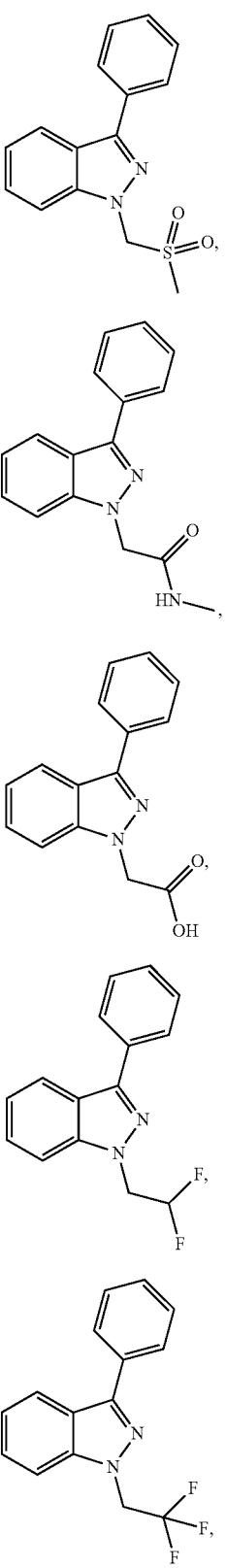

and pharmaceutically acceptable salts, solvates, hydrates, polymorphs, co-crystals, tautomers, stereoisomers, isotopically labeled derivatives, and prodrugs thereof.

In certain embodiments, the compound described herein is not any one of Formulae (I-4), (I-14)-(I-16), (I-31)-(I-51), (I-53)-(I-68), and pharmaceutically acceptable salts, solvates, hydrates, polymorphs, co-crystals, tautomers, stereoisomers, isotopically labeled derivatives, and prodrugs thereof.

In another aspect, the present invention provides pharmaceutical compositions comprising a compound described herein, or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of described herein, or a pharmaceutically acceptable salt, solvate, hydrate, polymorph, co-crystal, tautomer, stereoisomer, isotopically labeled derivative, or prodrug thereof, for treating or preventing a fungal or protozoan infection. The pharmaceutical composition may optional include another antifungal agent such as an azole antibiotic (e.g., fluconazole).

In one aspect, the present invention provides methods for the treatment of a fungal infection in a subject. In certain embodiments, the fungus causing the fungal infection is a *Candida* species (e.g., *Candida albicans* (e.g., CaCi-2 or CaCi-8)). In certain embodiments, the fungus is an *Aspergillus* species (e.g., *Aspergillus terreus*).

In another aspect, the present invention provides methods for the treatment of a protozoan infection in a subject. In certain embodiments, the protozoon causing the protozoan infection is a *Cryptosporidium*. In certain embodiments, the protozoon causing the protozoan infection is a member of genus *Trypanosoma*. In certain embodiments, the protozoon causing the protozoan infection is a member of genus *Pneumocystis*. In certain embodiments, the protozoon causing the protozoan infection is a member of genus *Plasmodium*. In certain embodiments, the protozoon causing the protozoan infection is a member of genus *Giardia*.

In still another aspect, the present invention provides methods of inhibiting the activity of fungal cytochrome b in a subject or biological sample.

In yet another aspect, the present invention provides methods of inhibiting the activity of fungal Hsp90 in a subject or biological sample.

Another aspect of the present invention relates to methods of killing a fungus or inhibiting the growth of a fungus.

In certain embodiments, the methods described herein include administering to a subject, contacting a biological sample, or contacting a fungus with an effective amount of a compound described herein, or a pharmaceutically acceptable salt, solvate, hydrate, polymorph, co-crystal, tautomer, stereoisomer, isotopically labeled derivative, or prodrug thereof, or a composition thereof. The inventive methods may be in vitro or in vivo.

The methods of the present invention may further comprise administering to a subject, contacting with a biological sample, or contacting with a fungus, one or more additional pharmaceutical agents in combination with a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. The additional pharmaceutical agent may be an antifungal agent (e.g., an azole antifungal agent (e.g., fluconazole)).

Another aspect of the invention relates to methods of screening a library of compounds to identify one or more compounds that are useful for the methods of the invention.

In certain embodiments, the compound identified by the methods of screening is useful in inhibiting the growth of or killing a fungus when the compound is employed without one or more additional pharmaceutical agents. In certain embodiments, the compound identified by the methods of screening is useful in inhibiting the growth of or killing a fungus when employed in combination with one or more additional pharmaceutical agents.

In yet another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in the treatment and/or prevention of a fungal infection in a subject, or in the killing a fungus or inhibition of the growth of a fungus.

In still another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in the treatment and/or prevention of a protozoan infection in a subject, or in the killing a protozoon or inhibition of the growth of a protozoon.

Another aspect provides methods of making compounds described herein, and methods of making compositions comprising one or more of the compounds.

Another aspect of the present invention relates to kits comprising a container with a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. The kits described herein may also include one or more additional pharmaceutical agents, such as antifungal agents (e.g., azole antifungal agents (e.g., fluconazole)). The provided kits may be useful for the treatment and/or prevention of a fungal and/or protozoan infection. In certain embodiments, the kits described herein further include instructions for administering a compound described herein, or a pharmaceutically acceptable salt, solvate, hydrate, polymorph, co-crystal, tautomer, stereoisomer, isotopically labeled derivative, or prodrug thereof, or a pharmaceutical composition thereof.

The details of particular embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

"Alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Haloalkyl" is a substituted alkyl group wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

"Heteroalkyl" refers to an alkyl group which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O) (R$^{aa}$)$_2$, —OP(=O)(R$^{aa}$)$_2$, —OP(=O)(OR$^{cc}$)$_2$, —P(=O)$_2$N (R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$ N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC (=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P (=O)$_2$R$^{ee}$, —P(=O)(R$^{ee}$)$_2$, —OP(=O)(R$^{ee}$)$_2$, —OP(=O) (OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ ($C_{1-6}$ alkyl), —NHC(=O)N($C_{1-6}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C (=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S) S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N ($R^{bb}$)$_2$, —C(=NR$^{bb}$)$R^{aa}$, —C(=NR$^{bb}$)OR$^{aa}$, —C(=NR$^{bb}$) N($R^{bb}$)$_2$, —C(=O)NR$^{bb}$SO$_2$$R^{aa}$, —C(=S)N($R^{bb}$)$_2$, —C(=O)SR$^{aa}$, or —C(=S)SR$^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N($R^{cc}$)$_2$, —CN, —C(=O)$R^{aa}$, —C(=O)N ($R^{cc}$)$_2$, —CO$_2$$R^{aa}$, —SO$_2$$R^{aa}$, —C(=NR$^{bb}$)$R^{aa}$, —C(=NR$^{cc}$)OR$^{aa}$, —C(=NR$^{cc}$)N($R^{cc}$)$_2$, —SO$_2$N($R^{cc}$)$_2$, —SO$_2$$R^{cc}$, —SO$_2$OR$^{cc}$, —SOR$^{aa}$, —C(=S)N($R^{cc}$)$_2$, —C(=O)SR$^{cc}$, —C(=S)SR$^{cc}$, —P(=O)$_2$$R^{aa}$, —P(=O) ($R^{aa}$)$_2$, —P(=O)$_2$N($R^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=NR$^{cc}$)$R^{aa}$, —C(=NR$^{cc}$)OR$^{aa}$, —C(=NR$^{cc}$)N ($R^{cc}$)$_2$, —SO$_2$N($R^{cc}$)$_2$, —SO$_2$$R^{cc}$, —SO$_2$OR$^{cc}$, —SOR$^{aa}$, —C(=S)N($R^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), tert-butyloxycarbonyl (BOC or Boc), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolylN-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)N(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.
Other Definitions The following definitions are more general terms used throughout the present application:

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish.

The terms "administer," "administering," or "administration" refers to implanting, absorbing, ingesting, injecting, inhaling, or otherwise introducing an inventive compound, or a pharmaceutical composition thereof, in or on a subject.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein, such as a fungal or protozoan infection. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment. For example, in treating a fungal or protozoan infection, an effective amount of an inventive compound may inhibit the growth of the fungi and/or kill the fungi.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "cytochrome" refers to a membrane-bound hemoprotein that contains heme groups and carries out electron transport. Several kinds of cytochrome exist, including cytochrome a, cytochrome b, cytochrome d, and cytochrome f. Cytochrome b is the main subunit of transmembrane cytochrome bc1 and b6f complexes. In the mitochondrion of eukaryotes and in aerobic prokaryotes, cytochrome b is a component of respiratory chain complex III (also known as the bc1 complex or ubiquinol-cytochrome c reductase). In plant chloroplasts and cyanobacteria, there is an analogous protein, cytochrome b6, a component of the plastoquinone-plastocyanin reductase (also known as the b6f complex). These complexes are involved in electron transport and the generation of ATP and thus play a vital role in the cell.

The present application refers to various issued patent, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

FIGS. 6A-E illustrate the dose-dependent activity of probe compound I-4 against various cell lines: C. albicans CaCi-2 in the presence of fluconazole ($IC_{50}$=440 nM, AID 493080) (A); C. albicans CaCi-8 in the presence of fluconazole ($IC_{50}$=1210 nM, AID 493149) (B); murine 3T3 fibroblasts in the absence of fluconazole (inactive, AID 493147) (C); C. albicans CaCi-2 in the absence of fluconazole (inactive, AID 493070) (D); and S. cerevisiae with Hsp90 construct ($IC_{50}$=4.18 µM, AID 493134) (E).

FIG. 14A shows the in vitro activity of compound I-3 against the cytochrome B enzyme activity of yeast Saccharomyces cerevisiae (wild type; curve 1), human Complex III (curve 2), and Saccharomyces cerevisiae selected for resistance to known antifungal agents (curve 3). FIG. 14B shows a mutation of the cytochrome B enzyme of an L275F strain of Saccharomyces cerevisiae. The mutation corresponds to a particular amino acid in the human ("H sapiens") protein and may account for L275F's resistance to known antifungal agents. The sequences in FIG. 14B, from top to bottom, correspond to SEQ ID NOs: 1-3.

DETAILED DESCRIPTION OF CERTAIN EMBODIMENTS OF THE INVENTION

Figure 1:
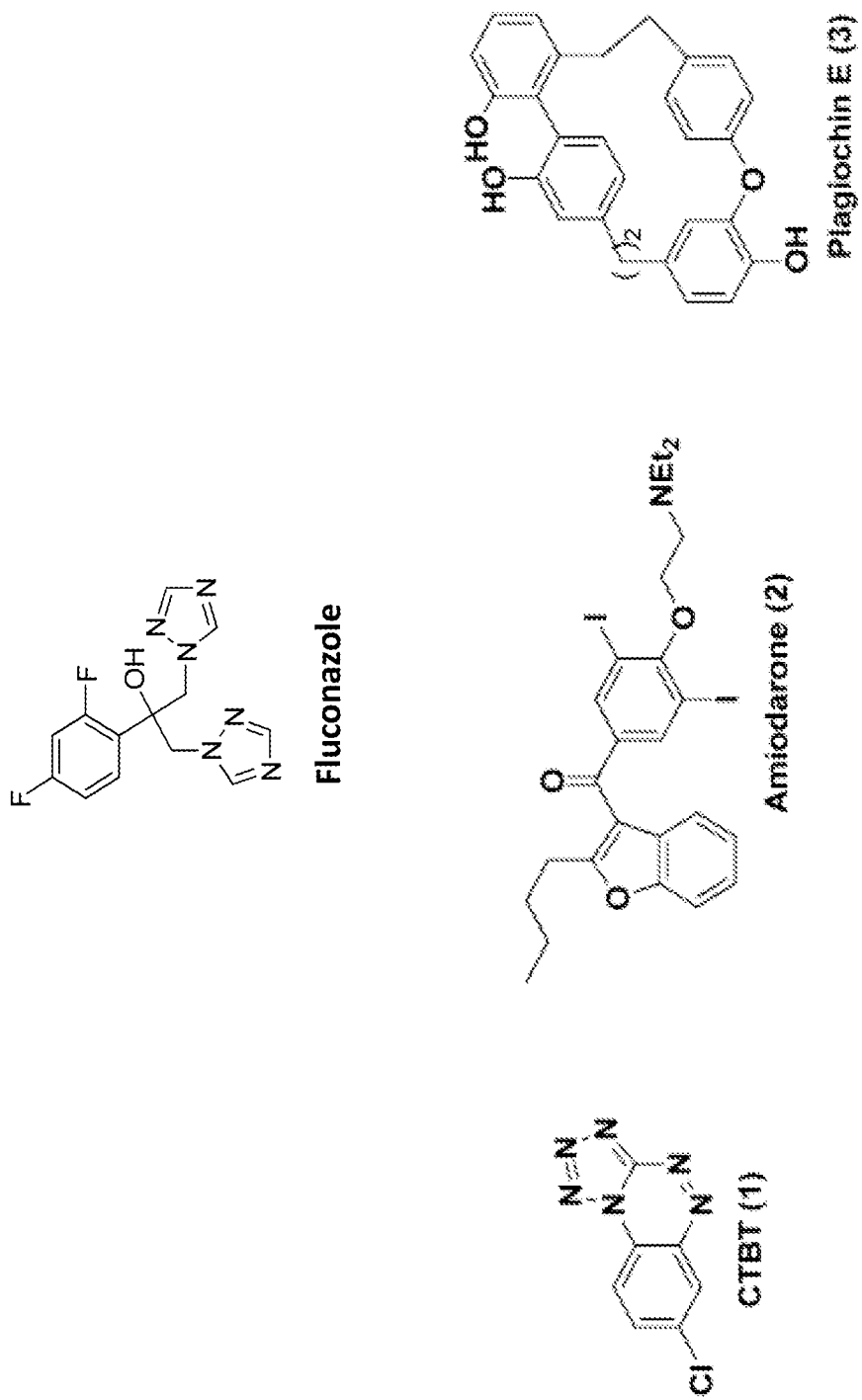
FIG. 1 shows the chemical structures of certain chemosensitizing agents reported to be capable of reversing fluconazole resistance.
Figure 2:
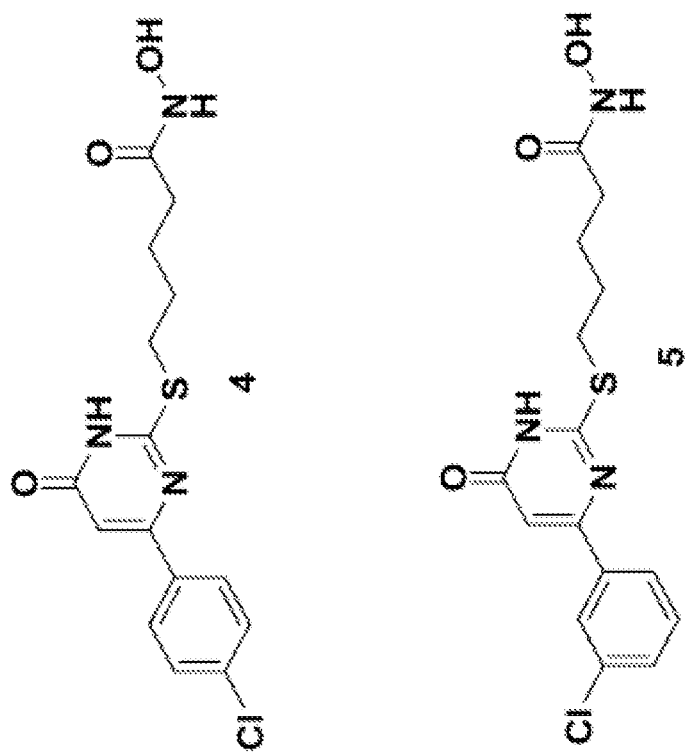
FIG. 2 shows the chemical structures of certain uracil-derived HDAC inhibitors reported to be capable of reversing antifungal drug resistance.

In one aspect, the present invention provides compounds described herein. In certain embodiments, the compounds are of Formula (I). These compounds have been found to be antifungal agents, antiprotozoan agents, and/or chemosensitizers capable of reversing the resistance of a fungus against an antifungal agent (e.g., fluconazole) and/or resistance of a protozoon against an antiprotozoan agent. Without wishing to be bound by any particular theory, the provided compounds may inhibit the activity of fungal cytochrome b and/or Hsp90. The invention also provides pharmaceutical compositions and kits comprising the compounds described herein. Also provided are methods of using the compounds described herein (e.g., compounds of Formula (I)), to treat and/or prevent a fungal or protozoan infection, and/or kill or inhibit the growth of a fungus or protozoon. In certain embodiments, the fungus described herein is a *Candida* or *Aspergillus* species. In certain embodiments, the compounds described herein are used in the inventive methods in combination with one or more additional pharmaceutical agents (e.g., an antifungal agent (such as an azole antifungal agent (e.g., fluconazole) and/or antiprotozoan agent). In certain embodiments, the fungus or protozoon described herein is resistant to the additional pharmaceutical agent(s).

Compounds

In one aspect of the present invention, provided are compounds of Formula (I):

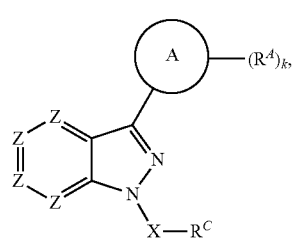

(I)

and pharmaceutically acceptable salts, solvates, hydrates, polymorphs, co-crystals, tautomers, stereoisomers, isotopically labeled derivatives, and prodrugs thereof;
wherein:

Ring A is a substituted or unsubstituted aryl ring, or substituted or unsubstituted heteroaryl ring;

each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-SCN$, $-C(=NR^{A1})R^{A1}$, $-C(NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, $-OC(=O)N(R^{A1})_2$, or a nitrogen protecting group when attached to a nitrogen atom, or optionally two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{A1}$ groups are joined to form a substituted or unsubstituted heterocyclic ring;

k is 0, 1, 2, 3, 4, or 5.

each instance of Z is independently nitrogen ($-N=$) or $-CR^B-$;

each instance of $R^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{B1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, or $-OC(=O)N(R^{B1})_2$, or optionally two $R^B$ groups are joined to form a substituted or unsubstituted carbocyclic, substituted or unsubstituted heterocyclic, substituted or unsubstituted aryl, or substituted or unsubstituted heteroaryl ring;

each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{B1}$ groups are joined to form a substituted or unsubstituted heterocyclic ring;

X is $-(C(R^X)_2)_n-$;

each instance of $R^X$ is independently hydrogen, halogen, or substituted or unsubstituted alkyl;

n is 0, 1, 2, or 3;

$R^C$ is $-C(=O)OR^{C1}$, $-C(=O)N(R^{C1})_2$, $-C(=O)R^{C1}$, $-S(=O)_2OR^{C1}$, $-S(=O)_2N(R^{C1})_2$, $-S(=O)_2R^{C1}$, $-C(CN)=NOR^{C1}$, $-C(=NR^{C1})R^{C1}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or optionally two $R^{C1}$ groups are joined to form a substituted or unsubstituted heterocyclic ring.

In certain embodiments, provided by the present invention are compounds as described herein, and pharmaceutically acceptable salts thereof.

Compounds of Formula (I) include a substituted or unsubstituted aryl ring, or substituted or unsubstituted heteroaryl ring as Ring A. In certain embodiments, Ring A is a substituted aryl ring. In certain embodiments, Ring A is an unsubstituted aryl ring. In certain embodiments, Ring A is a monocyclic aryl ring. In certain embodiments, Ring A is substituted phenyl. In certain embodiments, Ring A is of the formula:

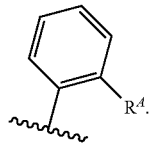

In certain embodiments, Ring A is of the formula:

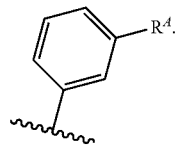

In certain embodiments, Ring A is of the formula:

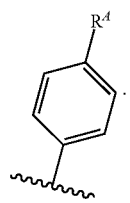

In certain embodiments, Ring A is of the formula:

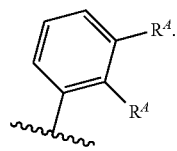

In certain embodiments, Ring A is of the formula:

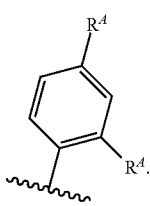

In certain embodiments, Ring A is of the formula:

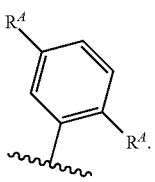

In certain embodiments, Ring A is of the formula:

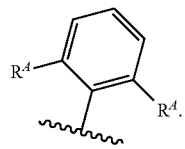

In certain embodiments, Ring A is of the formula:

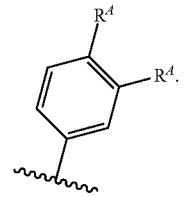

In certain embodiments, Ring A is of the formula:

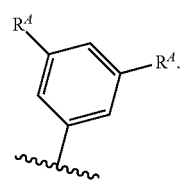

In certain embodiments, Ring A is unsubstituted phenyl. In certain embodiments, Ring A is a bicyclic aryl ring. In certain embodiments, Ring A is substituted naphthyl. In certain embodiments, Ring A is unsubstituted naphthyl. In certain embodiments, Ring A is a tricyclic aryl ring. In certain embodiments, Ring A is substituted anthracenyl. In certain embodiments, Ring A is unsubstituted anthracenyl. In certain embodiments, Ring A is an optionally substituted aryl ring fused with one or more optionally substituted carbocyclic, optionally substituted heterocyclic, optionally substituted aryl, or optionally substituted heteroaryl groups wherein the point of attachment is on the aryl ring.

Ring A of Formula (I) may also be an optionally substituted heteroaryl ring. In certain embodiments, Ring A is a substituted heteroaryl ring. In certain embodiments, Ring A is an unsubstituted heteroaryl ring. In certain embodiments, Ring A is a monocyclic heteroaryl ring. In certain embodiments, Ring A is a 6-membered monocyclic heteroaryl ring. In certain embodiments, Ring A is a 6-membered monocyclic heteroaryl ring, wherein only one of the six atoms in the ring of the heteroaryl is nitrogen. In certain embodiments, Ring A is of the formula:

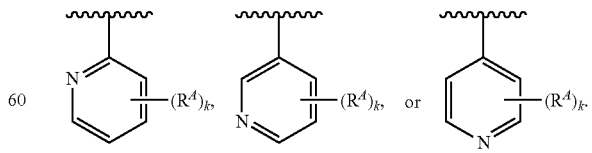

In certain embodiments, Ring A is a 6-membered monocyclic heteroaryl ring, wherein only two of the six atoms in the ring of the heteroaryl are nitrogen. In certain embodiments, Ring A is of the formula:

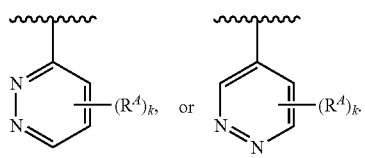

In certain embodiments, Ring A is of the formula:

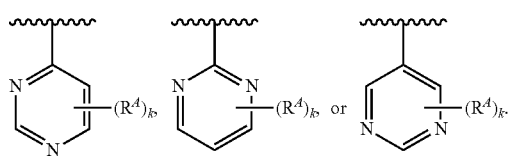

In certain embodiments, Ring A is of the formula:

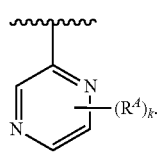

In certain embodiments, Ring A is a 6-membered monocyclic heteroaryl ring, wherein only three of the six atoms in the ring of the heteroaryl are nitrogen. In certain embodiments, Ring A is of the formula:

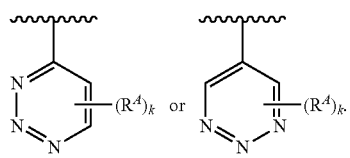

In certain embodiments, Ring A is of the formula:

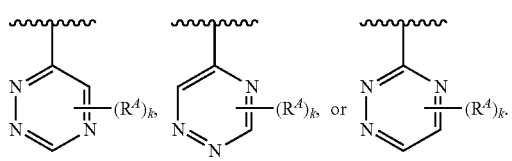

In certain embodiments, Ring A is of the formula:

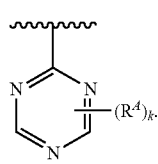

In certain embodiments, Ring A is a 5-membered monocyclic heteroaryl ring. In certain embodiments, Ring A is a 5-membered monocyclic heteroaryl ring, wherein only one of the five atoms in the ring of the heteroaryl is nitrogen, oxygen, or sulfur. In certain embodiments, Ring A is of the formula:

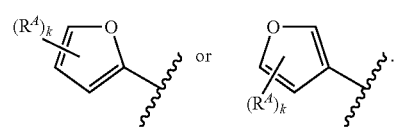

In certain embodiments, Ring A is of the formula:

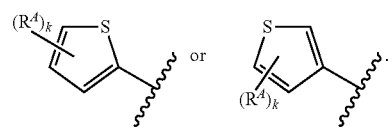

In certain embodiments, Ring A is of the formula:

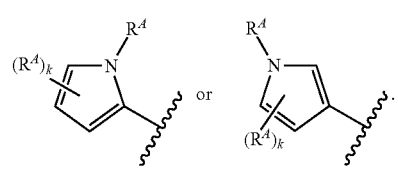

In certain embodiments, Ring A is a 5-membered monocyclic heteroaryl ring, wherein only two of the five atoms in the ring of the heteroaryl are independently nitrogen, oxygen, or sulfur. In certain embodiments, Ring A is of the formula:

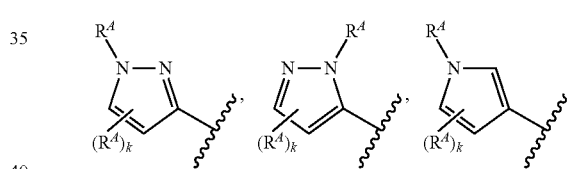

In certain embodiments, Ring A is of the formula:

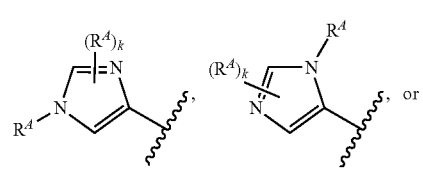

In certain embodiments, Ring A is of the formula:

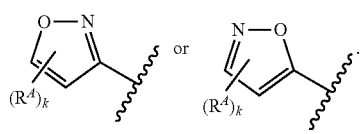

In certain embodiments, Ring A is of the formula:

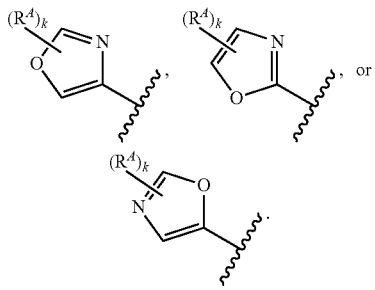, or

In certain embodiments, Ring A is of the formula:

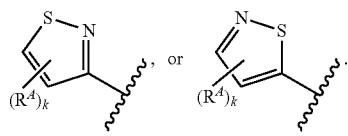, or

In certain embodiments, Ring A is of the formula:

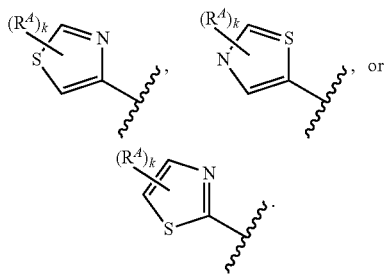, or

In certain embodiments, Ring A is a 5-membered monocyclic heteroaryl ring, wherein only three of the five atoms in the ring of the heteroaryl are independently nitrogen, oxygen, or sulfur. In certain embodiments, Ring A is of the formula:

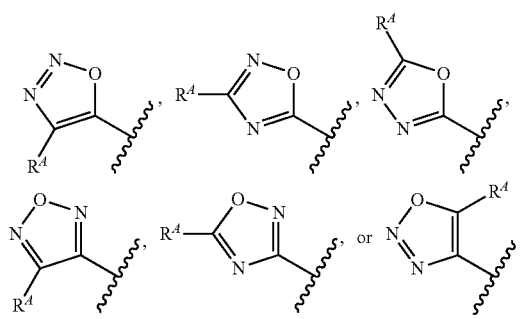, or

In certain embodiments, Ring A is of the formula:

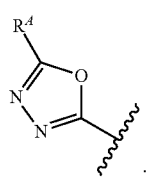

In certain embodiments, Ring A is of the formula:

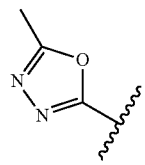

In certain embodiments, Ring A is of the formula:

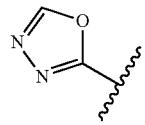

In certain embodiments, Ring A is of the formula:

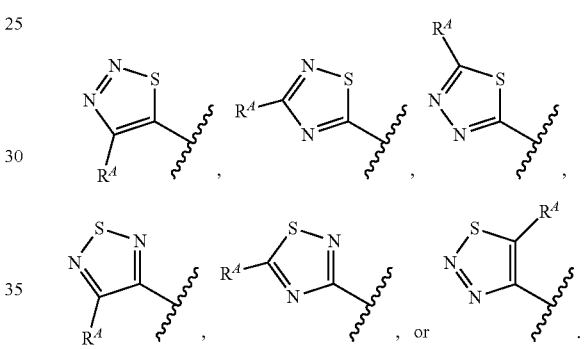, or

In certain embodiments, Ring A is of the formula:

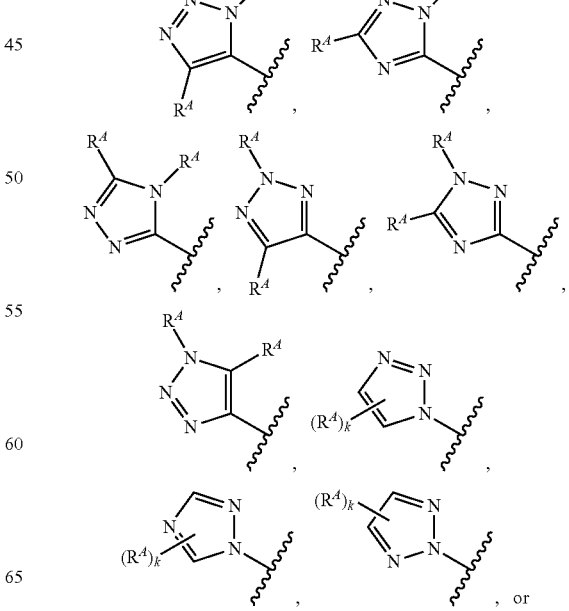, or

In certain embodiments, Ring A is a 5-membered monocyclic heteroaryl ring, wherein only four of the five atoms in the ring of the heteroaryl are nitrogen, oxygen, or sulfur. In certain embodiments, Ring A is of the formula:

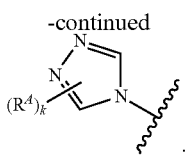

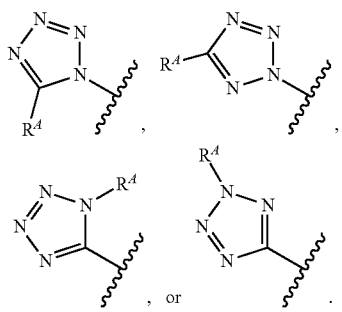

In certain embodiments, Ring A is bicyclic heteroaryl, wherein the point of attachment may be on any atom of the bicyclic heteroaryl ring system, as valency permits. In certain embodiments, Ring A is a monocyclic heteroaryl ring fused with phenyl. In certain embodiments, Ring A is a 5-membered monocyclic heteroaryl ring fused with phenyl. In certain embodiments, Ring A is a 6-membered monocyclic heteroaryl ring fused with phenyl. In certain embodiments, Ring A is a monocyclic heteroaryl ring fused with another monocyclic heteroaryl. In certain embodiments, Ring A is a 5-membered monocyclic heteroaryl ring fused with another 5-membered monocyclic heteroaryl. In certain embodiments, Ring A is a 5-membered monocyclic heteroaryl ring fused with a 6-membered monocyclic heteroaryl. In certain embodiments, Ring A is a 6-membered monocyclic heteroaryl ring fused with another 6-membered monocyclic heteroaryl.

Ring A of compounds described herein may include one or more substituents $R^A$. In certain embodiments, at least one $R^A$ is H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is substituted acyl. In certain embodiments, at least one $R^A$ is unsubstituted acyl. In certain embodiments, at least one $R^A$ is substituted alkyl. In certain embodiments, at least one $R^A$ is unsubstituted alkyl. In certain embodiments, at least one $R^A$ is $C_{1-6}$ alkyl. In certain embodiments, at least one $R^A$ is methyl. In certain embodiments, at least one $R^A$ is substituted methyl. In certain embodiments, at least one $R^A$ is —$CH_2F$. In certain embodiments, at least one $R^A$ is —$CHF_2$. In certain embodiments, at least one $R^A$ is —$CF_3$. In certain embodiments, at least one $R^A$ is benzyl (Bn). In certain embodiments, at least one $R^A$ is ethyl. In certain embodiments, at least one $R^A$ is substituted ethyl. In certain embodiments, at least one $R^A$ is —$(CH_2)_2Ph$. In certain embodiments, at least one $R^A$ is propyl. In certain embodiments, at least one $R^A$ is butyl. In certain embodiments, at least one $R^A$ is pentyl. In certain embodiments, at least one $R^A$ is adamantyl. In certain embodiments, at least one $R^A$ is substituted alkenyl. In certain embodiments, at least one $R^A$ is unsubstituted alkenyl. In certain embodiments, at least one $R^A$ is vinyl. In certain embodiments, at least one $R^A$ is substituted alkynyl. In certain embodiments, at least one $R^A$ is unsubstituted alkynyl. In certain embodiments, at least one $R^A$ is ethynyl. In certain embodiments, at least one $R^A$ is substituted carbocyclyl. In certain embodiments, at least one $R^A$ is unsubstituted carbocyclyl. In certain embodiments, at least one $R^A$ is cylcopropyl. In certain embodiments, at least one $R^A$ is cyclobutyl. In certain embodiments, at least one $R^A$ is cyclopentyl. In certain embodiments, at least one $R^A$ is cyclohexyl. In certain embodiments, at least one $R^A$ is cycloheptyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted naphthyl. In certain embodiments, at least one $R^A$ is unsubstituted naphthyl. In certain embodiments, at least one $R^A$ is substituted heteroaryl. In certain embodiments, at least one $R^A$ is unsubstituted heteroaryl. In certain embodiments, at least one $R^A$ is monocyclic heteroaryl. In certain embodiments, at least one $R^A$ is 5-membered monocyclic heteroaryl. In certain embodiments, at least one $R^A$ is 5-membered monocyclic heteroaryl, wherein only one of the five atoms in the ring of the heteroaryl is nitrogen, oxygen, or sulfur. In certain embodiments, at least one $R^A$ is 5-membered monocyclic heteroaryl, wherein only two of the five atoms in the ring of the heteroaryl are independently nitrogen, oxygen, or sulfur. In certain embodiments, at least one $R^A$ is 5-membered monocyclic heteroaryl, wherein only three of the five atoms in the ring of the heteroaryl are independently nitrogen, oxygen, or sulfur. In certain embodiments, at least one $R^A$ is tetrazolyl. In certain embodiments, at least one $R^A$ is 6-membered monocyclic heteroaryl. In certain embodiments, at least one $R^A$ is 6-membered monocyclic heteroaryl, wherein only one of the six atoms in the ring of the heteroaryl is nitrogen. In certain embodiments, at least one $R^A$ is 6-membered monocyclic heteroaryl, wherein only two of the six atoms in the ring of the heteroaryl are nitrogen. In certain embodiments, at least one $R^A$ is triazinyl. In certain embodiments, at least one $R^A$ is tetrazinyl. In certain embodiments, at least one $R^A$ is bicyclic heteroaryl, wherein the point of attachment may be on any atom of the bicyclic heteroaryl ring system, as valency permits. In certain embodiments, at least one $R^A$ is a monocyclic heteroaryl ring fused with phenyl. In certain embodiments, at least one $R^A$ is a 5-membered monocyclic heteroaryl ring fused with phenyl. In certain embodiments, at least one $R^A$ is a 6-membered monocyclic heteroaryl ring fused with phenyl. In certain embodiments, at least one $R^A$ is a monocyclic heteroaryl ring fused with another monocyclic heteroaryl. In certain embodiments, at least one $R^A$ is a 5-membered monocyclic heteroaryl ring fused with another 5-membered monocyclic heteroaryl. In certain embodiments, at least one $R^A$ is a 5-membered monocyclic heteroaryl ring fused with a 6-membered monocyclic heteroaryl. In certain embodiments, at least one $R^A$ is a 6-membered monocyclic heteroaryl fused with another 6-membered monocyclic heteroaryl. In certain embodiments, at least one $R^A$ is —$OR^{A1}$. In certain embodiments, at least one $R^A$ is —OMe. In certain embodiments, at least one $R^A$ is —OEt. In certain embodiments, at least one $R^A$ is —OPr. In certain embodiments, at least one $R^A$ is —OBu. In certain embodiments, at least one $R^A$ is —O(pentyl). In certain embodiments, at least one $R^A$ is —O(hexyl). In certain embodiments, at least one $R^A$ is —OCH$_2$(cyclopentyl). In certain embodiments, at least one $R^A$ is —O(CH$_2$)$_2$(cyclopentyl). In certain embodiments, at least one $R^A$ is —OCH$_2$(cyclohexyl). In certain embodiments, at least one $R^A$ is —O(CH$_2$)$_2$(cyclohexyl). In certain embodiments, at least one $R^A$ is —OPh. In certain embodiments, at least one $R^A$ is —OBn. In certain embodiments, at least one $R^A$ is —O(CH$_2$)$_2$Ph. In certain embodiments, at least one $R^A$ is —OH. In certain embodiments, at least one $R^A$ is —SR$^{A1}$. In certain embodiments, at least one $R^A$ is —SH. In certain embodiments, at least one $R^A$ is —N(R$^{A1}$)$_2$. In certain embodiments, at least one $R^A$ is —NH$_2$. In certain embodiments, at least one $R^A$ is —CN. In certain embodiments, at least one $R^A$ is —SCN. In certain embodiments, at least one $R^A$ is —C(=NR$^{A1}$)R$^{A1}$, —C(=NR$^{A1}$)OR$^{A1}$, or —C(=NR$^{A1}$)N(R$^{A1}$)$_2$. In certain embodiments, at least one $R^A$ is —C(=O)R$^{A1}$, —C(=O)OR$^{A1}$, or —C(=O)N(R$^{A1}$)$_2$. In certain embodiments, at least one $R^A$ is —NO$_2$. In certain embodiments, at least one $R^A$ is NR$^{A1}$C(=O)R$^{A1}$, —NR$^{A1}$C(=O)OR$^{A1}$, or —NR$^{A1}$C(=O)N(R$^{A1}$)$_2$. In certain embodiments, at least one $R^A$ is —OC(=O)R$^{A1}$, —OC(=O)OR$^{A1}$, or —OC(=O)N(R$^{A1}$)$_2$. In certain embodiments, at least one $R^A$ is a nitrogen protecting group when attached to a nitrogen atom. In certain embodiments, at least one $R^A$ is Bn, BOC, Cbz, Fmoc, trifluoroacetyl, triphenylmethyl, or Ts when attached to a nitrogen atom.

In certain embodiments, at least one $R^A$ is of the formula:

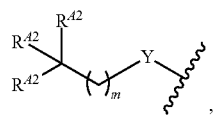

wherein:

each instance of $R^{A2}$ is independently hydrogen, or substituted or unsubstituted alkyl, or two or three $R^{A2}$ groups are joined to form a substituted or unsubstituted carbocyclic ring;

m is 0, 1, 2, or 3; and

Y is —CH$_2$— or —O—.

In certain embodiments, at least one $R^A$ is of the formula:

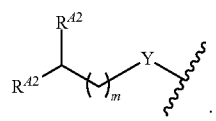

In certain embodiments, at least one $R^A$ is of the formula:

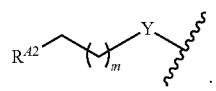

In certain embodiments, at least one $R^A$ is of the formula:

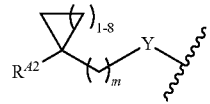

In certain embodiments, at least one $R^A$ is of the formula:

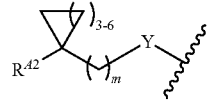

In certain embodiments, at least one $R^A$ is of the formula:

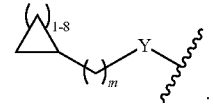

In certain embodiments, at least one $R^A$ is of the formula:

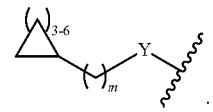

In compounds described herein, two $R^A$ groups may be joined to form a substituted or unsubstituted carbocyclic ring. In certain embodiments, two $R^A$ groups are joined to form a substituted or unsubstituted cyclopropyl ring. In certain embodiments, two $R^A$ groups are joined to form a substituted or unsubstituted cyclobutyl ring. In certain embodiments, two $R^A$ groups are joined to form a substituted or unsubstituted cyclopentyl ring. In certain embodiments, two $R^A$ groups are joined to form a substituted or unsubstituted cyclohexyl ring. In certain embodiments, two $R^A$ groups are joined to form a substituted or unsubstituted cycloheptyl ring. In certain embodiments, two $R^A$ groups are joined to form a substituted or unsubstituted cyclooctyl ring. In certain embodiments, two $R^A$ groups are joined to form a substituted or unsubstituted cyclononyl ring. In certain embodiments, two $R^A$ groups are joined to form a substituted or unsubstituted cyclodecyl ring.

In certain embodiments, two $R^A$ groups are joined to form a substituted or unsubstituted heterocyclic ring. In certain embodiments, two $R^A$ groups are joined to form a substituted or unsubstituted 4-membered heterocyclic ring. In certain embodiments, two $R^A$ groups are joined to form a substituted or unsubstituted 5-membered heterocyclic ring. In certain embodiments, two $R^A$ groups are joined to form a substituted or unsubstituted 6-membered heterocyclic ring. In certain embodiments, two $R^A$ groups are joined to form a substituted or unsubstituted 7-membered heterocyclic ring. In certain embodiments, two $R^A$ groups are joined to form a substituted or unsubstituted 8-membered heterocyclic ring. In certain embodiments, two $R^A$ groups are joined to form a substituted or unsubstituted 9-membered heterocyclic ring. In certain embodiments, two $R^A$ groups are joined to form a substituted or unsubstituted 10-membered heterocyclic ring.

In certain embodiments, two $R^A$ groups are joined to form a substituted or unsubstituted aryl ring. In certain embodiments, two $R^A$ groups are joined to form a substituted or unsubstituted monocyclic aryl ring. In certain embodiments, two $R^A$ groups are joined to form a substituted or unsubstituted phenyl ring. In certain embodiments, two $R^A$ groups are joined to form a substituted or unsubstituted bicyclic aryl ring. In certain embodiments, two $R^A$ groups are joined to form a substituted or unsubstituted naphthyl ring.

In certain embodiments, two $R^A$ groups are joined to form a substituted or unsubstituted heteroaryl ring. In certain embodiments, two $R^A$ groups are joined to form a substituted or unsubstituted monocyclic heteroaryl ring. In certain embodiments, two $R^A$ groups are joined to form a substituted or unsubstituted 5-membered monocyclic heteroaryl ring. In certain embodiments, two $R^A$ groups are joined to form a substituted or unsubstituted 6-membered monocyclic heteroaryl ring. In certain embodiments, two $R^A$ groups are joined to form a substituted or unsubstituted, bicyclic heteroaryl ring. In certain embodiments, two $R^A$ groups are joined to form a substituted or unsubstituted, 5,6-membered bicyclic heteroaryl ring. In certain embodiments, two $R^A$ groups are joined to form a substituted or unsubstituted, 6,5-membered bicyclic heteroaryl ring. In certain embodiments, two $R^A$ groups are joined to form a substituted or unsubstituted, 6,6-membered bicyclic heteroaryl ring.

In certain embodiments, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is pentyl. In certain embodiments, at least one $R^{A1}$ is adamantyl. In certain embodiments, at least one $R^{A1}$ is substituted alkenyl. In certain embodiments, at least one $R^{A1}$ is unsubstituted alkenyl. In certain embodiments, at least one $R^{A1}$ is vinyl. In certain embodiments, at least one $R^{A1}$ is substituted alkynyl. In certain embodiments, at least one $R^{A1}$ is unsubstituted alkynyl. In certain embodiments, at least one $R^{A1}$ is ethynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is cylcopropyl. In certain embodiments, at least one $R^{A1}$ is cyclobutyl. In certain embodiments, at least one $R^{A1}$ is cyclopentyl. In certain embodiments, at least one $R^{A1}$ is cyclohexyl. In certain embodiments, at least one $R^{A1}$ is cycloheptyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is Bn, Boc, Cbz, Fmoc, trifluoroacetyl, triphenylmethyl, or Ts when attached to a nitrogen atom. In certain embodiments $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom. In certain embodiments, two $R^{A1}$ groups are joined to form a substituted heterocyclic ring. In certain embodiments, two $R^{A1}$ groups are joined to form an unsubstituted heterocyclic ring. In certain embodiments, two $R^{A1}$ groups are joined to form a substituted heteroaryl ring. In certain embodiments, two $R^{A1}$ groups are joined to form an unsubstituted heteroaryl ring.

In certain embodiments, at least one $R^{A2}$ is H. In certain embodiments, at least one $R^{A2}$ is substituted alkyl. In certain embodiments, at least one $R^{A2}$ is unsubstituted alkyl. In certain embodiments, at least one $R^{A2}$ is $C_{1-6}$ alkyl. In certain embodiments, at least one $R^{A2}$ is methyl. In certain embodiments, at least one $R^{A2}$ is ethyl. In certain embodiments, at least one $R^{A2}$ is propyl. In certain embodiments, at least one $R^{A2}$ is butyl. In certain embodiments, at least one $R^{A2}$ is pentyl. In certain embodiments, at least one $R^{A2}$ is adamantyl.

In certain embodiments, two $R^{A2}$ groups are joined to form a substituted carbocyclic ring. In certain embodiments, two $R^{A2}$ groups are joined to form an unsubstituted carbocyclic ring. In certain embodiments, two $R^{A2}$ groups are joined to form a substituted or unsubstituted cyclopropyl ring. In certain embodiments, two $R^{A2}$ groups are joined to form a substituted or unsubstituted cyclobutyl ring. In certain embodiments, two $R^{A2}$ groups are joined to form a substituted or unsubstituted cyclopentyl ring. In certain embodiments, two $R^{A2}$ groups are joined to form a substituted or unsubstituted cyclohexyl ring. In certain embodiments, two $R^{A2}$ groups are joined to form a substituted or unsubstituted cycloheptyl ring. In certain embodiments, two $R^{A2}$ groups are joined to form a substituted or unsubstituted cyclooctyl ring. In certain embodiments, two $R^{A2}$ groups are joined to form a substituted or unsubstituted cyclononyl ring. In certain embodiments, two $R^{A2}$ groups are joined to form a substituted or unsubstituted cyclodecyl ring. In certain embodiments, three $R^{A2}$ groups are joined to form a substituted carbocyclic ring. In certain embodiments, three $R^{A2}$ groups are joined to form an unsubstituted carbocyclic ring. In certain embodiments, three $R^{A2}$ groups are joined to form adamantyl.

In certain embodiments, m is 0. In certain embodiments, m is 1. In certain embodiments, m is 2. In certain embodiments, m is 3.

In certain embodiments, Y is $-CH_2-$. In certain embodiments, Y is $-O-$.

In certain embodiments, k is 0. In certain embodiments, k is 1. In certain embodiments, k is 2. In certain embodiments, k is 3. In certain embodiments, k is 4. In certain embodiments, k is 5.

In compounds described herein, each instance of Z is independently nitrogen ($-N=$) or $-CR^B-$. In certain embodiments, all instances of Z are each $-CR^B-$. In certain embodiments, the compound described herein is of the formula:

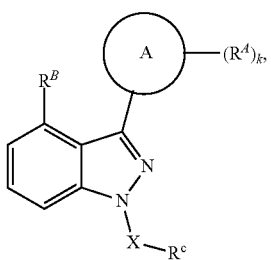

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

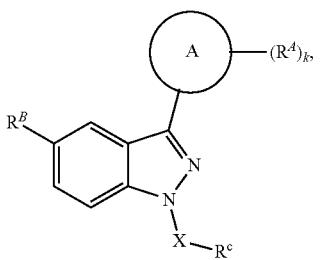

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

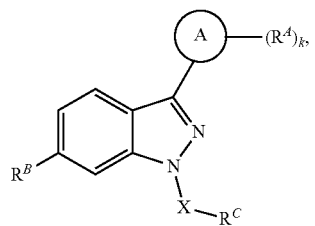

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

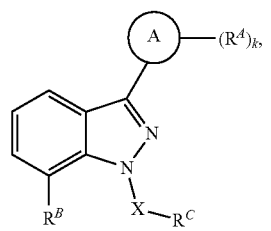

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

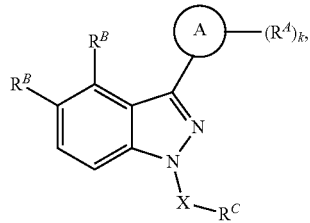

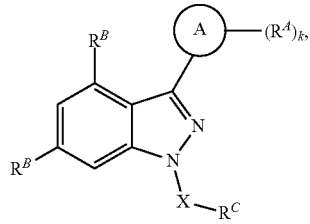

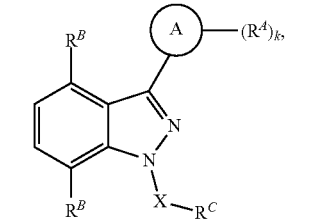

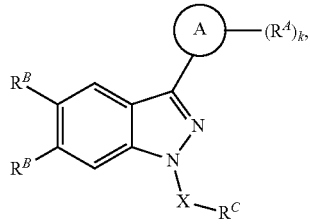

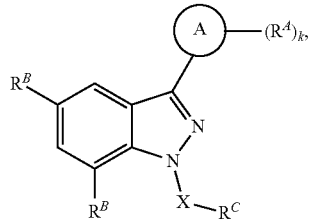

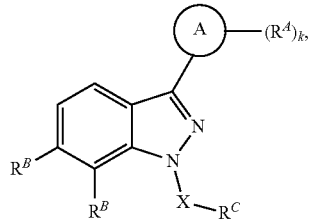

or a pharmaceutically acceptable salt, solvate, hydrate, polymorph, co-crystal, tautomer, stereoisomer, isotopically labeled derivative, or prodrug thereof.

In certain embodiments, all instances of Z are each CH.

In certain embodiments, only one instance of Z is nitrogen. In certain embodiments, the compound described herein is of the formula:

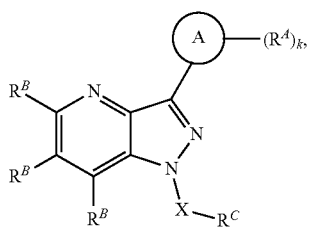

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

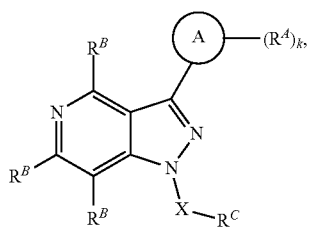

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

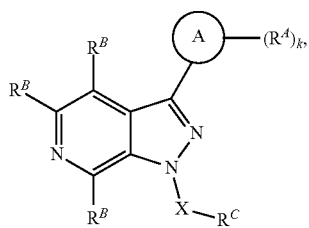

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

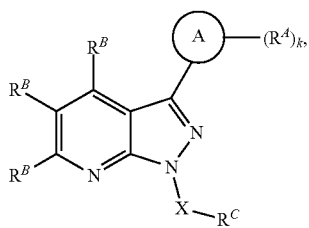

or a pharmaceutically acceptable salt, solvate, hydrate, polymorph, co-crystal, tautomer, stereoisomer, isotopically labeled derivative, or prodrug thereof.
[Did the inventors make any of these compounds wherein RB is anything other than H? If not, should we include formulae as above but with all RB simply hydrogen?]

In certain embodiments, only two instances of Z are nitrogen. In certain embodiments, the compound described herein is of the formula:

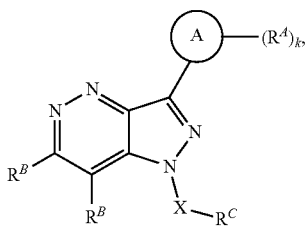

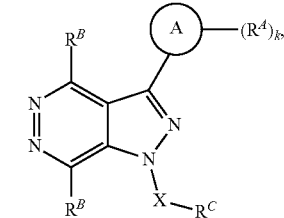

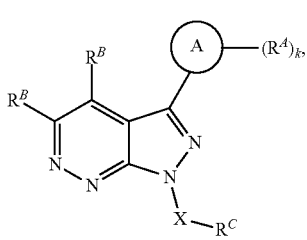

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

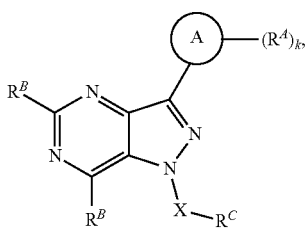

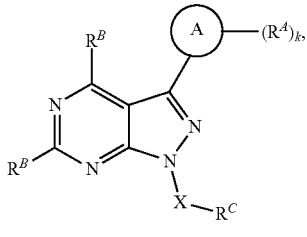

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

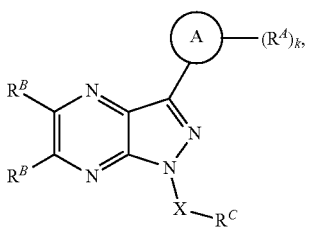

or a pharmaceutically acceptable salt, solvate, hydrate, polymorph, co-crystal, tautomer, stereoisomer, isotopically labeled derivative, or prodrug thereof.

In certain embodiments as described above and herein, when one or more instances of Z are —CR$^B$—, at least one R$^B$ is H. In certain embodiments, at least one R$^B$ is halogen. In certain embodiments, at least one R$^B$ is F. In certain embodiments, at least one R$^B$ is Cl. In certain embodiments, at least one R$^B$ is Br. In certain embodiments, at least one R$^B$ is I (iodine). In certain embodiments, at least one R$^B$ is substituted acyl. In certain embodiments, at least one R$^B$ is unsubstituted acyl. In certain embodiments, at least one R$^B$ is substituted alkyl. In certain embodiments, at least one R$^B$ is unsubstituted alkyl. In certain embodiments, at least one R$^B$ is $C_{1-6}$ alkyl. In certain embodiments, at least one R$^B$ is methyl. In certain embodiments, at least one R$^B$ is substituted methyl. In certain embodiments, at least one R$^B$ is —CH$_2$F. In certain embodiments, at least one R$^B$ is —CHF$_2$. In certain embodiments, at least one R$^B$ is —CF$_3$. In certain embodiments, at least one R$^B$ is Bn. In certain embodiments, at least one R$^B$ is ethyl. In certain embodiments, at least one R$^B$ is substituted ethyl. In certain embodiments, at least one R$^B$ is —(CH$_2$)$_2$Ph. In certain embodiments, at least one R$^B$ is propyl. In certain embodiments, at least one R$^B$ is butyl. In certain embodiments, at least one R$^B$ is pentyl. In certain embodiments, at least one R$^B$ is adamantyl. In certain embodiments, at least one R$^B$ is substituted alkenyl. In certain embodiments, at least one R$^B$ is unsubstituted alkenyl. In certain embodiments, at least one R$^B$ is vinyl. In certain embodiments, at least one R$^B$ is substituted alkynyl. In certain embodiments, at least one R$^B$ is unsubstituted alkynyl. In certain embodiments, at least one R$^B$ is ethynyl. In certain embodiments, at least one R$^B$ is substituted carbocyclyl. In certain embodiments, at least one R$^B$ is unsubstituted carbocyclyl. In certain embodiments, at least one R$^B$ is cylcopropyl. In certain embodiments, at least one R$^B$ is cyclobutyl. In certain embodiments, at least one R$^B$ is cyclopentyl. In certain embodiments, at least one R$^B$ is cyclohexyl. In certain embodiments, at least one R$^B$ is cycloheptyl. In certain embodiments, at least one R$^B$ is substituted heterocyclyl. In certain embodiments, at least one R$^B$ is unsubstituted heterocyclyl. In certain embodiments, at least one R$^B$ is substituted aryl. In certain embodiments, at least one R$^B$ is unsubstituted aryl. In certain embodiments, at least one R$^B$ is substituted phenyl. In certain embodiments, at least one R$^B$ is unsubstituted phenyl. In certain embodiments, at least one R$^B$ is substituted naphthyl. In certain embodiments, at least one R$^B$ is unsubstituted naphthyl. In certain embodiments, at least one R$^B$ is substituted heteroaryl. In certain embodiments, at least one R$^B$ is unsubstituted heteroaryl. In certain embodiments, at least one R$^B$ is monocyclic heteroaryl. In certain embodiments, at least one R$^B$ is 5-membered monocyclic heteroaryl. In certain embodiments, at least one R$^B$ is 5-membered monocyclic heteroaryl, wherein only one of the five atoms in the ring of the heteroaryl is nitrogen, oxygen, or sulfur. In certain embodiments, at least one R$^B$ is 5-membered monocyclic heteroaryl, wherein only two of the five atoms in the ring of the heteroaryl are independently nitrogen, oxygen, or sulfur. In certain embodiments, at least one R$^B$ is 5-membered monocyclic heteroaryl, wherein only three of the five atoms in the ring of the heteroaryl are independently nitrogen, oxygen, or sulfur. In certain embodiments, at least one R$^B$ is tetrazolyl. In certain embodiments, at least one R$^B$ is 6-membered monocyclic heteroaryl. In certain embodiments, at least one R$^B$ is 6-membered monocyclic heteroaryl, wherein only one of the six atoms in the ring of the heteroaryl is nitrogen. In certain embodiments, at least one R$^B$ is 6-membered monocyclic heteroaryl, wherein only two of the six atoms in the ring of the heteroaryl are nitrogen. In certain embodiments, at least one R$^B$ is triazinyl. In certain embodiments, at least one R$^B$ is tetrazinyl. In certain embodiments, at least one R$^B$ is bicyclic heteroaryl, wherein the point of attachment may be on any atom of the bicyclic heteroaryl, as valency permits. In certain embodiments, at least one R$^B$ is a monocyclic heteroaryl fused with phenyl. In certain embodiments, at least one R$^B$ is a 5-membered monocyclic heteroaryl fused with phenyl. In certain embodiments, at least one R$^B$ is a 6-membered monocyclic heteroaryl fused with phenyl. In certain embodiments, at least one R$^B$ is a monocyclic heteroaryl fused with another monocyclic heteroaryl. In certain embodiments, at least one R$^B$ is a 5-membered monocyclic heteroaryl fused with another 5-membered monocyclic heteroaryl. In certain embodiments, at least one R$^B$ is a 5-membered monocyclic heteroaryl fused with a 6-membered monocyclic heteroaryl. In certain embodiments, at least one R$^B$ is a 6-membered monocyclic heteroaryl fused with another 6-membered monocyclic heteroaryl. In certain embodiments, at least one R$^B$ is —OR$^{B1}$. In certain embodiments, at least one R$^B$ is —OMe. In certain embodiments, at least one R$^B$ is —OEt. In certain embodiments, at least one R$^B$ is —OPr. In certain embodiments, at least one R$^B$ is —OBu. In certain embodiments, at least one R$^B$ is —O(pentyl). In certain embodiments, at least one R$^B$ is —OCH$_2$(cyclohexyl). In certain embodiments, at least one R$^B$ is —OPh. In certain embodiments, at least one R$^B$ is —OBn. In certain embodiments, at least one R$^B$ is —O(CH$_2$)$_2$Ph. In certain embodiments, at least one R$^B$ is —OH. In certain embodiments, at least one R$^B$ is —SR$^{B1}$. In certain embodiments, at least one R$^B$ is —SMe. In certain embodiments, at least one R$^B$ is —SH. In certain embodiments, at least one R$^B$ is —N(R$^{B1}$)$_2$. In certain embodiments, at least one R$^B$ is —N(Me)$_2$. In certain embodiments, at least one R$^B$ is —NHMe. In certain embodiments, at least one R$^B$ is —NHAc. In certain embodiments, at least one R$^B$ is —NH$_2$. In certain embodiments, at least one R$^B$ is —CN. In certain embodiments, at least one R$^B$ is —SCN. In certain embodiments, at least one R$^B$ is —C(═NR$^{B1}$)R$^{B1}$, —C(═NR$^{B1}$)OR$^{B1}$, or —C(═NR$^{B1}$)N(R$^{B1}$)$_2$. In certain embodiments, at least one R$^B$ is —C(═O)R$^{B1}$. In certain embodiments, at least one R$^B$ is —C(═O)OR$^{B1}$. In certain embodiments, at least one R$^B$ is —C(═O)OMe. In certain embodiments, at least one R$^B$ is —C(═O)N(R$^{B1}$)$_2$. In certain embodiments, at least one R$^B$ is —C(═O)N(Me)$_2$. In certain embodiments, at least one R$^B$ is —C(═O)NHMe. In certain embodiments, at least one R$^B$ is —C(═O)NH$_2$. In certain embodiments, at least one R$^B$ is —NO$_2$. In certain embodiments, at least one R$^B$ is —NR$^{B1}$C(═O)R$^{B1}$, —NR$^{B1}$C(═O)OR$^{B1}$, or —NR$^{B1}$C(═O)N(R$^{B1}$)$_2$. In certain embodiments, at least one R$^B$ is —OC(═O)R$^{B1}$, —OC(═O)OR$^{B1}$, or —OC(═O)N(R$^{B1}$)$_2$.

In compounds described herein, two $R^B$ groups may be joined to form a substituted or unsubstituted carbocyclic ring. In certain embodiments, two $R^B$ groups are joined to form a substituted or unsubstituted cyclopropyl ring. In certain embodiments, two $R^B$ groups are joined to form a substituted or unsubstituted cyclobutyl ring. In certain embodiments, two $R^B$ groups are joined to form a substituted or unsubstituted cyclopentyl ring. In certain embodiments, two $R^B$ groups are joined to form a substituted or unsubstituted cyclohexyl ring. In certain embodiments, two $R^B$ groups are joined to form a substituted or unsubstituted cycloheptyl ring. In certain embodiments, two $R^B$ groups are joined to form a substituted or unsubstituted cyclooctyl ring. In certain embodiments, two $R^B$ groups are joined to form a substituted or unsubstituted cyclononyl ring. In certain embodiments, two $R^B$ groups are joined to form a substituted or unsubstituted cyclodecyl ring.

In certain embodiments, two $R^B$ groups are joined to form a substituted or unsubstituted heterocyclic ring. In certain embodiments, two $R^B$ groups are joined to form a substituted or unsubstituted 4-membered heterocyclic ring. In certain embodiments, two $R^B$ groups are joined to form a substituted or unsubstituted 5-membered heterocyclic ring. In certain embodiments, two $R^B$ groups are joined to form a substituted or unsubstituted 6-membered heterocyclic ring. In certain embodiments, two $R^B$ groups are joined to form a substituted or unsubstituted 7-membered heterocyclic ring. In certain embodiments, two $R^B$ groups are joined to form a substituted or unsubstituted 8-membered heterocyclic ring. In certain embodiments, two $R^B$ groups are joined to form a substituted or unsubstituted 9-membered heterocyclic ring. In certain embodiments, two $R^B$ groups are joined to form a substituted or unsubstituted 10-membered heterocyclic ring.

In certain embodiments, two $R^B$ groups are joined to form a substituted or unsubstituted aryl ring. In certain embodiments, two $R^B$ groups are joined to form a substituted or unsubstituted monocyclic aryl ring. In certain embodiments, two $R^B$ groups are joined to form a substituted or unsubstituted phenyl ring. In certain embodiments, two $R^B$ groups are joined to form a substituted or unsubstituted bicyclic aryl ring. In certain embodiments, two $R^B$ groups are joined to form a substituted or unsubstituted naphthyl ring.

In certain embodiments, two $R^B$ groups are joined to form a substituted or unsubstituted heteroaryl ring. In certain embodiments, two $R^B$ groups are joined to form a substituted or unsubstituted monocyclic heteroaryl ring. In certain embodiments, two $R^B$ groups are joined to form a substituted or unsubstituted, 5-membered monocyclic heteroaryl ring. In certain embodiments, two $R^B$ groups are joined to form a substituted or unsubstituted, 6-membered monocyclic heteroaryl ring. In certain embodiments, two $R^B$ groups are joined to form a substituted or unsubstituted, bicyclic heteroaryl ring. In certain embodiments, two $R^B$ groups are joined to form a substituted or unsubstituted, 5,6-membered bicyclic heteroaryl ring. In certain embodiments, two $R^B$ groups are joined to form a substituted or unsubstituted, 6,5-membered bicyclic heteroaryl ring. In certain embodiments, two $R^B$ groups are joined to form a substituted or unsubstituted, 6,6-membered bicyclic heteroaryl ring.

In certain embodiments, at least one $R^{B1}$ is H. In certain embodiments, at least one $R^{B1}$ is substituted acyl. In certain embodiments, at least one $R^{B1}$ is unsubstituted acyl. In certain embodiments, at least one $R^{B1}$ is acetyl. In certain embodiments, at least one $R^{B1}$ is substituted alkyl. In certain embodiments, at least one $R^{B1}$ is unsubstituted alkyl. In certain embodiments, at least one $R^{B1}$ is $C_{1-6}$ alkyl. In certain embodiments, at least one $R^{B1}$ is methyl. In certain embodiments, at least one $R^{B1}$ is ethyl. In certain embodiments, at least one $R^{B1}$ is propyl. In certain embodiments, at least one $R^{B1}$ is butyl. In certain embodiments, at least one $R^{B1}$ is pentyl. In certain embodiments, at least one $R^{B1}$ is adamantyl. In certain embodiments, at least one $R^{B1}$ is substituted alkenyl. In certain embodiments, at least one $R^{B1}$ is unsubstituted alkenyl. In certain embodiments, at least one $R^{B1}$ is vinyl. In certain embodiments, at least one $R^{B1}$ is substituted alkynyl. In certain embodiments, at least one $R^{B1}$ is unsubstituted alkynyl. In certain embodiments, at least one $R^{B1}$ is ethynyl. In certain embodiments, at least one $R^{B1}$ is substituted carbocyclyl. In certain embodiments, at least one $R^{B1}$ is unsubstituted carbocyclyl. In certain embodiments, at least one $R^{B1}$ is cylcopropyl. In certain embodiments, at least one $R^{B1}$ is cyclobutyl. In certain embodiments, at least one $R^{B1}$ is cyclopentyl. In certain embodiments, at least one $R^{B1}$ is cyclohexyl. In certain embodiments, at least one $R^{B1}$ is cycloheptyl. In certain embodiments, at least one $R^{B1}$ is substituted heterocyclyl. In certain embodiments, at least one $R^{B1}$ is unsubstituted heterocyclyl. In certain embodiments, at least one $R^{B1}$ is substituted aryl. In certain embodiments, at least one $R^{B1}$ is unsubstituted aryl. In certain embodiments, at least one $R^{B1}$ is substituted phenyl. In certain embodiments, at least one $R^{B1}$ is unsubstituted phenyl. In certain embodiments, at least one $R^{B1}$ is substituted heteroaryl. In certain embodiments, at least one $R^{B1}$ is unsubstituted heteroaryl. In certain embodiments, at least one $R^{B1}$ is substituted pyridyl. In certain embodiments, at least one $R^{B1}$ is unsubstituted pyridyl. In certain embodiments, at least one $R^{B1}$ is a nitrogen protecting group when attached to a nitrogen atom. In certain embodiments, at least one $R^{B1}$ is Bn, Boc, Cbz, Fmoc, trifluoroacetyl, triphenylmethyl, or Ts when attached to a nitrogen atom. In certain embodiments $R^{B1}$ is an oxygen protecting group when attached to an oxygen atom. In certain embodiments, $R^{B1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1}$ is a sulfur protecting group when attached to a sulfur atom. In certain embodiments, $R^{B1}$ is acetamidomethyl, t-Bu, 3-nitro-2-pyridine sulfenyl, 2-pyridine-sulfenyl, or triphenylmethyl when attached to a sulfur atom. In certain embodiments, two $R^{B1}$ groups are joined to form a substituted heterocyclic ring. In certain embodiments, two $R^{B1}$ groups are joined to form an unsubstituted heterocyclic ring. In certain embodiments, two $R^{B1}$ groups are joined to form a substituted heteroaryl ring. In certain embodiments, two $R^{B1}$ groups are joined to form an unsubstituted heteroaryl ring.

Compounds of Formula (I) include a divalent linker moiety X between the bicyclic ring system and the substitutent $R^C$. In certain embodiments, X is $—(C(R^X)_2)_n—$. In certain embodiments, X is a bond. In certain embodiments, X is $—C(R^X)_2—$. In certain embodiments, X is $—C(Me)_2-$. In certain embodiments, X is $—CHR^X—$. In certain embodiments, X is $—CHMe-$. In certain embodiments, X is $—CH_2—$. In certain embodiments, X is $—CF_2—$. In certain embodiments, X is $—C(R^X)_2—C(R^X)_2—$. In certain embodiments, X is $—C(R^X)_2—CHR^X—$ or $—CHR^X—C(R^X)_2—$. In certain embodiments, X is $—C(R^X)_2—CH_2—$ or $—CH_2—C(R^X)_2—$. In certain embodiments, X is $—CHR^X—CHR^X—$. In certain embodiments, X is $—CHR^X—CH_2—$ or $—CH_2—CHR^X—$. In certain embodiments, X is $—(CH_2)_2—$. In certain embodiments, X is $—C(R^X)_2—C(R^X)_2—C(R^X)_2—$. In certain embodiments, X is $—(CH_2)_3—$.

The linker moiety X may include one or more substituents $R^X$. In certain embodiments, at least one $R^X$ is H. In certain embodiments, all instances of $R^X$ are H. In certain embodiments, at least one $R^X$ is halogen. certain embodiments, at least one $R^X$ is F. In certain embodiments, at least one $R^X$ is Cl. In certain embodiments, at least one $R^X$ is Br. In certain embodiments, at least one $R^X$ is I (iodine). In certain embodiments, at least one $R^X$ is substituted alkyl. In certain embodiments, at least one $R^X$ is unsubstituted alkyl. In certain embodiments, at least one $R^X$ is $C_{1-6}$ alkyl. In certain embodiments, at least one $R^X$ is methyl. In certain embodiments, at least one $R^X$ is substituted methyl. In certain embodiments, at least one $R^X$ is —$CH_2F$. In certain embodiments, at least one $R^X$ is —$CHF_2$. In certain embodiments, at least one $R^X$ is —$CF_3$. In certain embodiments, at least one $R^X$ is Bn. In certain embodiments, at least one $R^X$ is ethyl. In certain embodiments, at least one $R^X$ is substituted ethyl. In certain embodiments, at least one $R^X$ is —$(CH_2)_2Ph$. In certain embodiments, at least one $R^X$ is propyl. In certain embodiments, at least one $R^X$ is butyl. In certain embodiments, at least one $R^X$ is pentyl. In certain embodiments, at least one $R^X$ is adamantyl.

In certain embodiments, n is 0. In certain embodiments, n is 1. In certain embodiments, n is 2. In certain embodiments, n is 3.

Compounds of Formula (I) include a substituent $R^C$ attached to the bicyclic ring system through linker X. In certain embodiments, $R^C$ is —$C(=O)OR^{C1}$. In certain embodiments, $R^C$ is —$C(=O)OMe$. In certain embodiments, $R^C$ is —$C(=O)N(R^{C1})_2$. In certain embodiments, $R^C$ is —$C(=O)N(Me)_2$. In certain embodiments, $R^C$ is —$C(=O)NHMe_2$. In certain embodiments, $R^C$ is —$C(=O)NH_2$. In certain embodiments, $R^C$ is —$C(=O)R^{C1}$. In certain embodiments, $R^C$ is —$S(=O)_2OR^{C1}$. In certain embodiments, $R^C$ is —$S(=O)_2OMe$. In certain embodiments, $R^C$ is —$S(=O)_2N(R^{C1})_2$. In certain embodiments, $R^C$ is —$S(=O)_2N(Me)_2$. In certain embodiments, $R^C$ is —$S(=O)_2NHMe$. In certain embodiments, $R^C$ is —$S(=O)_2NH_2$. In certain embodiments, $R^C$ is —$S(=O)_2R^{C1}$. In certain embodiments, $R^C$ is —$S(=O)_2Me$. In certain embodiments, $R^C$ is —$S(=O)_2CF_3$. In certain embodiments, $R^C$ is —$C(CN)=NOR^{C1}$. In certain embodiments, $R^C$ is —$C(CN)=NOMe$. In certain embodiments, $R^C$ is —$C(=NR^{C1})R^{C1}$.

In certain embodiments, $R^C$ is substituted alkyl. In certain embodiments, $R^C$ is unsubstituted alkyl. In certain embodiments, $R^C$ is $C_{1-6}$ alkyl. In certain embodiments, $R^C$ is methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$. In certain embodiments, $R^C$ is Bn. In certain embodiments, $R^C$ is ethyl. In certain embodiments, $R^C$ is substituted ethyl. In certain embodiments, $R^C$ is —$(CH_2)_2Ph$. In certain embodiments, $R^C$ is propyl. In certain embodiments, $R^C$ is butyl. In certain embodiments, $R^C$ is pentyl. In certain embodiments, $R^C$ is adamantyl. In certain embodiments, $R^C$ is substituted alkenyl. In certain embodiments, $R^C$ is unsubstituted alkenyl. In certain embodiments, $R^C$ is vinyl. In certain embodiments, $R^C$ is substituted alkynyl. In certain embodiments, $R^C$ is unsubstituted alkynyl. In certain embodiments, $R^C$ is ethynyl. In certain embodiments, $R^C$ is substituted carbocyclyl. In certain embodiments, $R^C$ is unsubstituted carbocyclyl. In certain embodiments, $R^C$ is cylcopropyl. In certain embodiments, $R^C$ is cyclobutyl. In certain embodiments, $R^C$ is cyclopentyl. In certain embodiments, $R^C$ is cyclohexyl. In certain embodiments, $R^C$ is cycloheptyl. In certain embodiments, $R^C$ is substituted heterocyclyl. In certain embodiments, $R^C$ is unsubstituted heterocyclyl. In certain embodiments, $R^C$ is substituted aryl. In certain embodiments, $R^C$ is unsubstituted aryl. In certain embodiments, $R^C$ is substituted phenyl. In certain embodiments, $R^C$ is unsubstituted phenyl. In certain embodiments, $R^C$ is substituted naphthyl. In certain embodiments, $R^C$ is unsubstituted naphthyl.

In certain embodiments, $R^C$ is substituted heteroaryl. In certain embodiments, $R^C$ is unsubstituted heteroaryl. In certain embodiments, $R^C$ is monocyclic heteroaryl. In certain embodiments, $R^C$ is a 6-membered monocyclic heteroaryl ring. In certain embodiments, $R^C$ is a 6-membered monocyclic heteroaryl ring, wherein only one of the six atoms in the ring of the heteroaryl is nitrogen. In certain embodiments, $R^C$ is of the formula:

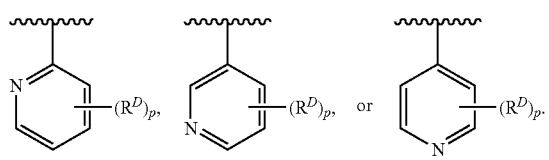

In certain embodiments, $R^C$ is a 6-membered monocyclic heteroaryl ring, wherein only two of the six atoms in the ring of the heteroaryl are nitrogen. In certain embodiments, $R^C$ is of the formula:

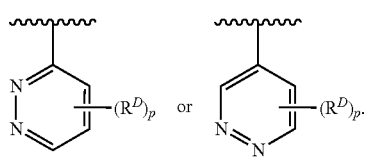

In certain embodiments, $R^C$ is of the formula:

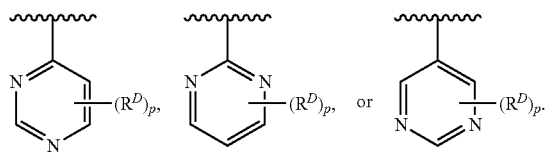

In certain embodiments, $R^C$ is of the formula:

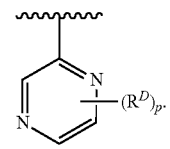

In certain embodiments, $R^C$ is a 6-membered monocyclic heteroaryl ring, wherein only three of the six atoms in the ring of the heteroaryl are nitrogen. In certain embodiments, $R^C$ is of the formula:

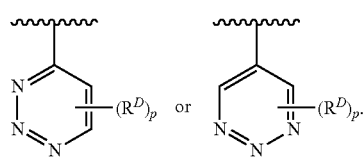

In certain embodiments, $R^C$ is of the formula:

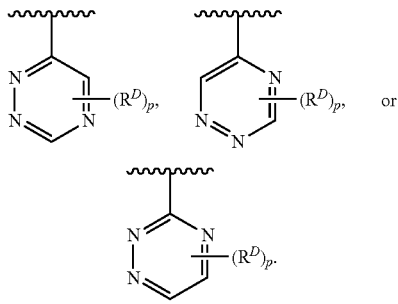

In certain embodiments, $R^C$ is of the formula:

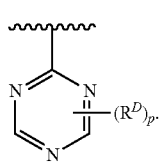

In certain embodiments, $R^C$ is 5-membered monocyclic heteroaryl. In certain embodiments, $R^C$ is 5-membered monocyclic heteroaryl, wherein only one of the five atoms in the ring of the heteroaryl is nitrogen, oxygen, or sulfur. In certain embodiments, $R^C$ is of the formula:

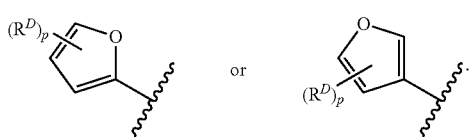

In certain embodiments, $R^C$ is of the formula:

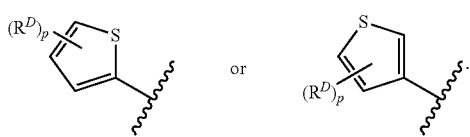

In certain embodiments, $R^C$ is of the formula:

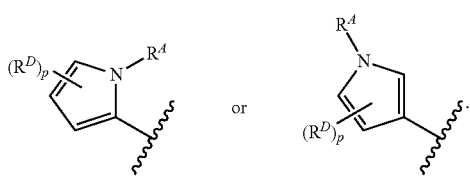

In certain embodiments, $R^C$ is 5-membered monocyclic heteroaryl, wherein only two of the five atoms in the ring of the heteroaryl are independently nitrogen, oxygen, or sulfur. In certain embodiments, $R^C$ is of the formula:

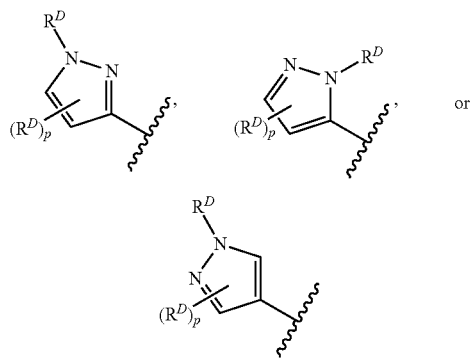

In certain embodiments, $R^C$ is of the formula:

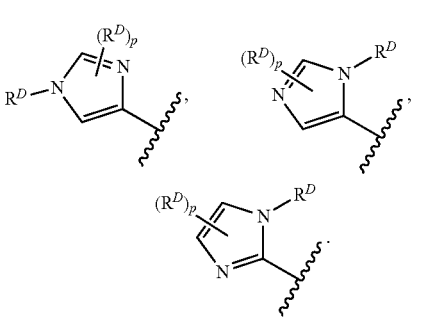

In certain embodiments, $R^C$ is of the formula:

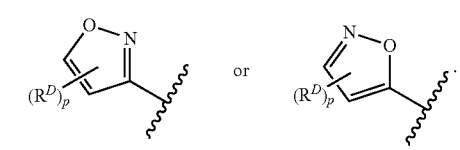

In certain embodiments, $R^C$ is of the formula:

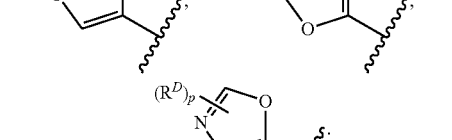

In certain embodiments, $R^C$ is of the formula:

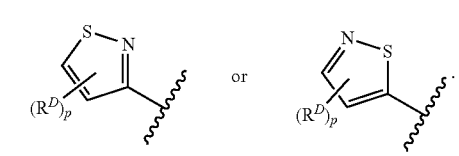

In certain embodiments, $R^C$ is of the formula:

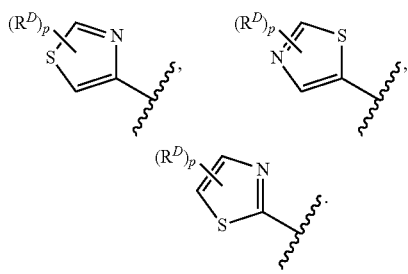

In certain embodiments, $R^C$ is 5-membered monocyclic heteroaryl, wherein only three of the five atoms in the ring of the heteroaryl are independently nitrogen, oxygen, or sulfur. In certain embodiments, $R^C$ is of the formula:

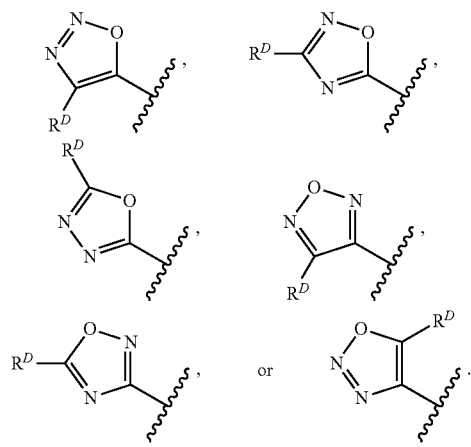

In certain embodiments, $R^C$ is of the formula:

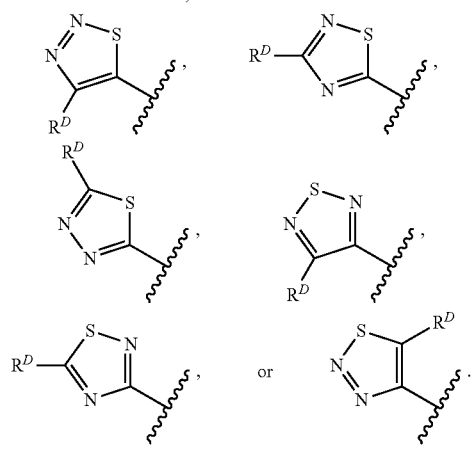

In certain embodiments, $R^C$ is of the formula:

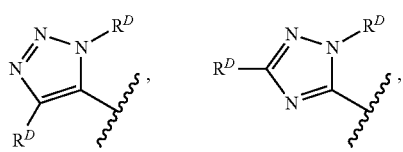

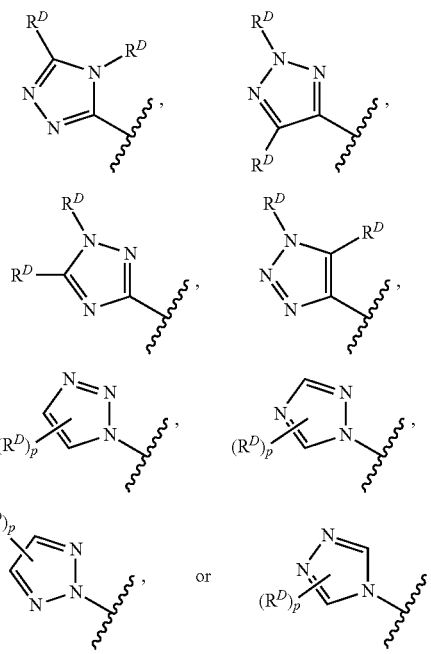

In certain embodiments, $R^C$ is a 5-membered monocyclic heteroaryl ring, wherein only four of the five atoms in the ring of the heteroaryl are nitrogen, oxygen, or sulfur. In certain embodiments, $R^C$ is of the formula:

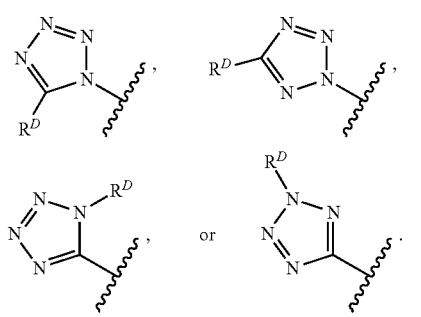

In certain embodiments, $R^C$ is of the formula:

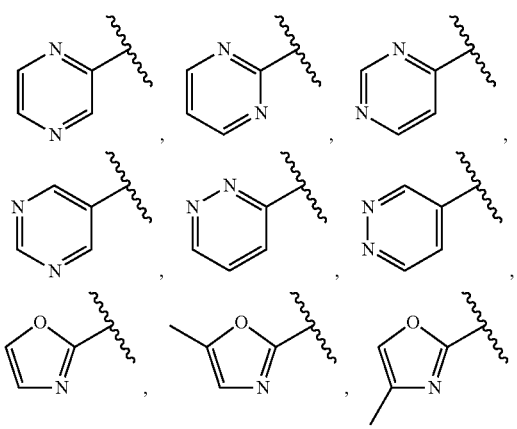

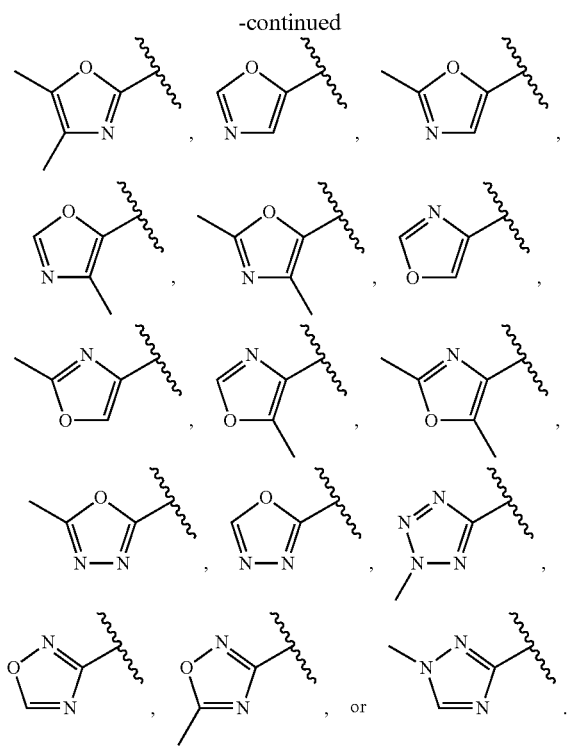

In certain embodiments, $R^C$ is bicyclic heteroaryl, wherein the point of attachment may be on any atom of the bicyclic heteroaryl, as valency permits. In certain embodiments, $R^C$ is a monocyclic heteroaryl fused with phenyl. In certain embodiments, $R^C$ is a 5-membered monocyclic heteroaryl fused with phenyl. In certain embodiments, $R^C$ is a 6-membered monocyclic heteroaryl fused with phenyl. In certain embodiments, $R^C$ is a monocyclic heteroaryl fused with another monocyclic heteroaryl. In certain embodiments, $R^C$ is a 5-membered monocyclic heteroaryl fused with another 5-membered monocyclic heteroaryl. In certain embodiments, $R^C$ is a 5-membered monocyclic heteroaryl fused with a 6-membered monocyclic heteroaryl. In certain embodiments, $R^C$ is a 6-membered monocyclic heteroaryl fused with another 6-membered monocyclic heteroaryl.

In certain embodiments, at least one $R^{C1}$ is H. In certain embodiments, at least one $R^{C1}$ is substituted acyl. In certain embodiments, at least one $R^{C1}$ is unsubstituted acyl. In certain embodiments, at least one $R^{C1}$ is acetyl. In certain embodiments, at least one $R^{C1}$ is substituted alkyl. In certain embodiments, at least one $R^{C1}$ is unsubstituted alkyl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl. In certain embodiments, at least one $R^{C1}$ is pentyl. In certain embodiments, at least one $R^{C1}$ is adamantyl. In certain embodiments, at least one $R^{C1}$ is substituted alkenyl. In certain embodiments, at least one $R^{C1}$ is unsubstituted alkenyl. In certain embodiments, at least one $R^{C1}$ is vinyl. In certain embodiments, at least one $R^{C1}$ is substituted alkynyl. In certain embodiments, at least one $R^{C1}$ is unsubstituted alkynyl. In certain embodiments, at least one $R^{C1}$ is ethynyl. In certain embodiments, at least one $R^{C1}$ is substituted carbocyclyl. In certain embodiments, at least one $R^{C1}$ is unsubstituted carbocyclyl. In certain embodiments, at least one $R^{C1}$ is cylcopropyl. In certain embodiments, at least one $R^{C1}$ is cyclobutyl. In certain embodiments, at least one $R^{C1}$ is cyclopentyl. In certain embodiments, at least one $R^{C1}$ is cyclohexyl. In certain embodiments, at least one $R^{C1}$ is cycloheptyl. In certain embodiments, at least one $R^{C1}$ is substituted heterocyclyl. In certain embodiments, at least one $R^{C1}$ is unsubstituted heterocyclyl. In certain embodiments, at least one $R^{C1}$ is substituted aryl. In certain embodiments, at least one $R^{C1}$ is unsubstituted aryl. In certain embodiments, at least one $R^{C1}$ is substituted phenyl. In certain embodiments, at least one $R^{C1}$ is unsubstituted phenyl. In certain embodiments, at least one $R^{C1}$ is substituted heteroaryl. In certain embodiments, at least one $R^{C1}$ is unsubstituted heteroaryl. In certain embodiments, at least one $R^{C1}$ is substituted pyridyl. In certain embodiments, at least one $R^{C1}$ is unsubstituted pyridyl. In certain embodiments, at least one $R^{C1}$ is a nitrogen protecting group when attached to a nitrogen atom. In certain embodiments, at least one $R^{C1}$ is Bn, Boc, Cbz, Fmoc, trifluoroacetyl, triphenylmethyl, or Ts when attached to a nitrogen atom. In certain embodiments $R^{C1}$ is an oxygen protecting group when attached to an oxygen atom. In certain embodiments, $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, two $R^{C1}$ groups are joined to form a substituted heterocyclic ring. In certain embodiments, two $R^{C1}$ groups are joined to form an unsubstituted heterocyclic ring. In certain embodiments, two $R^{C1}$ groups are joined to form a substituted heteroaryl ring. In certain embodiments, two $R^{C1}$ groups are joined to form an unsubstituted heteroaryl ring.

In certain embodiments, when $R^C$ of Formula (I) includes one or more substituents $R^D$, at least one $R^D$ is H. In certain embodiments, at least one $R^D$ is halogen. In certain embodiments, at least one $R^D$ is F. In certain embodiments, at least one $R^D$ is Cl. In certain embodiments, at least one $R^D$ is Br. In certain embodiments, at least one $R^D$ is I (iodine). In certain embodiments, at least one $R^D$ is substituted acyl. In certain embodiments, at least one $R^D$ is unsubstituted acyl. In certain embodiments, at least one $R^D$ is substituted alkyl. In certain embodiments, at least one $R^D$ is unsubstituted alkyl. In certain embodiments, at least one $R^D$ is $C_{1-6}$ alkyl. In certain embodiments, at least one $R^D$ is methyl. In certain embodiments, at least one $R^D$ is substituted methyl. In certain embodiments, at least one $R^D$ is —CH$_2$F. In certain embodiments, at least one $R^D$ is —CHF$_2$. In certain embodiments, at least one $R^D$ is —CF$_3$. In certain embodiments, at least one $R^D$ is Bn. In certain embodiments, at least one $R^D$ is ethyl. In certain embodiments, at least one $R^D$ is substituted ethyl. In certain embodiments, at least one $R^D$ is —(CH$_2$)$_2$Ph. In certain embodiments, at least one $R^D$ is propyl. In certain embodiments, at least one $R^D$ is butyl. In certain embodiments, at least one $R^D$ is pentyl. In certain embodiments, at least one $R^D$ is adamantyl. In certain embodiments, at least one $R^D$ is substituted alkenyl. In certain embodiments, at least one $R^D$ is unsubstituted alkenyl. In certain embodiments, at least one $R^D$ is vinyl. In certain embodiments, at least one $R^D$ is substituted alkynyl. In certain embodiments, at least one $R^D$ is unsubstituted alkynyl. In certain embodiments, at least one $R^D$ is ethynyl. In certain embodiments, at least one $R^D$ is substituted carbocyclyl. In certain embodiments, at least one $R^D$ is unsubstituted carbocyclyl. In certain embodiments, at least one $R^D$ is cylcopropyl. In certain embodiments, at least one $R^D$ is cyclobutyl. In certain embodiments, at least one $R^D$ is cyclopentyl. In certain embodiments, at least one $R^D$ is cyclohexyl. In certain embodiments, at least one $R^D$ is cycloheptyl. In certain embodiments, at least one $R^D$ is substituted heterocyclyl. In certain embodiments, at least one $R^D$ is unsubstituted heterocyclyl. In certain embodiments, at least one $R^D$ is substituted aryl. In certain embodiments, at least one $R^D$ is unsubstituted aryl. In certain embodiments, at least one $R^D$ is substituted phenyl. In certain embodiments, at least one $R^D$ is unsubstituted phenyl. In certain embodiments, at least one $R^D$ is substituted naphthyl. In certain embodiments, at least one $R^D$ is unsubstituted naphthyl. In certain embodiments, at least one $R^D$ is substituted heteroaryl. In certain embodiments, at least one $R^D$ is unsubstituted heteroaryl. In certain embodiments, at least one $R^D$ is monocyclic heteroaryl. In certain embodiments, at least one $R^D$ is 5-membered monocyclic heteroaryl. In certain embodiments, at least one $R^D$ is 5-membered monocyclic heteroaryl, wherein only one of the five atoms in the ring of the heteroaryl is nitrogen, oxygen, or sulfur. In certain embodiments, at least one $R^D$ is 5-membered monocyclic heteroaryl, wherein only two of the five atoms in the ring of the heteroaryl are independently nitrogen, oxygen, or sulfur. In certain embodiments, at least one $R^D$ is 5-membered monocyclic heteroaryl, wherein only three of the five atoms in the ring of the heteroaryl are independently nitrogen, oxygen, or sulfur. In certain embodiments, at least one $R^D$ is tetrazolyl. In certain embodiments, at least one $R^D$ is 6-membered monocyclic heteroaryl. In certain embodiments, at least one $R^D$ is 6-membered monocyclic heteroaryl, wherein only one of the six atoms in the ring of the heteroaryl is nitrogen. In certain embodiments, at least one $R^D$ is 6-membered monocyclic heteroaryl, wherein only two of the six atoms in the ring of the heteroaryl are nitrogen. In certain embodiments, at least one $R^D$ is triazinyl. In certain embodiments, at least one $R^D$ is tetrazinyl. In certain embodiments, at least one $R^D$ is bicyclic heteroaryl, wherein the point of attachment may be on any atom of the bicyclic heteroaryl, as valency permits. In certain embodiments, at least one $R^D$ is a monocyclic heteroaryl ring fused with phenyl. In certain embodiments, at least one $R^D$ is a 5-membered monocyclic heteroaryl ring fused with phenyl. In certain embodiments, at least one $R^D$ is a 6-membered monocyclic heteroaryl ring fused with phenyl. In certain embodiments, at least one $R^D$ is a monocyclic heteroaryl fused ring with another monocyclic heteroaryl. In certain embodiments, at least one $R^D$ is a 5-membered monocyclic heteroaryl ring fused with another 5-membered monocyclic heteroaryl. In certain embodiments, at least one $R^D$ is a 5-membered monocyclic heteroaryl ring fused with a 6-membered monocyclic heteroaryl. In certain embodiments, at least one $R^D$ is a 6-membered monocyclic heteroaryl ring fused with another 6-membered monocyclic heteroaryl. In certain embodiments, at least one $R^D$ is —$OR^{D1}$. In certain embodiments, at least one $R^D$ is —OMe. In certain embodiments, at least one $R^D$ is —OEt. In certain embodiments, at least one $R^D$ is —OPr. In certain embodiments, at least one $R^D$ is —OBu. In certain embodiments, at least one $R^D$ is —O(pentyl). In certain embodiments, at least one $R^D$ is —OCH$_2$(cyclohexyl). In certain embodiments, at least one $R^D$ is —OPh. In certain embodiments, at least one $R^D$ is —OBn. In certain embodiments, at least one $R^D$ is —O(CH$_2$)$_2$Ph. In certain embodiments, at least one $R^D$ is —OH. In certain embodiments, at least one $R^D$ is —$SR^{D1}$. In certain embodiments, at least one $R^D$ is —SMe. In certain embodiments, at least one $R^D$ is —SH. In certain embodiments, at least one $R^D$ is —N($R^{D1}$)$_2$. In certain embodiments, at least one $R^D$ is —N(Me)$_2$. In certain embodiments, at least one $R^D$ is —NHMe. In certain embodiments, at least one $R^D$ is —NHAc. In certain embodiments, at least one $R^D$ is —NH$_2$. In certain embodiments, at least one $R^D$ is —CN. In certain embodiments, at least one $R^D$ is —SCN. In certain embodiments, at least one $R^D$ is —C(=N$R^{D1}$)$R^{D1}$, C(=N$R^{D1}$)O$R^{D1}$, or —C(=N$R^{D1}$)N($R^{D1}$)$_2$. In certain embodiments, at least one $R^D$ is —C(=O)$R^{D1}$. In certain embodiments, at least one $R^D$ is —C(=O)O$R^{D1}$. In certain embodiments, at least one $R^D$ is —C(=O)OMe. In certain embodiments, at least one $R^D$ is —C(=O)N($R^{D1}$)$_2$. In certain embodiments, at least one $R^D$ is —C(=O)N(Me)$_2$. In certain embodiments, at least one $R^D$ is —C(=O)NHMe. In certain embodiments, at least one $R^D$ is —C(=O)NH$_2$. In certain embodiments, at least one $R^D$ is —NO$_2$. In certain embodiments, at least one $R^D$ is —N$R^{D1}$C(=O)$R^{D1}$, —N$R^{D1}$C(=O)O$R^{D1}$, or —N$R^{D1}$C(=O)N($R^{D1}$)$_2$. In certain embodiments, at least one $R^D$ is —OC(=O)$R^{D1}$, —OC(=O)O$R^{D1}$, or —OC(=O)N($R^{D1}$)$_2$.

In compounds described herein, two $R^D$ groups may be joined to form a substituted or unsubstituted carbocyclic ring. In certain embodiments, two $R^D$ groups are joined to form a substituted or unsubstituted cyclopropyl ring. In certain embodiments, two $R^D$ groups are joined to form a substituted or unsubstituted cyclobutyl ring. In certain embodiments, two $R^D$ groups are joined to form a substituted or unsubstituted cyclopentyl ring. In certain embodiments, two $R^D$ groups are joined to form a substituted or unsubstituted cyclohexyl ring. In certain embodiments, two $R^D$ groups are joined to form a substituted or unsubstituted cycloheptyl ring. In certain embodiments, two $R^D$ groups are joined to form a substituted or unsubstituted cyclooctyl ring. In certain embodiments, two $R^D$ groups are joined to form a substituted or unsubstituted cyclononyl ring. In certain embodiments, two $R^D$ groups are joined to form a substituted or unsubstituted cyclodecyl ring.

In certain embodiments, two $R^D$ groups are joined to form a substituted or unsubstituted heterocyclic ring. In certain embodiments, two $R^D$ groups are joined to form a substituted or unsubstituted 4-membered heterocyclic ring. In certain embodiments, two $R^D$ groups are joined to form a substituted or unsubstituted 5-membered heterocyclic ring. In certain embodiments, two $R^D$ groups are joined to form a substituted or unsubstituted 6-membered heterocyclic ring. In certain embodiments, two $R^D$ groups are joined to form a substituted or unsubstituted 7-membered heterocyclic ring. In certain embodiments, two $R^D$ groups are joined to form a substituted or unsubstituted 8-membered heterocyclic ring. In certain embodiments, two $R^D$ groups are joined to form a substituted or unsubstituted 9-membered heterocyclic ring. In certain embodiments, two $R^D$ groups are joined to form a substituted or unsubstituted 10-membered heterocyclic ring.

In certain embodiments, two $R^D$ groups are joined to form a substituted or unsubstituted aryl ring. In certain embodiments, two $R^D$ groups are joined to form a substituted or unsubstituted monocyclic aryl ring. In certain embodiments, two $R^D$ groups are joined to form a substituted or unsubstituted phenyl ring. In certain embodiments, two $R^D$ groups are joined to form a substituted or unsubstituted bicyclic aryl ring. In certain embodiments, two $R^D$ groups are joined to form a substituted or unsubstituted naphthyl ring.

In certain embodiments, two $R^D$ groups are joined to form a substituted or unsubstituted heteroaryl ring. In certain embodiments, two $R^D$ groups are joined to form a substituted or unsubstituted monocyclic heteroaryl ring. In certain embodiments, two $R^D$ groups are joined to form a substituted or unsubstituted, 5-membered monocyclic heteroaryl ring. In certain embodiments, two $R^D$ groups are joined to form a substituted or unsubstituted, 6-membered monocyclic heteroaryl ring. In certain embodiments, two $R^D$ groups are joined to form a substituted or unsubstituted bicyclic heteroaryl ring. In certain embodiments, two $R^D$ groups are joined to form a substituted or unsubstituted, 5,6-membered bicyclic heteroaryl ring. In certain embodiments, two $R^D$ groups are joined to form a substituted or unsubstituted, 6,5-membered bicyclic heteroaryl ring. In certain embodiments, two $R^D$ groups are joined to form a substituted or unsubstituted, 6,6-membered bicyclic heteroaryl ring.

In certain embodiments, at least one $R^{D1}$ is H. In certain embodiments, at least one $R^{D1}$ is substituted acyl. In certain embodiments, at least one $R^{D1}$ is unsubstituted acyl. In certain embodiments, at least one $R^{D1}$ is acetyl. In certain embodiments, at least one $R^{D1}$ is substituted alkyl. In certain embodiments, at least one $R^{D1}$ is unsubstituted alkyl. In certain embodiments, at least one $R^{D1}$ is $C_{1-6}$ alkyl. In certain embodiments, at least one $R^{D1}$ is methyl. In certain embodiments, at least one $R^{D1}$ is ethyl. In certain embodiments, at least one $R^{D1}$ is propyl. In certain embodiments, at least one $R^{D1}$ is butyl. In certain embodiments, at least one $R^{D1}$ is pentyl. In certain embodiments, at least one $R^{D1}$ is adamantyl. In certain embodiments, at least one $R^{D1}$ is substituted alkenyl. In certain embodiments, at least one $R^{D1}$ is unsubstituted alkenyl. In certain embodiments, at least one $R^{D1}$ is vinyl. In certain embodiments, at least one $R^{D1}$ is substituted alkynyl. In certain embodiments, at least one $R^{D1}$ is unsubstituted alkynyl. In certain embodiments, at least one $R^{D1}$ is ethynyl. In certain embodiments, at least one $R^{D1}$ is substituted carbocyclyl. In certain embodiments, at least one $R^{D1}$ is unsubstituted carbocyclyl. In certain embodiments, at least one $R^{D1}$ is cylcopropyl. In certain embodiments, at least one $R^{D1}$ is cyclobutyl. In certain embodiments, at least one $R^{D1}$ is cyclopentyl. In certain embodiments, at least one $R^{D1}$ is cyclohexyl. In certain embodiments, at least one $R^{D1}$ is cycloheptyl. In certain embodiments, at least one $R^{D1}$ is substituted heterocyclyl. In certain embodiments, at least one $R^{D1}$ is unsubstituted heterocyclyl. In certain embodiments, at least one $R^{D1}$ is substituted aryl. In certain embodiments, at least one $R^{D1}$ is unsubstituted aryl. In certain embodiments, at least one $R^{D1}$ is substituted phenyl. In certain embodiments, at least one $R^{D1}$ is unsubstituted phenyl. In certain embodiments, at least one $R^{D1}$ is substituted heteroaryl. In certain embodiments, at least one $R^{D1}$ is unsubstituted heteroaryl. In certain embodiments, at least one $R^{D1}$ is substituted pyridyl. In certain embodiments, at least one $R^{D1}$ is unsubstituted pyridyl. In certain embodiments, at least one $R^{D1}$ is a nitrogen protecting group when attached to a nitrogen atom. In certain embodiments, at least one $R^{D1}$ is Bn, Boc, Cbz, Fmoc, trifluoroacetyl, triphenylmethyl, or Ts when attached to a nitrogen atom. In certain embodiments $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1}$ groups are joined to form a substituted heterocyclic ring. In certain embodiments, two $R^{D1}$ groups are joined to form an unsubstituted heterocyclic ring. In certain embodiments, two $R^{D1}$ groups are joined to form a substituted heteroaryl ring. In certain embodiments, two $R^{D1}$ groups are joined to form an unsubstituted heteroaryl ring.

In certain embodiments, p is 0. In certain embodiments, p is 1. In certain embodiments, p is 2. In certain embodiments, p is 3. In certain embodiments, p is 4.

In certain embodiments, the compound described herein is of the formula:

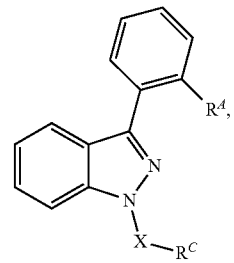

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

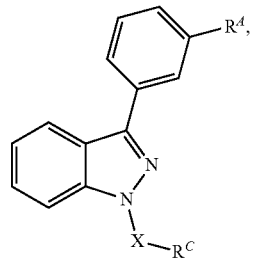

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

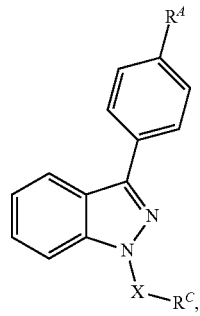

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

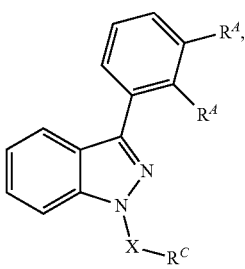

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

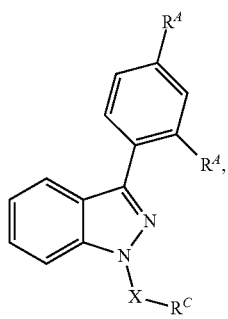

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

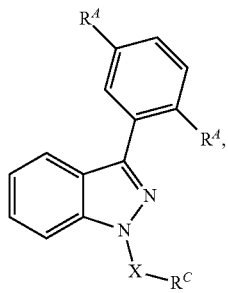

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

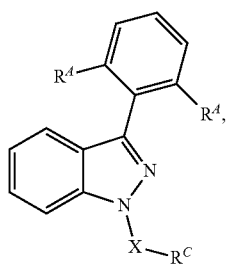

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

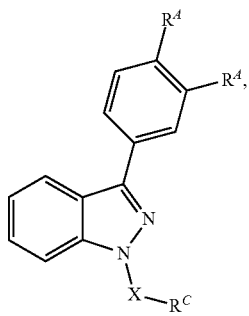

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

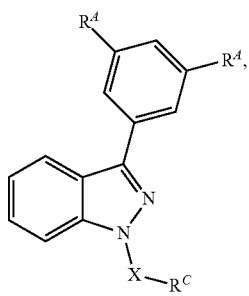

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

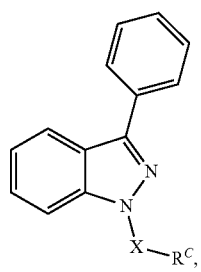

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

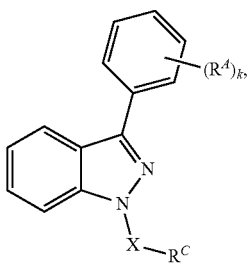

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

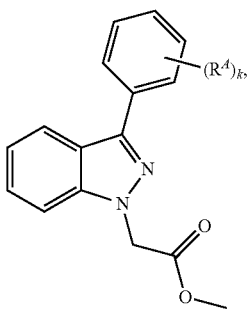

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

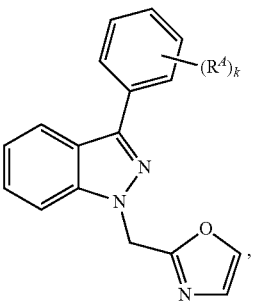

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

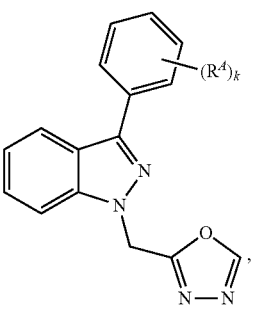

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

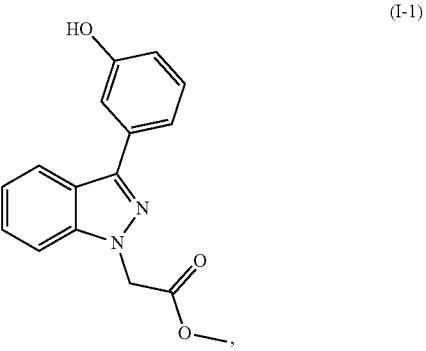

(I-1)

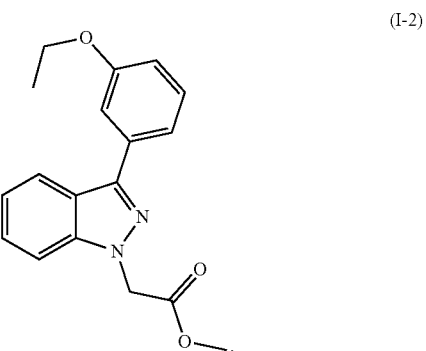

(I-2)

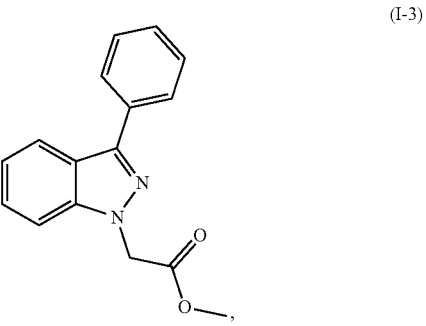

(I-3)

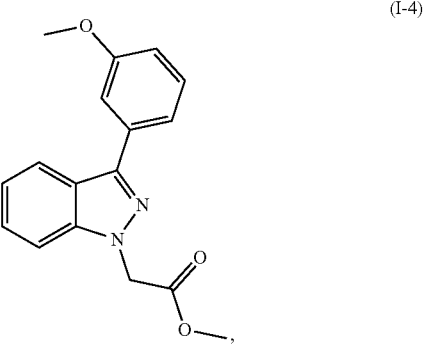

(I-4)

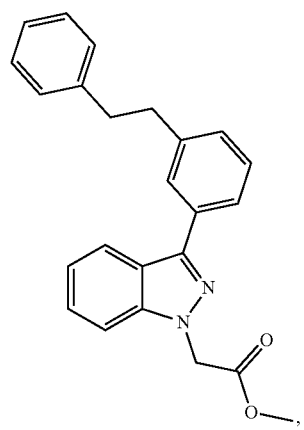
(I-5)
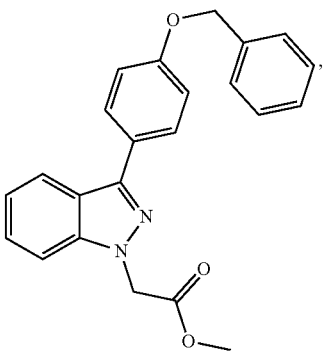
(I-9)
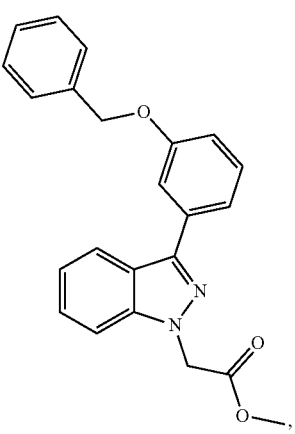
(I-10)
(I-6)
(I-7)
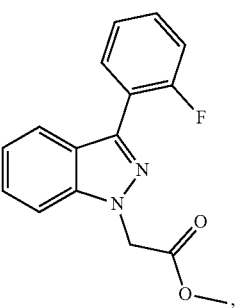
(I-11)
(I-8)
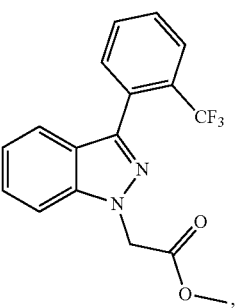
(I-12)

(I-13)
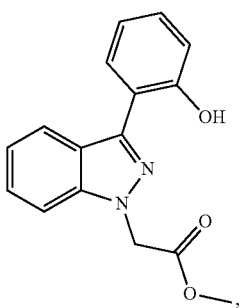
(I-14)
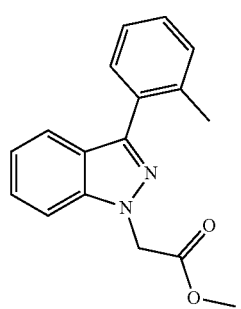
(I-15)
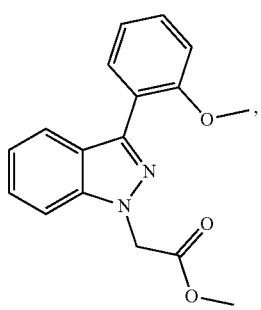
(I-16)
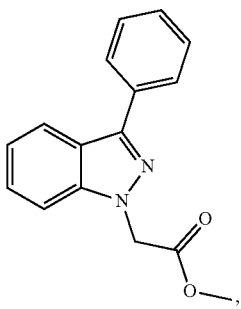
(I-17)
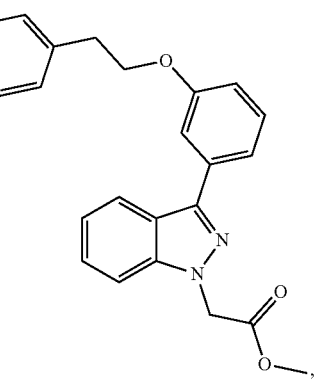
(I-18)
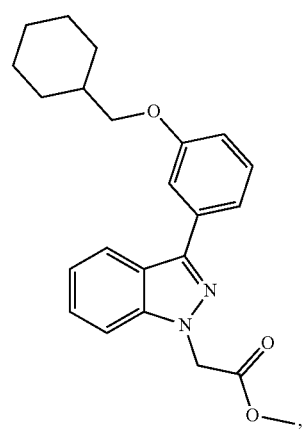
(I-19)
(I-20)
(I-21)
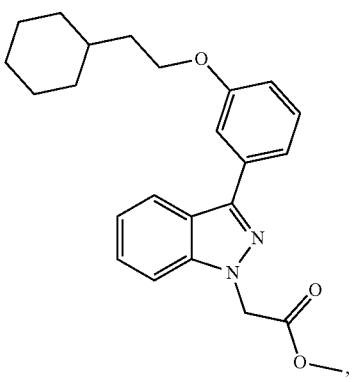

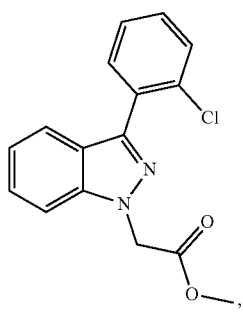
(I-22)
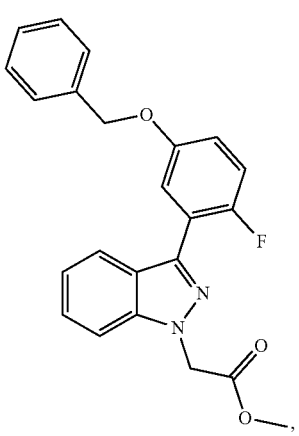
(I-23)
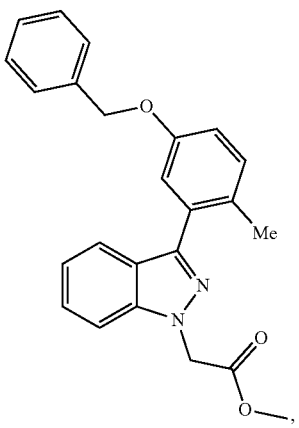
(I-24)
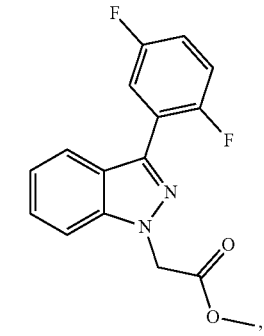
(I-25)
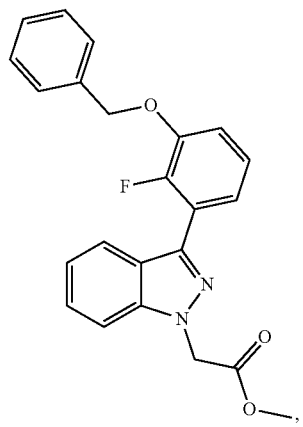
(I-26)
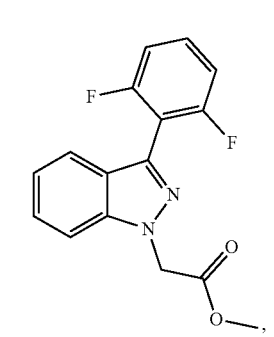
(I-27)
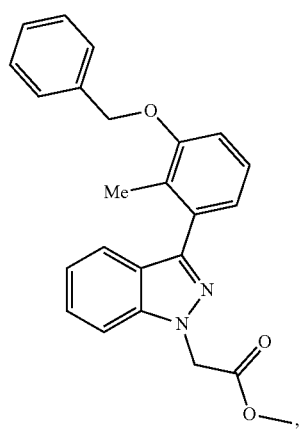
(I-28)
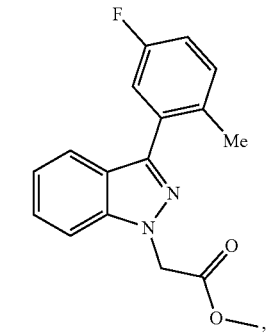
(I-29)

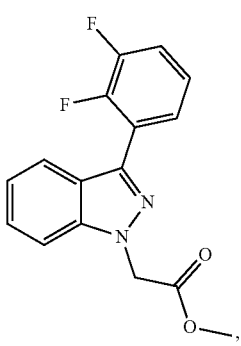
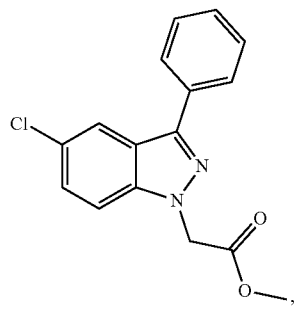

(I-40)
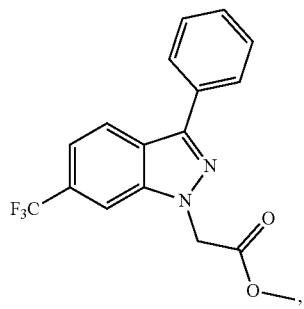
(I-41)
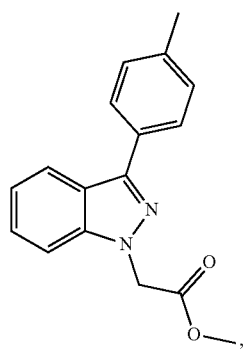
(I-42)
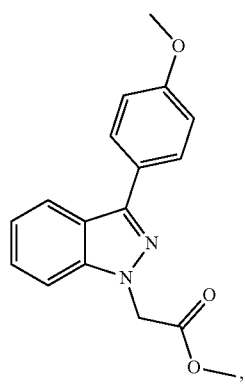
(I-43)
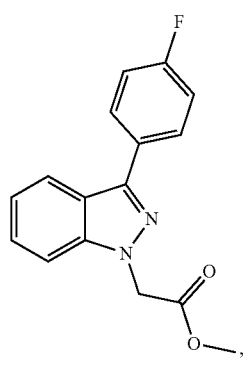
(I-44)
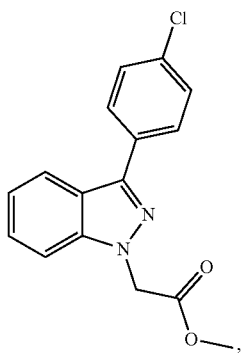
(I-45)
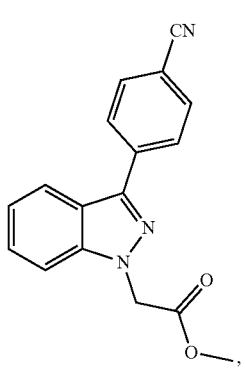
(I-46)
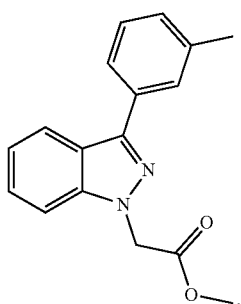
(I-47)
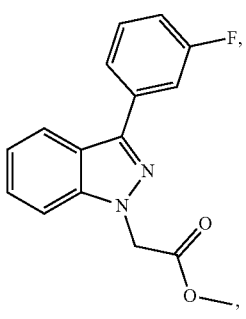

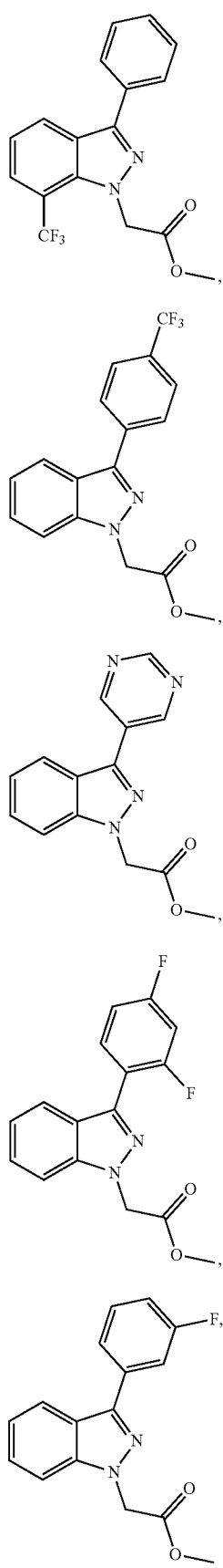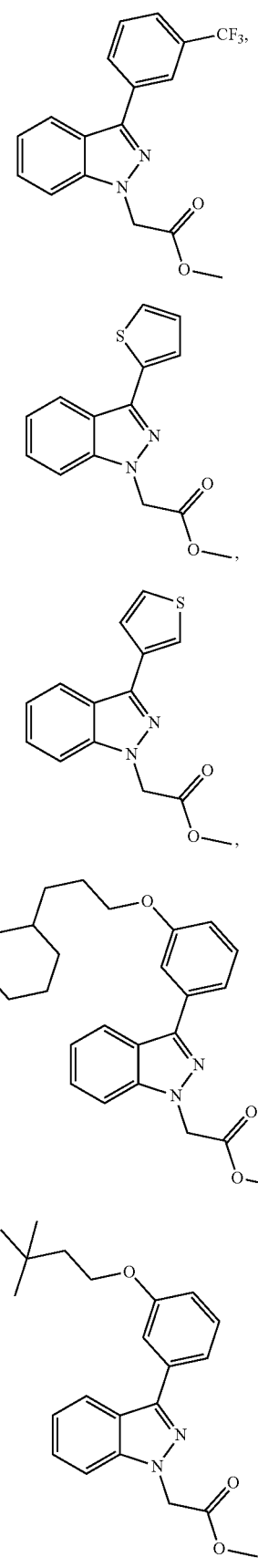

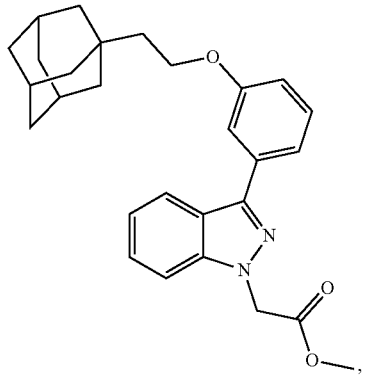
(I-80)
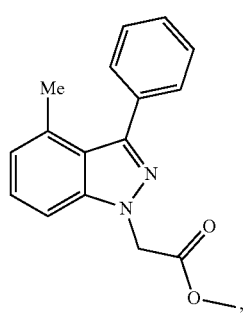
(I-81)
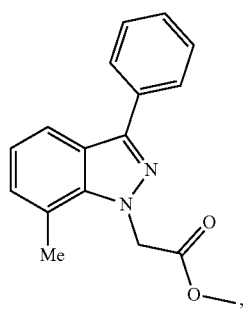
(I-82)
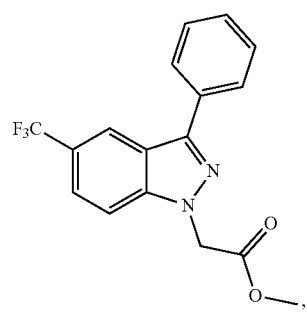
(I-83)
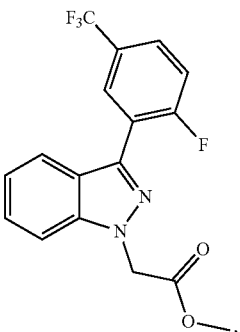
(I-88)
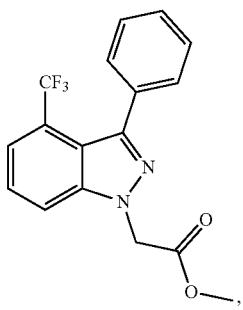
(I-89)
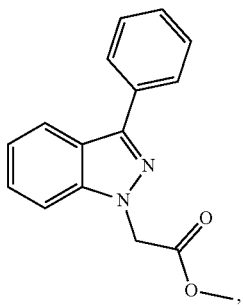
(I-96)
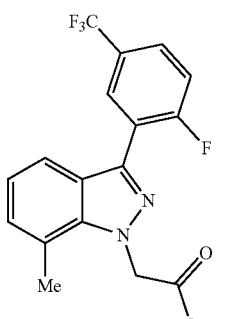
(I-97)

-continued
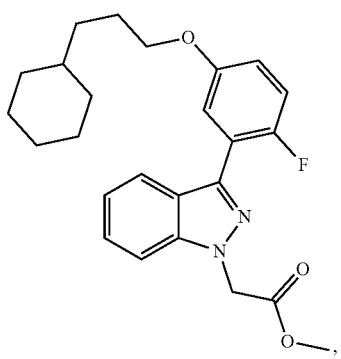 (I-100)
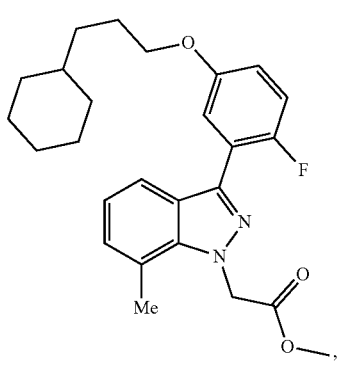 (I-101)
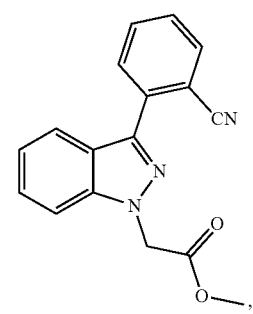 (I-117)
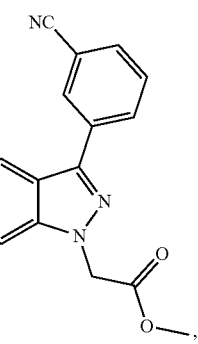 (I-118)
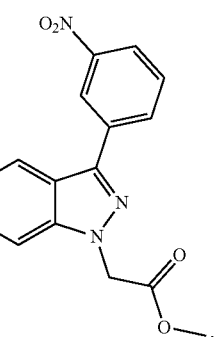 (I-119)
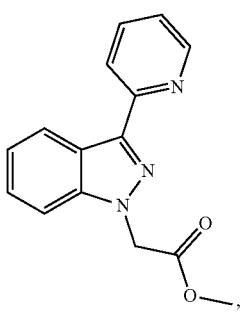 (I-120)
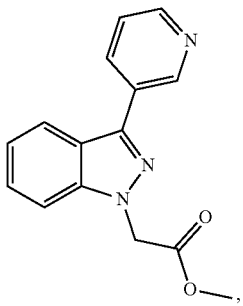 (I-121)
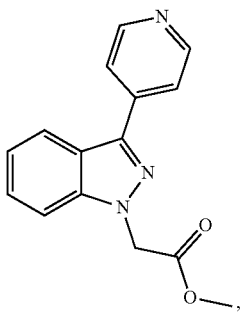 (I-122)
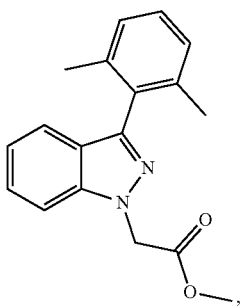 (I-127)

-continued
(I-128) 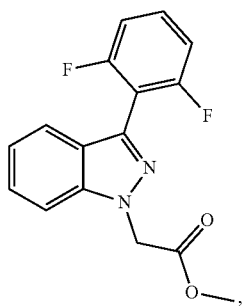
(I-129) 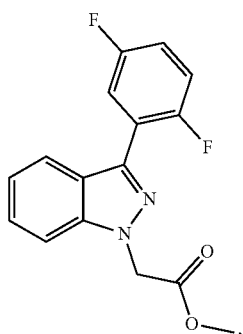
(I-130) 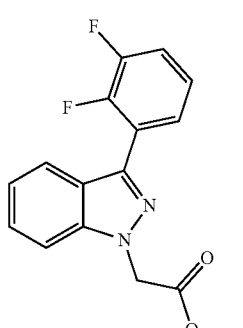
(I-131) 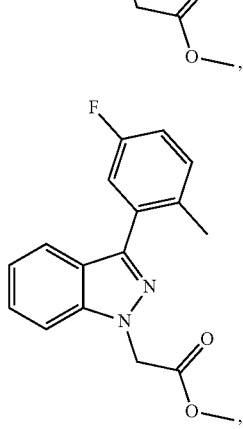
(I-132) 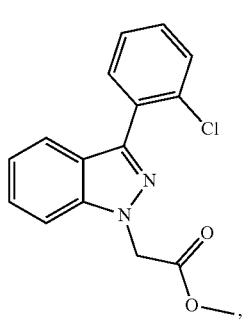
-continued
(I-133) 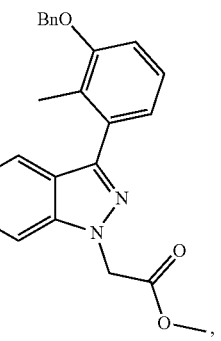
(I-134) 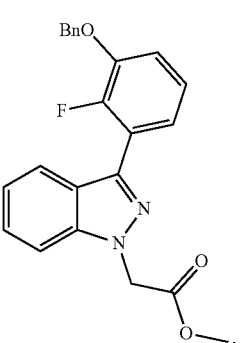
(I-135) 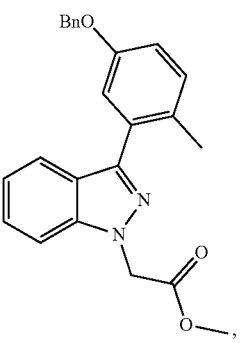
(I-136) 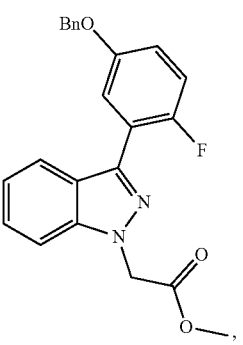

(I-137)
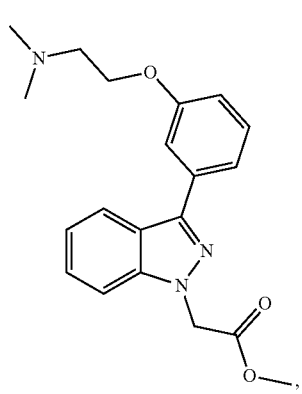

(I-138)
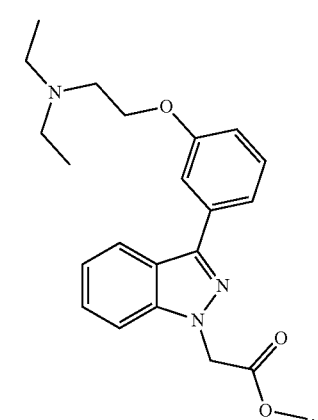

(I-139)
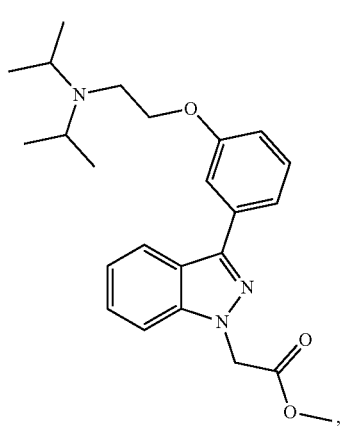

(I-140)
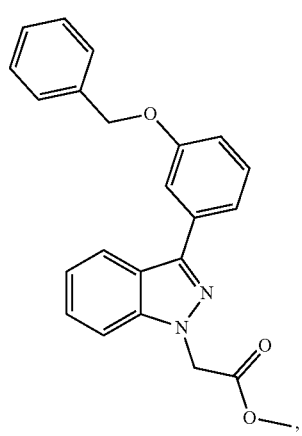

(I-141)
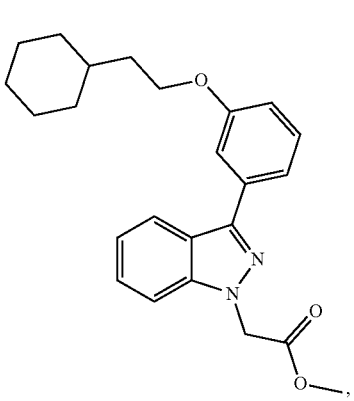

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

(I-51)
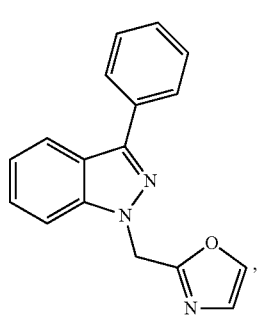

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

(I-52)
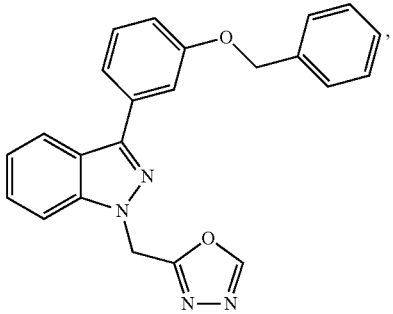

or a pharmaceutically acceptable salt, solvate, hydrate, polymorph, co-crystal, tautomer, stereoisomer, isotopically labeled derivative, or prodrug thereof.

In certain embodiments, the compound described herein is of the formula:

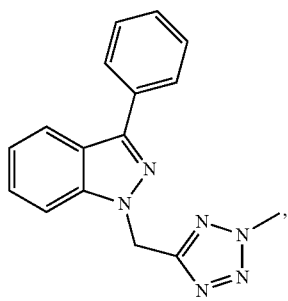
(I-69)
or a pharmaceutically acceptable salt, solvate, hydrate, polymorph, co-crystal, tautomer, stereoisomer, isotopically labeled derivative, or prodrug thereof.
In certain embodiments, the compound described herein is of the formula:
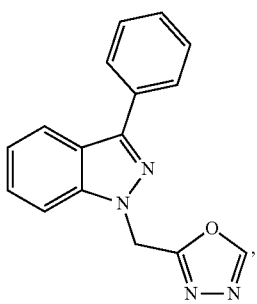
(I-74)
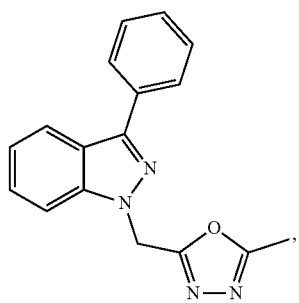
(I-84)
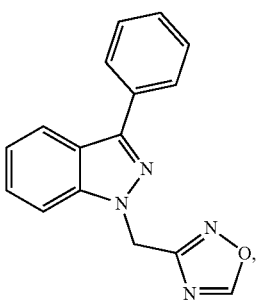
(I-85)
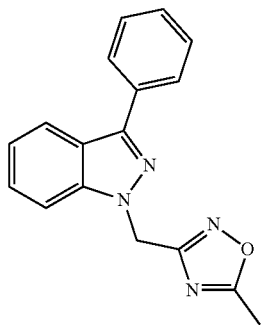
(I-86)
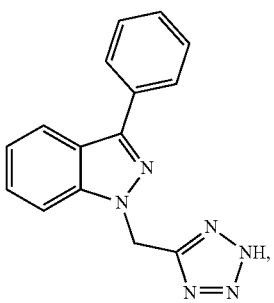
(I-87)
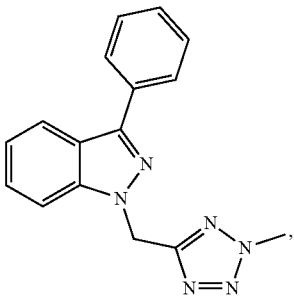
(I-90)
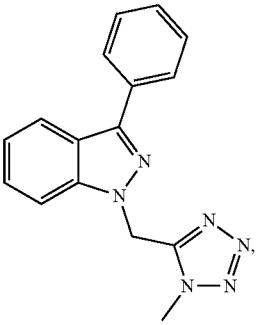
(I-91)
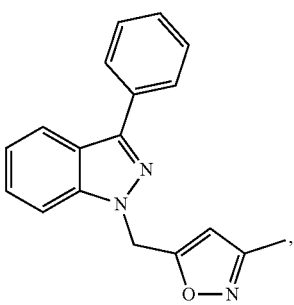
(I-92)

119
-continued
(I-93)
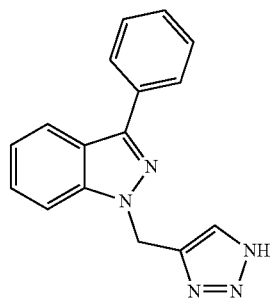
(I-94)
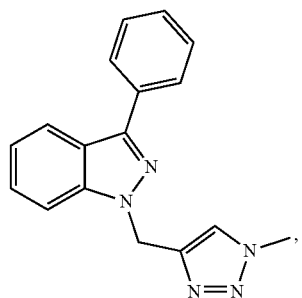
(I-95)
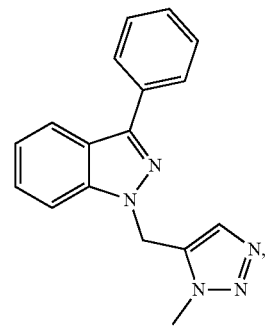
(I-98)
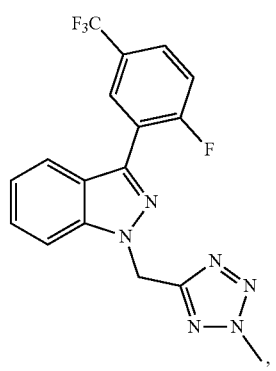
120
-continued
(I-99)
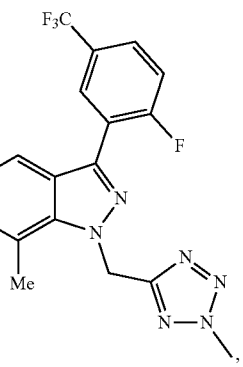
(I-102)
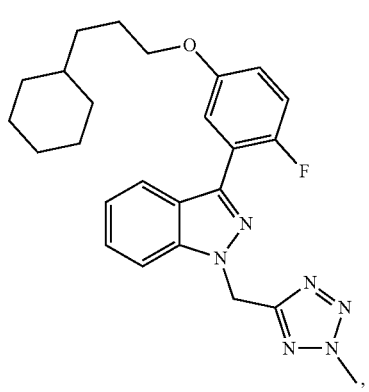
(I-103)
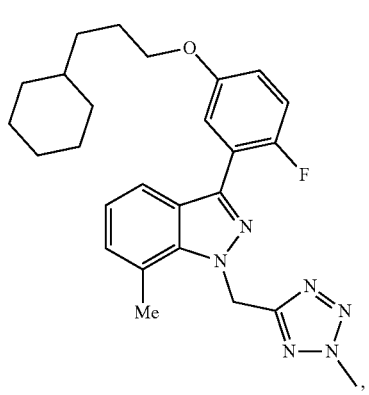
(I-108)
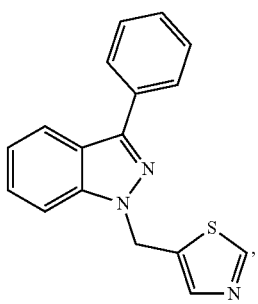

| 121 -continued | | 122 -continued | |
|---|---|---|---|
| 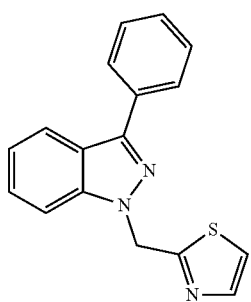 | (I-109) | 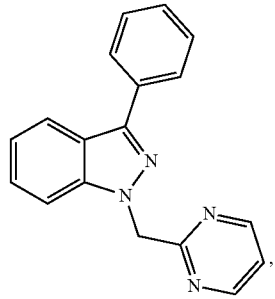 | (I-123) |
| 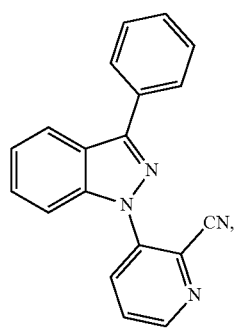 | (I-112) | 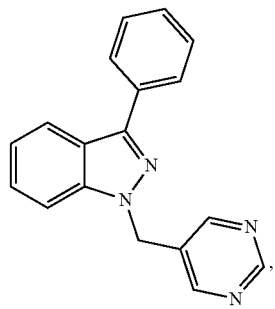 | (I-124) |
| 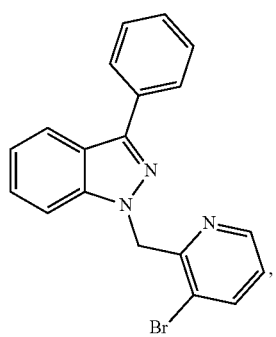 | (I-113) | 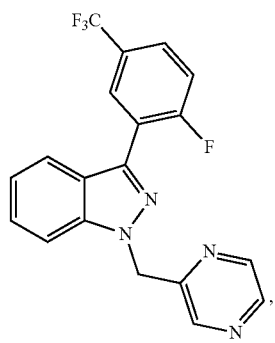 | (I-125) |
| 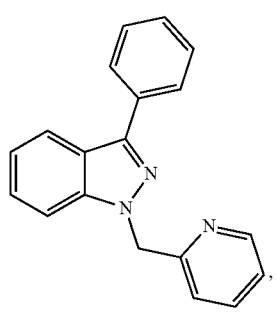 | (I-114) | 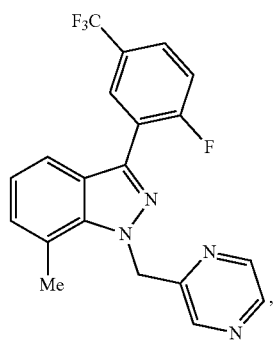 | (I-126) |
| 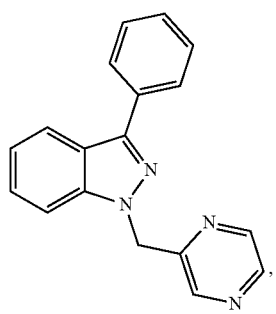 | (I-115) | 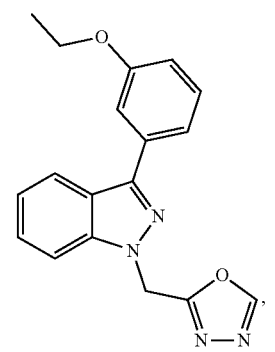 | (I-142) |

(I-143)
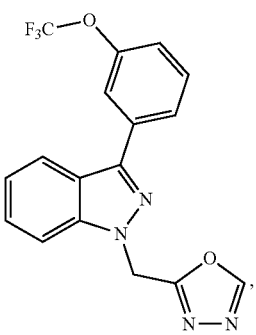
(I-144)
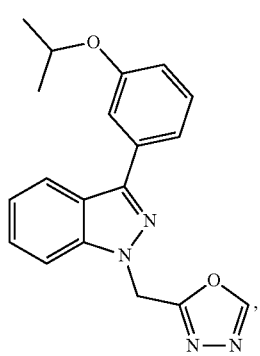
(I-145)
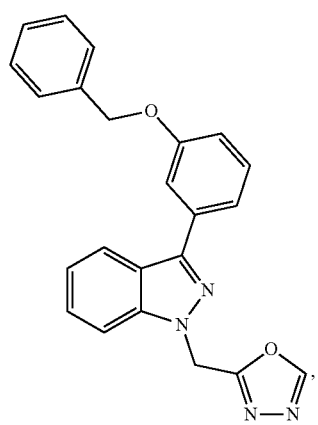
(I-146)
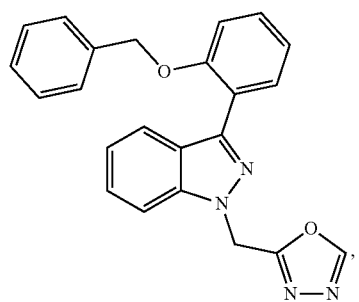
(I-147)
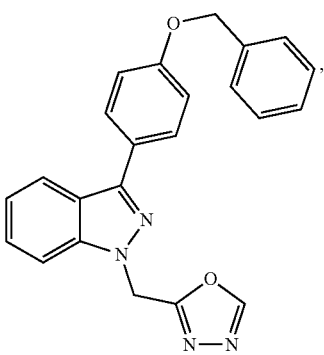
(I-148)
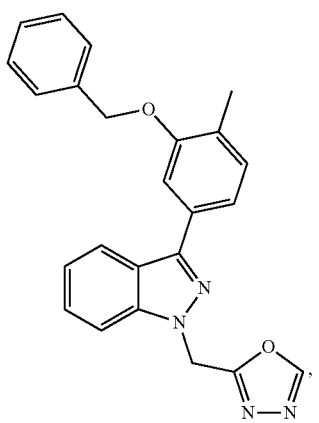
(I-149)
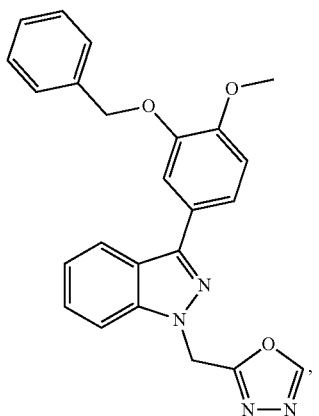
(I-150)
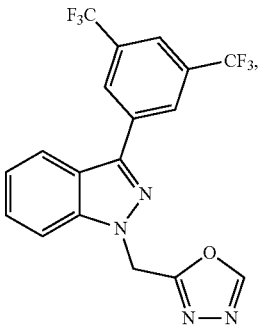
or a pharmaceutically acceptable salt, solvate, hydrate, polymorph, co-crystal, tautomer, stereoisomer, isotopically labeled derivative, or prodrug thereof.
In certain embodiments, the compound described herein is of the formula:

(I-53)
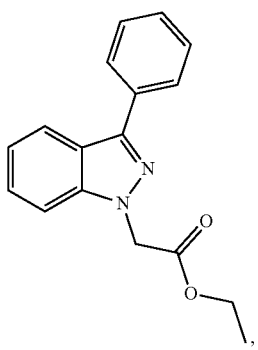
(I-54)
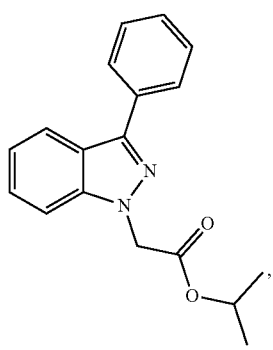
(I-55)
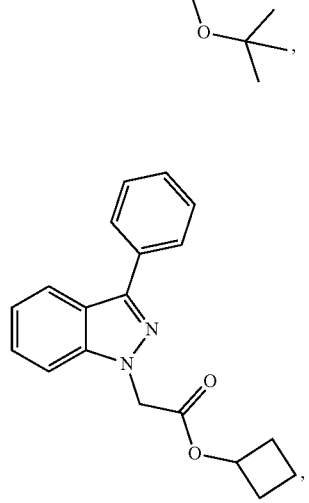
(I-56)
-continued
(I-57)
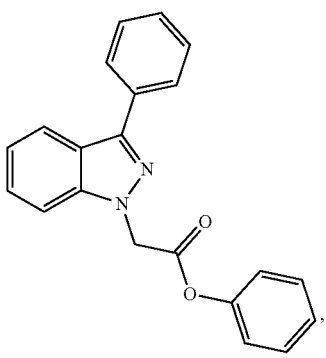
(I-58)
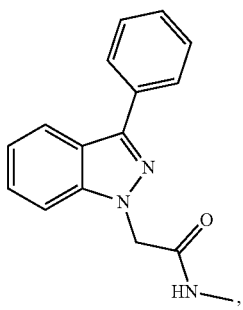
(I-59)
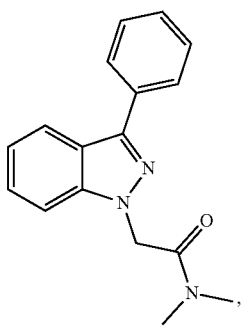
(I-60)
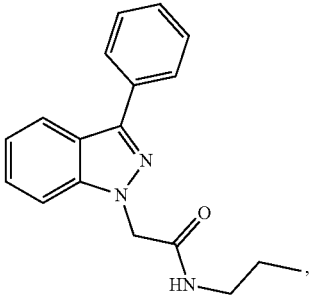
(I-61)
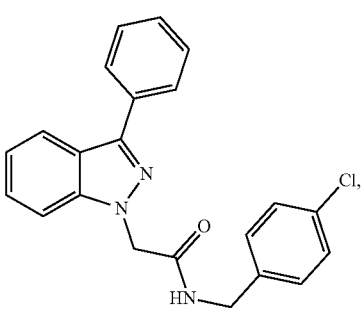

| 127 -continued | 128 -continued |
|---|---|
| 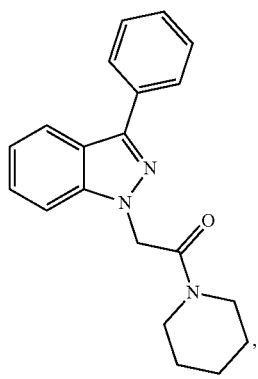 (I-62) | 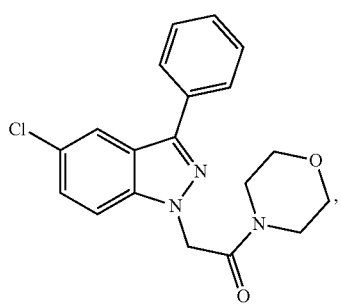 (I-67) |
| 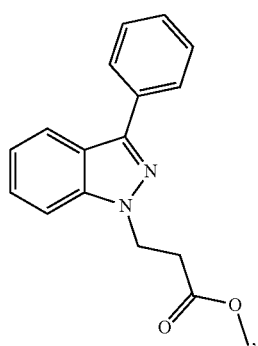 (I-63) | 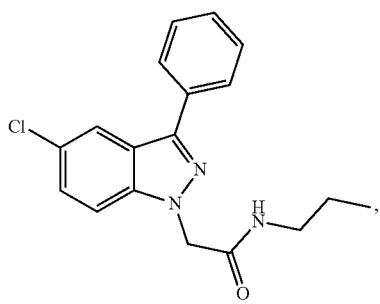 (I-68) |
| 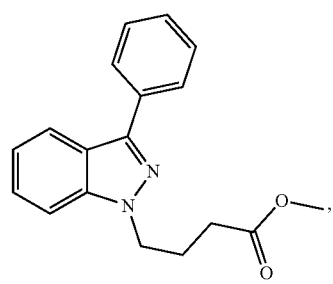 (I-64) | 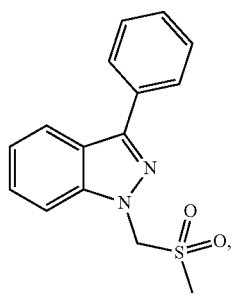 (I-73) |
| 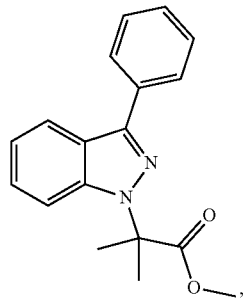 (I-65) | 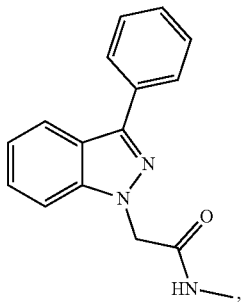 (I-75) |
| 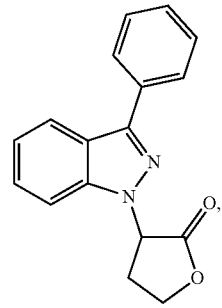 (I-66) | 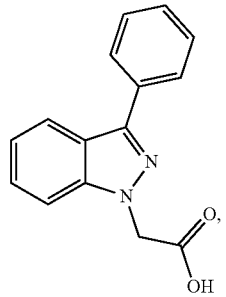 (I-107) |

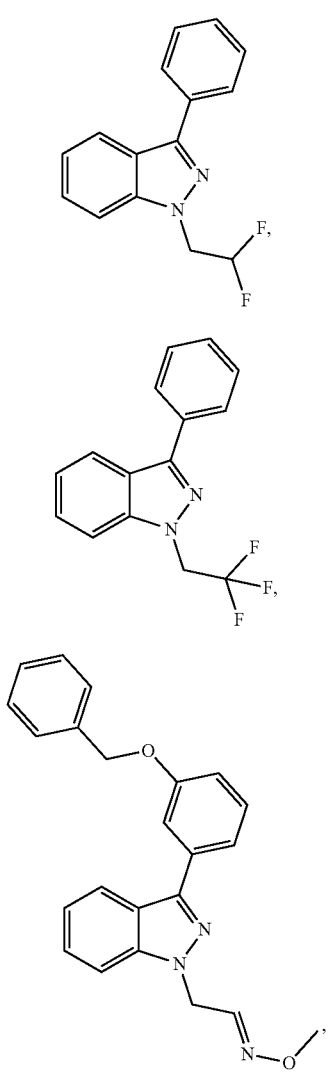

or a pharmaceutically acceptable salt, solvate, hydrate, polymorph, co-crystal, tautomer, stereoisomer, isotopically labeled derivative, or prodrug thereof.

In certain embodiments, the compound described herein is not any one of Formulae (I-4), (I-14)-(I-16), (I-31)-(I-51), (I-53)-(I-68), and pharmaceutically acceptable salts, solvates, hydrates, polymorphs, co-crystals, tautomers, stereoisomers, isotopically labeled derivatives, and prodrugs thereof.

The compounds described herein (e.g., compounds of Formula (I)) are shown to be antifungal agents, antiprotozoan, and/or chemosensitizers. In certain embodiments, the provided compounds are useful for reversing drug (e.g., fluconazole) resistance in fungi. In certain embodiments, the provided compounds are useful for reversing drug resistance in protozoa. Without wishing to be bound by a particular theory, these compounds may act by inhibiting the activity of fungal cytochrome b. In certain embodiments, the compound inhibits the activity of fungal cytochrome b without inhibiting, or at least not substantially, inhibiting the activity of the host's cytochrome b (e.g., human cytochrome b). These compounds may also inhibit the activity of fungal Hsp90. In certain embodiments, the compounds described herein are specific antifungal agents, that is, for example, the compounds described herein do not inhibit normal enzymatic activity in a subject (e.g., a human), biological sample, or plant as much as the compounds inhibit the analogous activity in a fungus. Thus, in some embodiments, it is desired that the compounds have high specificity for the fungal or protozoan target. The specificity of the inhibitor may be evaluated by comparing the $IC_{50}$ value with respect to the fungal or protozoan enzyme (i.e., target $IC_{50}$) as compared to that of the analogous host (e.g., human) enzyme (i.e., anti-target $IC_{50}$). An $IC_{50}$ value is defined as the concentration of the compound required to inhibit 50% of the enzymatic activity. In certain embodiments, the compound described herein exhibits an $IC_{50}$ value of <100 μM. In certain other embodiments, the compound exhibits an $IC_{50}$ value of <50 μM. In certain other embodiments, the compound exhibits an $IC_{50}$ value of <40 μM. In certain other embodiments, the compound exhibits an $IC_{50}$ value of <30 μM. In certain other embodiments, the compound exhibit an $IC_{50}$ value of <20 μM. In certain other embodiments, the compound exhibits an $IC_{50}$ value of <10 μM. In certain other embodiments, the compounds exhibit $IC_{50}$ values <7.5 μM. In certain embodiments, the compound exhibits an $IC_{50}$ value of <5 μM. In certain other embodiments, the compound exhibits an $IC_{50}$ value of <2.5 μM. In certain embodiments, the compound exhibits an $IC_{50}$ value of <1 μM. In certain embodiments, the compound exhibits an $IC_{50}$ value of <0.75 μM. In certain embodiments, the compound exhibits an $IC_{50}$ value of <0.5 μM. In certain embodiments, the compound exhibits an $IC_{50}$ value of <0.25 μM. In certain embodiments, the compound exhibits an $IC_{50}$ value of <0.1 μM. In certain other embodiments, the compound exhibit an $IC_{50}$ value of <75 nM. In certain other embodiments, the compound exhibits $IC_{50}$ value of <50 nM. In certain other embodiments, the compound exhibits an $IC_{50}$ value of <5 nM. In certain other embodiments, the compound exhibits $IC_{50}$ value of <10 nM. In other embodiments, the compound exhibits an $IC_{50}$ values of <7.5 nM. In other embodiments, the compound exhibits an $IC_{50}$ value of <5 nM.

In certain embodiments, the compound inhibits the fungal or protozoan enzyme at a concentration at least 2-fold, 5-fold, 10-fold, 50-fold, 100-fold, 500-fold, or 1000-fold lower than the concentration needed to inhibit the host's analogous enzyme to the same extent. In certain embodiments, the enzyme being inhibited is cytochrome b.

Pharmaceutical Compositions, Kits, and Administration

The present invention also provides pharmaceutical compositions comprising a compound described herein, or a pharmaceutically acceptable salt, solvate, hydrate, polymorph, co-crystals, tautomer, stereoisomer, isotopically labeled derivative, or prodrug thereof, and optionally a pharmaceutically acceptable excipient.

In certain embodiments, the compound described herein, or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount. In certain embodiments, the effective amount is an amount useful for the treatment and/or prevention of a fungal or protozoan infection. The effective amount of the compound in the composition may be useful for the treatment and/or prevention of a fungal or protozoan infection as a single agent or in combination with another agent such as another antifungal agent (e.g., fluconazole) or another antiprotozoan agent. In certain embodiments, the effective amount is an amount useful for inhibiting the activity of a fungal or protozoan enzyme. In certain embodiments, the effective amount is an amount useful for killing a fungus or inhibiting the growth of a fungus. An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., potency and/or efficacy in inhibiting one or more fungal or protozoan enzymes), bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

Exemplary additional pharmaceutical agents include, but are not limited to, antifungal agents, antiprotozoan agents, anti-bacterial agents, anti-viral agents, anti-inflammatory agents, and pain-relieving agents. The antifungal agents that may be used in combination with the compounds described herein include, but are not limited to, polyene antifungal agents (e.g., amphotericin B, candicidin, filipin, hamycin, natamycin, nystatin, rimocidin) and azole antifungal agents (e.g., imidazole antifungal agents (e.g., bifonazole, butoconazole, clotrimazole, econazole, fenticonazole, isoconazole, ketoconazole, miconazole, omoconazole, oxiconazole, sertaconazole, sulconazole, tioconazole), triazole antifungal agents (e.g., albaconazole, fluconazole, isavuconazole, itraconazole, posaconazole, ravuconazole, terconazole, voriconazole), and thiazole antifungal agents (e.g., abafungin). In certain embodiments, the antifungal agents are antifungal agents against which resistance is developed by the target fungus. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits described herein are useful in preventing and/or treating a fungal or protozoan infection in a subject. In certain embodiments, the kits are useful in inhibiting the activity of a fungal or protozoan enzyme (e.g., cytochrome b or Hsp90) in a subject or biological sample. In certain embodiments, the kits are useful in killing a fungus or inhibiting the growth of a fungus. In certain embodiments, the kits are useful in killing a protozoon or inhibiting the growth of a protozoon. In certain embodiments, the kits further include instructions for administering the compound, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits and instructions provide for treating and/or preventing a fungal or protozoan infection. In certain embodiments, the kits and instructions provide for inhibiting the activity of a fungal or protozoan enzyme. In certain embodiments, the kits and instructions provide for killing a fungus or inhibiting the growth of a fungus. In certain embodiments, the kits and instructions provide for killing a protozoon or inhibiting the growth of a protozoon. The kit may include one or more additional pharmaceutical agents described herein (such as antifungal agents (e.g., azole antifungal agents (e.g., fluconazole) and polyene antifungal agents (e.g., amphotericin B)) and/or antiprotozoan agents as a separate composition.

Methods of Preparing the Compounds

In one aspect, the present application provides methods of synthesizing the compounds described herein. In certain embodiments, the methods of synthesizing comprising:

contacting a compound of the formula

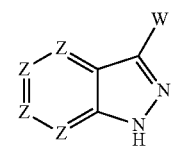

with a base and a compound of the formula

to provide a compound of the formula

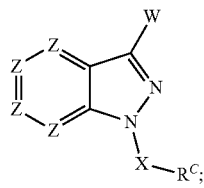

and
contacting the compound of the formula

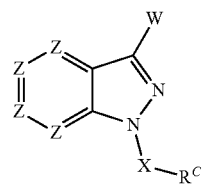

with a compound of the formula

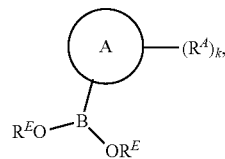

a palladium catalyst, and a base to provide a compound of the Formula (I);
wherein:
each instance of W is independently halogen, —OTf, or a leaving group;
each instance of $R^E$ is independently hydrogen, or substituted or unsubstituted alkyl, or two $R^E$ are joined to form a substituted or unsubstituted carbocyclic ring or substituted or unsubstituted aryl ring; and
Ring A, each instance of Z, X, $R^C$, each instance of $R^A$, and k are as defined herein.

In certain embodiments, the base is an inorganic base. In certain embodiments, the inorganic base is ammonia. In certain embodiments, the inorganic base is ammonium carbonate. In certain embodiments, the inorganic base is ammonium hydroxide. In certain embodiments, the inorganic base is an alkali metal phosphate tribasic. In certain embodiments, the inorganic base is $Li_3PO_4$, $Na_3PO_4$, $K_3PO_4$, $Rb_3PO_4$, or $Cs_3PO_4$. In certain embodiments, the inorganic base is an alkali metal phosphate dibasic. In certain embodiments, the inorganic base is $Li_2HPO_4$, $Na_2HPO_4$, $K_2HPO_4$, $Rb_2HPO_4$, or $Cs_2HPO_4$. In certain embodiments, the inorganic base is an alkali metal phosphate monobasic. In certain embodiments, the inorganic base is $LiH_2PO_4$, $NaH_2PO_4$, $KH_2PO_4$, $RbH_2PO_4$, or $CsH_2PO_4$. In certain embodiments, the inorganic base is an alkali metal carbonate. In certain embodiments, the inorganic base is $Li_2CO_3$, $Na_2CO_3$, $K_2CO_3$, $Rb_2CO_3$, or $Cs_2CO_3$. In certain embodiments, the inorganic base is an alkali metal bicarbonate. In certain embodiments, the inorganic base is $LiHCO_3$, $NaHCO_3$, $KHCO_3$, $RbHCO_3$, or $CsHCO_3$. In certain embodiments, the inorganic base is an alkali metal hydroxide. In certain embodiments, the inorganic base is LiOH, NaOH, KOH, RbOH, or CsOH. In certain embodiments, the inorganic base is an alkaline earth metal carbonate. In certain embodiments, the inorganic base is $BeCO_3$, $MgCO_3$, $CaCO_3$, $SrCO_3$, or $BaCO_3$. In certain embodiments, the inorganic base is an alkaline earth metal bicarbonate. In certain embodiments, the inorganic base is $Be(HCO_3)_2$, $Mg(HCO_3)_2$, $Ca(HCO_3)_2$, $Sr(HCO_3)_2$, or $Ba(HCO_3)_2$. In certain embodiments, the inorganic base is an alkaline earth metal hydroxide. In certain embodiments, the inorganic base is $Be(OH)_2$, $Mg(OH)_2$, $Ca(OH)_2$, $Sr(OH)_2$, or $Ba(OH)_2$. In certain embodiments, the base is an organic base. In certain embodiments, the organic base is an aliphatic amine. In certain embodiments, the organic base is an aromatic amine. In certain embodiments, the organic base is a primary amine. In certain embodiments, the organic base is a secondary amine. In certain embodiments, the organic base is a tertiary amine. In certain embodiments, the organic base is triethyl amine, N,N-diisopropylethylamine, or 1,8-diazabicyclo[5.4.0]undec-7-ene (DBU). In certain embodiments, the organic base is substituted pyridine. In certain embodiments, the organic base is 2,6-lutidine or 4-dimethylaminopyridine (DMAP). In certain embodiments, the organic base is unsubstituted pyridine.

In certain embodiments, the palladium catalyst is a Pd(0) catalyst. In certain embodiments, the palladium catalyst is a Pd(II) catalyst. In certain embodiments, the palladium catalyst is tetrakis(triphenylphosphine)palladium(0). In certain embodiments, the palladium catalyst is SPhos. In certain embodiments, the palladium catalyst is XPhos. In certain embodiments, the palladium catalyst is palladium(II) acetylacetonate.

Methods of Treatment and Uses

In one aspect, the present invention provides methods for the treatment and/or prevention of a fungal or protozoan infection in a subject. The fungal infection in the subject may be caused by a fungus. In certain embodiments, the fungus is a yeast. In certain embodiments, the fungus is a mold. In certain embodiments, the fungus that causes the fungal infection is a *Candida* species. In certain embodiments, the fungus is a *Candida albicans* strain. In certain embodiments, the fungus is CaCi-2. In certain embodiments, the fungus is CaCi-8. In certain embodiments, the fungus is *Candida albicans* strain 90028. In certain embodiments, the fungus is *Candida albicans* strain Gu5. In certain embodiments, the fungus is *Candida albicans* strain CTBT. Additional *Candida* species include, but are not limited to, *C. glabrata, C. krusii, C. rugosa, C. parapsilosis, C. tropicalis, C. dubliniensis, C. lusitaniae, C. guilliermondii, C. famata, C. kefyr, C. pelliculosa, C. lipolytica, C. inconspicua, C. sake, C. lambica, C. norvegensis,* and *C. zeylanoides*. In certain embodiments, the fungus is a *Aspergillus* species. In certain embodiments, the fungus is a *Aspergillus terreus* strain. Additional *Aspergillus* species include, but are not limited to, *A. clavatus, A. fumigatus, A. niger,* and *A. flavus*. In certain embodiments, the fungus is a *Saccharomyces* species. In certain embodiments, the fungus is a *Saccharomyces cerevisiae* strain. In certain embodiments, the fungus is *Saccharomyces cerevisiae* W303 reporter strain (ATCC 201238). In certain embodiments, the fungus is a *Cryptococcus* species. In certain embodiments, the fungus is a *Histoplasma* species. In certain embodiments, the fungus is a *Rhizopus* species. In certain embodiments, the fungus is a *Mucor* species. In some embodiments, the fungus is a member of the genus *Coccidioides*. In some embodiments, the fungus is a member of the phylum Ascomycota. In some embodiments, the fungus is a member of the phylum Basidiomycota, In some embodiments, the fungus is a member of the phylum Chytridiomycota, In some embodiments, the fungus is a member of the phylum Glomeromycota. In some embodiments, the fungus is a member of the phylum Zygomycota. The fungus may be any fungus including, but not limited to a member of a genus selected from the group consisting of *Aspergillus, Blastomyces Candida, Coccidioides, Cryptococcus, Fusarium, Histoplasma, Malassezia, Microsporum, Mucor, Paracoccidioide, Pneumocystis, Pseudallescheria, Rhizopus, Scedosporium, Sporothrix, Stachybotrys, Saccharomyces, Trichophyton,* or *Trichosporon*.

In some embodiments, the fungus of the genus *Blastomyces* is *Blastomyces dermatitidis*. In some embodiments, the fungus of the genus *Coccidioides* is *Coccidioides immitis* or *Coccidioides posadasii*. In some embodiments, the fungus of the genus *Cryptococcus* is *Cryptococcus neoformans C. gattii, C. albidus, C. laurentii,* or *C. uniguttulas*. In some embodiments, the fungus of the genus *Epidermophyton* is *E. floccosum*. In some embodiments, the fungus of the genus *Fusarium* is *Fusarium graminearum Fusarium oxysporum* fsp. *cubense*, a member of the *Fusarium solani* complex, *Fusarium oxysporum, Fusarium verticillioides,* or *Fusarium proliferatum*. In some embodiments, the fungus of the genus *Histoplasma* is *Histoplasma capsulatum*. In some embodiments, the fungus of the genus *Malassezia* is *Malassezia furfur*. In some embodiments, the fungus of the genus *Mucor* is *M. circinelloides* In some embodiments, the fungus of the genus *Paracoccidioides* is *Paracoccidioides brasiliensis*. In some embodiments, the fungus of the genus *Penicillium* is *Penicillium marneffei*. In some embodiments, the fungus of the genus *Pichia* is *Pichia anomala, Pichia guilliermondi*. In some embodiments, the fungus of the genus *Pneumocystis* is *Pneumocystis carinii* or *Pneumocystis jirovecii*. In some embodiments, the fungus of the genus *Pseudallescheria* is *Pseudallescheria boydii*. In some embodiments, a parasite of the genus *Rhizopus* is *Rhizopus oryzae*. In some embodiments, the fungus of the genus *Rhodotorula* is *Rhodotorula rubra*. In some embodiments, the fungus of the genus *Scedosporium* is *Scedosporium apiospermum*. In some embodiments, the fungus of the genus *Schizophyllum* is *Schizophyllum commune*. In some embodiments, the fungus of the genus *Sporothrix* is *Sporothrix schenckii*. In some embodiments, the fungus of the genus *Trichophyton* is *Trichophyton mentagrophytes, Trichophyton rubrum, Trichophyton verrucosum, Trichophyton tonsurans,* or *Trichophyton violaceum*. In some embodiments, the fungus of the genus *Trichosporon* is *Trichosporon asahii, Trichosporon cutaneum, Trichosporon inkin,* or *Trichosporon mucoides*.

In certain embodiments, the fungus is a fungus resistant to one or more azole antifungal agents. In certain embodiments, the fungus is a fungus resistant to fluconazole. In certain embodiments, the fungus is a fungus resistant to one or more polyene antifungal agents. In certain embodiments, the fungus is a fungus resistant to amphotericin B. In some embodiments, the fungus is pathogen that affects one or more cultivated plants. In some embodiments, the fungus is a member of the genus *Magnaporthe, Ophiostoma, Cryphonectria, Thielaviopsis, Verticillium, Fusarium, Ustilago, Alternaria, Rhizoctonia, Phakospora, Puccinia,* or *Cochliobolus*.

The protozoan infection in the subject may be caused by a protozoon. In some embodiments, the protozoon is an *Apicomplexan*, e.g., a member of the genus *Babesia, Plasmodium, Cryptosporidium, Isospora,* or *Toxoplasma*.

In certain embodiments, the compounds described herein, or a composition thereof, inhibits an eukaryotic parasite.

In certain embodiments, the compounds described herein, or a composition thereof, inhibits an enzyme of a microbial organism that requires mitochondrial respiratory function for virulence in a host of the microbial organism.

The compounds of the present invention, or pharmaceutical compositions thereof, may inhibit the fungal or protozoan cytochrome b (Cytochrome bc1 complex of the mitochondrial electron transport chain). In certain embodiments, the compounds of the present invention, or pharmaceutical compositions thereof, inhibit the fungal or protozoan cytochrome b with selectivity over the analogous human enzyme. This activity results in single-agent killing of pathogenic *Aspergillus* molds. In vitro, this activity sensitizes the fungal or protozoan pathogen *Candida albicans* to the commonly used antifungal agents (e.g., azole antifungal agents (e.g., fluconazole) and polyene antifungal agents (e.g., amphotericin B)) and/or antiprotozoan agents, and it is hypothesized that these compounds would have enhanced activity in a whole animal model of infection. In addition, these compounds may have use in the control of agricultural fungal or protozoan pathogens, as other cytochrome b inhibitors are widely used as pesticides (such as azoxystrobin).

The compounds of the present invention, or pharmaceutical compositions thereof, may also inhibit the mitochondrial respiratory function of a fungus or protozoon.

In certain embodiments, the subject described herein is a human. In certain embodiments, the subject is an animal. The animal may be of either sex and may be at any stage of development. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is immunocompromised. For example, the subject may have reduced immune system function as a result of a disease such as HIV infection, acquired immunodeficiency syndrome (AIDS), cancer (e.g., solid tumor or leukemia), bone marrow disorder, or a genetic immunodeficiency. In some embodiments, the subject is immunocompromised as a result of a medication, e.g., immunosuppressive therapy or chemotherapy, bone marrow transplant, stem cell transplant, or exposure to radiation. In some embodiments reduced immune system function comprises neutropenia. In some embodiments, the subject suffers from a nosocomial fungal infection.

Another aspect of the present invention involves methods of preventing a fungal infection in a subject who was or may be exposed to a fungus. In certain embodiments, the subject has been exposed to a fungus. In certain embodiments, the subject may have been exposed to a fungus. In these circumstances, the subject may not have developed the signs or symptoms of a fungal infection.

Another aspect of the present invention involves methods of preventing a protozoan infection in a subject who was or may be exposed to a protozoon. In certain embodiments, the subject has been exposed to a protozoon. In certain embodiments, the subject may have been exposed to a protozoon. In these circumstances, the subject may not have developed the signs or symptoms of a protozoan infection.

In another aspect, the present invention provides methods of inhibiting the activity of a fungal enzyme in a subject or biological sample. All types of biological samples described herein or known in the art are contemplated as being within the scope of the invention. In certain embodiments, the activity inhibited by the inventive methods is the activity of fungal cytochrome b. In certain embodiments, the activity inhibited by the inventive methods is the activity of fungal Hsp90.

In another aspect, the present invention provides methods of inhibiting the activity of a protozoan enzyme in a subject or biological sample. In certain embodiments, the activity inhibited by the inventive methods is the activity of protozoan cytochrome b. In certain embodiments, the activity inhibited by the inventive methods is the activity of protozoan Hsp90.

Another aspect of the present invention relates to methods of killing a fungus or inhibiting the growth of a fungus. In certain embodiments, the fungus is killed. In certain embodiments, the growth of the fungus is inhibited.

Another aspect of the present invention relates to methods of killing a protozoon or inhibiting the growth of a protozoon. In certain embodiments, the protozoon is killed. In certain embodiments, the growth of the protozoon is inhibited.

In certain embodiments, the methods described herein include administering to a subject, contacting a biological sample, or contacting a fungus and/or protozoon with an effective amount of a compound described herein, or a pharmaceutically acceptable salt, solvate, hydrate, polymorph, co-crystal, tautomer, stereoisomer, isotopically labeled derivative, or prodrug thereof, or a composition thereof. In certain embodiments, the methods described herein include administering to a subject, contacting a biological sample, or contacting a fungus and/or protozoon with an effective amount of a compound described herein, or a pharmaceutically acceptable salt thereof, or a composition thereof. In certain embodiments, the compound, or a composition thereof, is administered to a subject. In certain embodiments, the compound, or a composition thereof, is contacted with a biological sample. In certain embodiments, the compound, or a composition thereof, is contacted with a fungus and/or protozoon. In certain embodiments, the compound, or a composition thereof, is contacted with a fungus and/or protozoon in an agricultural setting. In certain embodiments, the compound, or a composition thereof, is contacted with a fungus and/or protozoon in an environmental setting. In certain embodiments, the compound, or a composition thereof, is contacted with a fungus and/or protozoon in a clinical setting. In certain embodiments, the compound, or a composition thereof, is contacted with a fungus and/or protozoon in or on a subject. In certain embodiments, the compound, or a composition thereof, is contacted with a fungus and/or protozoon in or on a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub. In certain embodiments, the compound is contacted with a leaf, branch, trunk, root, or seed. In some embodiments, the compound is contacted with a plant by spraying, dusting, introducing the compound into soil into which a seed is to be planted or has been planted or in which a plant is growing. A compound of the invention may be formulated with one or more vehicles appropriate for use in agricultural setting and/or may be present in a composition together with one or more other compounds useful for agricultural purposes, such as other antifungal and/or antiprotozoan agent(s). In some embodiments a compound of the invention is used to inhibit fungal and/or protozoan growth on a harvested plant material, e.g., crops or seeds, which may be stored for future use. In certain embodiments, the compound, or a composition thereof, is contacted with a fungus and/or protozoon in or on the soil. In certain embodiments, the compound, or a composition thereof, is contacted with a fungus and/or protozoon in water.

The methods of the present invention may further comprise administering to a subject, contacting a biological sample, or contacting a fungus and/or protozoon with one or more additional pharmaceutical agents in combination with a compound described herein, or a pharmaceutically acceptable salt, solvate, hydrate, polymorph, co-crystal, tautomer, stereoisomer, isotopically labeled derivative, or prodrug thereof, or composition thereof. In certain embodiments, the additional pharmaceutical agents are as described herein. The additional pharmaceutical agent may be an antifungal agent. In certain embodiments, the additional pharmaceutical agent is an azole antifungal agent. In certain embodiments, the additional pharmaceutical agent is fluconazole. In certain embodiments, the additional pharmaceutical agent is a polyene antifungal agent. In certain embodiments, the additional pharmaceutical agent is amphotericin B. The additional pharmaceutical agent may also be an antiprotozoal agent. In certain embodiments, the additional pharmaceutical agent is an inhibitor of fungal and/or protozoan cytochrome b. In certain embodiments, the additional pharmaceutical agent is an inhibitor of fungal and/or protozoan Hsp90.

In certain embodiments, the additional pharmaceutical agent inhibits synthesis of a component of the fungal plasma membrane, such as ergosterol. In certain embodiments, the additional pharmaceutical agent inhibits a fungal enzyme. In certain embodiments, the fungal enzyme is involved in synthesis of a component of the fungal membrane. In certain embodiments, the enzyme is fungal lanosterol 14α-demethylase. In certain embodiments, the additional pharmaceutical agent is an allylamine. Allylamines inhibit squalene epoxidase, an enzyme required for ergosterol synthesis. In some embodiments an allylamine is amorolfin, butenafine, naftifine, or terbinafine.

In certain embodiments, the additional pharmaceutical agent inhibits synthesis of a component of the fungal cell wall, such as fungal glucan. In some embodiments, the additional pharmaceutical agent inhibits fungal enzyme 1,3-β glucan synthase. In some embodiments, the additional pharmaceutical agent is an echinocandin, such as caspofungin, micafungin, or anidulafungin. In some embodiments, the additional pharmaceutical agent is a polyene antifungal agent such as amphotericin B, amphotericin A, nystatin, candicidin, filipin, hamycin, natamycin, timocidin, filipin, pimaricin, rimocidin, eurocidin, candidin, perimycin, levorin, or trichomycin.

In certain embodiments, the additional pharmaceutical agent is an inhibitor of mitochondrial respiration. In some embodiments, an inhibitor of mitochondrial respiration inhibits any one or more of complexes I, II, III, IV, and V of the mitochondrial respiratory chain. In some embodiments, an inhibitor of mitochondrial respiration is a complex I inhibitor. Complex I inhibitors include, e.g., pieridicin A, bullatacin, mycothiazol, and rotenone. In some embodiments, an inhibitor of mitochondrial respiration is a complex II inhibitor. Complex II inhibitors include, e.g., atpenin A5 (AAS; Axxora LLC, San Diego Calif.), malonate, diazoxide (DZX), 3-nitropropionic acid, and nitroxyl. In some embodiments, an inhibitor of mitochondrial respiration is a complex III inhibitor. Complex III inhibitors include, e.g., antimycin A, myxothiazol, and stigmatellin. In some embodiments, an inhibitor of mitochondrial respiration is a complex IV inhibitor. In some embodiments, an inhibitor of mitochondrial respiration is a complex V inhibitor. Complex V inhibitors include, e.g., oligomycin B, DCCD (dicyclohexylcarbodiimide), and venturicidin. In some embodiments, an inhibitor of mitochondrial respiration is an uncoupling agent (i.e., an agent that uncouples oxidation from phosphorylation so that ATP synthesis does not occur). Examples of uncoupling agents include ionophores that disrupt electron transfer by short-circuiting the proton gradient across mitochondrial membranes. Uncoupling agents include, e.g., dinitrophenol, valinomycin, nigericin, and FCCP (carbonylcyanide p-trifluoromethoxyphenylhydrazone). In certain embodiments, the inventive compositions include a compound of the invention and an inhibitor of mitochondrial respiration, and optionally an excipient. In certain embodiments, the inventive pharmaceutical compositions include a compound of the invention and an inhibitor of mitochondrial respiration, and optionally a pharmaceutically acceptable excipient, wherein the combination of the compound of the invention and the inhibitor of mitochondrial respiration is provided in a therapeutically effective amount for treating a fungal infection or protozoal infection.

The inventive compounds or compositions may synergistically augment the fungal- and/or protozoan-inhibitory activity of the additional pharmaceutical agent(s). Therefore, the combination of the inventive compound and the additional pharmaceutical agent(s) may be useful in inhibiting the activity of a fungal and/or protozoan enzyme that is resistant to the additional pharmaceutical agent(s) in the absence the inventive compounds. The combination of the inventive compound and the additional pharmaceutical agent(s) may also be useful in treating and/or preventing a fungal and/or protozoan infection caused by a fungus and/or protozoon resistant to the additional pharmaceutical agent(s) in the absence of the inventive compound. The combination of the inventive compound and the additional pharmaceutical agent(s) may further be useful in killing a fungus and/or protozoon or inhibiting the growth of a fungus and/or protozoon resistant to the additional pharmaceutical agent(s) in the absence of the inventive compound. In some embodiments, resistance is innate resistance. In some embodiments, resistance is acquired resistance. Resistance may be acquired as a result of a mutation. In some embodiments, a mutation is in a gene that encodes a target of an antifungal and/or antiprotozoan agent or a gene in the same biosynthetic pathway. In some embodiments, a mutation is in a gene that encodes a transcription factor that results in overexpression of a target of an antifungal and/or antiprotozoan agent or a gene in the same biosynthetic pathway.

In certain embodiments a compound of the invention or composition comprising such compound may be used to inhibit fungal and/or protozoan growth on or in an inanimate object or in an environment such as the interior of a building that may contain one or more fungal and/or protozoan cells or spores.

In some embodiments, the methods of the invention comprise detecting a fungus or protozoan. In some embodiments, the methods of the invention comprise diagnosing a subject as having a fungal infection or a protozoal infection. Methods for detecting fungi and protozoa, and methods for diagnosis of fungal or protozoal infections, are known in the art. In some embodiments, the methods of the invention comprise obtaining a sample and testing the sample for presence of a fungus, fungal product, protozoan, or protozoal product. In some embodiments, the methods of the invention comprise obtaining a biological sample from a subject and testing the sample for presence of a fungus, fungal product, protozoan, or protozoal product. In some embodiments, the methods of the invention comprise obtaining a biological sample from a subject and testing the sample for presence of an antibody to a fungus, protozoan, fungal antigen, or protozoal antigen. In some embodiments, a sample comprises soil, plant material, and/or dust.

Another aspect of the invention relates to methods of screening a library of compounds to identify one or more compounds that are useful in the methods of the invention. In certain embodiments, the one or more compounds identified are useful for treating and/or preventing a fungal and/or protozoan infection in a subject. In certain embodiments, the one or more compounds identified are useful for inhibiting the activity of a fungal and/or protozoan enzyme in a subject or biological sample. In certain embodiments, the one or more compounds identified are useful for killing a fungus or inhibiting the growth of a fungus. In certain embodiments, the one or more compounds identified are useful for killing a protozoon or inhibiting the growth of a protozoon. In certain embodiments, the library of compounds is a library of compounds described herein. In certain embodiments, the methods of screening a library include providing at least two different compounds described herein, or pharmaceutically acceptable salts, solvates, hydrates, polymorphs, co-crystals, tautomers, stereoisomers, isotopically labeled derivatives, or prodrugs thereof; and performing at least one assay using the different compounds described herein, to identify one or more compounds that potentiates the effect of an antifungal agent, reverses the resistance of a fungus to a particular antifungal agent, and/or that kills a fungus or inhibits the growth of a fungus. In certain embodiments, the methods of screening a library include providing at least two different compounds described herein, or pharmaceutically acceptable salts, solvates, hydrates, polymorphs, co-crystals, tautomers, stereoisomers, isotopically labeled derivatives, or prodrugs thereof; and performing at least one assay using the different compounds described herein, to identify one or more compounds that potentiates the effect of an antiprotozoan agent, reverses the resistance of a protozoon to a particular antiprotozoan agent, and/or that kills a protozoon or inhibits the growth of a protozoon.

The different compounds described herein may be generated by synthetic methods such as combinatorial chemistry (see, e.g., Ecker et al., *Bio/Technology*, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a library of compounds involve at least one assay. In certain embodiments, the assay is performed to detect one or more characteristics associated with the treatment of a fungal or protozoan infection. The assay may be an immunoassay, such as a sandwich-type assay, competitive binding assay, one-step direct test, two-step test, or blot assay. The step of performing at least one assay may be performed robotically or manually.

In yet another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in the treatment and/or prevention of a fungal or protozoan infection in a subject.

Another aspect of the present invention relates to the compounds described herein, and pharmaceutically acceptable salts, solvates, hydrates, polymorphs, co-crystals, tautomers, stereoisomers, isotopically labeled derivatives, prodrugs, and compositions thereof, for use in inhibiting the activity of a fungal or protozoan enzyme in a subject or biological sample.

In still another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in killing a fungus or inhibiting the growth of a fungus.

In yet another aspect, the present invention provides the compounds described herein, and pharmaceutically acceptable salts, solvates, hydrates, polymorphs, co-crystals, tautomers, stereoisomers, isotopically labeled derivatives, prodrugs, and compositions thereof, for use in killing a protozoon or inhibiting the growth of a protozoon.

In certain embodiments, the provided compounds, or compositions thereof, are useful as a pesticide. In certain embodiments, the provided compounds, or compositions thereof, are useful as a disinfectant.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Screening of the Compounds

In order to identify non-fungitoxic chemosensitizers ("probes" or "probe compounds") of *C. albicans*, compounds from the NIH's Molecular Libraries Small Molecule Repository (MLSMR) (mli.nih.gov/mli/secondary-menu/mlscn/ml-small-molecule-repository/) were evaluated in the screening cascade summarized in FIG. 3. The *C. albicans* strains used in the primary screen and secondary assay 1 (CaCi-2 and CaCi-8, respectively) are both clinical isolates that partially respond to fluconazole treatment (Redding et al., *Clin. Infect. Dis.* 1994, 18, 240-242). The minimum inhibitory concentration (MIC) of fluconazole against CaCi-2 and CaCi-8 was determined to be 2 µg/mL and 8 µg/mL, respectively. In the primary assay, CaCi-2 cells are exposed to 8 µg/mL fluconazole; this induces a basal level of 60-80% growth inhibition with additional suppression of the trailing growth associated with this particular strain (Redding et al., *Clin. Infect. Dis.* 1994, 18, 240-242).

Desired attributes of a probe compound include:
Compounds that inhibit yeast growth in the presence, but not in the absence of 8 µg/ml fluconazole;
Compounds that show at least 10-fold selectivity between the primary *Candida* test strain and mammalian cells;
Compounds that show activity toward resistant clinical isolates at an $IC_{50}$<50 µM;
$IC_{50}$<1 µM in primary or resistant screen cell line.

Figure 3A:
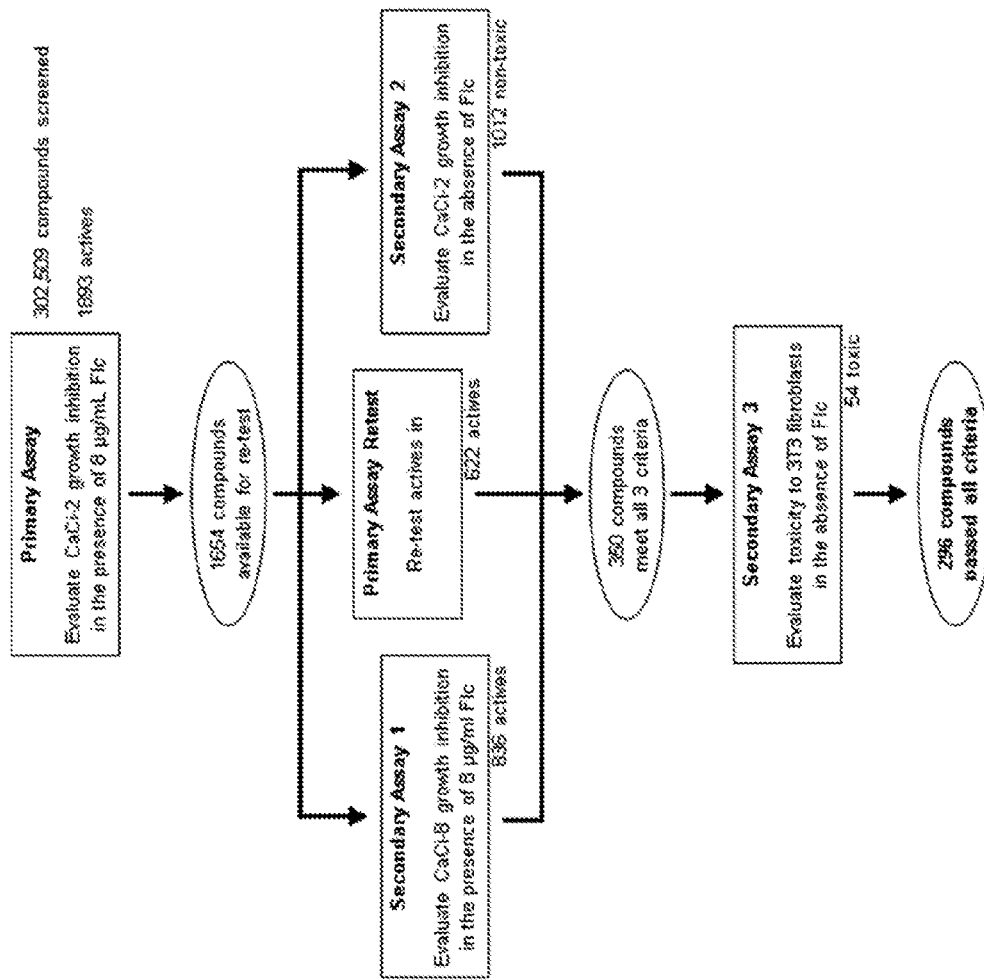
FIGS. 3A-B depicts the assay strategy for triaging hit compounds. Individual assay cut-offs are given in italics.
Figure 3B:
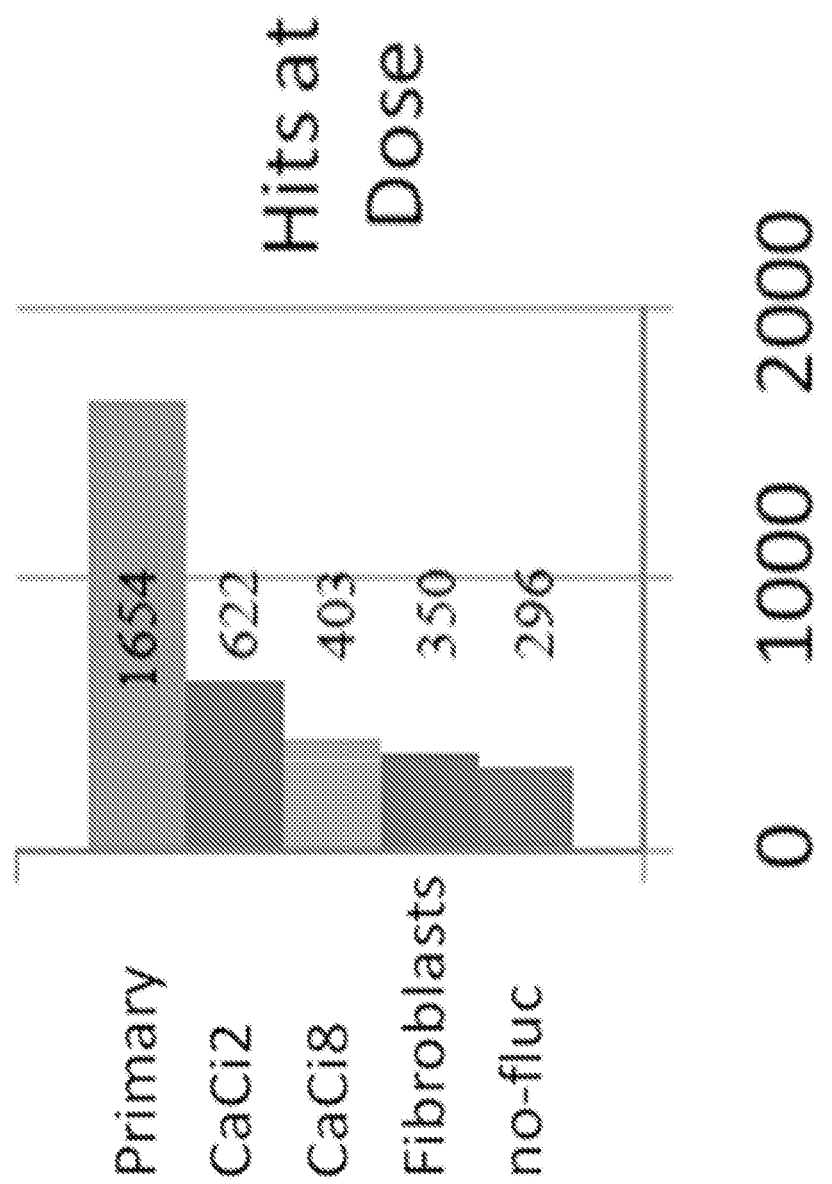

A total of 302,509 compounds from the MLSMR were tested at 7.5 µM for their ability to inhibit completely the growth of CaCi-2 cells that are concurrently treated with 8 µg/mL fluconazole (FIG. 3A). With a minimum requirement of 75% inhibition, 1,893 actives were recorded, corresponding to an overall hit rate of 0.6%. Of the active compounds, 1654 were available for re-testing in a dose-response format. This subset was re-subjected to the primary assay and was also tested concurrently in two secondary assays. Secondary assay 1 measured chemosensitization of the more resistant CaCi-8 strain. Secondary assay 2 eliminated anything with inherently antifungal activity. These three assays cooperatively removed almost 80% of the original hits, leaving 350 candidates. A final assay (secondary assay 3) was incorporated to discard any compound displaying toxicity to mammalian fibroblasts. The fibroblast toxicity assay removed another 54 compounds to leave a total of 296 hits. This screening campaign is also illustrated in FIG. 3B.

Two ancillary secondary assays were run to bin the remaining 296 compounds into three classes: Hsp90 inhibitors, calcineurin inhibitors, or other. The Hsp90 test used a *Saccharomyces cerevisiae* strain engineered to express beta-galactosidase driven by glucocorticoid response element. The glucocorticoid hormone receptor depends heavily on Hsp90 for function. From the 296 hits, 29 were selected for re-validation from dry powders obtained from commercial vendors or re-synthesis. Once their identity and purity was ascertained by LCMS and $^1$H NMR analysis, these 29 candidates were tested once more in the entire assay tree outlined previously in FIG. 3A. Of the 296 compounds, 17 compounds were active as defined by a 10 µM upper threshold of inhibition. The second binning assay for calcineurin inhibition was evaluated in a yeast carrying a construct encoding calcineurin-dependent response elements (CDRE) driving expression of beta-galactosidase.

Reporter activity with or without the prior addition of test compounds was measured following challenge with the stressor CaCl$_2$. Of the 296 compounds of interest, two compounds were active as defined by a 10 μM upper threshold of inhibition. The remaining 277 compounds were binned as "Other." Thirty compounds were chosen for initial dry powder confirmation studies from the 296 identified above by first clustering into small groups of related analogs, and then picking representative analogs from each of those families. After re-testing these dry powders in the test cascade, three compounds were chosen as potential probe candidates, and a first round of 31 analogs (plus three probe candidates) were obtained and assayed. Using the results from these assays as guidance, a second round of analogs (plus the probe candidate) was prepared for SAR analysis.

Example 2. Synthesis of the Compounds

Two different routes were adopted to access the various functionalized indazoles for the evaluation of the structure-activity relationships (SAR) of the compounds of the invention (Scheme 1). Suzuki-Miyaura reaction was selected for the preparation of analogs bearing substituents around the central indazole core. This approach also permitted rapid replacement of the phenyl ring at C3 with functionalized phenyl rings and alternative heterocycles. Preliminary attempts to couple substituted 3-iodoindazoles 4 directly failed to produce isolable amounts of desired product. Subsequently, the indazoles were protected as their tert-butyl carbamates (5) prior to undergoing palladium-mediated Suzuki reactions with various boronic acid partners. Under the reaction conditions, the carbamate protecting group was also cleaved to afford the desired 3-arylindazoles, albeit as the unprotected systems 6. Alkylation with methyl bromoacetate with potassium carbonate in hot acetone completed the synthesis of compounds 7.

In order to prepare 3-alkyl indazoles, 2-fluorobenzaldehyde was first treated with alkylmagnesium bromides, and the resulting benzyl alcohols were immediately oxidized with Dess-Martin reagent. Alkyl phenyl ketones 9 and hydrazine hydrate were then reacted under microwave conditions to assemble the indazole ring (10). The ester side chain of 11 was installed using the same conditions described above for the alkylation of 3-arylindazoles.

Synthesis of substituted 3-aryl indazoles

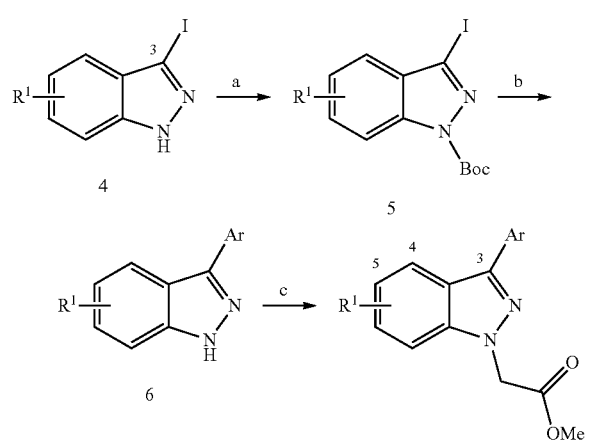

Synthesis of 3-alkyl indazoles

Scheme 1. Exemplary synthesis of substituted methyl 1-indazolyl acetates.

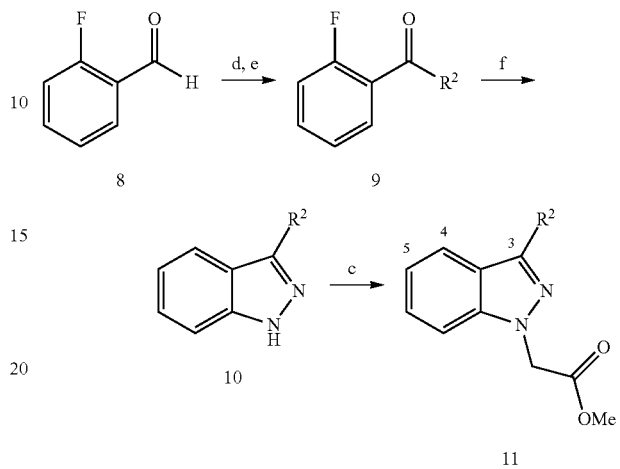

Reagents and conditions: a) Et$_3$N, Boc$_2$O, DMAP, tetrahydrofuran; b) ArB(OH)$_2$, Pd(PPh$_3$)$_4$, aqueous Na$_2$CO$_3$, 1,4-dioxane, 120° C.; c) methyl bromoacetate, K$_2$CO$_3$, acetone, 60° C.; d) alkylmagnesium bromide, Et$_2$O, 0° C.; e) Dess-Martin periodinane, Ch$_2$Cl$_2$; f) hydrazine hydrate, 175° C..

Functionalized indazoles for the evaluation of the SAR of the compounds of the invention may also be synthesized through other methods, such as ones illustrated in Schemes 2 and 3. Shown in Scheme 2 is an exemplary synthesis of substituted indazoles including a 1-heteroarylmethyl substituent.

Scheme 2. Exemplary synthesis of substituted 1-heteroarylmethyl indazoles.

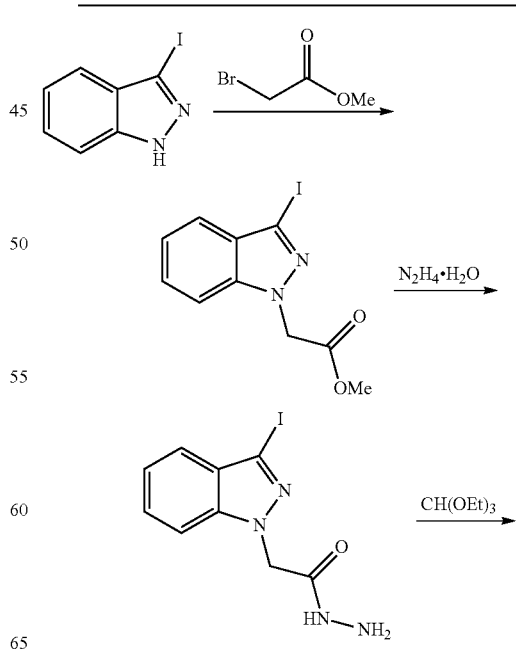

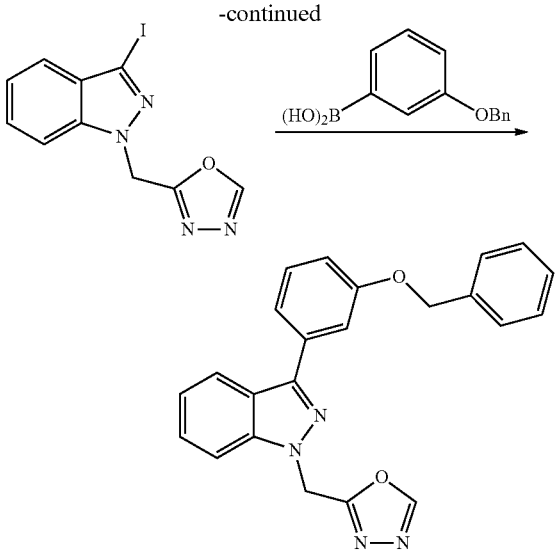

Shown in Scheme 3 is another exemplary synthesis of 1-substituted indazoles that involves a Suzuki-Miyaura coupling to install a substituted or unsubstituted aryl or substituted or unsubstituted heteroaryl at the 3-position of the indazolyl moiety (Kinzel et al., *J. Am. Chem. Soc.* 2010, 132, 14073-14075).

trometer as indicated. Proton and carbon chemical shifts are reported in ppm (δ) relative to tetramethylsilane ($^1$H δ 0.00) or residual chloroform in CDCl$_3$ solvent ($^1$H δ 7.24, $^{13}$C δ 77.0). NMR data are reported as follows: chemical shifts, multiplicity (obs.=obscured, br=broad, s=singlet, d=doublet, t=triplet, m=multiplet); coupling constant(s) in Hz; integration.

Unless otherwise indicated, NMR data were collected at 25° C. Flash chromatography was performed using 40-60 μm Silica Gel (60 Å mesh) on a Teledyne Isco Combiflash R$_f$ system. Tandem Liquid Chromatography/Mass Spectrometry (LC/MS) was performed on a Waters 2795 separations module and 3100 mass detector. Analytical thin layer chromatography (TLC) was performed on EM Reagent 0.25 mm silica gel 60-F plates. Visualization was accomplished with UV light and aqueous potassium permanganate (KMnO$_4$) stain followed by heating. Microwave reactions were performed with a Biotage Initiator 2.5 Microwave Synthesizer. High-resolution mass spectra were obtained at the MIT Mass Spectrometry Facility with a Bruker Daltonics APEXIV 4.7 Tesla Fourier Transform Ion Cyclotron Resonance mass spectrometer. Compound purity and identity were determined by UPLC-MS (Waters, Milford, Mass.). Purity was measured by UV absorbance at 210 nm. Identity was determined on an SQ mass spectrometer by positive electrospray ionization. Mobile Phase A consisted of either 0.1% ammonium hydroxide or 0.1% trifluoroacetic acid in water, while mobile Phase B consisted of the same additives in acetonitrile. The gradient ran from 5% to 95% mobile Phase B over 0.8 minutes at 0.45 ml/min. An Acquity

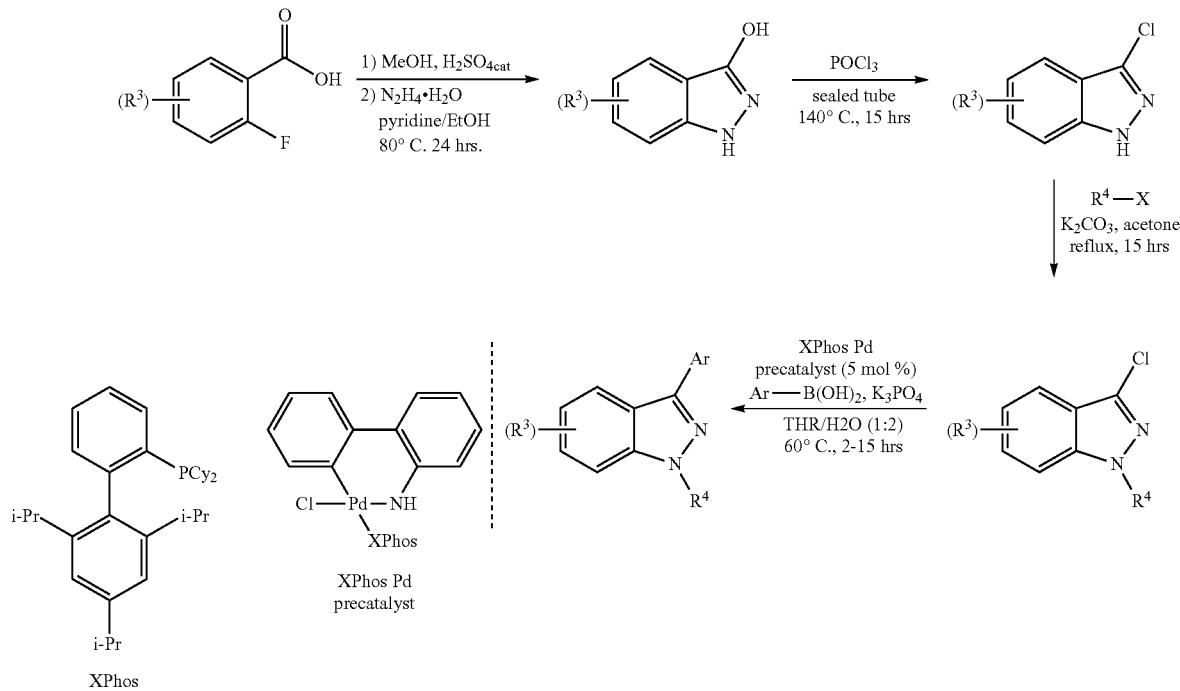

The term "Ar" in Scheme 3 refers to substituted or unsubstituted aryl or substituted or unsubstituted heteroaryl.

General Methods

All reagents and solvents were purchased from commercial vendors and used as received. NMR spectra were recorded on a Bruker 300 MHz or Varian 500 MHz spectrometer BEH C$_{18}$, 1.7 μm, 1.0×50 mm column was used with column temperature maintained at 65° C. Compounds were dissolved in DMSO at a nominal concentration of 1 mg/ml, and 0.25 μl of this solution was injected.

Example 2.1. Preparation of tert-butyl 3-iodo-1H-indazole-1-carboxylate

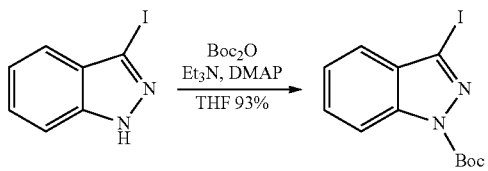 [SMILES: Ic1n[nH]c2ccccc12 ; "THF 93%" ; CC(C)(C)OC(=O)n1nc(I)c2ccccc21]

3-Iodo-1H-indazole (5.00 g, 19.5 mmol) was placed in a round-bottom flask and dissolved in tetrahydrofuran (100 ml). 4-Dimethylaminopyridine (0.24 g, 1.9 mmol, 0.1 equiv) was then added, followed by di-tert-butyl dicarbonate (5.4 ml, 24 mmol, 1.2 equiv). Triethylamine (5.4 ml, 39 mmol, 2.0 equiv) was slowly added to the clear brown solution by syringe. The resulting solution was stirred at room temperature and monitored by TLC until complete. The reaction required approximately 2 hours. Once complete, the reaction was diluted with water (75 ml) and ethyl acetate (50 ml). After separating the layers, the aqueous phase was extracted with additional ethyl acetate (3×50 ml). The combined organic layers were washed with brine (100 ml), shaken over magnesium sulfate, filtered, and concentrated under reduced pressure to give a dark red oil (8.40 g). The crude material was purified by column chromatography over silica gel (hexanes/ethyl acetate: 100/0 to 90/10) to give the title compound as an orange solid (6.20 g, 93%). $^1$H NMR (300 MHz, CDCl$_3$): δ 8.12 (d, J=8.4 Hz, 1H), 7.59 (t, J=7.7 Hz, 1H), 7.50 (d, J=7.9 Hz, 1H), 7.37 (t, J=7.5 Hz, 1H), 1.73 (s, 9H); $^{13}$C NMR (75 MHz, CDCl$_3$): δ 148.3, 139.6, 130.2, 129.9, 124.1, 121.9, 114.5, 102.8, 85.4, 28.1; ESI-MS (M-C$_4$H$_9$): m/z 288.

Example 2.2. Preparation of (3-(3-methoxyphenyl)-1H-indazole

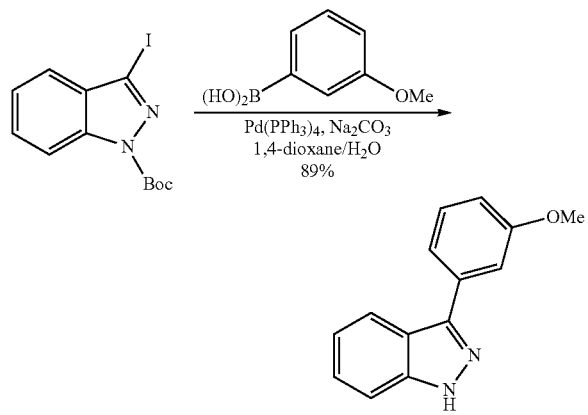

tert-Butyl 3-iodo-1H-indazole-1-carboxylate (100 mg, 0.29 mmol) was placed in a suitably sized microwave vial and dissolved in 1,4-dioxane (11.5 ml). 3-Methoxyphenyl boronic acid (88 mg, 0.58 mmol, 2.0 equiv) and tetrakis(triphenylphosphine) palladium (20 mg, 0.017 mmol, 0.06 equiv) were added, and the resulting turbid orange mixture was sparged thoroughly with nitrogen. An aqueous solution of sodium carbonate (2.0 M, 0.65 ml, 1.31 mmol, 4.5 equiv) was then added. The biphasic mixture was microwaved for 1 hour at a reaction temperature of 120° C. The reaction was diluted with ethyl acetate (2 ml), and then filtered through a Celite® pad with additional ethyl acetate. The filtrate was concentrated under reduced pressure to give an oil. The crude material was purified by column chromatography over silica gel (hexanes/ethyl acetate: 100/0 to 30/70) to give the title compound as an orange oil (58.0 mg, 89%). $^1$H NMR (300 MHz, CDCl$_3$): δ 12.71 (s, 1H), 8.00 (d, J=8.2, 1H), 7.69-7.53 (m, 2H), 7.44 (t, J=7.9, 1H), 7.31-7.22 (m, 1H), 7.17 (dd, J=4.9, 13.0, 1H), 7.05 (d, J=8.3, 1H), 7.03-6.98 (m, 1H), 3.79 (s, 3H); $^{13}$C NMR (75 MHz, CDCl$_3$): δ 160.1, 145.4, 141.7, 134.8, 130.0, 126.7, 121.3, 120.9, 120.8, 120.3, 114.2, 113.0, 110.5, 55.3; ESI-MS: m/z 224.

Example 2.3. Preparation of methyl 2-(3-(3-methoxyphenyl)-1H-indazol-1-yl)acetate

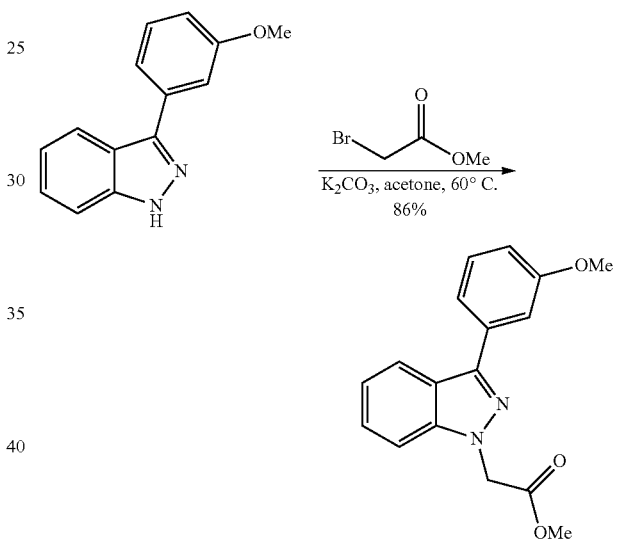

3-(3-methoxyphenyl)-1H-indazole (163 mg, 0.73 mmol) was dissolved in acetone (2.2 ml) and treated with methyl bromoacetate (0.21 ml, 2.2 mmol, 3.0 equiv). Finely powdered potassium carbonate (721 mg, 2.2 mmol, 3.0 equiv) was added in a single portion, and the resulting suspension was stirred overnight at 60° C. Upon completion, the reaction was cooled to room temperature and filtered through Celite® with acetone. The clear orange filtrate was concentrated under reduced pressure to give the crude product as a dark orange oil. This material was purified by column chromatography over silica gel (hexanes/ethyl acetate: 100/0 to 70/30) to give the title compound as an orange oil (186 mg, 86%). $^1$H NMR (300 MHz, CDCl3): δ 8.03 (d, J=8.2, 1H), 7.53 (obs. t, J=6.0, 1H), 7.50 (obs. s, 1H), 7.42 bs. q, J=7.7, 2H), 7.36 (obs. t, J=8.1, 1H), 7.24 (t, J=7.5, 1H), 6.96 (dd, J=2.5, 8.2, 1H), 5.22 (s, 2H), 3.89 (s, 3H), 3.75 (s, 3H). $^{13}$C NMR (75 MHz, CDCl$_3$): δ 168.4, 160.0, 145.1, 141.7, 134.6, 129.8, 126.9, 122.2, 121.6, 121.5, 120.1, 114.2, 112.8, 109.0, 55.4, 52.6, 50.3. HRMS (ESI): calculated mass for C$_{17}$H$_{16}$N$_2$O$_3$ [M+H] 297.1234. found 297.1246.

Example 2.4. Preparation of methyl 2-(3-iodo-1H-indazol-1-yl)acetate

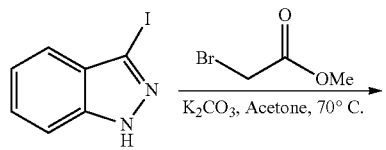

3-Iodo-1H-indazole (1.50 g, 6.15 mmol) was placed in a foil wrapped, 100 mL round-bottom flask equipped with a magnetic stir bar and dissolved in acetone (20.5 mL) to give a dark red-brown solution. Methyl bromoacetate (1.2 mL, 12.3 mmol, 2.0 equiv) was added, followed by anhydrous potassium carbonate (6.09 g, 18.4 mmol, 3.0 equiv). The flask was sealed under nitrogen, heated to 70° C., and stirred in the dark for 19 hours. The reaction was cooled to room temperature and filtered through Celite® with acetone. The clear red-brown filtrate was concentrated under reduced pressure to give a red oil. This crude material was purified by column chromatography over silica gel (hexanes/ethyl acetate: 100/0 to 80/20) to give the title compound as an orange oil (1.36 g, 70% yield). $^1$H NMR (300 MHz, CDCl$_3$) δ 7.52 (d, J=8.1 Hz, 1H), 7.48 (t, J=8.3 Hz, 1H), 7.31 (d, J=8.5 Hz, 1H), 7.26 (obs. t, J=8.3 Hz, 1H), 5.18 (s, 2H), 3.75 (s, 3H). LRMS (ESI$^+$) (M+H): 317.11 (found), 316.98 (expected).

Example 2.5. Preparation of 2-(3-Iodo-M-indazol-1-yl)acetohydrazide

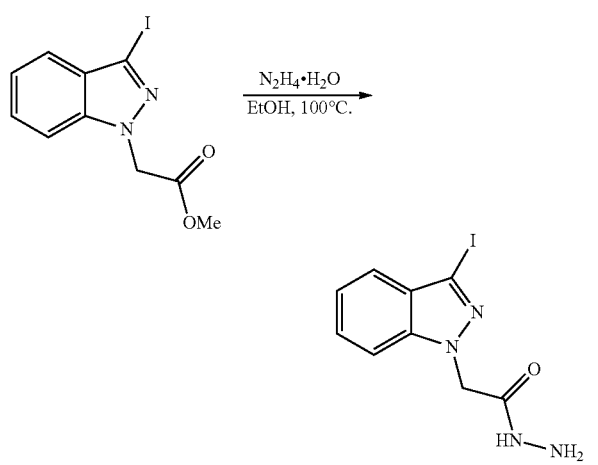

A 20 mL microwave vial equipped with a magnetic stir bar was charged with methyl 2-(3-iodo-1H-indazol-1-yl)acetate (1.23 g, 3.89 mmol) and anhydrous ethanol (7.8 mL) to give a clear, orange solution. Hydrazine hydrate (0.95 ml, 19.4 mmol, 5.0 equiv) was added, and the resulting mixture was heated to 100° C. by microwave for 30 minutes. After cooling to room temperature, the reaction was concentrated under reduced pressure to give the title compound as an ivory-white solid that was used immediately without further purification. LRMS (ESI$^+$) (M+H): 317.15 (found), 316.99 (expected).

Example 2.6. Preparation of 2-((3-Iodo-M-indazol-1-yl)methyl)-1,3,4-oxadiazole

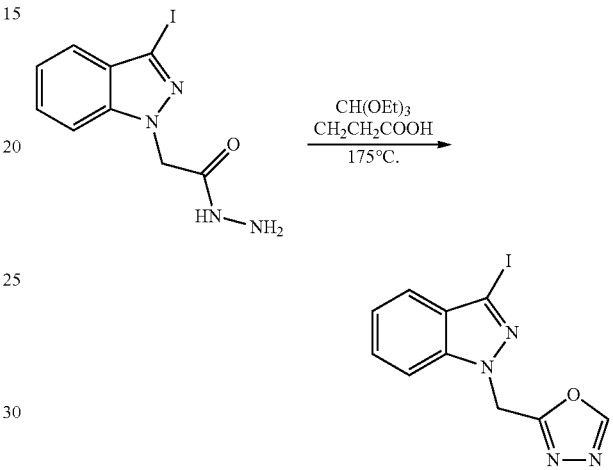

Crude 2-(3-iodo-1H-indazol-1-yl)acetohydrazide (1.23 g, 3.89 mmol) placed in a 50 mL sealed tube and suspended in triethyl orthoformate (15.6 mL). Propionic acid (0.3 mL, 3.9 mmol, 1.0 equiv) was added. The reaction was sealed under nitrogen, heated to 175° C., and stirred for overnight for 15 hours. After cooling to room temperature, the reaction mixture was purified immediately by column chromatography over silica gel (hexanes/ethyl acetate: 100/0 to 25/75) to give the title compound as a yellow-orange solid (0.57 g, 45% yield). A considerable amount of ethyl 2-(3-iodo-1H-indazol-1-yl)acetate (0.36 g, 28% yield) was also isolated as a clear, colorless oil. $^1$H NMR (300 MHz, CDCl$_3$) δ 8.36 (s, 1H), 7.54-7.48 (m, 3H), 7.28 (obs. dt, J=11.4, 3.8 Hz, 1H), 5.87 (s, 2H). LRMS (ESI$^+$) (M+H): 327.09 (found), 326.97 (expected).

Example 2.7. Preparation of 2-((3-(3-(Benzyloxy)phenyl)-1H-indazol-1-yl)methyl)-1,3,4-oxadiazole

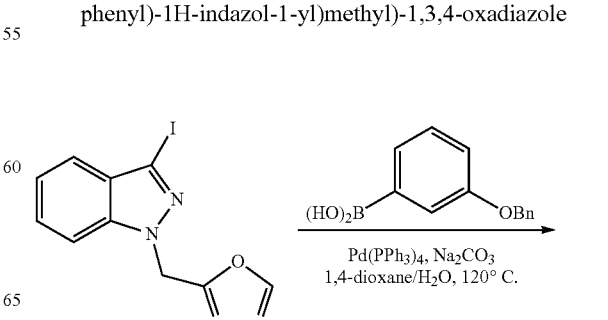

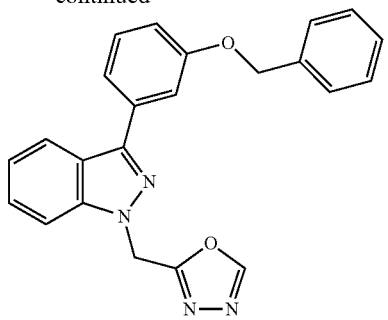

2 mL microwave tube equipped with a magnetic stir bar was charged with 2-((3-iodo-1H-indazol-1-yl)methyl)-1,3,4-oxadiazole (40 mg, 0.12 mmol), 3-(benzyloxy)phenylboronic acid (56 mg, 0.25 mmol, 2.0 equiv) and tetrakis(triphenylphosphine)palladium (7.1 mg, 6.1 μmol, 0.05 equiv). The tube was flushed thoroughly with nitrogen before adding 1,4-dioxane (0.8 mL) and 2.0 M aqueous solution of sodium carbonate (0.3 mL, 0.6 mmol, 5.0 equiv). This mixture heated to 120° C. by microwave for 90 minutes. After cooling to room temperature, the reaction was diluted with ethyl acetate (2 mL) and water (2 mL). The layers were separated and the aqueous phase was extracted with ethyl acetate (3×2 mL). All of the organic layers were combined, then shaken over magnesium sulfate, filtered, and concentrated under reduced pressure to give a brown oil. The crude material was purified by column chromatography over silica gel (hexanes/ethyl acetate: 100/0 to 60/40) to give the title compound as a clear oil (35 mg, 76% yield). $^1$H NMR (500 MHz, CDCl$_3$): δ 8.33 (s, 1H), 7.92 (d, J=8.1 Hz, 1H), 7.58-7.51 (m, 3H), 7.47 (t, J=7.3 Hz, 3H), 7.41 (dd, J=15.5, 7.8 Hz, 3H), 7.34 (t, J=7.1 Hz, 1H), 7.24 (obs. t, J=7.6 Hz, 1H), 7.04 (dd, J=8.2, 2.3 Hz, 1H), 5.89 (s, 2H), 5.16 (s, 2H). $^{13}$C NMR (125 MHz, CDCl$_3$): δ 161.8, 159.1, 153.7, 145.5, 141.2, 136.9, 134.1, 129.9, 128.6, 128.0, 127.5, 127.3, 122.3, 121.9, 121.7, 120.3, 115.1, 113.8, 109.1, 70.0, 43.4. LRMS (ESI$^+$) (M+H): 383.31 (found), 383.15 (expected).

Example 3. Chemical Characterization of the Compounds

Figure 5:
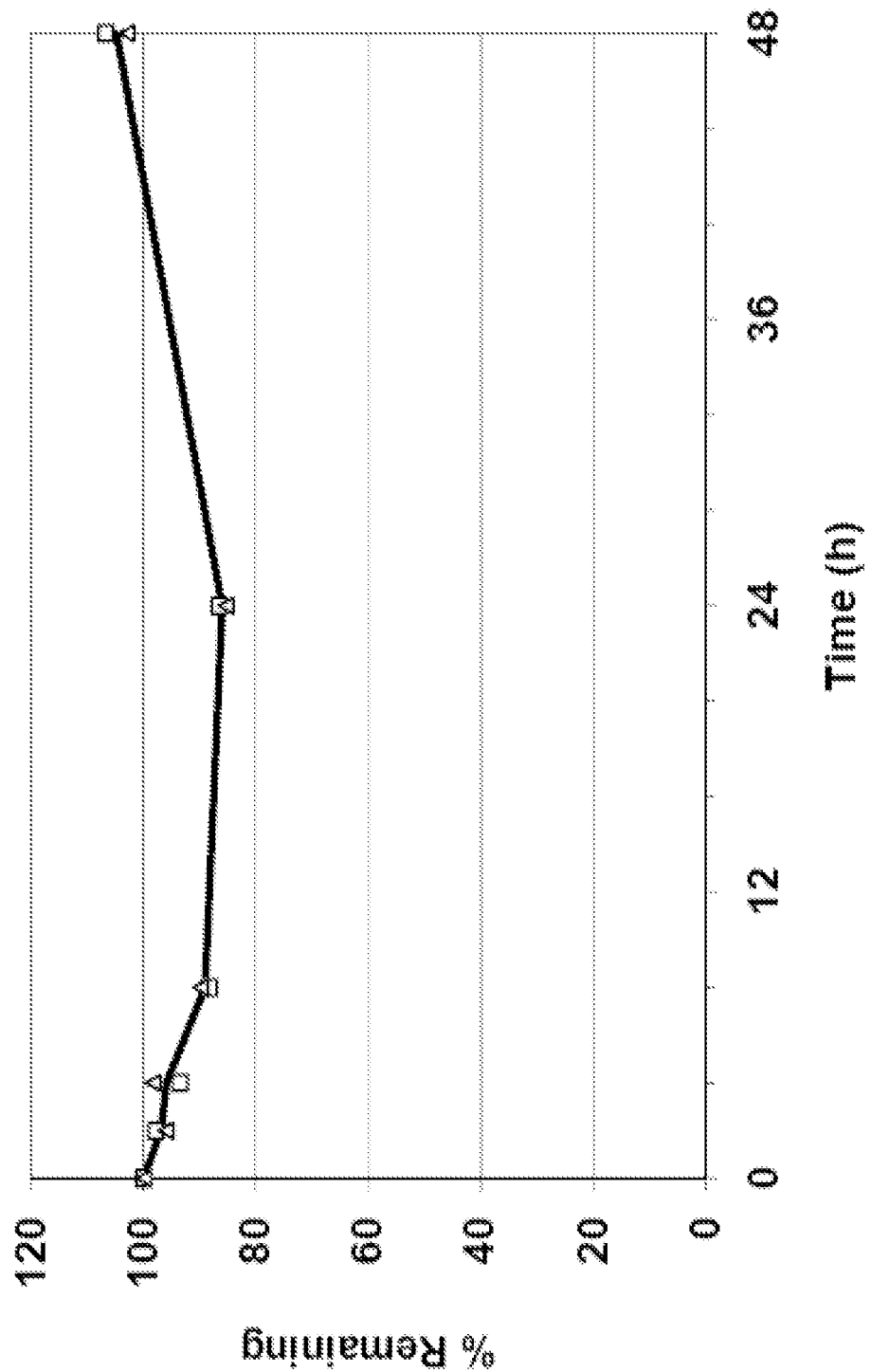
FIG. 5 illustrates the stability of probe compound I-4 in PBS at 23° C.
Figure 6C:
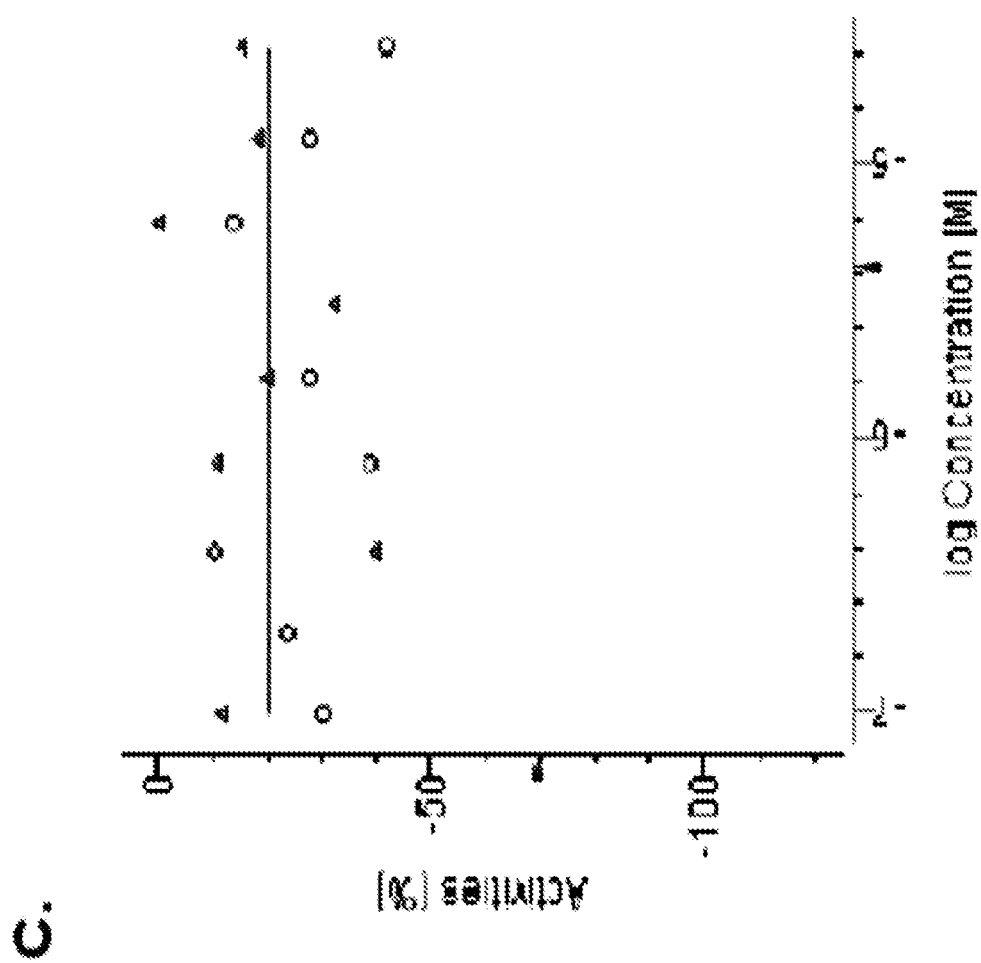

A probe compound I-4 was analyzed by ultra performance liquid chromatography (UPLC), $^1$H and $^{13}$C NMR spectroscopy, and high-resolution mass spectrometry. The data obtained from NMR and mass spectroscopy were consistent with the structure of compound I-4, and UPLC indicated an isolated purity of greater than 93%. The solubility of compound I-4 was experimentally determined to be less than 1 μM in PBS solution. Compound I-4 is exceptionally stable in PBS solution (>99% remaining after a 48-hour incubation). The data from the PBS stability assay is provided in FIG. 5. Plasma protein binding (PPB) was determined to be 95% bound in human plasma. Compound I-4 is unstable in human plasma with approximately 3% remaining after a 5-hour incubation period. Presumably, hydrolysis of the methyl ester is the primary contributor to instability. The solubility, PPB, and plasma stability results are summarized in Example 4 (entry 8, Table 6). Compound I-4 and four additional analogs were submitted to the SMR collection: MLS003271341 (Compound I-4; CID49835877/ML212), MLS003271340 (Compound I-51; CID49835836), MLS003271342 (Compound I-57; CID49835857), MLS003271343 (Compound I-16; CID3243873), and MLS003271344 (Compound I-48; CID49835842).

Example 4. Biological Assays of the Compounds

Materials and Methods

Figure 4:
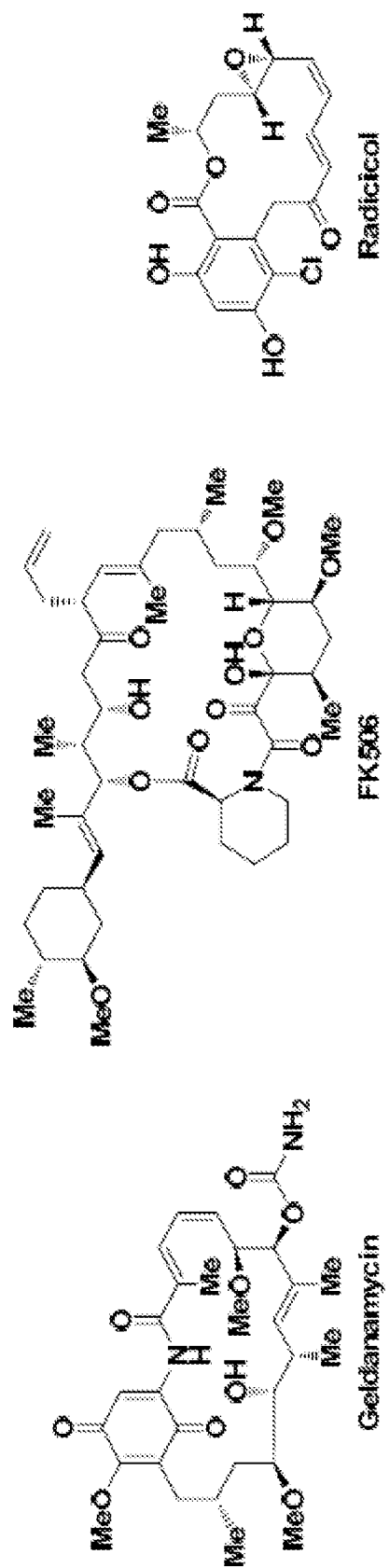
FIG. 4 shows the chemical structures of positive controls for biological assays of the compounds of the invention.

Compounds that can successfully inhibit *Candida* CaCi-2 cell growth in the presence of sublethal doses of fluconazole as measured in a fluorescence reporter assay were further tested against a highlyresistant *Candida* CaCi-8 strain in the presence of fluconazole. Those that inhibited growth in the resistant strain were also tested for toxicity against *Candida* in the absence of fluconazole and for toxicity against mammalian cells using a fluorescence reporter assay. The positive control for screening in the *Candida* and mammalian cell assays was the Hsp90 inhibitor geldanamycin (acting in concert with fluconazole; FIG. 4). Compounds that passed these four hurdles were binned through use of a *Saccharomyces* assay to determine whether the mechanism of action might be through the Hsp90 pathway, the calcineurin pathway, or an uncategorized mechanism.

A summary listing of completed assays and corresponding PubChem AID numbers is provided in Table 1.

TABLE 1

Summary of Completed Assays and AIDs

| PubChem AID | Type | Target | Concentration Range (μM) | Samples Tested |
|---|---|---|---|---|
| 1979 | Primary | CaCi-2 growth inhibition | 9.5 | 302509 |
| 2467 | Confirmatory | CaCi-2 growth inhibition | 3.8-0.03 | 1654 |
| 488836 | Confirmatory (powder) | CaCi-2 growth inhibition | 26-0.1 | 30 |
| 493089 | Analogs | CaCi-2 growth inhibition | 12-0.05 | 54 |
| 493081 | Analogs 2 | CaCi-2 growth inhibition | 12-0.05 | 29 |
| 493080 | Analogs 3 | CaCi-2 growth inhibition | 12-0.05 | 128 |
| 493150 | Analogs 4 | CaCi-2 growth inhibition | 12-0.05 | 33 |
| 2327 | Counterscreen | Fibroblast toxicity | 16-0.12 | 1654 |
| 488809 | Counterscreen (powder) | Fibroblast toxicity | 26-0.1 | 44 |
| 493099 | Counterscreen (analogs) | Fibroblast toxicity | 26-0.1 | 64 |
| 493147 | Counterscreen (analogs 2) | Fibroblast toxicity | 6-0.05 | 108 |
| 2423 | Orthogonal | CaCi-8 growth inhibition | 16-0.12 | 1654 |
| 488807 | Orthogonal (powder) | CaCi-8 growth inhibition | 26-0.1 | 44 |
| 493064 | Orthogonal (analogs) | CaCi-8 growth inhibition | 26-0.1 | 64 |
| 493069 | Orthogonal (analogs 2) | CaCi-8 growth inhibition | 26-0.1 | 27 |
| 493082 | Orthogonal (analogs 3) | CaCi-8 growth inhibition | 26-0.1 | 29 |
| 493149 | Orthogonal (analogs 3) | CaCi-8 growth inhibition | 26-0.1 | 33 |
| 2387 | Secondary | CaCi-2 growth inhibition | 16-0.12 | 350 |
| 488802 | Secondary (powder) | CaCi-2 growth inhibition | 26-0.1 | 30 |
| 493070 | Secondary (analogs2) | CaCi-2 growth inhibition | 26-0.1 | 27 |
| 493157 | Secondary (analogs3) | CaCi-2 growth inhibition | 26-0.1 | 29 |

TABLE 1-continued

Summary of Completed Assays and AIDs

| PubChem AID | Type | Target | Concentration Range (µM) | Samples Tested |
|---|---|---|---|---|
| 493134 | Secondary (analogs3) | CaCi-2 growth inhibition | 26-0.1 | 33 |
| 2400 | Secondary | Hsp90 | 16-0.12 | 350 |
| 504390 | Secondary (analogs) | Hsp90 | 26-0.1 | 18 |
| 2388 | Secondary | Calcineunn | 16-0.12 | 350 |
| 2007 | Summary | NA | NA | NA |

Example 4.1. Primary CaCi-2 (AID No. 1979), CaCi-2 dose-response retest (AID Nos. 2467, 488836)

Materials and Reagents.

Clear, flat-bottom, black, 384-well plates were obtained from Corning (Catalog No. 3712BC, Lot No. 35808016). Geldanamycin (Catalog No. G-1047) was obtained from AG Scientific and prepared in 15 mM stock solution in DMSO (control). Fluconazole was obtained from Sequoia Research Products, Ltd. and prepared in a 2 mg/ml stock solution in phosphate buffered saline (PBS). Alamar Blue was obtained from Biosource International (Catalog No. DAL1100; Lot No. 151016SA). PBS (Catalog No. 21-040-CV) without calcium and magnesium was obtained from Cellgro. Penicillin/Streptomycin (Pen/Strep) was obtained from Gibco and prepared 100× in PBS.

Synthetic Defined Growth Medium.

RPMI 1640 medium, (powder without sodium bicarbonate; Catalog No. 31800-089, Lot No. 648072) was obtained from Invitrogen. Uridine 8 mg/ml in water (Catalog No. U3750; Lot No. 028KO760), glucose 40% (w/v) in water (Catalog No. G-5400), and MOPS Buffer (Catalog No. M-1254; Lot No. 098K0033) were obtained from Sigma. RPMI medium (1×) was prepared by dissolving 10.4 g powdered medium in 800 ml water. A buffer of 34.52 g MOPS was added. While stirring, pH was adjusted to 7.0 with 10 N NaOH. Next, 10 ml uridine solution and 50 ml glucose solution were added. The final volume was adjusted to 1000 ml, and filter sterilized.

Fungal Inoculum.

The following yeast strains were used in this study: C. albicans CaCi-2. Fungal inoculum was prepared as follows: 500 µl of strain was inoculated from cryopreserved stock into a 250-ml shaker flask containing 30 ml growth medium and shaken overnight at 30° C. The optical density (OD 600) of 1 ml fungal culture in a cuvette was read using a standard optical density reader (Eppendorf BioPhotometer Plus), with growth medium as a background blank. The desired volume of fungal inoculums was diluted to desired volume of fungal inoculums according to the following formula: (1/OD measured)×(Desired Final Volume of Inoculum)×0.3=Volume of fungal culture (µl) to add to desired volume of growth medium. When added to media in wells, this yields a calculated starting OD of the fungal inoculum of 0.00015.

Procedures.

Fluconazole stock solution was added to the fungal inoculum to achieve 8 µg/ml. Pen/Strep was added to the media to a 1% concentration (v/v). A Thermo Combi nL was used to dispense 20 µl/well of assay media into all wells. Geldanamycin was dispensed in positive control wells using Thermo Combi nL for a final concentration of 3 µM. Then, 100 nl of test compound was pinned from compound plates into assay plates using a CyBi-Well pin tool. A further 20 µl/well of culture was dispensed into the assay media in all wells. The plates were incubated in a humidified (90% humidity) Liconic incubator at 37° C. without agitation for 48 hours. Alamar Blue was diluted 1:40 in Ca/Mg-free PBS. To all plates, 5 µl/well of the diluted Alamar Blue was added to the plates to a final dilution factor of 1:200. The plates were incubated for an additional 2 hours. Then, Relative Fluorescence Intensity (RFU) of each well was read on standard plate reader as a measure of relative fungal growth. Envision (Perkin Elmer) plate reader set-up: Ex 544 nm, Em 590 nm, Bandwidth 12 nm, Top read.

Example 4.2. Counterscreen Mammalian Cell Toxicity Assay (AID Nos. 2327, 488809, 493099, 493147)

Materials and Reagents.

Clear, flat-bottom, black, 384-well plates were obtained from Corning (Catalog No. 3712BC; Lot No. 35808016). Geldanamycin (Catalog No. G-1047) was obtained from AG Scientific and prepared in 15 mM stock solution in DMSO (control). Fluconazole was obtained from Sequoia Research Products, Ltd. and prepared in a 2 mg/ml stock solution in PBS. Alamar Blue was obtained from Biosource International (Catalog No. DAL1100; Lot No. 151016SA). Phosphate buffered saline (PBS; Catalog No. 21-040-CV) without calcium and magnesium was obtained from Cellgro.

Assay Medium.

Optimem medium (Catalog No. 31985-070, Lot No. 548536) and Pen/Strep 1% (v/v) solution (Catalog No. 15140-122, Lot No. 529891) were obtained from Invitrogen. Fetal bovine serum 2.5% (v/v) (FBS; Catalog No. 30071.03; Lot No. ARF26748) was obtained from Hyclone.

Cell Inoculum.

The following test strain was used in this study: NIH-3T3 mammalian fibroblasts (ATCC; CRL No. 1658). Cell inoculum was prepared as follows: Cells were plated at 6,000 cells/well in 20 µl assay medium and cultured overnight at 37° C. under 5% $CO_2$ in 384-well, clear bottom, black, tissue culture-treated, barcoded assay plates.

Procedures:

After overnight culture, compounds were pinned into wells at 100 nl/well using the CyBio CyBi-Well pinning instrument. After compounds were pinned, an additional 20 µl of assay medium supplemented with fluconazole (16 µg/ml) was added to each well. The final nominal concentration in the well was 50 µM of test compound and 8 µg/ml fluconazole. The plates were returned to the tissue culture incubator, and the culture continued for an additional 48 hours at 37° C. under 5% $CO_2$. At the completion of this incubation, Alamar Blue Reagent diluted 1:40 in Ca/Mg-free PBS was added to each well (10 µl/well) to achieve a final dilution of 1:200. The plates were incubated for an additional 2 to 3 hours at 37° C. under 5% $CO_2$, and then RFU as a measure of relative viable cell number was determined on an EnVision plate reading fluorometer. EnVision (Perkin Elmer) plate reader set-up: Ex 544 nm, Em 590 nm, Bandwidth 12 nm, Top read.

Example 4.3. Secondary Single-Agent (No-Fluconazole) Activity Assay (AID 488802)

Materials and Reagents.

Clear, flat-bottom, black, 384-well plates were obtained from Corning. Geldanamycin was obtained from AG Scientific G-1047 and prepared in 15 mM stock solution in DMSO. Pen/Strep was obtained from Gibco and prepared 100× in PBS. Fluconazole was obtained from Sigma and prepared in 2 mg/ml stock solution in PBS. Alamar Blue was obtained from Biosource International (Catalog No.

DAL1100). Phosphate buffered solution (PBS) without calcium and magnesium was obtained from Cellgro.

Synthetic Defined Growth Medium.

For the synthetic defined growth medium, RPMI 1640 medium (powder without sodium bicarbonate; was obtained from Invitrogen. Uridine (8 mg/ml in water), glucose 40% (w/v) in water, and MOPS buffer was obtained from Sigma. RPMI medium (1×) was prepared by dissolving 10.4 g powdered medium in 800 ml water. A buffer of 34.52 g MOPS was added. While stirring, pH was adjusted to 7.0 with 10N NaOH. Next, 10 ml uridine solution and 50 ml glucose solution were added. The final volume was adjusted to 1000 ml, and the solution was filter sterilized.

Fungal Inoculum.

The following yeast strain was used in this study: *C. albicans* CaCi-2 (Redding et al., *Clin. Infect. Dis.* 1994, 18(2): 240-42). Fungal inoculum was prepared as follows: 500 µl of yeast was inoculated from cryopreserved stock into a 250-ml shaker flask containing 30 ml growth medium and shaken overnight (16 hours) at 30° C. The culture was spun down, and the broth was poured off and washed with RPMI medium. The culture was spun down again, and the broth was poured off and resuspended in RPMI medium. The OD 600 of 1 ml of fungal culture in a cuvette was read using a standard optical density reader with growth medium as a background blank. The desired volume of fungal inoculum was diluted to starting OD of the fungal inoculum of 0.00015 A600.

Procedures:

Pen/Strep was added to the media to a final 1% concentration. A Combi NL (Thermo) was used to dispense 20 µl/well of assay media into all wells. Geldanamycin (1.5 mM) and fluconazole (0.2 mg/ml) were mixed for the positive control. Then, 80 nl of positive control solution was dispensed into the positive control wells using Thermo Combi nL for a final concentration of 3 µM geldanamycin and 8 µg/ml fluconazole. Then, 100 nl of test compound were pinned from the compound plates into assay plates using a CyBi-Well pin tool. A further 20 µl/well of RPMI synthetic defined medium culture was dispensed into 384-well, black plates. Fungal suspension (20 µl/well) was dispensed into all wells. The plates were incubated in a humidified (90% humidity) Liconic incubator at 37° C. without agitation for 48 hours. Alamar Blue Reagent was diluted 1:40 in Ca/Mg-free PBS. To all plates, 6.4 µl/well of the diluted Alamar Blue was added to the plates to a final dilution factor of 1:200. The plates were incubated for 2 hours at room temperature. Next, RFU of wells was read on a standard plate reader as a measure of relative fungal growth. Envision (Perkin Elmer) plate reader set-up: Ex 544 nm, Em 590 nm, Bandwidth 12 nm, Top read.

Example 4.4. Hsp90 Binning

Materials and Reagents.

Corning white, 384-well plates were obtained from Corning (Catalog No. 8867BC; Lot No. 22609019). Tropix Gal-Screen was obtained from Applied Biosystems (Catalog No. T2359; Lot No. 0903044).

Assay Media.

(1) SD-ADE Yeast Nitrogen Base without Ammonium Sulfate, Minus Adenine.

SD Growth Media was obtained from MP Biomedical (Catalog No. 4027-012; Lot No. 119458). Complete Supplement minus adenine was obtained from Sunrise Science (Catalog No. 1029-100; Lot No. 070409). Deoxycorticosterone (DOC) steroid was obtained from Sigma. To prepare the assay media, 100 ml (20% (w/v) dextrose and 780 mg Complete Supplement) was added to 100 ml SD Growth Media. Water was added to a final volume of 1 liter, and the solution was filter sterilized.

(2) DOC Media.

For DOC media, 1 ml DOC was added to 100 ml SD-ADE media.

Cell Inoculum.

The following test strain was used in this study: *Saccharomyces cerevisiae* W303 reporter strain (ATCC 201238). Cell Inoculum was prepared as follows: Reporter *Saccharomyces* strain was inoculated from cryopreserved stock into a 250 ml shaker flask containing 20 ml SD-ADE media. The reporter strain W303 was incubated overnight (16 hours) at 37° C. and 150 rpm.

Procedures:

The OD 600 of 1 ml of culture in a cuvette was read using a standard optical density reader with growth medium as a background blank. Cells were diluted to OD=0.04 in SD-ADE media. To each 384-well, white plate, 20 µl of diluted culture was dispensed using a Combi NL (Thermo). Then, 100 nl of test compound were pinned into plates with a CyBi-Well pin tool. Next, 5 µM radicicol was added as positive control in the control wells, dispensing with a Combi NL (Thermo). With Combi, 20 µl of 20 µM DOC (steroid) in SD-ADE media was dispensed in pinned plates. The plates were incubated at 30° C. for 75 minutes with agitation. Using Combi, 40 µl Gal-Screen reagent was dispensed. The plates were incubated at 30° C. for 25 minutes. Luminescence of the wells was read on a standard plate reader as a measure of relative fungal growth. Envision (Perkin Elmer) plate reader set-up: Top read; Luminescence filter (560 nm) at 0.1 seconds.

Example 4.5. In Vitro Inhibition of Complex III (Cytochrome bc1, Ubiquinol-Cytochrome c Reductase)

Mitochondrial membranes were prepared from yeast (Meisinger et al., *Methods Mol. Biol.* 2006, 313:33-9.) or HEK293 cells (Johnson et al., *LoS ONE* 2009, 4(9): e7100) as previously described. Compounds described herein were added to plates in a buffer containing 50 mM Tris-Cl pH 7.3, 10 mM $NaN_3$, 0.01% BSA, and 0.05% Tween-20. Mitochondrial membranes (2-5 µg protein) were added to the buffer, followed by oxidized equine cytochrome C (Sigma) at a final concentration of 50 µM. Reactions were initiated by adding decylubiquinol to a final concentration of 50 µM. Reaction progress was monitored by reading the increase in signal at 550 nm on a Tecan Evo plate reader. $IC_{50}$'s were interpolated as the concentration that resulted in 50% decreased activity after 3 minutes of incubation. All measurements were performed in triplicate. Exemplary results are shown in FIGS. 6, 10, 11, and 14.

Example 4.6. In Vivo Inhibition of Fungal Respiration

*Saccharomyces cerevisiae* (*S. cerevisiae*) strain W303-1a was grown overnight in Yeast-Peptone-Dextrose media, washed, and diluted into Yeast Nitrogen Base media with 2.5% glycerol containing compounds at a range of dilutions. $IC_{50}$ was determined as the concentration that reduced growth relative to no-drug control by 50% after 48 hours, as determined by measuring OD600 of agitated plates. Exemplary results are shown in FIGS. 8 to 10 and 12, wherein each of compounds I-52, I-3, and I-7 shows inhibitory activity against *S. cerevisiae*.

Example 4.7. *Candida Albicans* Susceptibility Test

*Candida albicans* susceptibility testing was performed as described in Clinical Laboratory Standards Institute document M27-A3 (CLSI M27-A3) (CLSI. *Reference Method for Broth Dilution Antifungal Susceptibility Testing of Yeasts; Approved Standard—Third Edition*. CLSI, 940 West Valley Road, Suite 1400, Wayne, Pa. 19087-1898 USA, 2003).

Example 4.8. *Aspergillus Terreus* Susceptibility Test

Figure 8:
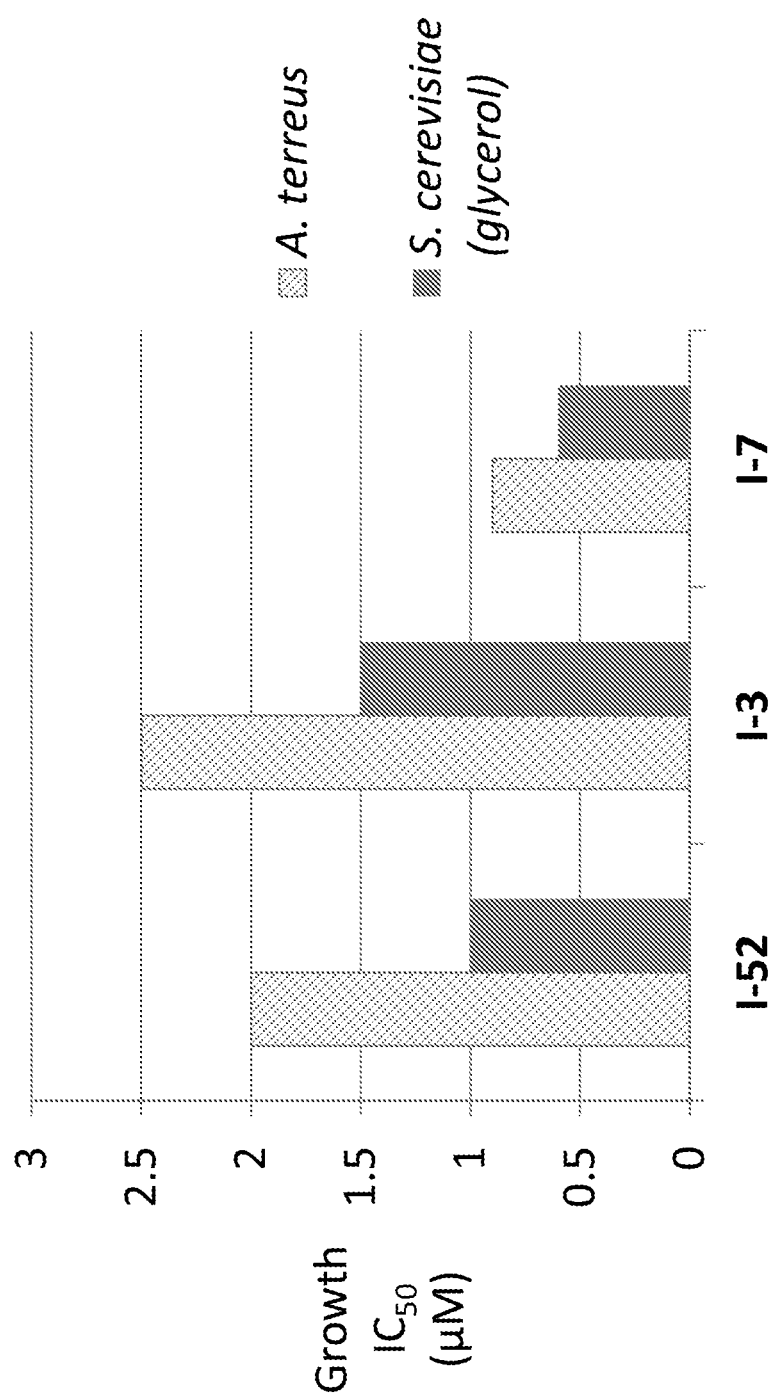
FIG. 8 shows the inhibitory activities of compounds I-52, I-3, and I-7 against A. terreus and S. cerevisiae.

*Aspergillus terreus* (*A. terreus*) susceptibility testing was performed as described in Clinical Laboratory Standards Institute document M38-A2 (CLSI M38-A2) (CLSI. *Reference Method for Broth Dilution Antifungal Susceptibility Testing of Filamentous Fungi; Approved Standard—Second Edition*. CLSI, 940 West Valley Road, Suite 1400, Wayne, Pa. 19087-1898 USA, 2003). Exemplary results are shown in FIG. 8, wherein each of compounds I-52, I-3, and I-7 shows inhibitory activity against *A. terreus*.

Example 4.9. Combination of Compound I-97 and Fluconazole Prevented De Novo Emergence of the Resistance of *Candida Albicans* Against Fluconazole

Figure 13:
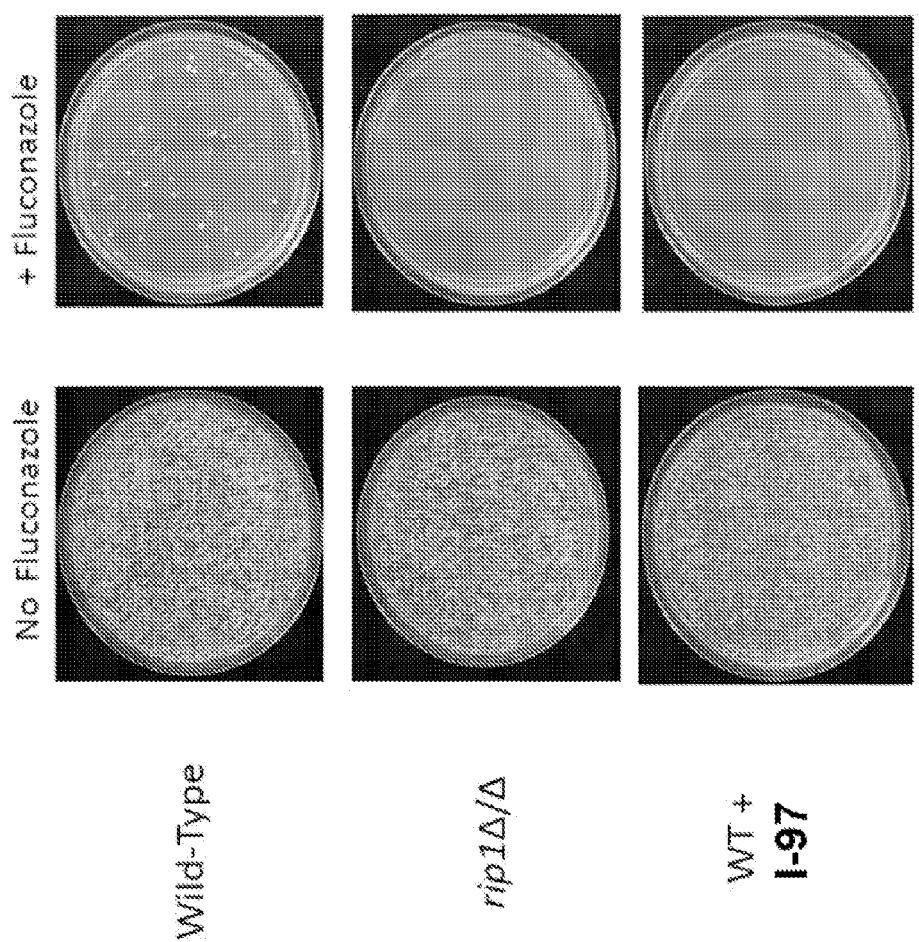
FIG. 13 shows that genetic or pharmacological abrogation of the activity of a combination of compound I-97 and fluconazole prevented the emergence of the resistance to fluconazole in Candida albicans.

*Candida albicans* wild-type (WT, FIG. 13, top panel) or rip1/rip1 homozygous deletion mutant (rip1 Δ/Δ, FIG. 13, middle panel) were plated on media in the presence of fluconazole (32 mg/L) or in the absence of fluconazole. The emergence of colonies was monitored after six days. Wild-type strain plated on media containing compound I-97 (0.5 μM) in the presence of fluconazole (32 mg/L) or absence of fluconazole is shown in FIG. 13, bottom panel. The results show that abrogation of the activity of a combination of compound I-97 and fluconazole prevented the emergence of the resistance to fluconazole in *Candida albicans* (FIG. 13).

Example 4.10. Combination of Compound I-97 and Fluconazole was Cytotoxic Against Fluconazole-Sensitive *Candida Albicans* Strain SC5314 and Fluconazole-Resistant *Candida Albicans* Strain CaCi-2

Figure 15A:
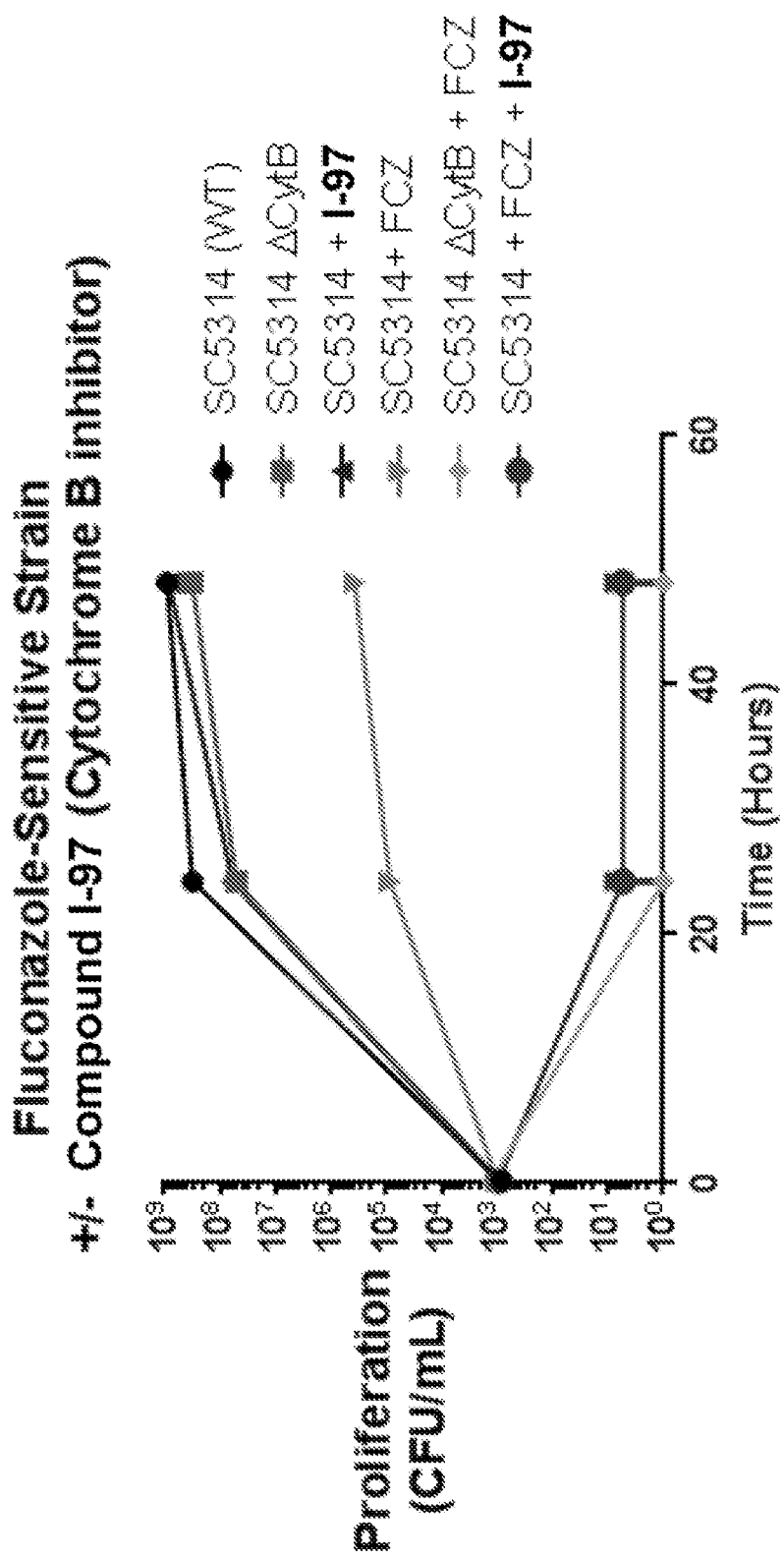
FIG. 15 shows that a combination of compound I-97 and fluconazole (FCZ) was cytotoxic to fluconazole-sensitive Candida albicans strain SC5314 (FIG. 15A) and fluconazole-resistant Candida albicans strain CaCi-2 (FIG. 15B). WT: wild type. ΔCytB: mutated at cytochrome B.

*Candida albicans* strain SC5314 is sensitive to fluconazole. However, fluconazole is cytostatic, but not cytotoxic, to SC5314 (FIG. 15A). *Candida albicans* strain CaCi-2 is resistant to fluconazole, and fluconazole is not cytostatic or cytotoxic to CaCi-2 (FIG. 15B).

Figure 15B:
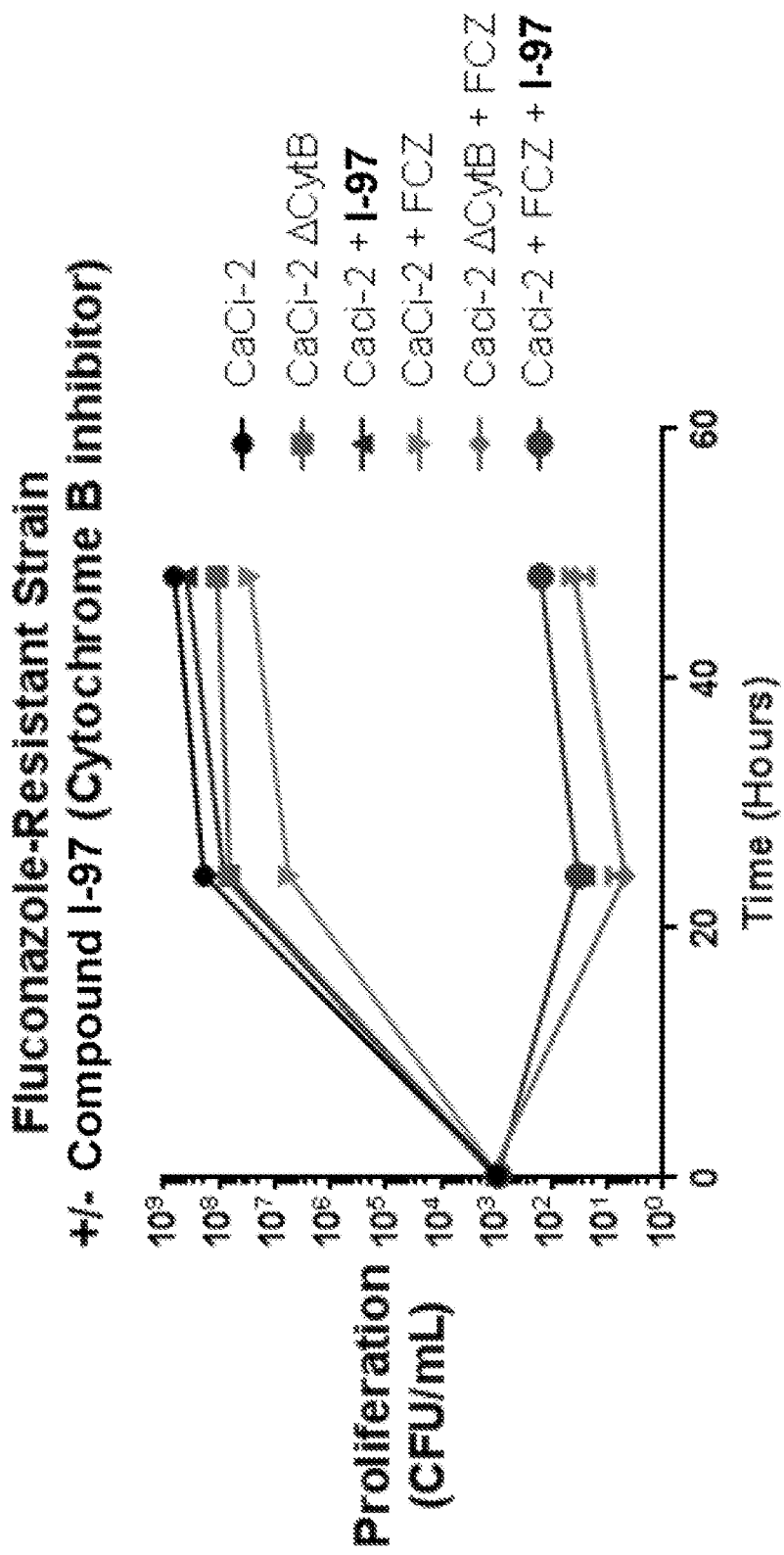

Surprisingly, the combination of fluconazole and compound I-97 was found cytotoxic to both SC5314 (FIG. 15A) and CaCi-2 (FIG. 15B). This result indicates that a combination of an azole (e.g., fluconazole) and an inhibitor of mitochondrial respiratory function (e.g., an inventive compound, such as compound I-97) may be cytotoxic to a fungus or protozoon, compared to the azole, which is cytostatic to the fungus or protozoon or has no significant effect on the proliferation of the fungus or protozoon.

Figure 16:
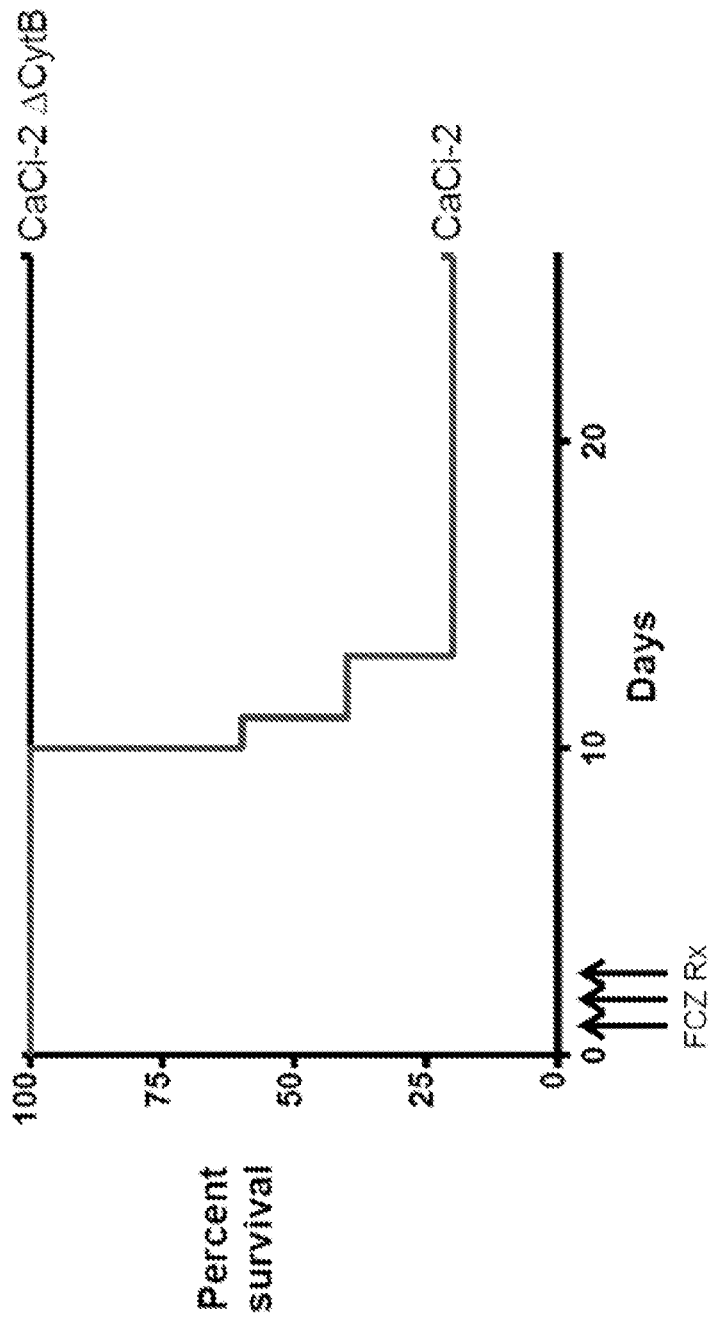
FIG. 16 shows that mitochondrial respiration of a fungus or protozoon may be required for the resistance of the fungus or protozoon against fluconazole in vivo. FCZ Rx: one or more doses of fluconazole. CaCi-2: Candida albicans strain CaCi-2 wild type. CaCi-2 ΔCytB: *Candida albicans* strain CaCi-2 mutated at cytochrome B.

Since mitochondrial respiratory function of a fungus or protozoon may be required for the resistance of the fungus or protozoon to fluconazole in vivo (FIG. 16, where mice were infected with 106 CFU of CaCi-2 (wild type) or CaCi-2 ΔCytB (mutated at cytochrome B), dosed Q.D. with fluconazole at 24 mg/kg for 3 days, and monitored for the mice's survival, body weight, and kidney CFU for 3 weeks), a combination of an azole (e.g., fluconazole) and an inhibitor of mitochondrial respiratory function (e.g., an inventive compound, such as compound I-97) may be cytotoxic to a fungus or protozoon resistant to the azole or the inhibitor of mitochondrial respiratory function.

Results

Dose Response Curves for Probe.

The results of does responses of the compounds described herein are shown in FIGS. 6A-E.

Scaffold/Moiety Chemical Liabilities.

A search of PubChem for the probe compound I-4 (CID 49835877/ML212) indicated that the probe compound I-4 has not been previously evaluated in any other assay. A structure-based search in SciFinder and Reaxys did not identify any publications or patents in which the probe appeared. The only potential chemical liability associated with the probe may be the hydrolysis of the methyl ester.

Structure-Activity-Relationship (SAR) Results.

In order to investigate the activity of this structural class, a collection of structurally related analogs were synthesized and evaluated for their ability to reverse fluconazole resistance in the *C. albicans* test strains.

The biological assay data and physical properties of these analogs are presented in Tables 2-10 and 10A.

The initial hit from the screening campaign described in Example 1 was methyl 3-phenyl-1H-indazole acetate (compound I-16). The side chain methyl ester of the hit was predicted to be susceptible to hydrolysis, and a series of ester and amide analogs were prepared accordingly to evaluate the necessity of this latent acid (Table 3). From this screen, it was determined that replacement of the methyl ester with metabolically more stable derivatives was detrimental to cellular activity. The inactivity of these compounds suggested that perhaps the free acid was the active species. Unfortunately, when this predicted metabolite was prepared and tested, it also proved ineffective at countering fluconazole resistance in *C. albicans* (entry 12, Table 2).

Following the investigation of alternative esters and amides, efforts were undertaken to substantially modify the entire side chain. To this end, 10 analogs were prepared and tested (Table 3). The absence of the methyl acetate was not tolerated (entry 1, Table 3), and excision of any oxygen atoms from the ester system (entries 2-4, Table 3) was also not tolerated. Extension of the side chain length was similarly ineffective (entries 5 and 6, Table 3). Several compounds incorporating substitutions adjacent to the ester were also prepared (entries 7-9, Table 3). However, only the mono-methyl derivative (entry 7, Table 3) retained any activity in the cellular assay; but, this analog was less potent than the original hit. While the γ-lactone (entry 9, Table 3) was clean by NMR spectroscopy, UPLC indicated hydrolysis to the seco-acid readily occurs; this phenomenon may have contributed to the inactivity of this compound.

Finally, an oxazole conjugate was investigated as a possible ester surrogate. Although this derivative displayed very weak activity against CaCi-8, there was no measurable efficacy towards the less resistant CaCi-2 (entry 10, Table 3).

Table 4 presents several derivatives of the initial hit wherein the indazole core was modified to incorporate additional functional groups. This series of analogs focused predominantly on the 5- and 6-positions of the aromatic system. With regards to the 5-position (i.e. $R_1$), only the methyl or fluoro derivatives displayed low micromolar potency against CaCi-2 (entries 1 and 3, Table 4). Conversely, no activity was recorded for the methoxy or chloro counterparts (entries 2 and 4, Table 4). $R_2$, or the 6-position, appeared more amenable to manipulation as four of five conjugates demonstrated mild inhibitory effects towards CaCi-2 (entries 5-9, Table 4); only the 6-trifluoromethyl variant was inactive (entry 9, Table 4). It is notable that all of the 5- and 6-substituted variants were slightly active against the more resistant CaCi-8 strain ($IC_{50}$ values 5.3 µM to 32.1 µM). SAR of the indazole core suggests the 6-position is an attractive site for future exploration, in particular for further optimization of aqueous solubility.

The last point of diversity explored was the 3-phenyl ring of the parent indazole scaffold. Fifteen analogs were synthesized to probe the SAR of this region, and the results are summarized in Table 5 and Table 6. Table 5 presents several nonaromatic analogs that were prepared to replace the benzene ring. Removal of the phenyl ring adversely affected potency; both the unsubstituted 1H-indazole and 3-methyl compounds were inactive in the primary assay (entries 1 and 3, Table 5). The 3-iodo derivative was likewise an ineffective chemosensitizing agent (entry 2, Table 5). Incidentally, this series of analogs boasted high PBS solubility, but sacrificed all cellular potency. To complement the previous nonaromatic series, a collection of monosubstituted phenyl conjugates was prepared (Table 6). Substitution at the para-position was generally not productive (entries 1-6, Table 6); only the methoxy and fluoro compounds displayed measurable activity in the primary screen (entries 2 and 3, Table 6). This trend stands in stark contrast to modification of the meta site. All three indazoles bearing a meta-substituted phenyl ring were very potent chemosensitizers (entries 7-9, Table 6). Both the 3-(3-tolyl) and 3-(3-anisolyl)-1H-indazoles demonstrated nanomolar potency against CaCi-2 ($IC_{50}$=650 nM and 440 nM, respectively) and low micromolar activity against CaCi-8 ($IC_{50}$=1.3 µM and 1.2 µM, respectively). The 3-fluoro counterpart was marginally less effective ($IC_{50}$=1.4 µM against CaCi-2 and 2.1 µM against CaCi-8). The meta-position was clearly the pivotal site for potency; the two ortho-substituted analogs were considerably less potent than the meta-series although there were small gains in solubility (entries 10-11, Table 6). SAR evaluation of the original scaffold was concluded with a series of compounds encompassing larger structural perturbations (Table 7). For several analogs, the aromatic and acetate side chains were relocated to alternative sites around the indazole system (entries 1-6, Table 7). Not surprisingly, these drastic alterations failed to yield any beneficial increase to cellular potency. Entries 7 and 8 (Table 7) re-affirmed SAR trends previously observed—neither the 5-chloro indazole nor acetamide analogs were efficacious chemosensitizers (Table 4 and Table 2, respectively), and their corresponding hybrids were just as impotent. Various fragmented indazole systems did not exhibit any bioactivity when evaluated (entries 9-11, Table 7). It can be concluded from these SAR studies that the methyl acetate side chain is invaluable to cellular bioactivity. Similarly, replacement of the 3-phenyl ring system with nonaromatic functionalities strongly attenuated potency. However, it was identified that meta-substituted phenyl rings were equipotent to or more potent than the original screening hit. Modification of the para- or ortho-positions was generally counterproductive. The indazole core itself could tolerate functionalization at the 5-position to a limited degree while the adjacent 6-position could accommodate substituents with only a small loss in activity. Most of the compounds evaluated exhibited poor solubility in PBS (<1 µM).

As a result of these synthetic efforts, it was possible to increase the potency of the original hit (compound I-16; CID3243873) from 1.8 µM to 0.44 µM and led to the identification of 3-(3-methoxyphenyl)-1Hindazole as a new probe compound (compound I-4; CID49835877/ML212) (Table 11).

Figure 9:
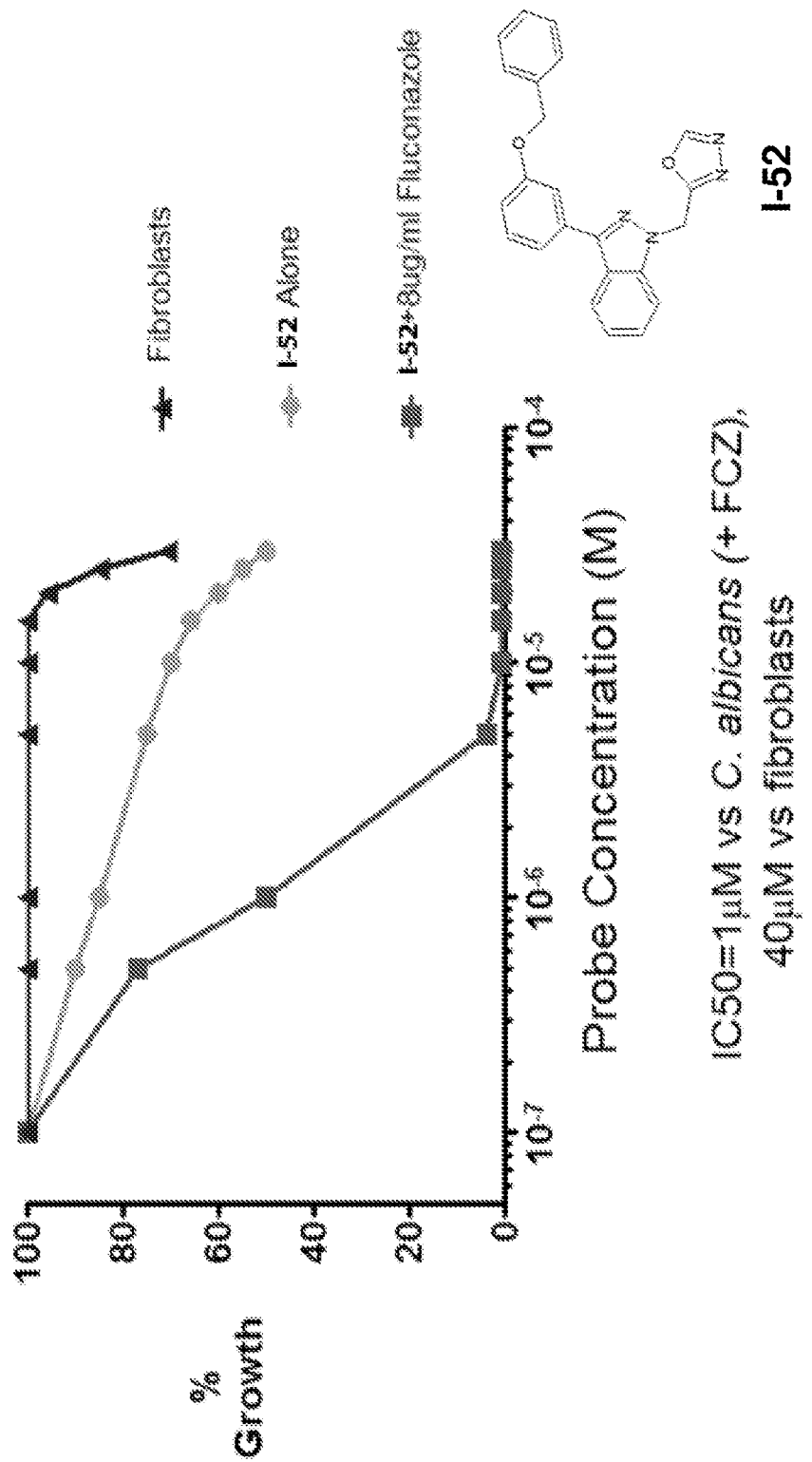
FIG. 9 shows the inhibitory activities of compound I-52 against C. albicans in absence and presence of fluconazole (FCZ).

FIG. 9 shows that compound I-52 is more active in inhibiting *C. albicans* in presence of fluconazole (FCZ) than in absence thereof.

TABLE 2

Evaluation of 12 Synthetic Ester and Amide Analogs

| Entry | SARAnalysis | | | | $R_1$ | Target Potency (µM) Mean±S.E.M | | | | | | Anti-target Potency (µM) Mean ± S.E.M | |
|---|---|---|---|---|---|---|---|---|---|---|---|---|---|
| | | | | | | CaCi-2[a] | | CaCi-2[b] | | CaCi-8[a] | | Fibroblasts[b] | |
| No. | CID | SID | Broad ID | * | $R_1$ | $n^c$ | $IC_{50}$ | $n^c$ | $IC_{50}$ | $n^c$ | $IC_{50}$ | $n^b$ $IC_{50}$ | ** |
| 1 | 3243873 | 99245544 | BRD-K37150847 | S | —OMe | 8 | 1.86 ± 0.99 | 6 | IA | 8 | 2.53 ± 1.13 | 3 IA | ND |

PBS Solubility: 2.5 µM Plasma Protein Binding: 96% Plasma Stability: <1.0% Purity (UPLC): 97%

| 2 | 13330959 | 103910831 | BRD-K17670538 | S | —OEt | 3 | IA | 2 | IA | 3 | IA | 1 IA | ND |

PBS Solubility: <1.0 µM Plasma Protein Binding: 99% Plasma Stability: 20% Purity (UPLC): 99%

TABLE 2-continued

Evaluation of 12 Synthetic Ester and Amide Analogs

Structure: 3-phenyl-1H-indazole with N-CH2-C(=O)-R1 substituent

| Entry No. | CID | SID | Broad ID | * | R1 | CaCi-2[a] n[c] | CaCi-2[a] IC50 | CaCi-2[b] n[c] | CaCi-2[b] IC50 | CaCi-8[a] n[c] | CaCi-8[a] IC50 | Fibroblasts[b] n[b] | Fibroblasts[b] IC50 | ** |
|---|---|---|---|---|---|---|---|---|---|---|---|---|---|---|
| 3 | 49835820 | 103910829 | BRD-K51391281 | S | —Oi-Pr | 3 | IA | 2 | IA | 3 | IA | 1 | IA | ND |

PBS Solubility: <1.0 μM Plasma Protein Binding: 99% Plasma Stability: 53% Purity (UPLC): >99%

| 4 | 49835839 | 103910847 | BRD-K85640513 | S | —Ot-Bu | 3 | IA | 2 | IA | 3 | IA | 1 | IA | ND |

PBS Solubility: <1.0 μM Plasma Protein Binding: >99% Plasma Stability: 85% Purity (UPLC): 100%

| 5 | 49835870 | 103910819 | BRD-K39846706 | S | —O-cyclobutyl | 1 | IA | 2 | IA | 1 | IA | 1 | 0.19 | ND |

PBS Solubility: <1.0 μM Plasma Protein Binding: >99% Plasma Stability: 2.0% Purity (UPLC): 97%

| 6 | 49835857 | 103910827 | BRD-K98546361 | S | —OPh | 3 | IA | 2 | IA | 3 | IA | 1 | IA | ND |

PBS Solubility: <1.0 μM Plasma Protein Binding: ND Plasma Stability: 13% Purity (UPLC): 74%

| 7 | 13330955 | 99245536 | BRD-K79487335 | S | —NHMe | 3 | IA | 4 | IA | 3 | IA | 3 | IA | ND |

PBS Solubility: <18.5 μM Plasma Protein Binding: 93% Plasma Stability: >99% Purity (UPLC): >99%

| 8 | 49835882 | 103910836 | BRD-K11584268 | S | —NMe2 | 3 | IA | 2 | IA | 3 | IA | 1 | IA | ND |

PBS Solubility: 325.5 μM Plasma Protein Binding: 98% Plasma Stability: 98% Purity (UPLC): >99%

| 9 | 20877568 | 99245533 | BRD-K24457958 | P | —NH-CH2CH2-Me | 3 | IA | 4 | IA | 3 | IA | 3 | IA | ND |

PBS Solubility: 5.4 μM Plasma Protein Binding: 97% Plasma Stability: >99% Purity (UPLC): 96%

| 10 | 20877568 | 99245584 | BRD-K38464168 | P | —NH-CH2-(4-Cl-cyclohexyl) | 3 | IA | 4 | IA | 3 | IA | 3 | IA | ND |

PBS Solubility: <1.0 μM Plasma Protein Binding: 95% Plasma Stability: >99% Purity (UPLC): 96%

TABLE 2-continued

Evaluation of 12 Synthetic Ester and Amide Analogs

Structure: 3-phenyl-1H-indazole with N-CH2-C(=O)-R1 substituent

| Entry No. | SAR Analysis CID | SAR Analysis SID | SAR Analysis Broad ID | * | R1 | Target Potency (µM) Mean±S.E.M CaCi-2[a] n[c] | IC50 | CaCi-2[b] n[c] | IC50 | CaCi-8[a] n[c] | IC50 | Anti-target Potency (µM) Mean ± S.E.M Fibroblasts[b] n[b] | IC50 | ** |
|---|---|---|---|---|---|---|---|---|---|---|---|---|---|---|
| 11 | 20877557 | 9924586 | BRD-K19712641 | S | (1,2,3,4-tetrahydroisoquinolin-2-yl) | 3 | IA | 4 | IA | 3 | IA | 3 | IA | ND |

PBS Solubility: <1.0 µM  Plasma Protein Binding: >99%  Plasma Stability: 97%  Purity (UPLC): >99%

| 12 | 5309553 | 99376506 | BRD-K85225856 | S | —OH | 3 | IA | 3 | IA | 3 | IA | 2 | IA | ND |

PBS Solubility: 534.6 µM  Plasma Protein Binding: 97%  Plasma Stability: >99%  Purity (UPLC): 94%

IA = Inactive; ND = Not determined; S = synthesized; P = purchased.
** CaCi-2 to anti-target fold selectivity.
[a] In the presence of fluconazole.
[b] In the absence of fluconazole.
[c] Number of replicates.

TABLE 3

Synthetic Replacements of the Methyl Acetate Side Chain (10 analogs)

Structure: 3-phenyl-1H-indazole with N-R1 substituent

| Entry No. | SAR Analysis CID | SAR Analysis SID | SAR Analysis Broad ID | * | R1 | Target Potency (µM) Mean±S.E.M CaCi-2[a] n[c] | IC50 | CaCi-2[b] n[c] | IC50 | CaCi-8[a] n[c] | IC50 | Anti-target Potency (µM) Mean ± S.E.M Fibroblasts[b] n[c] | IC50 | ** |
|---|---|---|---|---|---|---|---|---|---|---|---|---|---|---|
| 1 | 300385 | 99245532 | BRD-K54502992 | S | —CH2—H | 3 | 3 | 4 | IA | 2 | IA | 2 | IA | ND |

PBS Solubility: 91.0 µM  Plasma Protein Binding: 98%  Plasma Stability: >99%  Purity (UPLC): 98%

| 2 | 49835816 | 103910823 | BRD-K23177474 | S | —CH2—C(=O)—CH2—Me | 1 | IA | 2 | IA | 1 | IA | 1 | IA | ND |

PBS Solubility: <1.0 µM  Plasma Protein Binding: 99%  Plasma Stability: 98%  Purity (UPLC): 98%

TABLE 3-continued

Synthetic Replacements of the Methyl Acetate Side Chain (10 analogs)

Structure

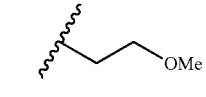

| | SARAnalysis | | | | | Target Potency (μM) Mean±S.E.M | | | | | Anti-target Potency (μM) Mean ± S.E.M Fibroblasts[b] | | |
|---|---|---|---|---|---|---|---|---|---|---|---|---|---|
| | | | | | | CaCi-2[a] | | CaCi-2[b] | | CaCi-8[a] | | | |
| Entry No. | CID | SID | Broad ID | * | $R_1$ | $n^c$ | $IC_{50}$ | $n^c$ | $IC_{50}$ | $n^c$ | $IC_{50}$ | $n^c$ | $IC_{50}$ | ** |
| 3 | 49835825 | 103910830 | BRD-K10798115 | S | 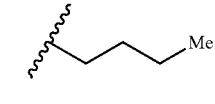 [SMILES: *CCCC] | 3 | IA | 2 | IA | 3 | IA | 1 | IA | ND |

PBS Solubility: <1.0 μM  Plasma Protein Binding: >99%  Plasma Stability: 70%  Purity (UPLC): 99%

| 4 | 49835848 | 103910810 | BRD-K16789019 | S | 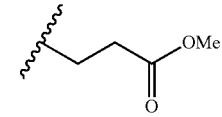 [SMILES: *CCC(=O)OC] | 1 | IA | 2 | IA | 1 | IA | 1 | IA | ND |

PBS Solubility: <1.0 μM  Plasma Protein Binding: >99%  Plasma Stability: 81%  Purity (UPLC): >99%

| 5 | 49835835 | 103910835 | BRD-K48860244 | S | 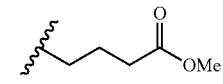 | 3 | IA | 2 | IA | 3 | IA | 1 | IA | ND |

PBS Solubility: <1.0 μM  Plasma Protein Binding: >99%  Plasma Stability: 74%  Purity (UPLC): >99%

| 6 | 49835981 | 103910822 | BRD-K48854225 | S | 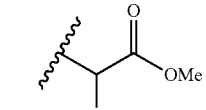 | 1 | IA | 2 | IA | 1 | IA | 1 | IA | ND |

PBS Solubility: <1.0 μM  Plasma Protein Binding: >99%  Plasma Stability: 57%  Purity (UPLC): >99%

| 7 | 49835813 | 103910834 | BRD-M84860065 | S | 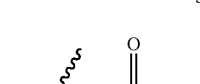 | 2 | 6.56 ± 0.79 | 2 | IA | 2 | 15.8 2.2 | 1 | IA | ND |

PBS Solubility: <1.0 μM  Plasma Protein Binding: >99%  Plasma Stability: 61%  Purity (UPLC): 99%

| 8 | 49835873 | 103910811 | BRD-K04729536 | S | 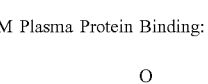 | 1 | IA | 2 | IA | 1 | IA | 1 | IA | ND |

PBS Solubility: <1.0 μM  Plasma Protein Binding: >99%  Plasma Stability: 63%  Purity (UPLC): >99%

| 9 | 49835834 | 103910812 | BRD-A41230630 | S |  | 1 | IA | 2 | IA | 1 | IA | 1 | IA | ND |

PBS Solubility: <1.0 μM  Plasma Protein Binding: ND  Plasma Stability: <1.0%  Purity (UPLC): 65%

TABLE 3-continued

Synthetic Replacements of the Methyl Acetate Side Chain (10 analogs)

Structure: 3-phenyl-1H-indazole with N-R₁ substituent

| Entry No. | SARAnalysis CID | SID | Broad ID | * | R₁ | Target Potency (μM) Mean±S.E.M ||||||| Anti-target Potency (μM) Mean ± S.E.M Fibroblasts[b] || ** |
|---|---|---|---|---|---|---|---|---|---|---|---|---|---|---|
| | | | | | | CaCi-2[a] || CaCi-2[b] || CaCi-8[a] || | | |
| | | | | | | n[c] | IC$_{50}$ | n[c] | IC$_{50}$ | n[c] | IC$_{50}$ | n[c] | IC$_{50}$ | |
| 10 | 49835836 | 103910824 | BRD-K71142328 | S | (oxazol-2-ylmethyl) | 3 | IA | 2 | IA | 3 | 34.2 ± 7.9 | 1 | IA | ND |

PBS Solubility: <1.0 μM  Plasma Protein Binding: >99%  Plasma Stability: 97%  Purity (UPLC): >99%

IA = Inactive; ND = Not determined; S = synthesized; P = purchased.
** CaCi-2 to anti-target fold selectivity.
[a] In the presence of fluconazole.
[b] In the absence of fluconazole.
[c] Number of replicates.

TABLE 4

Biological and Physical Properties of Substituted Indazoles (10 analogs)

Structure: 3-phenyl-1H-indazole with R₄, R₂ substituents on benzene ring and N-CH₂C(O)OMe

| Entry No. | SARAnalysis CID | SID | Broad ID | * | R₁ | R₂ | Target Potency (μM) Mean±S.E.M ||||||| Anti-target Potency (μM) Mean ± S.E.M Fibroblasts[b] || ** |
|---|---|---|---|---|---|---|---|---|---|---|---|---|---|---|---|
| | | | | | | | CaCi-2[a] || CaCi-2[b] || CaCi-8[a] || | | |
| | | | | | | | n[c] | IC$_{50}$ | n[c] | IC$_{50}$ | n[c] | IC$_{50}$ | n[c] | IC$_{50}$ | |
| 1 | 49835874 | 103910845 | BRD-K76441112 | S | Me | H | 3 | 3.28 ± 1.06 | 2 | IA | 3 | 5.33 ± 0.72 | 2 | 69.5 | 21 |
| | PBS Solubility: <1.0 μM  Plasma Protein Binding: 95%  Plasma Stability: <1.0%  Purity (UPLC): 97% ||||||||||||||||
| 2 | 49835837 | 103910851 | BRD-K03923773 | S | OMe | H | 3 | IA | 2 | IA | 3 | 18.5 ± 7.6 | 1 | IA | ND |
| | PBS Solubility: <1.0 μM  Plasma Protein Binding: <1.0%  Plasma Stability: <1.0%  Purity (UPLC): >99% ||||||||||||||||
| 3 | 49835889 | 103910846 | BRD-K89892330 | S | F | H | 3 | 4.63 ± 0.30 | 2 | IA | 3 | 6.98 ± 0.69 | 1 | IA | ND |
| | PBS Solubility: <1.0 μM  Plasma Protein Binding: >96%  Plasma Stability: 1.0%  Purity (UPLC): 82% ||||||||||||||||
| 4 | 9551137 | 99245555 | BRD-K17052831 | S | Cl | H | 3 | IA | 4 | IA | 3 | 9.84 ± 1.03 | 1 | IA | ND |
| | PBS Solubility: <1.0 μM  Plasma Protein Binding: >99%  Plasma Stability: <1.0%  Purity (UPLC): >93% ||||||||||||||||
| 5 | 49835872 | 103910833 | BRD-K17372907 | S | H | Me | 3 | 3.14 ± 0.99 | 2 | IA | 2 | 9.62 ± 0.34 | 1 | 31.6 | 10 |
| | PBS Solubility: <1.0 μM  Plasma Protein Binding: 98%  Plasma Stability: 6.5%  Purity (UPLC): 87% ||||||||||||||||
| 6 | 49835812 | 103910841 | BRD-K59965621 | S | H | OMe | 3 | 7.37 ± 1.49 | 2 | IA | 3 | 12.7 ± 0.6 | 1 | 0.80 | 0.01 |
| | PBS Solubility: <1.0 μM  Plasma Protein Binding: 38%  Plasma Stability: 1.3%  Purity (UPLC): 93% ||||||||||||||||
| 7 | 49835815 | 103910832 | BRD-K21644500 | S | H | F | 3 | 5.10 ± 0.96 | 2 | IA | 3 | 8.34 ± 4.30 | 1 | IA | ND |
| | PBS Solubility: <1.0 μM  Plasma Protein Binding: 97%  Plasma Stability: 1.1%  Purity (UPLC): 92% ||||||||||||||||

TABLE 4-continued

Biological and Physical Properties of Substituted Indazoles (10 analogs)

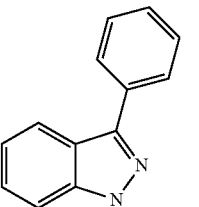

| Entry No. | CID | SID | Broad ID | * | $R_1$ | $R_2$ | $n^c$ | CaCi-2$^a$ IC$_{50}$ | $n^c$ | CaCi-2$^b$ IC$_{50}$ | $n^c$ | CaCi-8$^a$ IC$_{50}$ | $n^c$ | Fibroblasts$^b$ IC$_{50}$ | ** |
|---|---|---|---|---|---|---|---|---|---|---|---|---|---|---|---|
| 8 | 49835818 | 103910839 | BRD-K77651440 | S | H | Cl | 3 | 3.79 ± 1.97 | 2 | IA | 2 | 8.57 ± 0.69 | 1 | 29.9 | 7.9 |
| | | | | | | PBS Solubility: <1.0 μM Plasma Protein Binding: 18% Plasma Stability: 90% Purity (UPLC): 92% | | | | | | | | | |
| 9 | 49835849 | 103910808 | BRD-K95485521 | S | H | $CF_3$ | 4 | IA | 3 | IA | 4 | 32.1 ± 17.4 | 1 | IA | ND |
| | | | | | | PBS Solubility: <1.0 μM Plasma Protein Binding: 62% Plasma Stability: 1.7% Purity (UPLC): 95% | | | | | | | | | |
| 10 | 49835842 | 103910809 | BRD-K32112425 | S | | | 1 | IA | 2 | IA | 1 | IA | 1 | IA | ND |

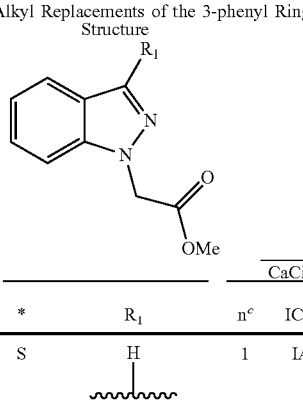

PBS Solubility: <1.0 μM Plasma Protein Binding: >99% Plasma Stability: 50% Purity (UPLC): >99%

IA = Inactive; ND = Not determined; S = synthesized; P = purchased.
** CaCi-2 to anti-target fold selectivity.
$^a$In the presence of fluconazole.
$^b$In the absence of fluconazole.
$^c$Number of replicates.

TABLE 5

Alkyl Replacements of the 3-phenyl Ring (3 Analogs)

| Entry No. | CID | SID | Broad ID | * | $R_1$ | $n^c$ | CaCi-2$^a$ IC$_{50}$ | $n^c$ | CaCi-2$^b$ IC$_{50}$ | $n^c$ | CaCi-8$^a$ IC$_{50}$ | $n^c$ | Fibroblasts$^b$ IC$_{50}$ | ** |
|---|---|---|---|---|---|---|---|---|---|---|---|---|---|---|
| 1 | 49835852 | 103910820 | BRD-K65977579 | S | H | 1 | IA | 2 | IA | 1 | IA | 1 | 0.74 | ND |

PBS Solubility: 154.7 μM Plasma Protein Binding: <1.0% Plasma Stability: <1.0% Purity (UPLC): >99%

TABLE 5-continued

Alkyl Replacements of the 3-phenyl Ring (3 Analogs)

Structure

| | SARAnalysis | | | | | Target Potency (µM) Mean±S.E.M | | | | | | Anti-target Potency (µM) Mean ± S.E.M Fibroblasts[b] | | |
|---|---|---|---|---|---|---|---|---|---|---|---|---|---|---|
| Entry | | | | | | CaCi-2[a] | | CaCi-2[b] | | CaCi-8[a] | | | | |
| No. | CID | SID | Broad ID | * | $R_1$ | $n^c$ | $IC_{50}$ | $n^c$ | $IC_{50}$ | $n^c$ | $IC_{50}$ | $n^c$ | $IC_{50}$ | ** |
| 2 | 49835832 | 103910818 | BRD-K67191613 | S | I | 1 | IA | 2 | IA | 1 | 18.8 | 1 | 0.53 | ND |
| | PBS Solubility: 143.5 µM Plasma Protein Binding: 98% Plasma Stability: 1.3% Purity (UPLC): 91% | | | | | | | | | | | | | |
| 3 | 46856254 | 992455741 | BRD-K61868295 | S | Me | 3 | IA | 4 | IA | 3 | 21.3 ± 8.1 | 3 | IA | ND |
| | PBS Solubility: 287.5 µM Plasma Protein Binding: 42% Plasma Stability: 3.0% Purity (UPLC): >99% | | | | | | | | | | | | | |

IA = Inactive; ND = Not determined; S = synthesized; P = purchased.
** CaCi-2 to anti-target fold selectivity.
[a]In the presence of fluconazole.
[b]In the absence of fluconazole.
[c]Number of replicates.

TABLE 6

Effect of Substitution on the 3-phenyl Ring System (12 analogs)

Structure

| | SARAnalysis | | | | | Target Potency (µM) Mean±S.E.M | | | | | | Anti-target Potency (µM) Mean ± S.E.M Fibroblasts[b] | | |
|---|---|---|---|---|---|---|---|---|---|---|---|---|---|---|
| Entry | | | | | | CaCi-2[a] | | CaCi-2[b] | | CaCi-8[a] | | | | |
| No. | CID | SID | Broad ID | * | $R_1$ | $n^c$ | $IC_{50}$ | $n^c$ | $IC_{50}$ | $n^c$ | $IC_{50}$ | $n^c$ | $IC_{50}$ | ** |
| 1 | 46856255 | 99245540 | BRD-K66205757 | S | 4-Me | 3 | IA | 4 | IA | 3 | 11.0 ± 3.2 | 3 | IA | ND |
| | PBS Solubility: 1.7 µM Plasma Protein Binding: 96% Plasma Stability: 4.1% Purity (UPLC): 95% | | | | | | | | | | | | | |
| 2 | 49835664 | 103910840 | BRD-K00916099 | S | 4-OMe | 3 | 4.23 ± 1.67 | 1 | IA | 3 | 8.30 ± 0.20 | 1 | 1.02 | 0.24 |
| | PBS Solubility: <1.0 µM Plasma Protein Binding: 94% Plasma Stability: 2.7% Purity (UPLC): 97% | | | | | | | | | | | | | |
| 3 | 49835876 | 103910817 | BRD-K83306461 | S | 4-F | 4 | 6.26 ± 1.63 | 3 | IA | 4 | 10.2 ± 4.0 | 1 | IA | ND |
| | PBS Solubility: <1.0 µM Plasma Protein Binding: 93% Plasma Stability: <1.0% Purity (UPLC): 95% | | | | | | | | | | | | | |
| 4 | 46856253 | 99245538 | BRD-K13053491 | S | 4-Cl | 4 | IA | 4 | IA | 3 | 11.6 ± 4.7 | 3 | IA | ND |
| | PBS Solubility: <1.0 µM Plasma Protein Binding: >99% Plasma Stability: 6.4% Purity (UPLC): 95% | | | | | | | | | | | | | |
| 5 | 49835854 | 103910826 | BRD-K89702943 | S | 4CF$_3$ | 3 | IA | 3 | IA | 1 | IA | 1 | 0.68 | ND |
| | PBS Solubility: <1.0 µM Plasma Protein Binding: 97% Plasma Stability: 17% Purity (UPLC): 97% | | | | | | | | | | | | | |
| 6 | 49835863 | 103910815 | BRD-K09194947 | S | 4-CN | 1 | IA | 2 | IA | 1 | 20.0 | 1 | IA | ND |
| | PBS Solubility: <1.0 µM Plasma Protein Binding: 92% Plasma Stability: <1.0% Purity (UPLC): 92% | | | | | | | | | | | | | |
| 7 | 49835823 | 103910848 | BRD-K33918068 | S | 3-Me | 3 | 0.65 ± 0.25 | 2 | IA | 3 | 1.34 ± 0.26 | 1 | IA | ND |
| | PBS Solubility: <1.0 µM Plasma Protein Binding: 98% Plasma Stability: 4.7% Purity (UPLC): 97% | | | | | | | | | | | | | |

TABLE 6-continued

Effect of Substitution on the 3-phenyl Ring System (12 analogs)

Structure

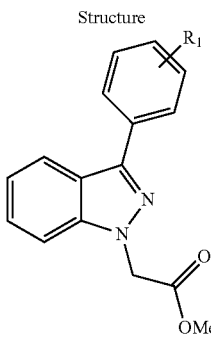

| | SARAnalysis | | | | | Target Potency (μM) Mean±S.E.M | | | | | | Anti-target Potency (μM) Mean ± S.E.M | | |
|---|---|---|---|---|---|---|---|---|---|---|---|---|---|---|
| | | | | | | CaCi-2[a] | | CaCi-2[b] | | CaCi-8[a] | | Fibroblasts[b] | | |
| Entry No. | CID | SID | Broad ID | * | $R_1$ | $n^c$ | $IC_{50}$ | $n^c$ | $IC_{50}$ | $n^c$ | $IC_{50}$ | $n^c$ | $IC_{50}$ | ** |
| 8 | 49835877 | 103910843 | BRD-K14324645 | S | 3-OMe | 3 | 0.44 ± 0.08 | 2 | IA | 3 | 1.21 ± 0.17 | 1 | IA | ND |
| | PBS Solubility: <1.0 μM Plasma Protein Binding: 95% Plasma Stability: 2.6% Purity (UPLC): 93% | | | | | | | | | | | | | |
| 9 | 49835858 | 103910816 | BRD-K34975656 | S | 3-F | 3 | 1.41 ± 0.08 | 3 | IA | 3 | 2.14 ± 0.44 | 1 | 12.9 | 9.1 |
| | PBS Solubility: <1.0 μM Plasma Protein Binding: 96% Plasma Stability: <1.0% Purity (UPLC): 95% | | | | | | | | | | | | | |
| 10 | 49835865 | 103910813 | BRD-K13238786 | S | 2-Me | 3 | 5.50 ± 0.65 | 3 | IA | 3 | 7.25 ± 3.52 | 1 | IA | ND |
| | PBS Solubility: 3.7 μM Plasma Protein Binding: <1.0% Plasma Stability: <1.0% Purity (UPLC): 93% | | | | | | | | | | | | | |
| 11 | 49835850 | 103910838 | BRD-K39093020 | S | 2-OMe | 3 | 6.21 ± 1.73 | 2 | IA | 3 | 10.2 ± 1.8 | 1 | 1.54 | 0.17 |
| | PBS Solubility: 26.7 μM Plasma Protein Binding: 92% Plasma Stability: <1.0% Purity (UPLC): 97% | | | | | | | | | | | | | |
| 12 | 49835858 | 103910849 | BRD-K39093020 | S | 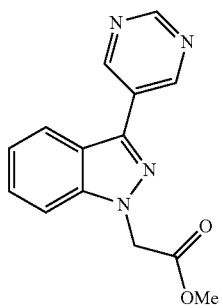 [SMILES: COC(=O)Cn1nc(-c2cncnc2)c2ccccc21] | 3 | IA | 2 | IA | 1 | IA | 1 | IA | ND |
| | PBS Solubility: 154.6 μM Plasma Protein Binding: ND Plasma Stability: <1.0% Purity (UPLC): 93% | | | | | | | | | | | | | |

IA = Inactive; ND = Not determined; S = synthesized; P = purchased.
** CaCi-2 to anti-target fold selectivity.
[a]In the presence of fluconazole.
[b]In the absence of fluconazole.
[c]Number of replicates.

TABLE 7

Miscellaneous Analogs of the 3-phenyl-1H-indazole Scaffold (11 analogs)

| | SAR Analysis | | | | | Target Potency (μM) Mean ± S.E.M | | | | | | Anti-Target Potency (μM) Mean ± S.E.M | |
|---|---|---|---|---|---|---|---|---|---|---|---|---|---|
| Entry | | | | | | CaCi-2[a] | | CaCi-2[b] | | CaCi-8[a] | | Fibroblasts[b] | |
| No. | CID | SID | Broad ID | * | Structure | $n^c$ | $IC_{50}$ | $n^c$ | $IC_{50}$ | $n^c$ | $IC_{50}$ | $n^b$ $IC_{50}$ | ** |
| 1 | 12312246 | 99245565 | BRD-K08771473 | S | 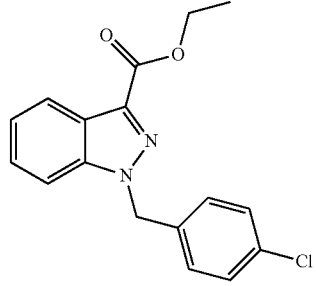 [SMILES: CCOC(=O)c1nn(Cc2ccc(Cl)cc2)c2ccccc12] | 3 | IA | 4 | IA | 3 | IA | 3 IA | ND |

PBS Solubility: <0.1 μM Plasma Protein Binding: >99% Plasma Stability: 93% Purity (UPLC): >99%

| 2 | 100493 | 99245554 | BRD-K67484673 | S | 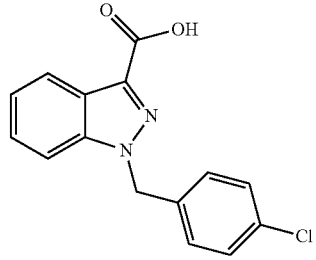 [SMILES: O=C(O)c1nn(Cc2ccc(Cl)cc2)c2ccccc12] | 3 | IA | 4 | IA | 2 | IA | 3 IA | ND |

PBS Solubility: 516.1 μM Plasma Protein Binding: >99% Plasma Stability: >99% Purity (UPLC): 99%

| 3 | 46856252 | 99245530 | BRD-K96609729 | S | 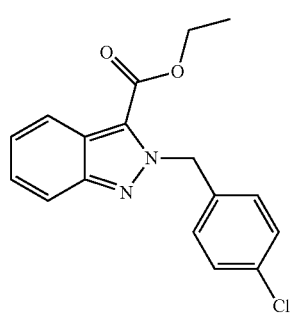 [SMILES: CCOC(=O)c1c2ccccc2nn1Cc1ccc(Cl)cc1] | 3 | IA | 4 | IA | 3 | IA | 3 IA | ND |

PBS Solubility: <1.0 μM Plasma Protein Binding: >99% Plasma Stability: 70% Purity (UPLC): 99%

| 4 | 14420592 | 99245552 | BRD-K03169838 | S | 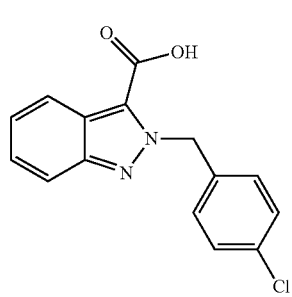 [SMILES: O=C(O)c1c2ccccc2nn1Cc1ccc(Cl)cc1] | 3 | IA | 3 | IA | 3 | IA | 3 IA | ND |

PBS Solubility: 502.6 μM Plasma Protein Binding: >99% Plasma Stability: 96% Purity (UPLC): 95%

TABLE 7-continued

Miscellaneous Analogs of the 3-phenyl-1H-indazole Scaffold (11 analogs)

| | | | SAR Analysis | | | Target Potency (μM) Mean ± S.E.M | | | | | | Anti-Target Potency (μM) Mean ± S.E.M | |
|---|---|---|---|---|---|---|---|---|---|---|---|---|---|
| Entry | | | | | | CaCi-2[a] | | CaCi-2[b] | | CaCi-8[a] | | Fibroblasts[b] | |
| No. | CID | SID | Broad ID | * | Structure | n[c] | IC$_{50}$ | n[c] | IC$_{50}$ | n[c] | IC$_{50}$ | n[b] | IC$_{50}$ | ** |
| 5 | 46378661 | 99245545 | BRD-K77711392 | P | | 3 | IA | 4 | IA | 3 | IA | 3 | IA | ND |

PBS Solubility: 529.1 μM   Plasma Protein Binding: 52%   Plasma Stability: >99%   Purity (UPLC): 96%

| 6 | 4131200 | 103023261 | BRD-K61757267 | S | | 3 | IA | 3 | IA | 3 | IA | 2 | IA | ND |

PBS Solubility: 438.2 μM   Plasma Protein Binding: 95%   Plasma Stability: 46%   Purity (UPLC): 96%

| 7 | 20877381 | 99245558 | BRD-K89784498 | P | | 3 | IA | 4 | IA | 3 | IA | 3 | IA | ND |

PBS Solubility: 8.0 μM   Plasma Protein Binding: 96%   Plasma Stability: 99%   Purity (UPLC): >99%

| 8 | 20877322 | 99245547 | BRD-K50197321 | P | | 3 | IA | 4 | IA | 2 | IA | 3 | IA | ND |

PBS Solubility: <1.0 μM   Plasma Protein Binding: >99%   Plasma Stability: 97%   Purity (UPLC): >99%

TABLE 7-continued

Miscellaneous Analogs of the 3-phenyl-1H-indazole Scaffold (11 analogs)

| Entry No. | CID | SID | Broad ID | * | Structure | Target Potency (μM) Mean ± S.E.M ||||||| Anti-Target Potency (μM) Mean ± S.E.M ||| |
|---|---|---|---|---|---|---|---|---|---|---|---|---|---|---|
| | | | | | | CaCi-2[a] || CaCi-2[b] || CaCi-8[a] || Fibroblasts[b] |||
| | | | | | | $n^c$ | $IC_{50}$ | $n^c$ | $IC_{50}$ | $n^c$ | $IC_{50}$ | $n^b$ | $IC_{50}$ | ** |
| 9 | 46856251 | 99245549 | BRD-K42988725 | S | *(3-methyl-1-methanesulfonyl-1H-indazole)* | 3 | IA | 4 | IA | 3 | IA | 3 | IA | ND |
| 10 | 9855970 | 103910621 | BRD-K20739871 | | *(3-(4-methoxyphenyl)-1H-indazole)* | 1 | IA | 2 | IA | 1 | IA | 1 | IA | ND |
| 11 | 49635869 | 103910814 | BRD-K52595598 | | *(3-(4-trifluoromethylphenyl)-1H-indazole)* | 1 | IA | 2 | IA | 1 | IA | 1 | IA | ND |

Entry 9: PBS Solubility: 494.5 μM  Plasma Protein Binding: 63%  Plasma Stability: >99%  Purity (UPLC): 98%

Entry 10: PBS Solubility: <1.0 μM  Plasma Protein Binding: 98%  Plasma Stability: 89%  Purity (UPLC): 98%

Entry 11: PBS Solubility: <1.0 μM  Plasma Protein Binding: >99%  Plasma Stability: 79%  Purity (UPLC): >99%

IA = Inactive; ND = Not determined; S = synthesized; P = purchased.
** CaCi-2 to anti-target fold selectivity.
[a] In the presence of fluconazole.
[b] In the absence of fluconazole.
[c] Number of replicates.

TABLE 8

IC$_{50}$ values of certain exemplary compounds

| R | CaCi-2 IC$_{50}$ (μM)[b] | CaCi-8 IC$_{50}$ (μM)[b] |
|---|---|---|
| H | 2.2 ± 1.0 | 3.5 ± 1.9 |
| 5-Me | 5.2 ± 2.2 | 8.2 ± 3.2 |
| 5-OMe | 14.9 ± 5.7 | 22.1 ± 6.2 |
| 5-F | 11.2 ± 7.2 | inactive |
| 6-Me | 5.9 ± 3.1 | inactive |
| 6-OMe | 9.5 ± 2.5 | 12.4 ± 0.5 |
| 6-Cl | 4.0 ± 1.3 | 8.4 ± 0.5 |
| 6-CF$_3$ | inactive | inactive |
| 6-CN | inactive | inactive |
| 7-CF$_3$ | inactive | inactive |
| Ph | inactive | inactive |

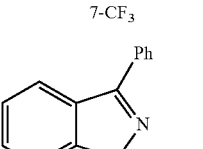

[a]CaCi-2 and CaCi-8 cells were incubated at 37° C. for 48 hours with test compound and 8 μg/mL (26 μM) fluconazole.
[b]Average of at least three independent experiments, performed in duplicate. Inactive compounds displayed negligible activity at concentrations below 26 μM.

TABLE 9

IC$_{50}$ values of certain exemplary compounds

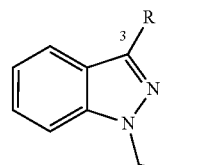

| R | CaCi-2 IC$_{50}$ (μM)[b] | CaCi-8 IC$_{50}$ (μM)[b] |
|---|---|---|
| —H | inactive | inactive |
| —Et | inactive | inactive |
| 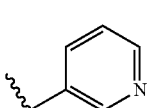 | inactive | inactive |
| 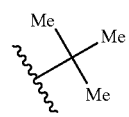 | inactive | Inactive |
| 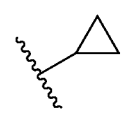 [SMILES: *C1CC1] | 2.3 ± 0.3 | 6.0 ± 1.7 |

TABLE 9-continued

IC$_{50}$ values of certain exemplary compounds

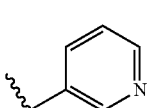

| R | CaCi-2 IC$_{50}$ (μM)[b] | CaCi-8 IC$_{50}$ (μM)[b] |
|---|---|---|
| 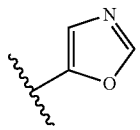 | inactive | inactive |
| 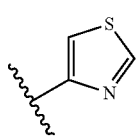 | inactive | 21.1 ± 3.3 |
| 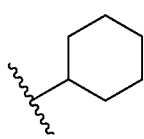 [SMILES: *C1CCCCC1] | inactive | inactive |
| | 12.9 ± 1.7 | inactive |

[a]CaCi-2 and CaCi-8 cells were incubated at 37° C. for 48 hours with test compound and 8 μg/mL (26 μM) fluconazole.
[b]Average of at least three independent experiments, performed in duplicate. Inactive compounds displayed negligible activity at concentrations below 26 μM.

TABLE 10

IC$_5$0 values of certain exemplary compounds

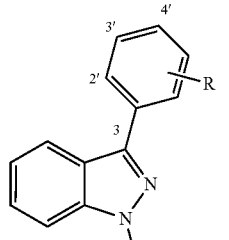

| Cpd | R | CaCi-2 IC$_{50}$ (μM)[b] | CaCi-8 IC$_{50}$ (μM)[b] |
|---|---|---|---|
| 1 | H | 2.2 ± 1.0 | 3.5 ± 1.9 |
| 30 | 4'-Me | 4.8 ± 2.5 | 19.5 ± 14.2 |
| 31 | 4'-OMe | 4.2 ± 1.7 | 14.1 ± 6.4 |
| 32 | 4'-F | 8.3 ± 2.8 | 12.3 ± 3.9 |
| 33 | 4'-CF$_3$ | inactive | inactive |
| 34 | 4'-CN | inactive | 20.5 ± 0.3 |
| 35 | 3'-Me | 1.1 ± 0.6 | 1.9 ± 0.9 |
| 36 | 3'-OMe | 0.7 ± 0.3 | 1.5 ± 0.6 |
| 37 | 3'-NMe$_2$ | 0.8 ± 0.1 | 2.0 ± 0.2 |
| 38 | 3'-F | 1.7 ± 0.4 | 4.2 ± 4.1 |
| 39 | 2'-Me | 5.3 ± 0.5 | 7.8 ± 2.6 |
| 40 | 2'-OMe | 9.3 ± 3.6 | 11.4 ± 1.7 |
| 41 | 3',5'-di-OMe | inactive | inactive |

[a] CaCi-2 and CaCi-8 cells were incubated at 37° C. for 48 hours with test compound and 8 μg/mL (26 μM) fluconazole.
[b] Average of at least three independent experiments, performed in duplicate. Inactive compounds displayed negligible activity at concentrations below 26 μM.

TABLE 10A

IC$_{50}$ values and selectivity of certain exemplary compounds

| Compound | IC$_{50}$ (nM) | Selectivity* |
|---|---|---|
| I-70 | 275 | 58.2 |
| I-71 | 250 | 80 |
| I-72 | 40 | 200 |
| I-73 | >80,000 | |
| I-74 | 3,000 | 53 |
| I-75 | >80,000 | |
| I-76 | 1,250 | 32 |
| I-77 | 625 | 48 |
| I-78 | 10 | 100 |
| I-79 | 40 | 50 |
| I-80 | 12.5 | 20 |
| I-81 | 1,250 | 8 |
| I-82 | 125 | 40 |
| I-83 | 40,000 | 3 |
| I-84 | 8,000 | >32 |
| I-85 | 2,000 | 40 |
| I-86 | 5,000 | >32 |
| I-87 | >160,000 | |
| I-88 | 25 | 200 |
| I-89 | 10,000 | 3.75 |
| I-90 | 1,250 | 32 |
| I-91 | >20,000 | |
| I-92 | 30,000 | >5 |
| I-93 | 25,000 | >6 |
| I-94 | 40,000 | >4 |
| I-95 | >20,000 | |
| I-96 | 600 | 13.3 |
| I-97 | 4 | 200 |
| I-98 | 63 | 48 |
| I-99 | 23 | 160 |
| I-100 | 7 | 54 |
| I-101 | 1.5 | 49 |
| I-102 | 46 | 16 |
| I-103 | 7 | 71 |
| I-107 | >120,000 | |
| I-108 | 20,000 | |
| I-109 | 80,000 | |
| I-110 | >120,000 | |
| I-112 | >120,000 | |
| I-113 | >120,000 | |
| I-114 | >120,000 | |
| I-115 | 630 | 128 |
| I-117 | 20,000 | |
| I-118 | 1,250 | 96 |
| I-119 | 500 | 160 |
| I-120 | 15,000 | |
| I-121 | 15,000 | |
| I-122 | 80,000 | |
| I-123 | >120,000 | |
| I-124 | 80,000 | |
| I-125 | 59 | 340 |
| I-126 | 94 | 320 |
| I-127 | >32,000 | |
| I-128 | 500 | 32 |
| I-129 | 150 | 133 |
| I-130 | 250 | 32 |
| I-131 | 400 | 40 |
| I-132 | 750 | 32 |
| I-133 | 400 | 30 |
| I-134 | 200 | 20 |
| I-135 | 800 | 3.75 |
| I-136 | 60 | 8.3 |
| I-137 | >32,000 | |
| I-138 | >32,000 | |
| I-139 | 1,000 | 6 |
| I-140 | 400 | 8 |
| I-141 | 62.5 | 12 |

*The term "selectivety" refers to the value of (anti-target IC$_{50}$)/(target IC$_{50}$). As used in this table, the target is yeast, and the anti-target is human cytochrome.

TABLE 11

Properties of Probe Compound I-4 (CID 49835877/ML212)

| CID/ML No. | Target Name | IC$_{50}$ (nM) [SID, AID] | Anti-Target Names | IC$_{50}$ (nM) [SID, AID] | Fold Selective* | Secondary Assay(s) IC$_{50}$ (nM) [SID, AID] |
|---|---|---|---|---|---|---|
| 49835877/ 212 | CaCi-2 growth inhibition | 440 [103910843, 493080] | Fibroblast toxicity | >26,000 (103910843, 493147] | 59 | CaCi-8 growth inhibition 1210 [103910843, 493149] |
| | | | Activity without fluconazole | >26,000 [103910843, 493070] | 59 | |

*Selectivity = Anti-target IC$_{50}$/Target IC$_{50}$.

Cellular Activity Results.

All assays were performed with whole cells. A murine 3T3 fibroblast mammalian cell toxicity assay was included as a secondary screen. Experimental details are provided herein in Example 4.2. The probe (compound I-4; CID 49835877/ML212) clearly met the established probe criteria specified in Example 1 (Table 12).

TABLE 12

Properties of Probe Compound I-4 (CID 49835877/ML212) Meet the Requirements

| No. | Property | Requirement | Probe |
|---|---|---|---|
| 1 | CaCi-2 $IC_{50}$ with 8 µg/ml fluconazole | Less than 1 µM | 0.44 µM |
| 2 | CaCi-8 $IC_{50}$ with 8 µg/ml fluconazole | Less than 50 µM | 1.21 µM |
| 3 | CaCi-2 $IC_{50}$ without fluconazole | Greater than 10 µM | >26 µM |
| 4 | Mammalian fibroblast $IC_{50}$ | At least 10-fold greater than (1) | >59-fold |

Profiling Assays.

The probe compound I-4 (CID 49835877/ML212) was evaluated for inhibitory activity against calcinuerin and Hsp90. Assay results indicated the probe was a mild inhibitor of the Hsp90 pathway ($IC_{50}$=4.18 µM). Additional details are provided below in the Discussion section.

Discussion

Comparison to Existing Art and how the New Probe is an Improvement.

Investigation into relevant prior art entailed searching the following databases: SciFinder, Reaxys, PubChem, PubMed, US Patent and Trademark Office (USPTO), PatFT, AppFT, and World Intellectual Property Organization (WIPO). The search terms applied and hit statistics are provided in Table 13. The searches were performed on and are current as of Feb. 7, 2011.

TABLE 13

Search Strings and Databases Employed in the Prior Art Search

| Search String | Database | Hits Found |
|---|---|---|
| "fluconazole resistance" | SciFinder | 3071 |
| "fluconazole sensitivity" | SciFinder | 702 |
| "fluconazole chemosensitizer" | SciFinder | 12 |
| "fluconazole resistance" | Reaxys | 162 |
| "fluconazole AND sensitivity" | Reaxys | 20 |
| "fluconazole AND chemosensitize" | Reaxys | 1 |
| "fluconazole resistance" | PubChem Bioassay | 250 |
| "fluconazole sensitivity" | PubChem Bioassay | 34 |
| "fluconazole chemosensitize" | PubChem Bioassay | 0 |
| "fluconazole resistance" | PubMed | 1923 |
| "fluconazole sensitivity" | PubMed | 2153 |
| "fluconazole chemosensitize" | PubMed | 1 |
| "fluconazole resistance" | USPTO PatFT | 16 |
| "fluconazole resistance" | USPTO AppFT | 28 |
| "fluconazole sensitivity" | WIPO | 1225 |

Figure 7:
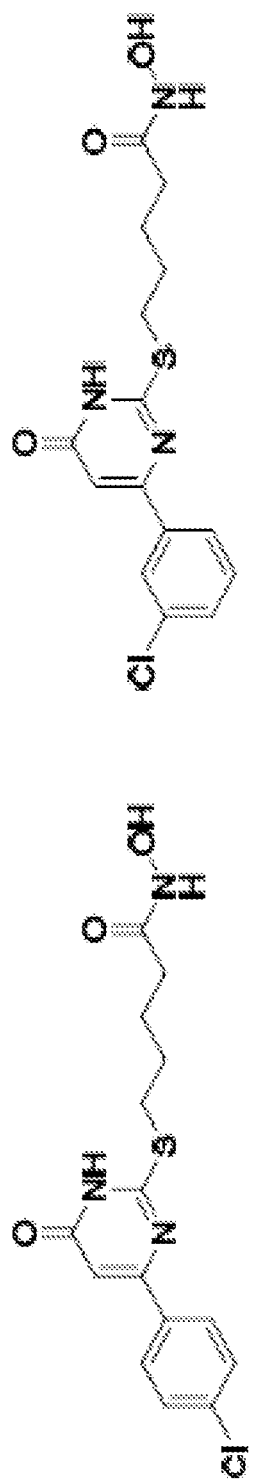
FIG. 7 shows the chemical structure of two exemplary chemosensitizers for reversing fluconazole resistance (MIC=1.2-2.8 µM).

Several compounds have been previously identified as chemosensitizers, increasing the susceptibility of various *C. albicans* strains to fluconazole treatment (DiGirolamo et al., *J. Nat. Prod.* 2009, 72(8):1524-28; Cernicka et al., *Int. J. Antimicrobial Agents*. 2007, 29 (2):170-8; Gamarra et al., *Antimicrob. Agents Chemother.* 2010, 54(5):1753-61; Guo et al., *J. Appl. Microbio.* 2008, 104(3):831-38; Courchesne, *J. Pharmacol. Exp. Ther.* 2002, 300:195-99; Mai et al., *Bioorg. Med. Chem. Lett.* 2007, 17(5):1221-25). The most potent belonged to a series of HDAC inhibitors reported by Mai et al. (Mai et al., *Bioorg. Med. Chem. Lett.* 2007, 17(5):1221-25). Depicted in FIG. 7, these compounds are uracil-derived hydroxamic acids and exhibited MIC values ranging from 1.2 µM to 2.8 µM when combined with fluconazole. When tested in the absence of fluconazole, neither compound demonstrated activity against *C. albicans* at concentrations up to 368 µM. The potent activity of these compounds against murine HDAC1 ($IC_{50}$<51 nM) indicates they would not likely possess the fungal selectivity required for the probe.

Mechanism-of-Action Studies.

All compounds were binned into one of three categories: 1) Hsp90-inhibitors, 2) Calcineurin inhibitors, or 3) Other mechanism.

Potential inhibition of the Hsp90-based chaperone machinery was evaluated using yeast reporter assays involving the glucocorticoid hormone receptor and the tyrosine kinase, v-Src. Both of these well established client proteins depend heavily on Hsp90 for their function. Refer to Example 4.4 for method details.

Potential inhibition of calcineurin function was evaluated in yeast carrying a construct encoding calcineurin-dependent response elements (CDRE) driving expression of a reporter enzyme. Reporter activity with or without the prior addition of test compounds was measured following challenge with the stressor $CaCl_2$.

The probe compound I-4 (CID 49835877/ML212) exhibited Hsp90 pathway inhibition with $IC_{50}$=4.18 µM in the *S. cerevisiae* model. The inactivity of the compound in the mammalian fibroblast assay ($IC_{50}$>26 µM) suggests that compound I-4 may be a fungal-selective Hsp90 inhibitor.

Figure 10:
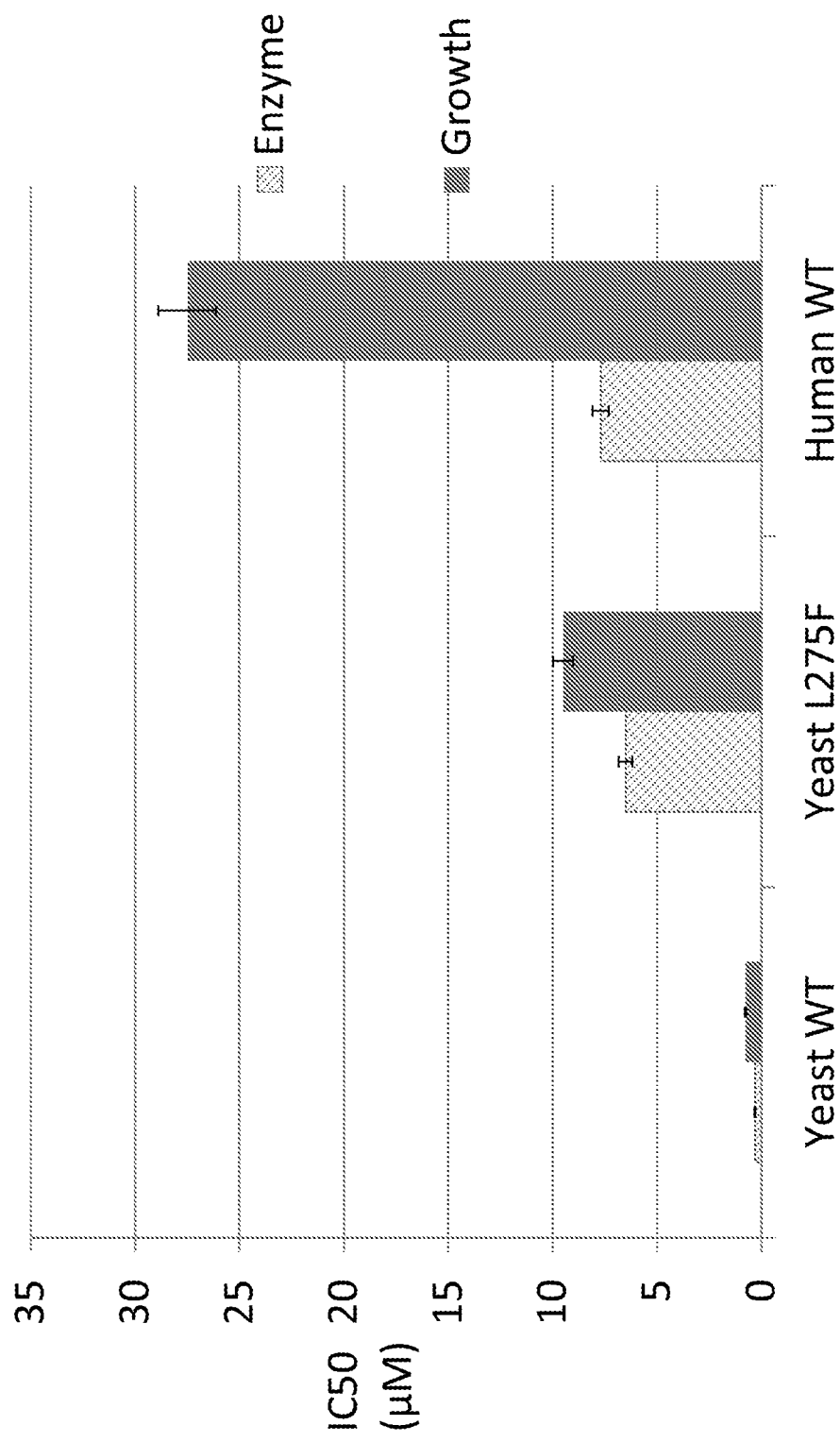
FIG. 10 shows the inhibitory activities compound I-52 against various cytochrome b enzyme sources in vitro and in vivo.
Figure 11:
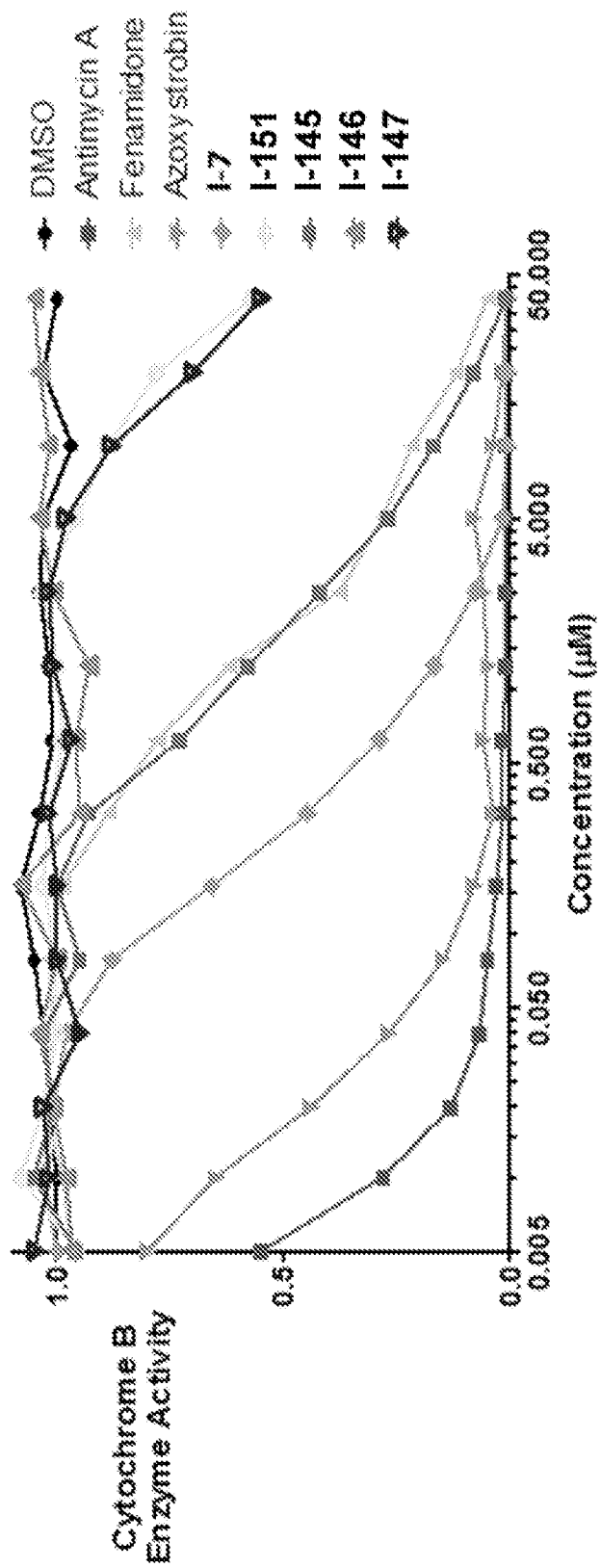
FIG. 11 shows the in vitro inhibitory activities of certain compounds described herein against cytochrome b enzyme.
Figure 12:
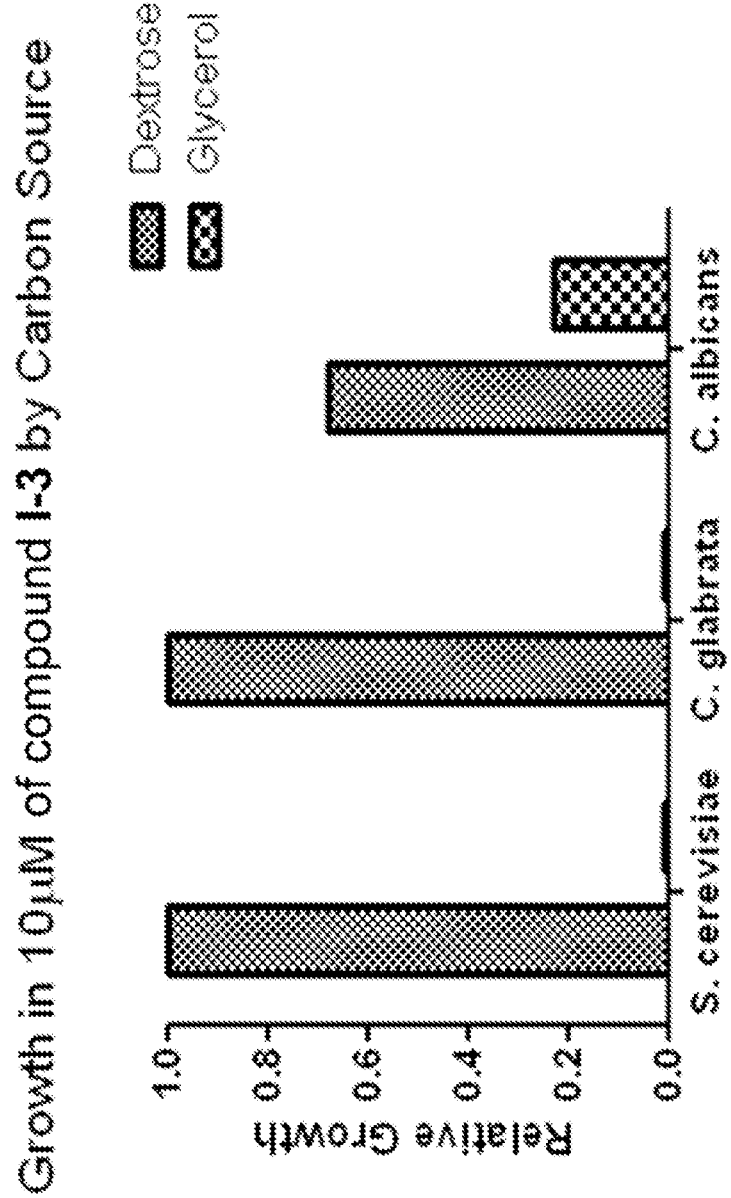
FIG. 12 shows that compound I-3 completely inhibits respiratory growth of genetically tractable yeast.

Cytochrome B was identified as the target by selection of mutants resistant to the probe compound. Whole genome sequencing of resistant mutants and genome alignment to parental drug-sensitive strains identified several unique mutations in the mitochondrial COB (cytochrome B) gene, including L275F, L275S, N256Y in resistant strains. Assay of purified cytochrome bc1 enzymatic activity in the presence of various indazole derivatives (e.g., compounds described herein (e.g., compounds of Formula (I)) exhibited dose-dependent inhibition of enzyme activity at similar concentrations as necessary to inhibit whole cell growth. FIG. 10 shows that resistance in vivo gives resistance in vitro, and FIG. 11 shows that the compounds of the invention are active in vitro in inhibiting the activity of cytochrome b enzyme. Shown in FIG. 12 is the carbon source-dependent toxicity result, wherein compounds described herein may inhibit respiratory growth of genetically tractable yeast. This may allow for selection of resistant mutants and genome sequencing. FIG. 14A shows that compound I-3 was active in inhibiting in vitro the activity of cytochrome B of yeast *S. cerevisiae* (wild type; curve 1) and human Complex III (curve 2). The $IC_{50}$ of compound I-3 against cytochrome B of the wild type of *S. cerevisiae* was about 0.6 µM. Compound I-3's fungal selectivity (i.e., $IC_{50}$ against yeast enzyme over $IC_{50}$ against human enzyme) was about 15. Compound I-3 also showed inhibitory activity against a *S. cerevisiae* that was resistant to known antifungal agents (curve 3). FIG. 14B shows a mutation of the cytochrome B enzyme of an L275F strain of *S. cerevisiae*. The mutation corresponds to a particular amino acid in the human ("*H sapiens*") protein and may account for L275F's resistance to known antifungal agents.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

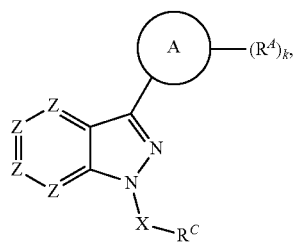

(I)

or a pharmaceutically acceptable salt thereof;
wherein:
Ring A is phenyl
each instance of $R^A$ is independently halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —C(=$NR^{A1}$)$R^{A1}$, —C(=$NR^{A1}$)$OR^{A1}$, —C(=$NR^{A1}$)$N(R^{A1})_2$, —C(=O)$R^{A1}$, —C(=O)$OR^{A1}$, —C(=O)$N(R^{A1})_2$, —$NO_2$, —$NR^{A1}$C(=O)$R^{A1}$, —$NR^{A1}$C(=O)$OR^{A1}$, —$NR^{A1}$C(=O)$N(R^{A1})_2$, —OC(=O)$R^{A1}$, —OC(=O)$OR^{A1}$, or —OC(=O)$N(R^{A1})_2$, or optionally two $R^A$ groups are joined to form a substituted or unsubstituted carbocyclic, substituted or unsubstituted heterocyclic, substituted or unsubstituted aryl, or substituted or unsubstituted heteroaryl ring;
each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{A1}$ groups are joined to form a substituted or unsubstituted heterocyclic ring; provided that when $R^A$ is —$OR^{A1}$, $R^{A1}$ is substituted or unsubstituted acyl, substituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
k is 1, 2, 3, 4, or 5;
each instance of Z is $CR^B$;
each instance of $R^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1}$, —$N(R^{B1})_2$, —$SR^{B1}$, —CN, —SCN, —C(=$NR^{B1}$)$R^{B1}$, —C(=$NR^{B1}$)$OR^{B1}$, —C(=$NR^{B1}$)$N(R^{B1})_2$, —C(=O)$R^{B1}$, —C(=O)$OR^{B1}$, —C(=O)$N(R^{B1})_2$, —$NO_2$, —$NR^{B1}$C(=O)$R^{B1}$, —$NR^{B1}$C(=O)$OR^{B1}$, —$NR^{B1}$C(=O)$N(R^{B1})_2$, —OC(=O)$R^{B1}$, —OC(=O)$OR^{B1}$, or —OC(=O)$N(R^{B1})_2$, or optionally two $R^B$ groups are joined to form a substituted or unsubstituted carbocyclic, substituted or unsubstituted heterocyclic, substituted or unsubstituted aryl, or substituted or unsubstituted heteroaryl ring;
each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{B1}$ groups are joined to form a substituted or unsubstituted heterocyclic ring;
X is —$(C(R^x)_2)_n$—;
each instance of $R^x$ is independently hydrogen, or substituted or unsubstituted alkyl;
n is 1;
$R^C$ is —C(=O)$OR^{C1}$; and
$R^{C1}$ is methyl.

2. The compound of claim 1, or a pharmaceutically acceptable salt thereof, wherein Ring A is of the formula:

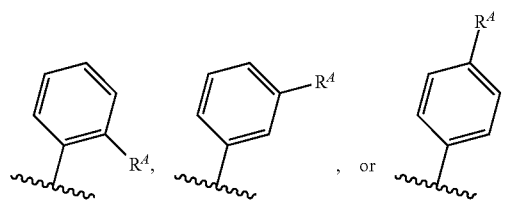

3. The compound of claim 1, or a pharmaceutically acceptable salt thereof, wherein Ring A is of the formula:

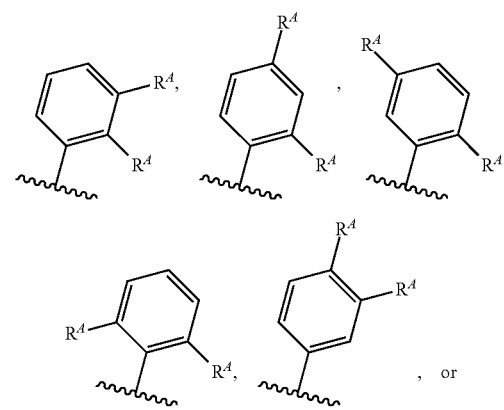

-continued

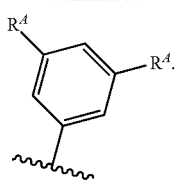

4. The compound of claim 1, or a pharmaceutically acceptable salt thereof, wherein $R^B$ is halogen, substituted or unsubstituted alkyl, $-OR^{B1}$, $-N(R^{B1})_2$, $-SR^{B1}$, $-C(=O)OR^{B1}$, or $-C(=O)N(R^{B1})_2$.

5. The compound of claim 1, wherein the compound is of the formula:

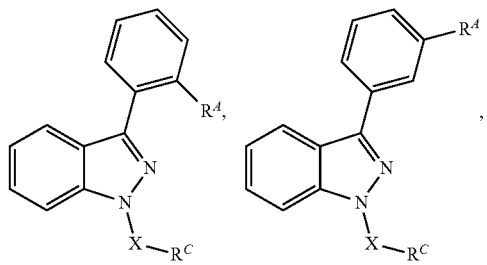

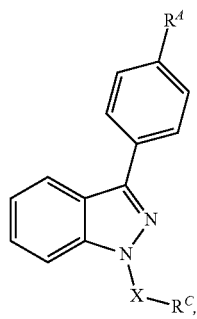

or a pharmaceutically acceptable salt thereof.

6. The compound of claim 1, wherein the compound is of the formula:

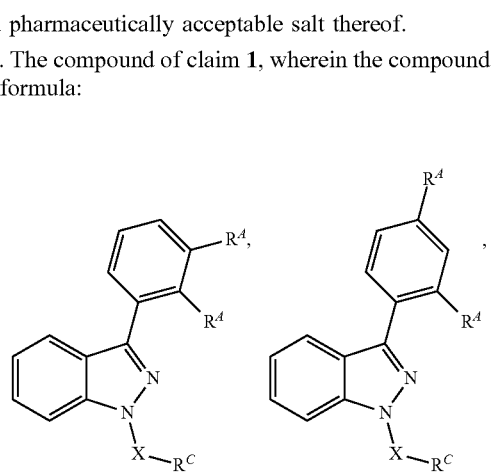

-continued

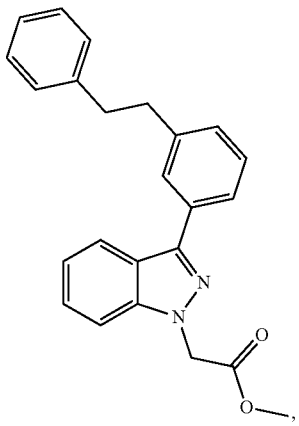

or a pharmaceutically acceptable salt thereof.

7. The compound of claim 1, wherein the compound is of the formula:

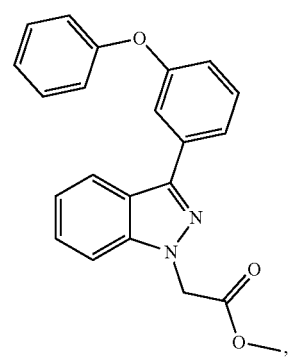

(I-7)
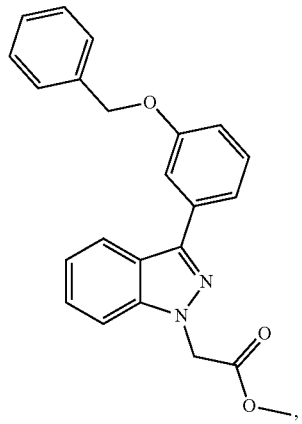
(I-8)
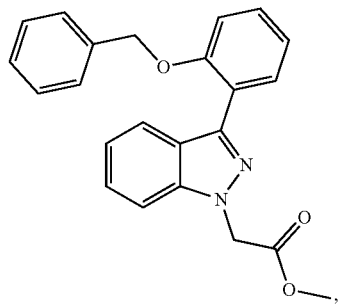
(I-9)
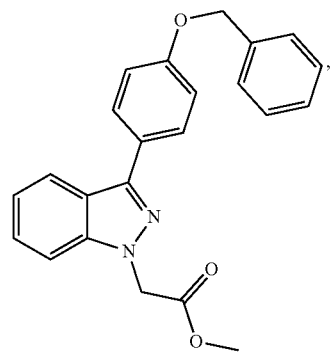
(I-10)
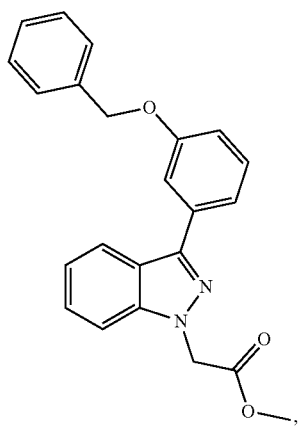
(I-11)
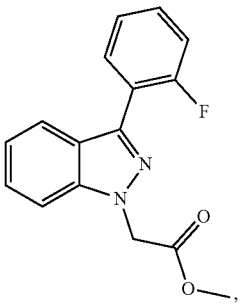
(I-12)
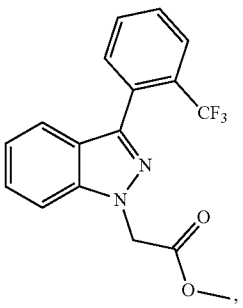
(I-14)
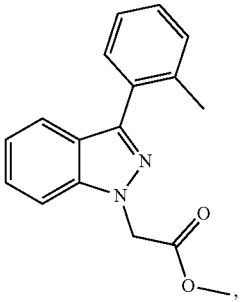
(I-17)
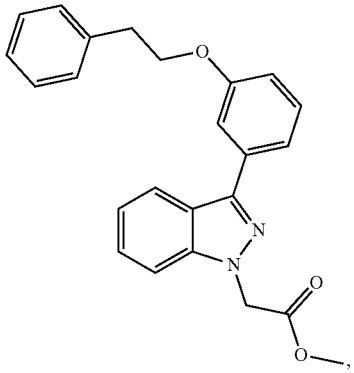

(I-18)
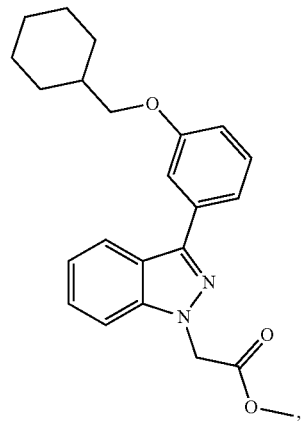
(I-19)
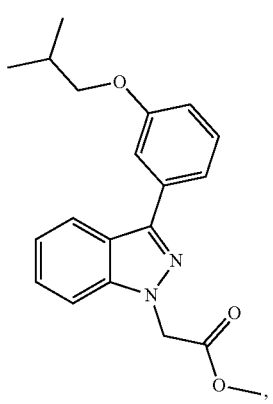
(I-20)
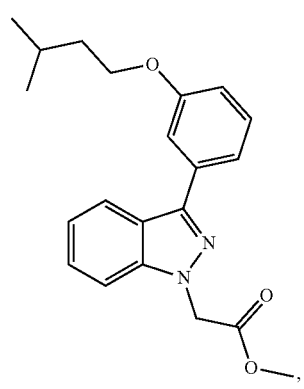
(I-21)
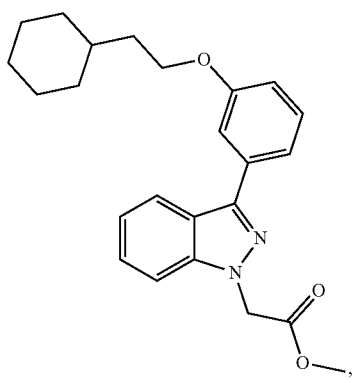
(I-22)
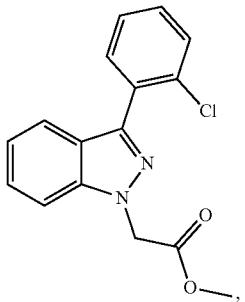
(I-23)
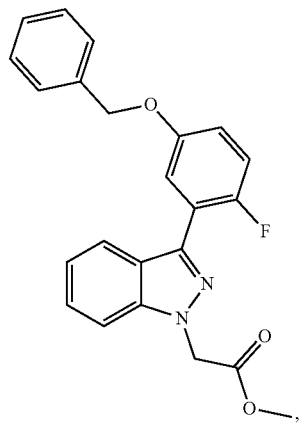
(I-24)
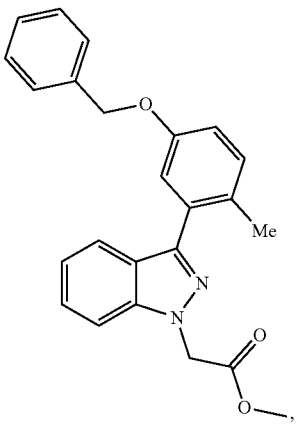
(I-25)
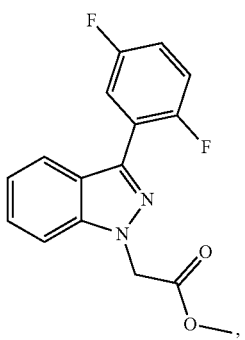

(I-26)
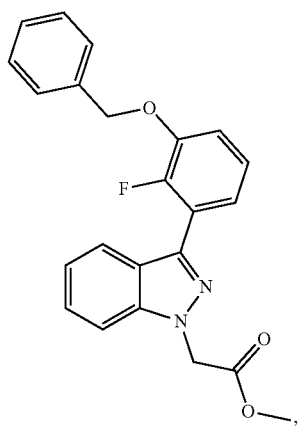
(I-27)
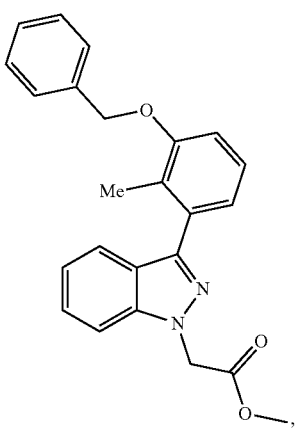
(I-28)
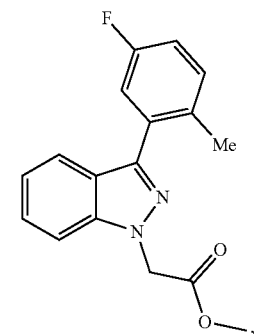
(I-29)
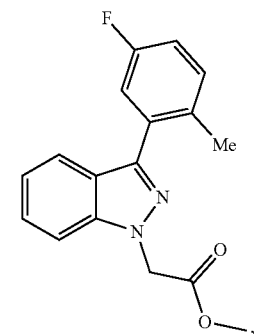
(I-30)
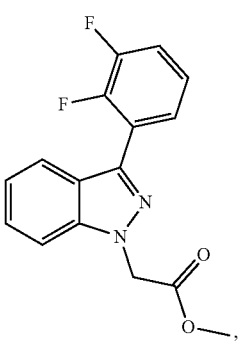
(I-41)
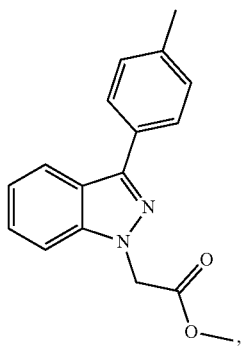
(I-43)
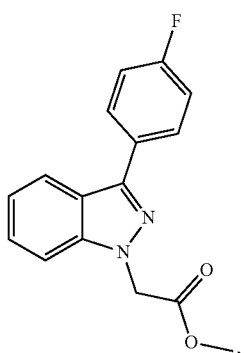
(I-44)
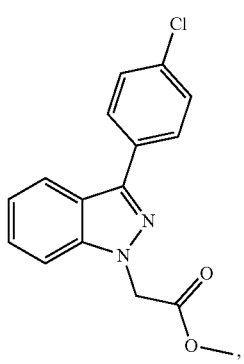

207
-continued
(I-45)
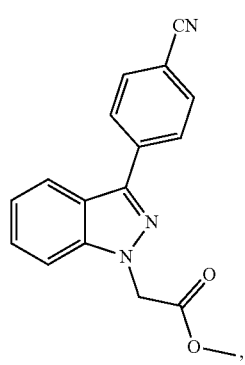
(I-46)
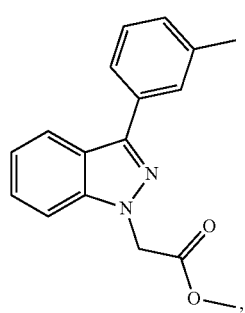
(I-47)
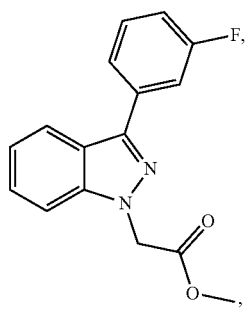
(I-70)
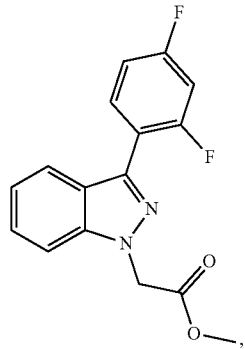
(I-72)
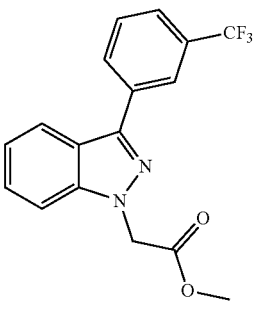
208
-continued
(I-78)
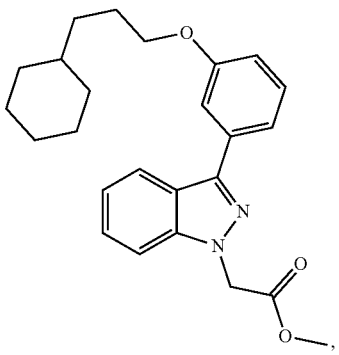
(I-79)
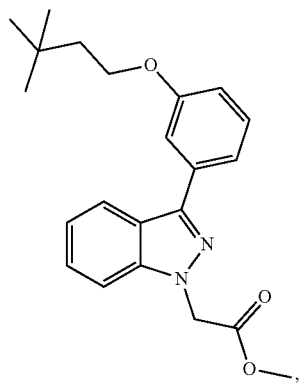
(I-80)
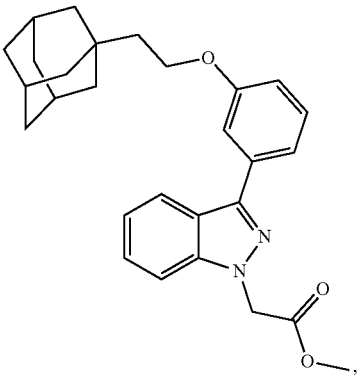
(I-88)
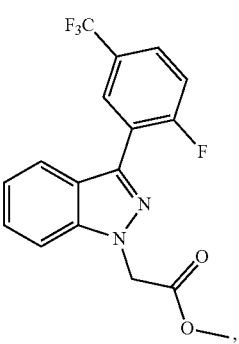

(I-97)
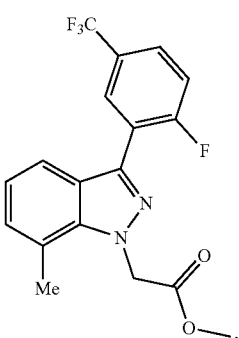

(I-100)
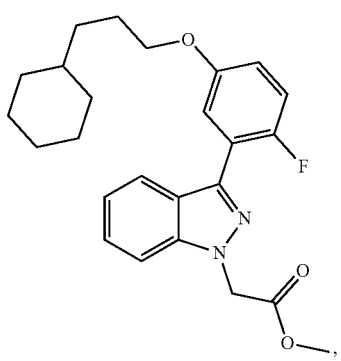

(I-101)
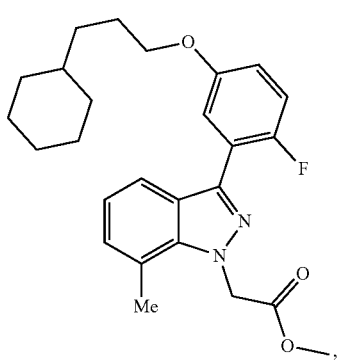

(I-117)
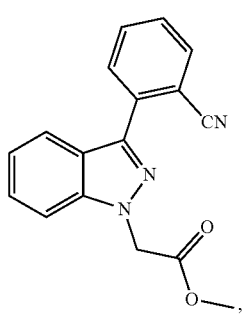

(I-118)
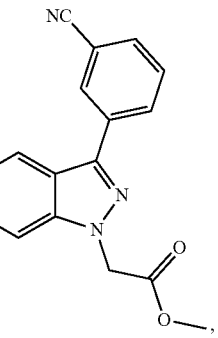

(I-119)
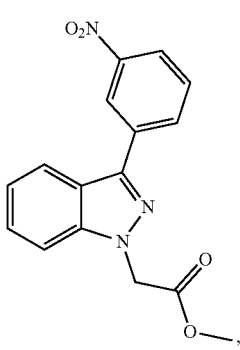

or a pharmaceutically acceptable salt thereof.

8. A pharmaceutical composition comprising a compound of claim 1, or a pharmaceutically acceptable salt thereof, and optionally a pharmaceutically acceptable excipient.

9. A method of treating a fungal infection caused by *Candida albicans*, *Aspergillus terreus*, or *Saccharomyces cerevisiae* in a subject in need thereof, the method comprising:
   administering to the subject a therapeutically effective amount of a compound of claim 1, or a pharmaceutically acceptable salt thereof.

10. A method of inhibiting the activity of *Candida albicans*, *Aspergillus terreus*, or *Saccharomyces cerevisiae* cytochrome b in a subject in need thereof, or biological sample, the method comprising:
   administering to the subject or contacting the biological sample with a therapeutically effective amount of a compound of claim 1, or a pharmaceutically acceptable salt thereof.

11. A method of killing or inhibiting the growth of *Candida albicans*, *Aspergillus terreus*, or *Saccharomyces cerevisiae*, the method comprising:
   contacting the fungus with an effective amount of a compound of claim 1, or a pharmaceutically acceptable salt thereof.

12. The compound of claim 1, or a pharmaceutically acceptable salt thereof, wherein at least one $R^A$ is halogen, substituted or unsubstituted alkyl, $-OR^{A1}$, $-CN$, or $-NO_2$.

13. The compound of claim 1, or a pharmaceutically acceptable salt thereof, wherein at least one $R^A$ is of the formula:

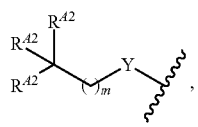

wherein:
each instance of $R^{A2}$ is independently hydrogen, or substituted or unsubstituted alkyl, or two or three $R^{A2}$ groups are joined to form a substituted or unsubstituted carbocyclic ring;
m is 0, 1, 2, or 3; and
Y is —CH$_2$— or —O—.

14. The compound of claim 1, or a pharmaceutically acceptable salt thereof, wherein $R^A$ is F, Cl, Me, —CH$_2$F, —CHF$_2$, —CF$_3$, —(CH$_2$)$_2$Ph, —OH, —OEt, —OPr, —OBu, —O(pentyl), —OCH$_2$(cyclohexyl), —OPh, —OBn, —O(CH$_2$)$_2$Ph, or —CN.

15. The compound of claim 1, wherein the compound is of the formula:

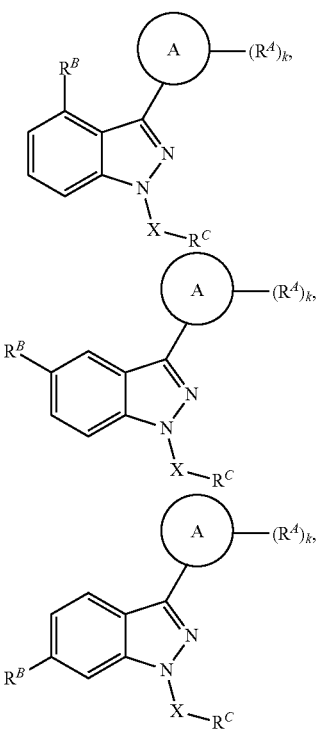

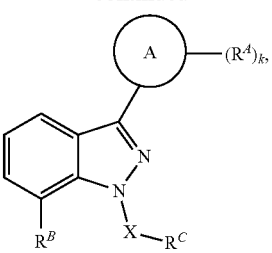

or a pharmaceutically acceptable salt thereof.

16. The compound of claim 1, or a pharmaceutically acceptable salt thereof, wherein all instances of Z are CH.

17. The compound of claim 1, or a pharmaceutically acceptable salt thereof, wherein $R^B$ is F, Cl, Me, —CH$_2$F, —CHF$_2$, —CF$_3$, —OH, —OMe, —NH$_2$, —NHMe, —NHAc, —N(Me)$_2$, —SH, —SMe, —C(=O)OMe, —C(=O)NH$_2$, —C(=O)NHMe, or —C(=O)N(Me)$_2$.

18. The compound of claim 1, or a pharmaceutically acceptable salt thereof, wherein all instances of $R^X$ are hydrogen.

19. The compound of claim 1, wherein the compound is of the formula:

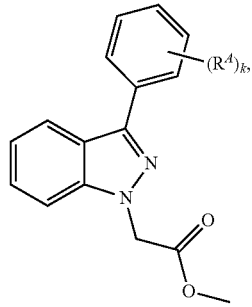

or a pharmaceutically acceptable salt thereof.

* * * * *